US012528850B2

(12) United States Patent
Seidel, III et al.

(10) Patent No.: US 12,528,850 B2
(45) Date of Patent: Jan. 20, 2026

(54) TGF-β POLYPEPTIDES

(71) Applicant: Cue Biopharma, Inc., Boston, MA (US)

(72) Inventors: Ronald D. Seidel, III, Natick, MA (US); Rodolfo J. Chaparro, Cambridge, MA (US); John F. Ross, Arlington, MA (US); Chee Meng Low, Cambridge, MA (US)

(73) Assignee: Cue Biopharma, Inc., Boston, MA (US)

( * ) Notice: Subject to any disclaimer, the term of this patent is extended or adjusted under 35 U.S.C. 154(b) by 151 days.

(21) Appl. No.: 18/134,016

(22) Filed: Apr. 12, 2023

(65) Prior Publication Data

US 2023/0416322 A1 Dec. 28, 2023

Related U.S. Application Data

(60) Division of application No. 17/722,328, filed on Apr. 16, 2022, now Pat. No. 11,692,018, which is a continuation of application No. PCT/US2020/056937, filed on Oct. 22, 2020.

(60) Provisional application No. 62/925,227, filed on Oct. 23, 2019.

(51) Int. Cl.

| | |
|---|---|
| ***C07K 14/495*** | (2006.01) |
| ***A61P 37/06*** | (2006.01) |
| ***C07K 14/54*** | (2006.01) |
| ***C07K 14/545*** | (2006.01) |
| ***C07K 14/55*** | (2006.01) |
| ***C07K 14/705*** | (2006.01) |
| ***C12N 5/00*** | (2006.01) |
| ***C12N 15/62*** | (2006.01) |
| *A61K 38/00* | (2006.01) |

(52) U.S. Cl.

CPC ............ *C07K 14/495* (2013.01); *A61P 37/06* (2018.01); *C07K 14/54* (2013.01); *C07K 14/5406* (2013.01); *C07K 14/5412* (2013.01); *C07K 14/5418* (2013.01); *C07K 14/5428* (2013.01); *C07K 14/5443* (2013.01); *C07K 14/545* (2013.01); *C07K 14/55* (2013.01); *C07K 14/70532* (2013.01); *C07K 14/70575* (2013.01); *C12N 5/00* (2013.01); *C12N 15/62* (2013.01); *A61K 38/00* (2013.01); *C07K 2318/10* (2013.01); *C07K 2319/74* (2013.01)

(58) Field of Classification Search

CPC .................................................... C07K 14/495

See application file for complete search history.

(56) References Cited

U.S. PATENT DOCUMENTS

| | | | | |
|---|---|---|---|---|
| 9,090,685 | B2 | 7/2015 | Ledbetter et al. | |
| 11,692,018 | B2 * | 7/2023 | Seidel, III .......... | C07K 14/5418 424/85.2 |
| 2010/0221777 | A1 | 9/2010 | Choe et al. | |
| 2011/0165623 | A1 | 7/2011 | Sun et al. | |
| 2018/0221508 | A1 | 8/2018 | Kadiyala et al. | |
| 2018/0327477 | A1 | 11/2018 | Kumar et al. | |
| 2019/0062400 | A1 | 2/2019 | Seidel, III et al. | |
| 2020/0308243 | A1 | 10/2020 | Stagliano et al. | |
| 2020/0325212 | A1 | 10/2020 | Williams et al. | |
| 2020/0377571 | A1 | 12/2020 | Loew et al. | |

FOREIGN PATENT DOCUMENTS

| | | | |
|---|---|---|---|
| EP | 3 093 295 | A1 | 11/2016 |
| WO | WO 2008/016356 | A2 | 2/2008 |
| WO | WO 2011/109789 | A2 | 9/2011 |
| WO | WO 2015/027082 | A1 | 2/2015 |
| WO | WO 2019/113464 | A1 | 6/2019 |
| WO | WO 2020/069398 | A1 | 4/2020 |
| WO | WO 2021/081258 | A1 | 4/2021 |

OTHER PUBLICATIONS

Bork. Powers and Pitfalls in Sequence Analysis: The 70% Hurdle. Genome Research, 2000, 10:398-400 (Year: 2000).*

Greenspan et al. 1999. Defining epitopes: It's not as easy as it seems; Nature Biotechnology, 17:936-937 (Year: 1999).*

Bowie et al. Deciphering the Message in Protein Sequences: Tolerance to Amino Acid Substitutions. Science, 1990, 247:1306-1310 (Year: 1990).*

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine ResidueJ. Cell Biol. 111:2129-2138, 1990 (Year: 1990).*

Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*

International Search Report and Written Opinion, International Application No. PCT/US2022/025479 (published under WO/2022/226024), 10 pages (Aug. 2, 2022).

(Continued)

*Primary Examiner* — Prema M Mertz

(74) *Attorney, Agent, or Firm* — Hoffmann & Baron, LLP

(57) ABSTRACT

The present disclosure provides T-cell modulatory multimeric polypeptides (T-Cell-MMP) and their epitope conjugates comprising at least one immunomodulatory polypeptide ("MOD") that may be selected to exhibit reduced binding affinity to a cognate co-immunomodulatory polypeptide ("Co-MOD"). The epitope may be, for example, a cancer-associated epitope, an infectious disease-associated epitope, or a self-epitope. The T-Cell-MMP-epitope conjugates are useful for modulating the activity of a T-cell by delivering immunomodulatory peptides, such as IL-2 or IL-2 variants that exhibit reduced binding affinity for the IL-2R, to T-cells in an epitope selective/specific manner, and accordingly, for treating individuals with a cancer, infectious disease or autoimmune disorder.

17 Claims, 37 Drawing Sheets

Specification includes a Sequence Listing.

(56) References Cited

OTHER PUBLICATIONS

International Search Report and Written Opinion, International Application No. PCT/US2022/025499 (published under WO/2022/226037), 18 pages (Sep. 21, 2022).
International Search Report and Written Opinion, International Application No. PCT/US2022/025532 (published under WO/2022/226058), 11 pages (Jul. 19, 2022).
International Search Report and Written Opinion, International Application No. PCT/US2022/025526 (published under WO/2022/226054), 15 pages (Oct. 18, 2022).
International Search Report and Written Opinion, International Application No. PCT/US2022/025547 (published under WO/2022/226069), 20 pages (Sep. 2, 2022).
International Search Report and Written Opinion, International Application No. PCT/US2022/025552 (published under WO/2022/226073), 17 pages (Sep. 2, 2022).
Invitation to Pay Additional Fees, International Application No. PCT/US2021/060357 (published under WO/2022/109399), 3 pages (Feb. 1, 2022).
Invitation to Correct Defects in the International Application, International Application No. PCT/US2021/060357 (published under WO/2022/109399), 5 pages (Dec. 14, 2021).
Preliminary International Preliminary Report on Patentability, International Application No. PCT/US2020/056937 (published under WO 2021/081258), 20 pages (Nov. 15, 2021).
Bettini et al., Development of Thymically-Derived Natural Regulatory T Cells; Ann N Y Acad Sci. Jan. 2010; 1183:1-2. Doi:10.1111/j.1749-6632.2009.05129.x.
Chen et al., Cotransfection with IL-10 and TGF-_1 into immature dendritic cells enhances immune tolerance in a rat liver transplantation model; Am J Physiol Gastrointest Liver Physiol 306: G575-G581, 2014. First published Feb. 6, 2014; doi:10.1152/ajpgi.00283.2013.
Ch'ng et al., Celiac Disease and Autoimmune Thyroid Disease; Clinical Medicine & Research vol. 5, No. 3: 184-19; © 2007 Marshfield Clinic.
De Crescenzo et al., Three Key Residues Underlie the Differential Affinity ofthe TGFb Isoforms for the TGFb Type II Receptor; J. Mol. Biol. (2006) 355, 47-62.
Docagne et al., A Soluble Transforming Growth Factor-b (TGF-b) Type I Receptor Mimics TGF-_Responses; The Journal of Biological Chemistry; vol. 276, No. 49, Issue of Dec. 7, pp. 46243-46250, 2001.
Elyaman et al., Notch Receptors and Smad3 Signaling Cooperate in the Induction of Interleukin-9-Producing T Cells, Immunity. Apr. 20, 2012; 36(4): 623-634. doi:10.1016/j.immuni.2012.01.020.
Faghih et al., The role of Th1 and Th17 in the pathogenesis of celiac disease; Gastroenterology & Hepatology: Open Access; Nov. 8, 2017;Published: Apr. 13, 2018; vol. 9, Issue 2-2018.
Francisco et al., PD-L1 regulates the development, maintenance, and function of induced regulatory T cells; Published Online: Dec. 14, 2009 | Supp Info: http://doi.org/10.1084/jem.20090847.
Genestier et al., Transforming Growth Factor b1 Inhibits Fas Ligand Expression and Subsequent Activation-induced Cell Death in T Cells via Downregulation of c-Myc; The Journal of Experimental Medicine; 189 (1999), 2.-S. 231-239.
Groppe et al., Cooperative Assembly of TGF-b Superfamily Signaling Complexes Is Mediated by Two Disparate Mechanisms and Distinct Modes of Receptor Binding; Molecular Cell 29, 157-168, Feb. 1, 2008.
Ha et al., Immunoglobulin Fc Heterodimer Platform Technology From Design to Applications in Therapeutic Antibodies and Proteins; Frontiers in Immunolog; Oct. 2016, vol. 7, pp. 1-10, Article 394.
Herbertz et al., Clinical development of galunisertib (LY2157299 monohydrate), a small molecule inhibitor of transforming growth factor-beta signaling pathway; Drug Design, Development and Therapy 2015:9, pp. 4479-4499.
Hezareh et al., Effector Function Activities of a Panel of Mutants of a Broadly Neutralizing Antibody against Human Immunodeficiency Virus Type 1; Journal of Virology, Dec. 2001, p. 12161-12168, vol. 75, No. 24.
Jacobsen, et al.; Engineering an IgG Scaffold Lacking Effector Function with Optimized Developability; JBC Papers in Press. Published on Dec. 19, 2016.
Jiang et al., NADPH oxidase-dependent redox signaling in TGF-β-mediated fibrotic responses; Redox Biology 2, 2014, pp. 267-272.
Josephson et al., Design and Analysis of an Engineered Human Interleukin-10 Monomer; The Journal of Biological Chemistry; vol. 275, No. 18, Issue of May 5, 2000, pp. 13552-13557.
Kaur et al., Interplay between Type 1 Diabetes Mellitus and Celiac Disease: Implications in Treatment; Dig Dis 2018;36:399-408.
Komai et al., Transforming growth Factor-β and interleukin-10 synergistically regulate humoral immunity via Modulating Metabolic Signals; Frontiers in Immunology | www.frontiersin.org Jun. 2018 | vol. 9 | Article 1364, pp. 1-15.
Kubiczkova et al., TGF-β—an excellent servant but a bad master; Journal of Translational Medicine 2012, 10:183, pp. 1-24.
Lord et al., Structure-based engineering to restore high affinity binding of an isoform-selective anti-TGFβ1 antibody, mAbs, 10:3, 444-452, DOI:10.1080/19420862.2018.1426421; ISSN: 1942-0862.
Mazzarella, Effector and suppressor T cells in celiac disease; World J Gastroenterol Jun. 28, 2015; 21(24): 7349-7356; ISSN 1007-9327 (print).
McNally et al., CD4+CD25+ regulatory T cells control CD8+ T-cell effector differentiation by modulating IL-2 homeostasis; PNAS, May 3, 2011, vol. 108, No. 18, 7529.
Ogasawara et al., IL-10, TGF-β and glucocorticoid prevent the production of type 2 cytokines in human group 2 innate lymphoid cells; J Allergy Clin Immunol, vol. 141, # 3, pp. 1147-1152.
Pakyari et al., Critical Role of Transforming Growth Factor Beta in Different Phases of Wound Healing; Advance in Wound Care, vol. 2, No. 5, pp. 215-225.
Parra-Medina et al., Prevalence of Celiac Disease in Latin America: a Systematic Review and Meta-Regression; PLOS ONE | DOI:10.1371/journal.pone.0124040 May 5, 2015 pp. 1-19.
Perry et al., Fragment-based screening of programmed death ligand 1 (PD-L1); Bioorganic & Medicinal Chemistry Letters 29 (2019) 786-790.
Gerald J. Prud'homme, Pathobiology of transforming growth factor b in cancer, fibrosis and immunologic disease, and therapeutic considerations; Laboratory Investigation (2007) 87, 1077-1091; doi:10.1038/labinvest.3700669; published online Aug. 27, 2007.
Read et al., IL-2, IL-7, and IL-15: Multistage regulators of CD4ρ T helper cell Differentiation; Experimental Hematology 2016;44:799-808.
Rigas et al., Type 2 innate lymphoid cell suppression by regulatory T cells attenuates airway hyperreactivity and requires inducible T-cell costimulator-inducible T-cell costimulator ligand interaction; J Allergy Clin Immunol. vol. 139, No. 5, pp. 1468-1477.
Rubio-Tapia et al., Liver Involvement in Celiac Disease; Minerva Med. Dec. 2008: 99(6): 595-604.
Sanjabi et al., Anti- and Pro-inflammatory Roles of TGF-β, IL-10, and IL-22 In Immunity and Autoimmunity; Curr Opin Pharmacol. Aug. 2009 ; 9(4): 447-453. doi:10.1016/j.coph.2009.04.008.
Sanjabi et al., Regulation of the Immune Response by TGF-b: From Conception to Autoimmunity and Infection; Cold Spring Harb Perspect Biol 2017;9:a022236, pp. 1-33.
Stathopoulou et al., Programmed death-1 receptor signaling downregulates asparaginyl endopeptidase to maintain Foxp3 stability in induced Regulatory T cells; Immunity. Aug. 21, 2018; 49(2): 247-263.e7. doi:10.1016/j.immuni.2018.05.006.
Tovoli et al., Autoimmune Hepatitis and Celiac Disease: Case Report, Showing an Entero-Hepatic Link Case Rep Gastroenterol 2010;4:469-475;DOI: 10.1159/000321992; Published online: Oct. 26, 2010.
Villarreal et al., Binding Properties of the Transforming Growth Factor-β Coreceptor Betaglycan: Proposed Mechanism for Potentiation of Receptor Complex Assembly and Signaling; Biochemistry 2016, 55, 6880-6896.

(56) References Cited

OTHER PUBLICATIONS

Ward et al., IL-2/CD25: a Long-Fusion Protein That Promotes Immune Tolerance by Selectively Targeting the IL-2 Receptor on Regulatory T Cells; J Immunol 2018; 201:2579-2592; Pre-published online Oct. 3, 2018; doi: 10.4049/jimmunol.1800907.
Wu et al., Developmental and Functional Control of Natural Killer Cells by Cytokines; Frontiers in Immunology, Aug. 2017, vol. 8, Article 930.
Xu et al., Transforming growth factor-β in stem cells and tissue homeostasis; Bone Research (2018) 6:2 https://doi.org/10.1038/s41413-017-0005-4.
Yen, et al., IL-23 is essential for T cell-mediated colitis and promotes inflammation via IL-17 and IL-6; J ClinInvest. 2006;116(5):1310-1316. https://doi.org/10.1172/JCI21404.
Zak et al., Structure of the Complex of Human Programmed Death 1, PD-1, and Its Ligand PD-L1; Structure 23, 2341-2348, Dec. 1, 2015; http://dx.doi.org/10.1016/j.str.2015.09.010.
Ying E. Zhang, Non-Smad pathways in TGF-β signaling; Cell Res. Jan. 2009; 19(1): 128-139 doi:10.1038/cr.2008.328.
Zwaagstra et al., Engineering and Therapeutic Application of Single-Chain Bivalent TGF-b Family Traps; Mol Cancer Ther 2012;11(7), 1477-1487. Published Online First May 4, 2012.

* cited by examiner

VII. Fig 2

FIG. 2A

*Homo sapiens* IgA Fc GenBank P01876 (amino acids 120-353) (SEQ ID NO:68) 234 aa

```
1   ASPTSPKVFP LSLCSTQPDG NVVIACLVQG FFPQEPLSVT WSESGQGVTA RNFPPSQDAS
61  GDLYTTSSQL TLPATQCLAG KSVTCHVKHY TNPSQDVTVP CPVPSTPPTP SPSTPPTPSP
121 SCCHPRLSLH RPALEDLLLG SEANLTCTLT GLRDASGVTF TWTPSSGKSA VQGPPERDLC
181 GCYSVSSVLP GCAEPWNHGK TFTCTAAYPE SKTPLTATLS KSGNTFRPEV HLLPPPSEEL
241 ALNELVTLTC LARGFSPKDV LVRWLQGSQE LPREKYLTWA SRQEPSQGTT TFAVTSILRV
301 AAEDWKKGDT FSCMVGHEAL PLAFTQKTID RLAGKPTHVN VSVVMAEVDG TCY
```

FIG. 2B

*Homo sapiens* IgD Fc GenBank AAA52770 (amino acids 162-383) (SEQ ID NO:69) 222 aa

```
1   PTKAPDVFPI ISGCRHPKDN SPVVLACLIT GYHPTSVTVT WYMGTQSQPQ RTFPEIQRRD
61  SYYMTSSQLS TPLQQWRQGE YKCVVQHTAS KSKKEIFRWP ESPKAQASSV PTAQPQAEGS
121 LAKATTAPAT TRNTGRGGEE KKKEKEKEEQ EERETKTPEC PSHTQPLGVY LLTPAVQDLW
181 LRDKATFTCF VVGSDLKDAH LTWEVAGKVP TGGVEEGLLE RHSNGSQSQH SRLTLPRSLW
241 NAGTSVTCTL NHPSLPPQRL MALREPAAQA PVKLSLNLLA SSDPPEAASW LLCEVSGFSP
301 PNILLMWLED QREVNTSGFA PARPPPQPRS TTFWAWSVLR VPAPPSPQPA TYTCVVSHED
361 SRTLLNASRS LEVSYVTDHG PMK
```

FIG. 2C

*Homo sapiens* IgE Fc GenBank 1F6A_B (amino acids 6-222) (SEQ ID NO:70) 212 aa

```
1   ADPCDSNPRG VSAYLSRPSP FDLFIRKSPT ITCLVVDLAP SKGTVNLTWS RASGKPVNHS
61  TRKEEKQRNG TLTVTSTLPV GTRDWIEGET YQCRVTHPHL PRALMRSTTK TSGPRAAPEV
121 YAFATPEWPG SRDKRTLACL IQNFMPEDIS VQWLHNEVQL PDARHSTTQP RKTKGSGFFV
181 FSRLEVTRAE WEQKDEFICR AVHEAASPSQ TVQRAVSVNP GK
```

FIG. 2D

**WT *Homo sapiens* IgG1 Fc Sequence (SEQ ID NO:71) 227 aa**

```
1   DKTHTCPPCP APELLGGPSV FLFPPKPKDT LMISRTPEVT CVVVDVSHED PEVKFNWYVD
61  GVEVHNAKTK PREEQYNSTY RVVSVLTVLH QDWLNGKEYK CKVSNKALPA PIEKTISKAK
121 GQPREPQVYT LPPSREEMTK NQVSLTCLVK GFYPSDIAVE WESNGQPENN YKTTPPVLDS
181 DGSFFLYSKL TVDKSRWQQG NVFSCSVMHE ALHNHYTQKS LSLSPGK
```

*Homo sapiens* IgG1 Fc GenBank 3S7G_A (SEQ ID NO:72) 227 aa

```
1   DKTHTCPPCP APELLGGPSV FLFPPKPKDT LMISRTPEVT CVVVDVSHED PEVKFNWYVD
61  GVEVHNAKTK PREEQYNSTY RVVSVLTVLH QDWLNGKEYK CKVSNKALPA PIEKTISKAK
121 GQPREPQVYT LPPSRDELTK NQVSLTCLVK GFYPSDIAVE WESNGQPENN YKTTPPVLDS
181 DGSFFLYSKL TVDKSRWQQG NVFSCSVMHE ALHNHYTQKS LSLSPGK
```

*Homo sapiens* IgG1 Fc Mutant: L234F/L235E/P331S (Triple Mutant "TM") (SEQ ID NO:73)

DKTHTCPPCP APE*<u>FE</u>*GGPSV FLFPPKPKDT LMISRTPEVT CVVVDVSHED PEVKFNWYVD
GVEVHNAKTK PREEQYNSTY RVVSVLTVLH QDWLNGKEYK CKVSNKALPA <u>S</u>IEKTISKAK
GQPREPQVYT LPPSREEMTK NQVSLTCLVK GFYPSDIAVE WESNGQPENN YKTTPPVLDS
DGSFFLYSKL TVDKSRWQQG NVFSCSVMHE ALHNHYTQKS LSLSPGK

*Homo sapiens* <u>IgG1 Fc Mutant: N297A</u> (SEQ ID NO:74)

DKTHTCPPCP APELLGGPSV FLFPPKPKDT LMISRTPEVT CVVVDVSHED PEVKFNWYVD
GVEVHNAKTK PREEQY*<u>A</u>*STY RVVSVLTVLH QDWLNGKEYK CKVSNKALPA PIEKTISKAK
GQPREPQVYT LPPSREEMTK NQVSLTCLVK GFYPSDIAVE WESNGQPENN YKTTPPVLDS
DGSFFLYSKL TVDKSRWQQG NVFSCSVMHE ALHNHYTQKS LSLSPGK

FIG. 2D (continued)

***Homo sapiens* IgG1 Fc Mutant: L234A/L235A ("LALA") (SEQ ID NO:75)**

```
DKTHTCPPCP APEAAGGPSV FLFPPKPKDT LMISRTPEVT CVVVDVSHED PEVKFNWYVD
GVEVHNAKTK PREEQYNSTY RVVSVLTVLH QDWLNGKEYK CKVSNKALPA PIEKTISKAK
GQPREPQVYT LPPSREEMTK NQVSLTCLVK GFYPSDIAVE WESNGQPENN YKTTPPVLDS
DGSFFLYSKL TVDKSRWQQG NVFSCSVMHE ALHNHYTQKS LSLSPGK
```

***Homo sapiens* IgG1 Fc Mutant: (N-terminal Δ10) L234A/L235A ("LALA") L351K, T366S, P395V, F405R, Y407A, and K409Y (SEQ ID NO:76)**

```
APEAAGGPS VFLFPPKPK DTLMISRTP EVTCVVVDV SHEDPEVKF NWYVDGVEV HNAKTKPRE
EQYNSTYRV VSVLTVLHQ DWLNGKEYK CKVSNKALP APIEKTISK AKGQPREPQ VYTKPPSRE
EMTKNQVSL SCLVKGFYP SDIAVEWES NGQPENNYK TTVPVLDSD GSFRLASYL TVDKSRWQQ
GNVFSCSVM HEALHNHYT QKSLSLSP
```

***Homo sapiens* IgG1 Fc Mutant: L234A/L235A ("LALA") and T366W Knob-in-Hole "Knob"(SEQ ID NO:77)**

```
DKTHTCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVYTLPPSREEMTK
NQVSLWCLVKGFYPSDIAVEWESNGQPENNYKTTPPVLDSDGSFFLYSKLTVDKSRWQQGNVFSCSVMHE
ALHNHYTQKSLSLSP
```

***Homo sapiens* IgG1 Fc Mutant: L234A/L235A ("LALA") and T366S and L368A Knob-in-Hole "Hole" (SEQ ID NO:78)**

DKTHTCPPCPAPE*AA*GGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISKAKGQPREPQ
VYTLPPSREEMTKNQVSL*S*C*A*VKGFYPSDIAVEWESNGQPENNYKTTPPVLDSDGSFFL*V*SKLTV
DKSRWQQGNVFSCSVMHEALHNHYTQKSLSLSP

Residue numbered according to EU index (Kabat Numbering)

FIG. 2E

***Homo sapiens* IgG2 Fc GenBank AAN76044 (amino acids 99-325) (SEQ ID NO:79) 227 aa**

```
1   STKGPSVFPL APCSRSTSES TAALGCLVKD YFPEPVTVSW NSGALTSGVH TFPAVLQSSG
61  LYSLSSVVTV PSSNFGTQTY TCNVDHKPSN TKVDKTVERK CCVECPPCPA PPVAGPSVFL
121 FPPKPKDTLM ISRTPEVTCV VVDVSHEDPE VQFNWYVDGV EVHNAKTKPR EEQFNSTFRV
181 VSVLTVVHQD WLNGKEYKCK VSNKGLPAPI EKTISKTKGQ PREPQVYTLP PSREEMTKNQ
241 VSLTCLVKGF YPSDIAVEWE SNGQPENNYK TTPPMLDSDG SFFLYSKLTV DKSRWQQGNV
301 FSCSVMHEAL HNHYTQKSLS LSPGK
```

FIG. 2F

***Homo sapiens* IgG3 Fc GenBank AAW65947(amino acids 19-246) (SEQ ID NO:80) 238 aa**

```
1   HKPSNTKVDK RVELKTPLGD TTHTCPPCPA PELLGGPSVF LFPPKPKDTL MISRTPEVTC
61  VVVDVSHEDP EVKFNWYVDG VEVHNAKTKP REEQYNSTYR VVSVLTVLHQ DWLNGKEYKC
121 KVSNKALPAP IEKTISKAKG QPREPQVYTL PPSRDELTKN QVSLTCLVKG FYPSDIAVEW
181 ESNGQPENNY KTTPPVLDSD GSFFLYSKLT VDKSRWQQGN VFSCSVMHEA LHNHYTQKSL
241 SLSPGK
```

FIG. 2G

*Homo sapiens* IgG4 Fc GenBank P01861 (amino acids 100-327) (SEQ ID NO:81) 228 aa

```
1   ASTKGPSVFP LAPCSRSTSE STAALGCLVK DYFPEPVTVS WNSGALTSGV HTFPAVLQSS
61  GLYSLSSVVT VPSSSLGTKT YTCNVDHKPS NTKVDKRVES KYGPPCPSCP APEFLGGPSV
121 FLFPPKPKDT LMISRTPEVT CVVVDVSQED PEVQFNWYVD GVEVHNAKTK PREEQFNSTY
181 RVVSVLTVLH QDWLNGKEYK CKVSNKGLPS SIEKTISKAK GQPREPQVYT LPPSQEEMTK
241 NQVSLTCLVK GFYPSDIAVE WESNGQPENN YKTTPPVLDS DGSFFLYSRL TVDKSRWQEG
301 NVFSCSVMHE ALHNHYTQKS LSLSLGK
```

*Homo sapiens* IgG4 Fc Segment (SEQ ID NO:82) 223 aa

```
1   PPCPSCPAPE FLGGPSVFLF PPKPKDTLMI SRTPEVTCVV VDVSQEDPEV QFNWYVDGVE
61  VHNAKTKPRE EQFNSTYRVV SVLTVLHQDW LNGKEYKCKV SNKGLPSSIE KTISKAKGQP
121 REPQVYTLPP SQEEMTKNQV SLTCLVKGFY PSDIAVEWES NGQPENNYKT TPPVLDSDGS
181 FFLYSRLTVD KSRWQEGNVF SCSVMHEALH NHYTQKSLSL SPG
```

FIG. 2H

*Homo sapiens* IgM Fc GenBank 0308221A (SEQ ID NO:83) 276 aa

```
1   VTSTLTIKZS DWLGESMFTC RVDHRGLTFQ QNASSMCVPD QDTAIRVFAI PPSFASIFLT
61  KSTKLTCLVT DLTTYBSVTI SWTREENGAV KTHTNISESH PNATFSAVGE ASICEDBDWS
121 GERFTCTVTH TDLPSPLKQT ISRPKGVALH RPBVYLLPPA RZZLNLRESA TITCLVTGFS
181 PADVFVEWMQ RGEPLSPQKY VTSAPMPEPQ APGRYFAHSI LTVSEEEWNT GGTYTCVVAH
241 EALPNRVTER TVDKSTGKPT LYNVSLVMSD TAGTCY
```

FIG. 2I

*Homo sapiens* J-Chain NCBI Reference Sequence: NP_653247.1 SEQ ID NO:84)

MKNHLLFWGV LAVFIKAVHV KAQEDERIVL VDNKCKCARI TSRIIRSSED PNEDIVERNI
RIIVPLNNRE NISDPTSPLR TRFVYHLSDL CKKCDPTEVE LDNQIVTATQ SNICDEDSAT
ETCYTYDRNK CYTAVVPLVY GGETKMVETA LTPDACYPD

Amino acids 1-22 (underlined) are the signal peptide.

FIG. 2J

*Homo sapiens* Ig CH1 domain (SEQ ID NO:85)

1 FTVRETASTK GPSVFPLAPS SKSTSGGTAA LGCLVKDYFP EPVTVSWNSG ALTSGVHTFP
61 AVLQSSGLYS LSSVVTVPSS SLGTQTYICN VNHKPSNTKV DKKVEPKSCD KT

FIG. 2K

*Homo sapiens* Ig κ chain constant region (SEQ ID NO:86)

1 TVAAPSVFIF PPSDEQLKSG TASVVCLLNN FYPREAKVQW KVDNALQSGN SQESVTEQDS
61 KDSTYSLSST LTLSKADYEK HKVYACEVTH QGLSSPVTKS FNRGEC

*Homo sapiens* Ig λ chain constant region(SEQ ID NO:87)

```
1 GQPKANPTVT LFPPSSEELQ ANKATLVCLI SDFYPGAVTV AWKADGSPVK AGVETTKPSK
61 QSNNKYAASS YLSLTPEQWK SHRSYSCQVT HEGSTVEKTV APTECS
```

FIG. 3

*Homo sapiens* TGF-β -1 preproprotein NCBI Ref. Seq. NP_000651.3 (SEQ ID NO:106)

1 MPPSGLRLLP LLLPLLWLLV LTPGRPAAGL STCKTIDMEL VKRKRIEAIR GQILSKLRLA
61 SPPSQGEVPP GPLPEAVLAL YNSTRDRVAG ESAEPEPEPE ADYYAKEVTR VLMVETHNEI
121 YDKFKQSTHS IYMFFNTSEL REAVPEPVLL SRAELRLLRL KLKVEQHVEL YQKYSNNSWR
181 YLSNRLLAPS DSPEWLSFDV TGVVRQWLSR GGEIEGFRLS AHCSCDSRDN TLQVDINGFT
241 TGRRGDLATI HGMNRPFLLL MATPLERAQH LQSSRHRRAL DTNYCFSSTE KNCCVRQLYI
301 DF*R*KDLGWKW IHEPKGYHAN FCLGPCPYIW SLDTQYSKVL ALYNQHNPGA SAAPCCVPQA
361 LEPLPIVYY*V* G*R*KPKVEQLS NMIVRSCKCS

1..29 Signal Peptide
29..261 TGF-β propeptide
244..246 Cell attachment site
279..390 mature peptide
See also UniProtKB - P01137 having a P10L substitution in the signal sequence (SEQ ID NO:190)

*Homo sapiens* TGF-β-2 preproprotein GenBank: AAA50405.1 (SEQ ID NO:109)

1 MHYCVLSAFL ILHLVTVALS LSTCSTLDMD QFMRKRIEAI RGQILSKLKL TSPPEDYPEP
61 EEVPPEVISI YNSTRDLLQE KASRRAAACE RERSDEEYYA KEVYKIDMPP FFPSEAIPPT
121 FYRPYFRIVR FDVSAMEKNA SNLVKAEFRV FRLQNPKARV PEQRIELYQI LKSKDLTSPT
181 QRYIDSKVVK TRAEGEWLSF DVTDAVHEWL HHKDRNLGFK ISLHCPCCTF VPSNNYIIPN
241 KSEELEARFA GIDGTSTYTS GDQKTIKSTR KKNSGKTPHL LLMLLPSYRL ESQQTNRRKK
301 RALDAAYCFR NVQDNCCLRP LYIDF*K*RDLG WKWIHEPKGY NANFCAGACP YLWSSDTQHS
361 RVLSLYNTIN PEASASPCCV SQDLEPLTIL YY*I*G*K*TPKIE QLSNMIVKSC KCS

1..20 Signal Peptide
21..227 TGF-β propeptide
302..413 mature peptide
Lys 25, Ile 92, and Lys 94 of the mature peptide are emphasized by bolding, italicization, and underline

*Homo sapiens* TGF-β-3 preproprotein isoform 1 NCBI Ref. Seq. NP_001316868.1 UniProt Ref.: P10600.1 (SEQ ID NO:112)

1 MKMHLQRALV VLALLNFATV SLSLSTCTTL DFGHIKKKRV EAIRGQILSK LRLTSPPEPT
61 VMTHVPYQVL ALYNSTRELL EEMHGEREEG CTQENTESEY YAKEIHKFDM IQGLAEHNEL
121 AVCPKGITSK VFRFNVSSVE KNRTNLFRAE FRVLRVPNPS SKRNEQRIEL FQILRPDEHI
181 AKQRYIGGKN LPTRGTAEWL SFDVTDTVRE WLLRRESNLG LEISIHCPCH TFQPNGDILE
241 NIHEVMEIKF KGVDNEDDHG RGDLGRLKKQ KDHHNPHLIL MMIPPHRLDN PGQGGQRKKR
301 ALDTNYCFRN LEENCCVRPL YIDFRQDLGW KWVHEPKGYY ANFCSGPCPY LRSADTTHST
361 VLGLYNTLNP EASASPCCVP QDLEPLTILY YVGRTPKVEQ LSNMVVKSCK CS

1..23 Signal Peptide
24..300 mature latency associated peptide
24..230 TGF-β propeptide`
261..263 Cell attachment site
301..412 mature peptide

FIG. 3 (continued)

***Homo sapiens* Mature TGF-β-3 isoform 1 NCBI Ref. Seq. NP_001316868.1 UniProt Ref.: P10600.1, SEQ ID NO:111 (aas 301-412 of SEQ ID NO:112)**

```
1  ALDTNYCFRN LEENCCVRPL YIDFRQDLGW KWVHEPKGYY ANFCSGPCPY LRSADTTHST
61 VLGLYNTLNP EASASPCCVP QDLEPLTILY YVGRTPKVEQ LSNMVVKSCK CS
```

***Homo sapiens* Mature TGF-β-3 isoform 1 Mutant: C77S NCBI Ref. Seq. NP_001316868.1 UniProt Ref.: P10600.1, SEQ ID NO:113 (aas 301-412 of SEQ ID NO:112 with a C77S substitution)**

1  ALDTNYCFRN LEENCCVRPL YIDFRQDLGW KWVHEPKGYY ANFCSGPCPY LRSADTTHST
61 VLGLYNTLNP EASASP*S*CVP QDLEPLTILY YVGRTPKVEQ LSNMVVKSCK CS

C77S substitution bolded, underlined, and italicized.

FIG. 4

**Alignment of *Homo sapiens* TGF-β sequences**

```
NP_000651.3    MPPSGLRLLPLLLPLLWLLVLTPGRPAAGLSTCKTIDMELVKRKRIEAIRGQILSKLRLA 60
P01137         MPPSGLRLLLLLLPLLWLLVLTPGRPAAGLSTCKTIDMELVKRKRIEAIRGQILSKLRLA 60
AAA50405.1     --------MHY-CVLSAFLILHLVTVALSLSTCSTLDMDQFMRKRIEAIRGQILSKLKLT 51
NP_001316868.1 ------MKMHLQRALVVLALLNFATVSLSLSTCTTLDFGHIKKKRVEAIRGQILSKLRLT 54
                       :     *  : :*     : .****.*:*:  . :**:***********:*:

NP_000651.3    SPPSQGEVPPGPLPEAVLALYNSTRDRVAGESAE-----PEPEPEADYYAKEVTRVLMVE 115
P01137         SPPSQGEVPPGPLPEAVLALYNSTRDRVAGESAE-----PEPEPEADYYAKEVTRVLMVE 115
AAA50405.1     SPPEDY-PEPEEVPPEVISIYNSTRDLLQEKASRRAAACERERSDEEYYAKEVYKIDMPP 110
NP_001316868.1 SPPEPT-V-MTHVPYQVLALYNSTRELLEEMHGEREEGCTQENTESEYYAKEIHKFDMIQ 112
               ***.        :*  *:::*****: :    ..      . . : :*****: :. *

NP_000651.3    TH---NEIYDKFKQSTHSIYMFFNTSELREAVPEPVLLSRAELRLLRLKL----KVEQHV 168
P01137         TH---NEIYDKFKQSTHSIYMFFNTSELREAVPEPVLLSRAELRLLRLKL----KVEQHV 168
AAA50405.1     FFPSEAI-PPTFYRPYFRIVR-FDVSAME---KNASNLVKAEFRVFRLQNPKARVPEQRI 165
NP_001316868.1 GLAEHNELAVCPKGITSKVFR-FNVSSVE---KNRTNLFRAEFRVLRVPNPSSKRNEQRI 168
                                 :   *:.* :.    :   * :**:*::*:        **::

NP_000651.3    ELYQKYSN-----NSWRYLSNRLLAPSDSPEWLSFDVTGVVRQWLSRGGEIEGFRLSAHC 223
P01137         ELYQKYSN-----NSWRYLSNRLLAPSDSPEWLSFDVTGVVRQWLSRGGEIEGFRLSAHC 223
AAA50405.1     ELYQILKSKDLTSPTQRYIDSKVVKTRAEGEWLSFDVTDAVHEWLHHKDRNLGFKISLHC 225
NP_001316868.1 ELFQILRPDEH-IAKQRYIGGKNLPTRGTAEWLSFDVTDTVREWLLRRESNLGLEISIHC 227
               **:*          . **:..: :      ********..*::** :     *:.:* **

NP_000651.3    SCDSRDNTLQ-----------V---DINGFTTGRRGDLATIH------GMNRPFLLLMAT 263
P01137         SCDSRDNTLQ-----------V---DINGFTTGRRGDLATIH------GMNRPFLLLMAT 263
AAA50405.1     PCCTFVPSNNYIIPNKSEELEARFAGIDGTSTYTSGDQKTIKSTRKKNSGKTPHLLLMLL 285
NP_001316868.1 PCHTFQPNGD-ILENIHEVMEIKFKGVDNEDDHGRGDLGRLK---KQKDHHNPHLILMMI 283
                * :   . :               .::.      **   ::      . : *.*:**

NP_000651.3    PLERAQH--LQSSRHRRALDTNYCFSSTEKNCCVRQLYIDFRKDLGWKWIHEPKGYHANF 321
P01137         PLERAQH--LQSSRHRRALDTNYCFSSTEKNCCVRQLYIDFRKDLGWKWIHEPKGYHANF 321
AAA50405.1     PSYRLESQ-QTNRRKKRALDAAYCFRNVQDNCCLRPLYIDFKRDLGWKWIHEPKGYNANF 344
NP_001316868.1 PPHRLDNPGQGGQRKKRALDTNYCFRNLEENCCVRPLYIDFRQDLGWKWVHEPKGYYANF 343
               *  * :     . *::****: *** . :.***:* *****::******:****** ***
```

FIG. 4 (continued)

```
NP_000651.3    CLGPCPYIWSLDTQYSKVLALYNQHNPGASAAPCCVPQALEPLPIVYYVGRKPKVEQLSN 381
P01137         CLGPCPYIWSLDTQYSKVLALYNQHNPGASAAPCCVPQALEPLPIVYYVGRKPKVEQLSN 381
AAA50405.1     CAGACPYLWSSDTQHSRVLSLYNTINPEASASPCCVSQDLEPLTILYYIGKTPKIEQLSN 404
NP_001316868.1 CSGPCPYLRSADTTHSTVLGLYNTLNPEASASPCCVPQDLEPLTILYYVGRTPKVEQLSN 403
               * * ***: * ** :* **.***  ** ***:**** * **** *:**:*:.**:*****

NP_000651.3    MIVRSCKCS 390
P01137         MIVRSCKCS 390
AAA50405.1     MIVKSCKCS 413
NP_001316868.1 MVVKSCKCS 412
               *:*:*****
```

Amino acid positions 25, 77, 92 and 94 of the mature TGF-β sequences are underlinded, and italicized, but not bolded.

FIG. 5A

*Homo sapiens* TGF-β receptor type-1 isoform 1 precursor, NCBI Ref. Seq. NP_004603.1 and UniProtKB/Swiss-Prot: P36897.1 (SEQ ID NO:114)

```
1   MEAAVAAPRP RLLLLVLAAA AAAAAALLPG ATALQCFCHL CTKDNFTCVT DGLCFVSVTE
61  TTDKVIHNSM CIAEIDLIPR DRPFVCAPSS KTGSVTTTYC CNQDHCNKIE LPTTVKSSPG
121 LGPVELAAVI AGPVCFVCIS LMLMVYICHN RTVIHHRVPN EEDPSLDRPF ISEGTTLKDL
181 IYDMTTSGSG SGLPLLVQRT IARTIVLQES IGKGRFGEVW RGKWRGEEVA VKIFSSREER
241 SWFREAEIYQ TVMLRHENIL GFIAADNKDN GTWTQLWLVS DYHEHGSLFD YLNRYTVTVE
301 GMIKLALSTA SGLAHLHMEI VGTQGKPAIA HRDLKSKNIL VKKNGTCCIA DLGLAVRHDS
361 ATDTIDIAPN HRVGTKRYMA PEVLDDSINM KHFESFKRAD IYAMGLVFWE IARRCSIGGI
421 HEDYQLPYYD LVPSDPSVEE MRKVVCEQKL RPNIPNRWQS CEALRVMAKI MRECWYANGA
481 ARLTALRIKK TLSQLSQQEG IKM
```

| | |
|---|---|
| 1..33 | signal peptide |
| 34-126 | extracellular region (ectodomain) |
| 127-147 | transmembrane region |
| 176..203 | Transforming growth factor beta type I GS-motif |
| 205..492 | Protein tyrosine kinase |
| 209..496 | Catalytic domain of the Serine/Threonine Kinases, |

*Homo sapiens* TGF-β receptor type-1 isoform 1 ectodomain (SEQ ID NO:115)

```
34   LQCFCHL CTKDNFTCVT DGLCFVSVTE TTDKVIHNSM CIAEIDLIPR DRPFVCAPSS

91   KTGSVTTTYC CNQDHCNKIE LPTTVKSSPG LGPVEL
```

FIG. 5B

*Homo sapiens* TGF-β receptor type-2 (TβRII) isoform A precursor NCBI Ref. Seq. NP_001020018.1 (SEQ ID NO:116)

1 MGRGLLRGLW PLHIVLWTRI ASTIPPHVQK SDVEMEAQKD EIICPSCNRT AHPLRHINND
61 MIVTDNNGAV KFPQLCKFCD VRFSTCDNQK SCMSNCSITS ICEKPQEVCV AVWRKNDENI
121 TLETVCHDPK LPYHDFILED AASPKCIMKE KKKPGETFFM CSCSSDECND NIIFSEEYNT
181 *SNPD*LLLVIF QVTGISLLPP LGVAISVIII FYCYRVNRQQ KLSSTWETGK TRKLMEFSEH
241 CAIILEDDRS DISSTCANNI NHNTELLPIE LDTLVGKGRF AEVYKAKLKQ NTSEQFETVA
301 VKIFPYEEYA SWKTEKDIFS DINLKHENIL QFLTAEERKT ELGKQYWLIT AFHAKGNLQE
361 YLTRHVISWE DLRKLGSSLA RGIAHLHSDH TPCGRPKMPI VHRDLKSSNI LVKNDLTCCL
421 CDFGLSLRLD PTLSVDDLAN SGQVGTARYM APEVLESRMN LENVESFKQT DVYSMALVLW
481 EMTSRCNAVG EVKDYEPPFG SKVREHPCVE SMKDNVLRDR GRPEIPSFWL NHQGIQMVCE
541 TLTECWDHDP EARLTAQCVA ERFSELEHLD RLSGRSCSEE KIPEDGSLNT TK

1..23 signal peptide
24..592 mature peptide
24..177 extracellular region (ectodomain)

*Homo sapiens* TGF-β receptor type-2 (TβRII) isoform A ectodomain(SEQ ID NO:117)

24 IPPHVQK SDVEMEAQKD EIICPSCNRT AHPLRHINND MIVTDNNGAV KFP*QLCKFCD*
*80 VRFSTCDNQK SCMSNCSITS ICEKPQEVCV AVWRKNDENI TLETVCHDPK*
*130 LPYHDFILED AASPKCIMKE KKKPGETFFM CSCSSDECND NIIFSEE*

*Homo sapiens* TGF-β receptor type-2 (TβRII) isoform B precursor, UniProtKB Ref. P37173, NCBI Ref. Seq. NP_003233.4 (SEQ ID NO:118)

1 MGRGLLRGLW PLHIVLWTRI ASTIPPHVQK SVNNDMIVTD NNGAVKFP*QL CKFCDVRFST*
61 *CDNQKSCMSN CSITSICEKP QEVCVAVWRK NDENITLETV CHDPKLPYHD FILEDAASPK*
121 *CIMKEKKKPG ETFFMCSCSS DECNDNIIFS EE*YNTSNPDL LLVIFQVTGI SLLPPLGVAI
181 SVIIIFYCYR VNRQQKLSST WETGKTRKLM EFSEHCAIIL EDDRSDISST CANNINHNTE
241 LLPIELDTLV GKGRFAEVYK AKLKQNTSEQ FETVAVKIFP YEEYASWKTE KDIFSDINLK
301 HENILQFLTA EERKTELGKQ YWLITAFHAK GNLQEYLTRH VISWEDLRKL GSSLARGIAH
361 LHSDHTPCGR PKMPIVHRDL KSSNILVKND LTCCLCDFGL SLRLDPTLSV DDLANSGQVG
421 TARYMAPEVL ESRMNLENVE SFKQTDVYSM ALVLWEMTSR CNAVGEVKDY EPPFGSKVRE
481 HPCVESMKDN VLRDRGRPEI PSFWLNHQGI QMVCETLTEC WDHDPEARLT AQCVAERFSE
541 LEHLDRLSGR SCSEEKIPED GSLNTTK

1..23 Signal peptide (As noted below, NCBI records report the signal sequence to be aas 1-22.)
24..567 Mature peptide
24..166 Transforming growth factor beta receptor 2 ectodomain

*Homo sapiens* TGF-β receptor type-2 (TβRII) isoform B, ectodomain sequence (SEQ ID NO:119)

30 32 52 55

1 IPPHVQKSVN NDMIVTDNNG AVKFPQLCKF CDVRFSTCDN QKSCMSNCSI TSICEKPQEV

118

61 CVAVWRKNDE NITLETVCHD PKLPYHDFIL EDAASPKCIM KEKKKPGETF FMCSCSSDEC

121 NDNIIFSEEY NTSNPDLLLV IFQ

FIG. 5B (Continued)

*Homo sapiens* TGF-β receptor type-2 (TβRII) isoform B, ectodomain fragment sequence (SEQ ID NO:120)

30 32 52 55

1 IPPHVQKSVN NDMIVTDNNG AVKFPQLCKF CDVRFSTCDN QKSCMSNCSI TSICEKPQEV

118

61 CVAVWRKNDE NITLETVCHD PKLPYHDFIL EDAASPKCIM KEKKKPGETF FMCSCSSDEC

121 NDNIIFSEE

*Homo sapiens* TGF-β receptor type-2 isoform B, ectodomain fragment Δ14 (N-terminus) D118A (SEQ ID NO:121)

30 32 52 55

15 TDNNG AVKFPQLCKF CDVRFSTCDN QKSCMSNCSI TSICEKPQEV CVAVWRKNDE NITLETVCHD

118

80 PKLPYHDFIL EDAASPKCIM KEKKKPGETF FMCSCSSAEC NDNIIFSEE

*Homo sapiens* TGF-β receptor type-2 (TβRII) isoform B, ectodomain fragment Δ25 (N-terminus) D118A (SEQ ID NO:122)

30 32 52 55

26 QLCKF CDVRFSTCDN QKSCMSNCSI TSICEKPQEV CVAVWRKNDE NITLETVCHD

118

80 PKLPYHDFIL EDAASPKCIM KEKKKPGETF FMCSCSSAEC NDNIIFSEE

*Homo sapiens* TGF-β receptor type-2 (TβRII) isoform B, ectodomain fragment Δ25 (N-terminus), D118A ectodomain sequence (SEQ ID NO:123)

26 QLCKF C*D*VRFSTCDN QKSCMSNCSI TSIC*E*KPQEV CVAVWRKNDE NITLETVCH

80 DPKLPYHDFI LEDAASPKCI MKEKKKPGET FFMCSCSS*A*E CNDNIIFSE EYNTSNPD

Based upon NCBI Ref. Seq. NP_003233.4, and UniProtKB Ref. P37173; with the sequence corresponding to aas 49 to 159 of those sequences. The substitution at aspartic acid "D119" of the mature protein with an alanine "*A*" (bolded, italicized, and underlined) is marked as a "D118A" substitution for consistency with the literature describing that substitution. Note that aa D119 numbering is based on the mature protein, and accordingly it is D 141 of the precursor protein when the 22 aa signal sequence is included. The location of D32, sometimes substituted with asparagine (D32N), is also shown bolded, italicized, and underlined. D32 in corresponds to D55 in the precursor protein.

FIG. 5C

***Homo sapiens* TGF-β receptor type 3 isoform A precursor, (BETA Glycan), NCBI Ref. Seq. NP_003234.2 and UniProtKB/Swiss-Prot: Q03167.3 (SEQ ID NO:124)**

```
1   MTSHYVIAIF ALMSSCLATA GPEPGALCEL SPVSASHPVQ ALMESFTVLS GCASRGTTGL
61  PQEVHVLNLR TAGQGPGQLQ REVTLHLNPI SSVHIHHKSV VFLLNSPHPL VWHLKTERLA
121 TGVSRLFLVS EGSVVQFSSA NFSLTAETEE RNFPHGNEHL LNWARKEYGA VTSFTELKIA
181 RNIYIKVGED QVFPPKCNIG KNFLSLNYLA EYLQPKAAEG CVMSSQPQNE EVHIIELITP
241 NSNPYSAFQV DITIDIRPSQ EDLEVVKNLI LILKCKKSVN WVIKSFDVKG SLKIIAPNSI
301 GFGKESERSM TMTKSIRDDI PSTQGNLVKW ALDNGYSPIT SYTMAPVANR FHLRLENNAE
361 EMGDEEVHTI PPELRILLDP GALPALQNPP IRGGEGQNGG LPFPFPDISR RVWNEEGEDG
421 LPRPKDPVIP SIQLFPGLRE PEEVQGSVDI ALSVKCDNEK MIVAVEKDSF QASGYSGMDV
481 TLLDPTCKAK MNGTHFVLES PLNGCGTRPR WSALDGVVYY NSIVIQVPAL GDSSGWPDGY
541 EDLESGDNGF PGDMDEGDAS LFTRPEIVVF NCSLQQVRNP SSFQEQPHGN ITFNMELYNT
601 DLFLVPSQGV FSVPENGHVY VEVSVTKAEQ ELGFAIQTCF ISPYSNPDRM SHYTIIENIC
661 PKDESVKFYS PKRVHFPIPQ ADMDKKRFSF VFKPVFNTSL LFLQCELTLC TKMEKHPQKL
721 PKCVPPDEAC TSLDASIIWA MMQNKKTFTK PLAVIHHEAE SKEKGPSMKE PNPISPPIFH
781 GLDTLTVMGI AFAAFVIGAL LTGALWYIYS HTGETAGRQQ VPTSPPASEN SSAAHSIGST
841 QSTPCSSSST A
```

| | |
|---|---|
| 1..18 | Signal peptide |
| 27..787 | Extracellular domain (ectodomain) |
| 788-809 | Transmembrane domain |
| 567..724 | Zona pellucida-like domain |
| 737..751 | Interaction with TGF-beta ligand |
| 788..809 | site_type="transmembrane region" |

***Homo sapiens* TGF-β receptor type 3 isoform B precursor, (BETA Glycan) NCBI Ref. Seq. NP_001182612.1 and (SEQ ID NO:125)**

```
1   MTSHYVIAIF ALMSSCLATA GPEPGALCEL SPVSASHPVQ ALMESFTVLS GCASRGTTGL
61  PQEVHVLNLR TAGQGPGQLQ REVTLHLNPI SSVHIHHKSV VFLLNSPHPL VWHLKTERLA
121 TGVSRLFLVS EGSVVQFSSA NFSLTAETEE RNFPHGNEHL LNWARKEYGA VTSFTELKIA
181 RNIYIKVGED QVFPPKCNIG KNFLSLNYLA EYLQPKAAEG CVMSSQPQNE EVHIIELITP
241 NSNPYSAFQV DITIDIRPSQ EDLEVVKNLI LILKCKKSVN WVIKSFDVKG SLKIIAPNSI
301 GFGKESERSM TMTKSIRDDI PSTQGNLVKW ALDNGYSPIT SYTMAPVANR FHLRLENNEE
361 MGDEEVHTIP PELRILLDPG ALPALQNPPI RGGEGQNGGL PFPFPDISRR VWNEEGEDGL
421 PRPKDPVIPS IQLFPGLREP EEVQGSVDIA LSVKCDNEKM IVAVEKDSFQ ASGYSGMDVT
481 LLDPTCKAKM NGTHFVLESP LNGCGTRPRW SALDGVVYYN SIVIQVPALG DSSGWPDGYE
541 DLESGDNGFP GDMDEGDASL FTRPEIVVFN CSLQQVRNPS SFQEQPHGNI TFNMELYNTD
601 LFLVPSQGVF SVPENGHVYV EVSVTKAEQE LGFAIQTCFI SPYSNPDRMS HYTIIENICP
661 KDESVKFYSP KRVHFPIPQA DMDKKRFSFV FKPVFNTSLL FLQCELTLCT KMEKHPQKLP
721 KCVPPDEACT SLDASIIWAM MQNKKTFTKP LAVIHHEAES KEKGPSMKEP NPISPPIFHG
781 LDTLTVMGIA FAAFVIGALL TGALWYIYSH TGETAGRQQV PTSPPASENS SAAHSIGSTQ
841 STPCSSSSTA
```

| | |
|---|---|
| 1..18 | Signal peptide |
| 27..786 | Extracellular domain (ectodomain) |
| 566..723 | Zona pellucida-like domain |
| 736..750 | Interaction with TGF-beta ligand |
| 787..808 | site_type="transmembrane region" |

FIG. 7A

APTSSSTKKTQLQLEHLLLDLQMILNGINNYKNPKLTRMLTFKFYMPKKATELKHLQCLEEELKPLEEVLNLAQSKNFHLRPRDL
ISNINVIVLELKGSETTFMCEYADETATIVEFLNRWITFCQSIISTLT*GGGGSGGGGSGGGGS*APE*AA*GGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISK
AKGQPREPQVYT*K*PPSREEMTKNQVSL*S*CLVKGFYPSDIAVEWESNGQPENNYKTT*V*PVLDSDGSF*R*L*A*S*Y*LTVDKSRWQQGNV
FSCSVMHEALHNHYTQKSLSLSP*GGGGGSGGGGSGGGGS*QLCKFCDVRFSTCDNQKSCMSNCSITSICEKPQEVCVAVWRKND
ENITLETVCHDPKLPYHDFILEDAASPKCIMKEKKKPGETFFMCSCSSAECNDNIIFSEEYNTSNPD*GGGGSGGGGSGGGGSGGGG*
*SGGGGS*ALDTNYCFRNLEENCCVRPLYIDFRQDLGWKWVHEPKGYYANFCSGPCPYLRSADTTHSTVLGLYNTLNPEASASP*S*C
VPQDLEPLTILYYVGRTPKVEQLSNMVVKSCKCS

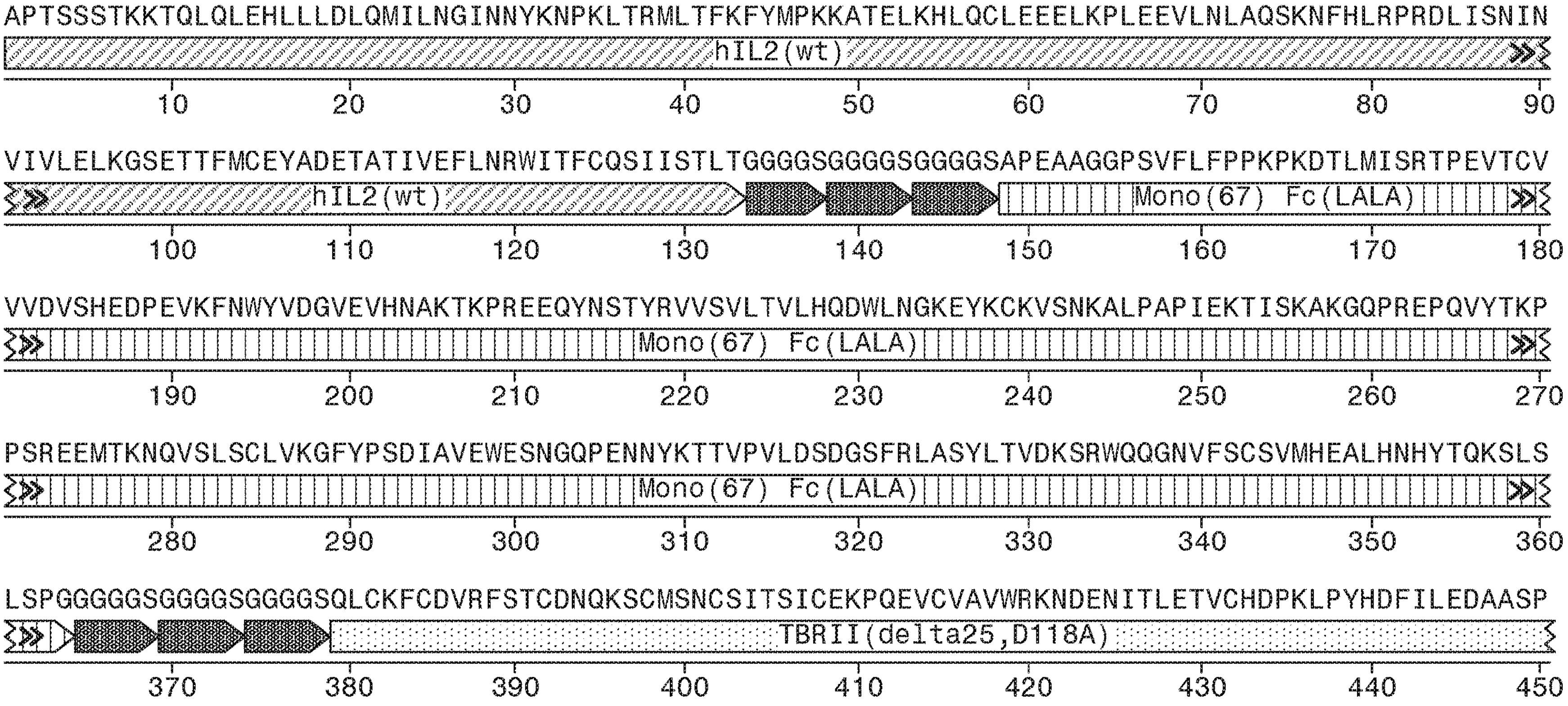

FIG. 7B

APTSSSTKKTQLQLETLLLDLQMILNGINNYKNPKLTRMLTAKFYMPKKATELKHLQCLEEELKPLEEVLNLAQSKNFHLRPRDL
ISNINVIVLELKGSETTFMCEYADETATIVEFLNRWITFCQSIISTLT*GGGGSGGGGSGGGGS*DKTHTCPPCPAPE*AA*GGPSVFLFPP
KPKDTLMISRTPEVTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWESNGQPENNYKTTPPVLDSDGSFFLYSKLTV
DKSRWQQGNVFSCSVMHEALHNHYTQKSLSLSP*GGGGGSGGGGSGGGGS*QLCKFCDVRFSTCDNQKSCMSNCSITSICEKPQE
VCVAVWRKNDENITLETVCHDPKLPYHDFILEDAASPKCIMKEKKKPGETFFMCSCSSAECNDNIIFSEEYNTSNPD*GGGGSGGG*
*GSGGGGSGGGGSGGGGS*ALDTNYCFRNLEENCCVRPLYIDFRQDLGWKWVHEPKGYYANFCSGPCPYLRSADTTHSTVLGLY
NTLNPEASASPCCVPQDLEPLTILYYVGRTPKVEQLSNMVVKSCKCS

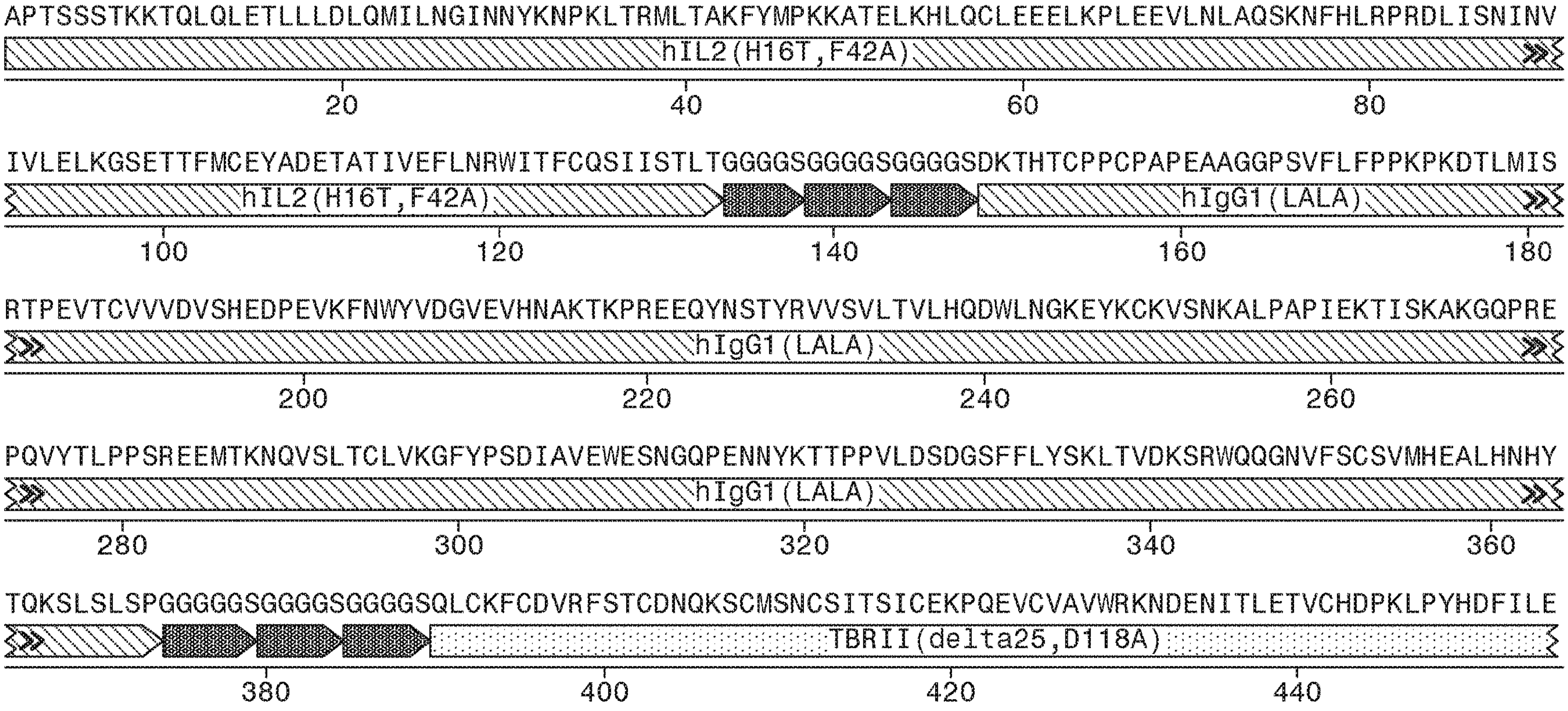

FIG. 7C

APTSSSTKKTQLQLEHLLLDLQMILNGINNYKNPKLTRMLTFKFYMPKKATELKHLQCLEEELKPLEEVLNLAQSKNFHLRPRDL
ISNINVIVLELKGSETTFMCEYADETATIVEFLNRWITFCQSIISTLT*GGGGSGGGGSGGGGS*DKTHTCPPCPAPE*AA*GGPSVFLFPP
KPKDTLMISRTPEVTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSL*W*CLVKGFYPSDIAVEWESNGQPENNYKTTPPVLDSDGSFFLYSKLT
VDKSRWQQGNVFSCSVMHEALHNHYTQKSLSLSP*GGGGGSGGGGSGGGGSGGGGSGGGGS*ALDTNYCFRNLEENCCVRPLYI
DFRQDLGWKWVHEPKGYYANFCSGPCPYLRSADTTHSTVLGLYNTLNPEASASP*S*CVPQDLEPLTILYYVGRTPKVEQLSNMV
VKSCKCS

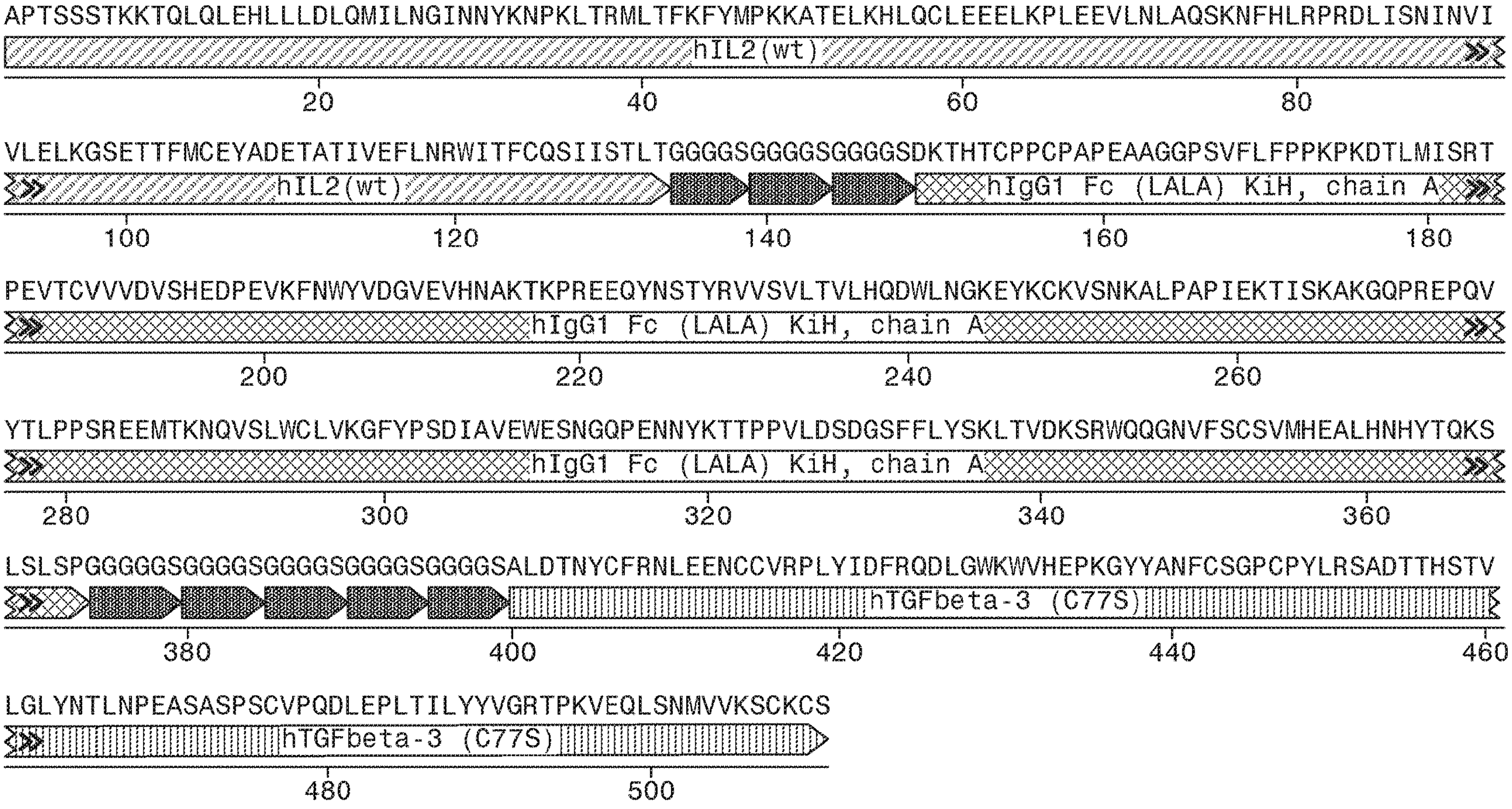

FIG. 7C (continued)

APTSSSTKKTQLQLEHLLLDLQMILNGINNYKNPKLTRMLTFKFYMPKKATELKHLQCLEEELKPLEEVLNLAQSKNFHLRPRDL
ISNINVIVLELKGSETTFMCEYADETATIVEFLNRWITFCQSIISTLT*GGGGSGGGGSGGGGS*DKTHTCPPCPAPE*AA*GGPSVFLFPP
KPKDTLMISRTPEVTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSL*S*C*A*VKGFYPSDIAVEWESNGQPENNYKTTPPVLDSDGSFFLVSKLTV
DKSRWQQGNVFSCSVMHEALHNHYTQKSLSLSP*GGGGSGGGGSGGGGS*QLCKFCDVRFSTCDNQKSCMSNCSITSICEKPQE
VCVAVWRKNDENITLETVCHDPKLPYHDFILEDAASPKCIMKEKKKPGETFFMCSCSSAECNDNIIFSEEYNTSNPD

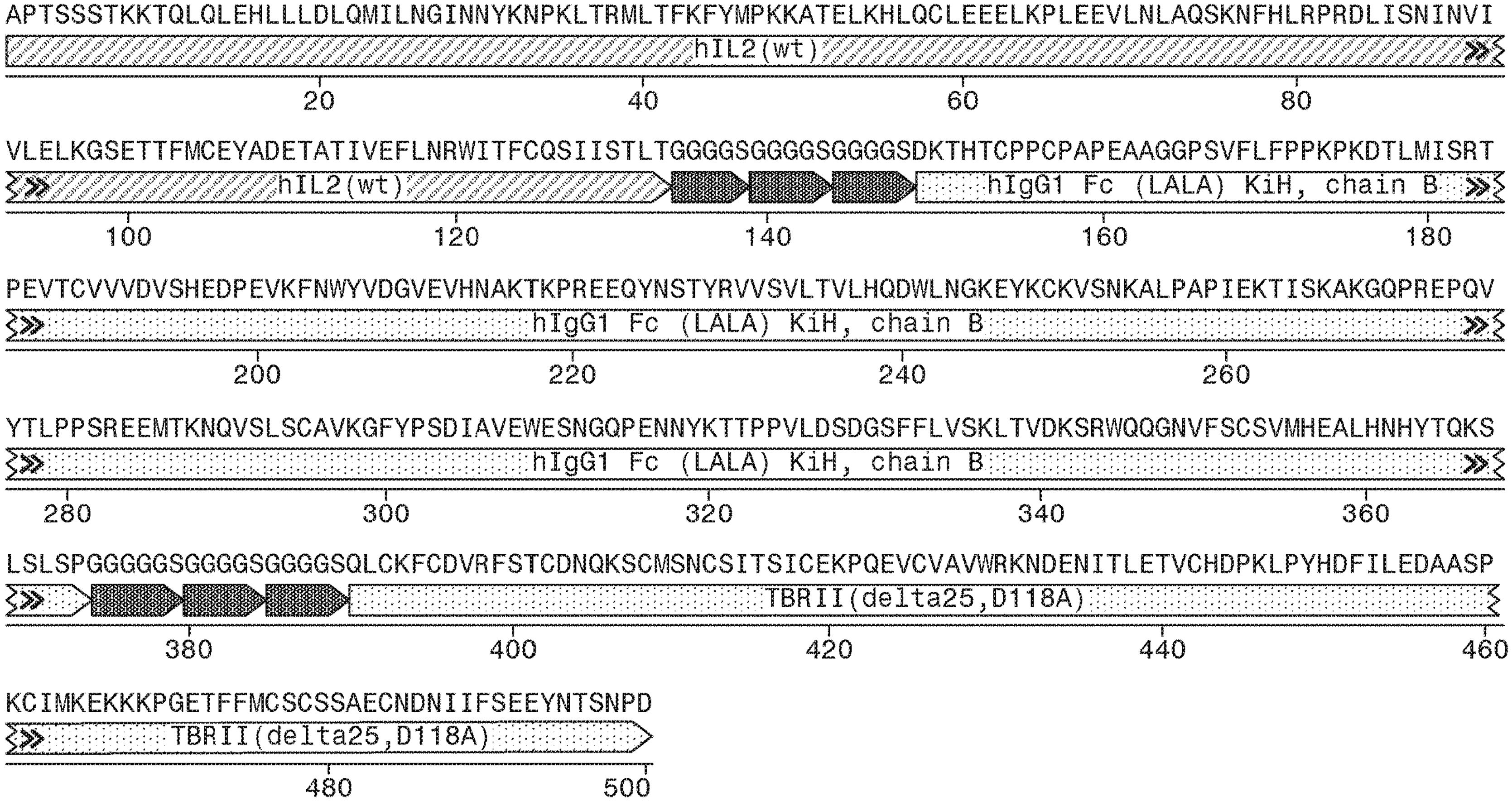

FIG. 7D

APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFCQSIISTLT*GGGGSGGGGSGGGGS*DKTHTCPPCPAPE<u>*AA*</u>GGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSL<u>*W*</u>CLVKGFYPSDIAVEWESNGQPENNYKTTPPVLDSDGSFFLYSKLTVDKSRWQQGNVFSCSVMHEALHNHYTQKSLSLSP*GGGGGSGGGGSGGGGSGGGGSGGGGS*ALDTNYCFRNLEENCCVRPLYIDFRQDLGWKWVHEPKGYYANFCSGPCPYLRSADTTHSTVLGLYNTLNPEASASP<u>*S*</u>CVPQDLEPLTILYYVGRTPKVEQLSNMVVKSCKCS

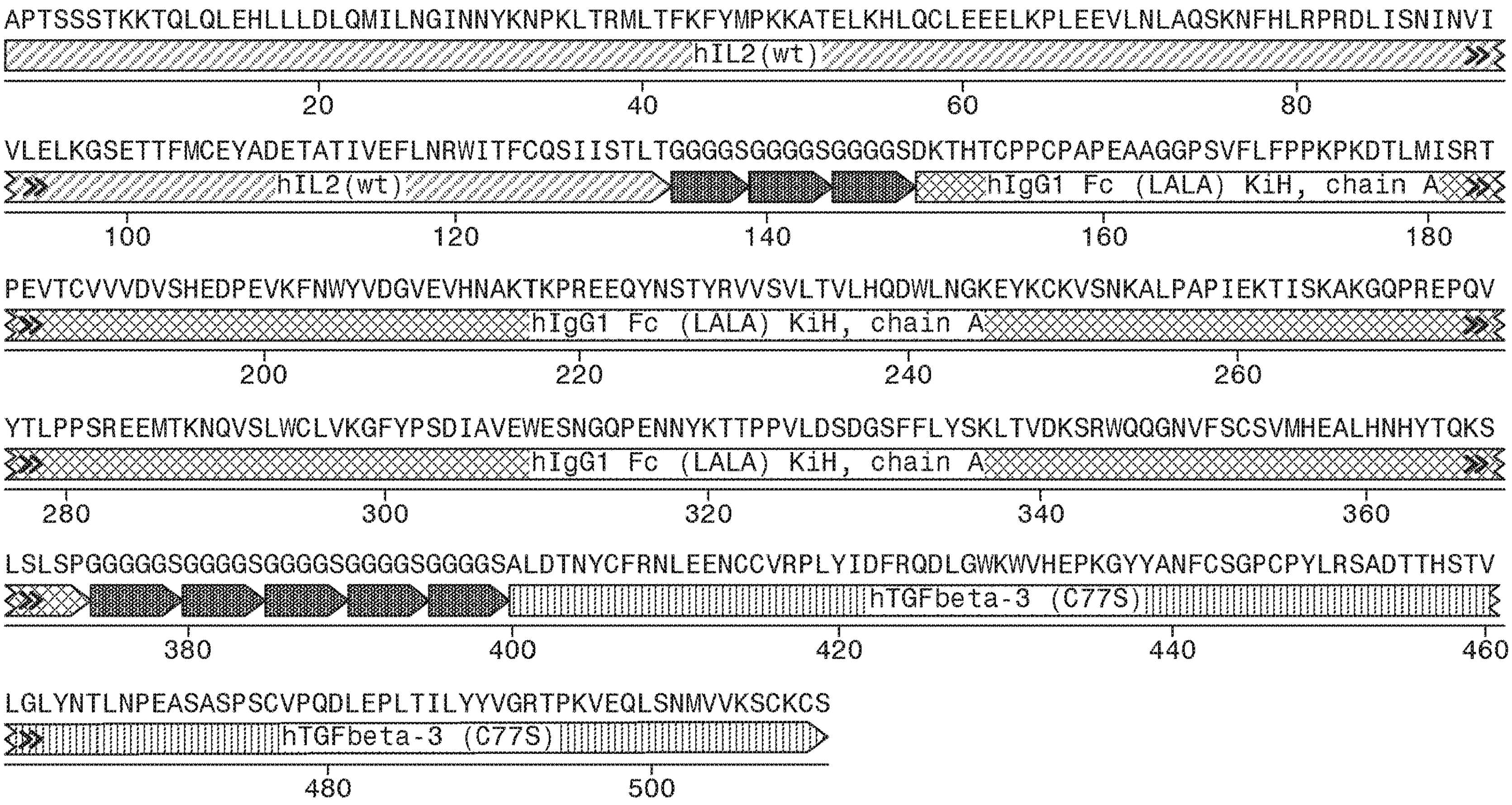

FIG. 7D (continued)

and 3855

DKTHTCPPCPAPE<u>*AA*</u>GGPSVFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSL<u>*S*</u>C<u>*A*</u>VKGFYPSDIAVEWESNGQPE
NNYKTTPPVLDSDGSFFLVSKLTVDKSRWQQGNVFSCSVMHEALHNHYTQKSLSLSP*GGGGGSGGGGSGGGG*SQLCKFCDVRF
STCDNQKSCMSNCSITSICEKPQEVCVAVWRKNDENITLETVCHDPKLPYHDFILEDAASPKCIMKEKKKPGETFFMCSCSSAEC
NDNIIFSEEYNTSNPD

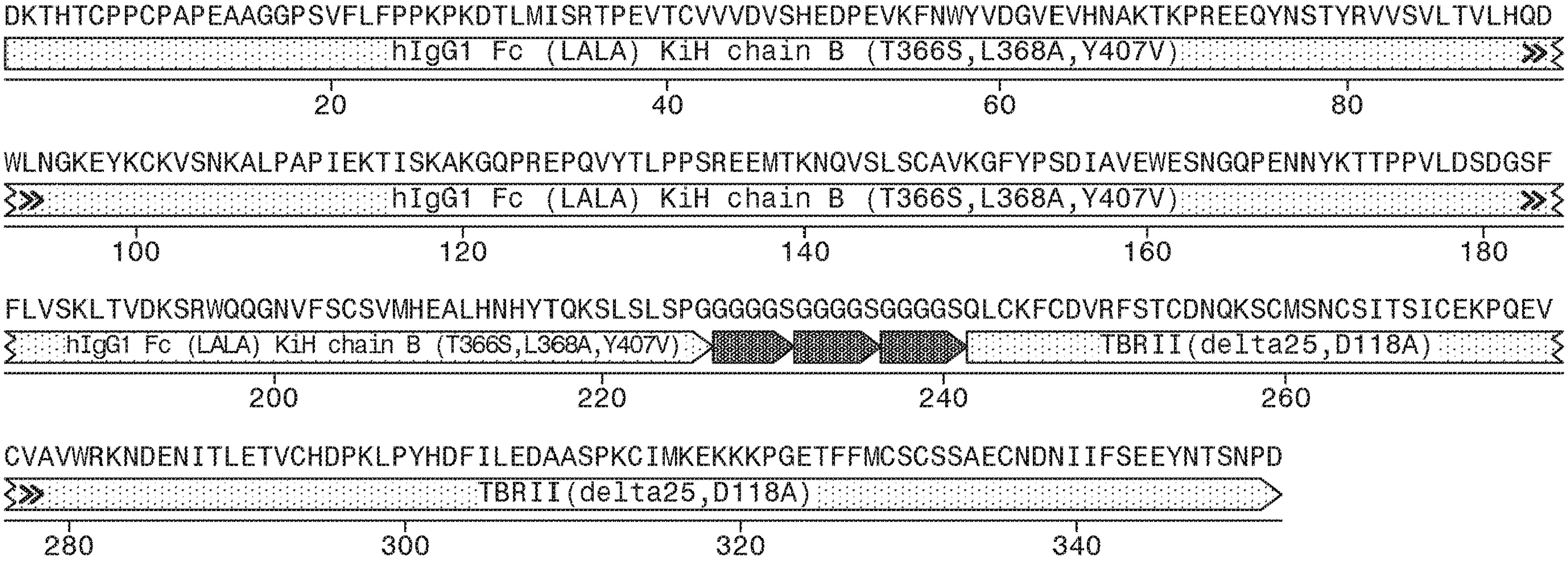

FIG. 7E

APTSSSTKKTQLQLETLLLDLQMILNGINNYKNPKLTRMLTAKFYMPKKATELKHLQCLEEELKPLEEVLNLAQSKNFHLRPRDL
ISNINVIVLELKGSETTFMCEYADETATIVEFLNRWITFCQSIISTLT*GGGGSGGGGSGGGGS*DKTHTCPPCPAPE*AA*GGPSVFLFPP
KPKDTLMISRTPEVTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSL*W*CLVKGFYPSDIAVEWESNGQPENNYKTTPPVLDSDGSFFLYSKLT
VDKSRWQQGNVFSCSVMHEALHNHYTQKSLSLSP*GGGGGSGGGGSGGGGS*QLCKFCDVRFSTCDNQKSCMSNCSITSICEKPQ
EVCVAVWRKNDENITLETVCHDPKLPYHDFILEDAASPKCIMKEKKKPGETFFMCSCSSAECNDNIIFSEEYNTSNPD***GGGGSGG
GGSGGGGSGGGGSGGGGS***ALDTNYCFRNLEENCCVRPLYIDFRQDLGWKWVHEPKGYYANFCSGPCPYLRSADTTHSTVLGL
YNTLNPEASASP*S*CVPQDLEPLTILYYVGRTPKVEQLSNMVVKSCKCS

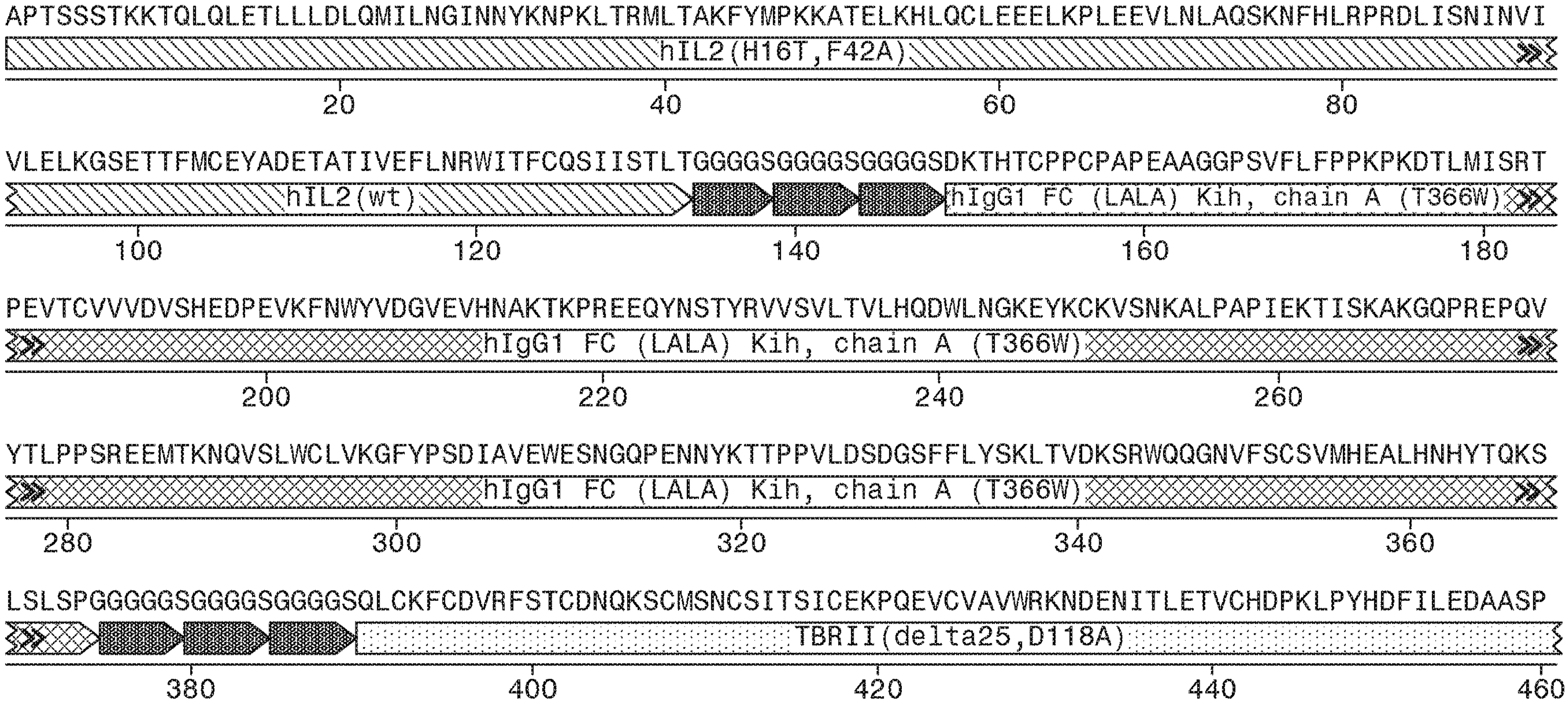

FIG. 7E (continued)

KCIMKEKKKPGETFFMCSCSSAECNDNIIFSEEYNTSNPDGGGGSGGGGSGGGGSGGGGSGGGGSALDTNYCFRNLEENCCVRPLYIDFRQD

TBRII(delta25,D118A) hTGFbeta-3 (C77S)

480 500 520 540

LGWKWVHEPKGYYANFCSGPCPYLRSADTTHSTVLGLYNTLNPEASASPSCVPQDLEPLTILYYVGRTPKVEQLSNMVVKSCKCS hTGFbeta-3 (C77S)

560 580 600 620

3664

DKTHTCPPCPAPEAAGGPSVFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEWESNGQPE
NNYKTTPPVLDSDGSFFLVSKLTVDKSRWQQGNVFSCSVMHEALHNHYTQKSLSLSPG

DKTHTCPPCPAPEAAGGPSVFLFPPKPKDTLMISRTPEVTCVVVDVSHEDPEVKFNWYVDGVEVHNAKTKPREEQYNSTYRVVSVLTVLHQD hIgG1 Fc (LALA), KiH chain B 20 40 60 80

WLNGKEYKCKVSNKALPAPIEKTISKAKGQPREPQVYTLPPSREEMTKNQVSLSCAVKGFYPSDIAVEWESNGQPENNYKTTPPVLDSDGSF hIgG1 Fc (LALA), KiH chain B 100 120 140 160 180

FLVSKLTVDKSRWQQGNVFSCSVMHEALHNHYTQKSLSLSPG hIgG1 Fc (LALA), KiH chain B 200 220

FIG. 7F

DKTHTCPPCPAPEAAGGPSVFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLSCAVKGFYPSDIAVEWESNGQPE
NNYKTTPPVLDSDGSFFLVSKLTVDKSRWQQGNVFSCSVMHEALHNHYTQKSLSLSPGGGGGSGGGGSGGGGSQLCKFCNVRF
STCDNQKSCMSNCSITSICEKPQEVCVAVWRKNDENITLETVCHDPKLPYHDFILEDAASPKCIMKEKKKPGETFFMCSCSSAEC
NDNIIFSEEYNTSNPDGGGGSGGGGSGGGGSGGGGSGGGGSALDTNYCFRNLEENCCVRPLYIDFRQDLGWKWVHEPKGYYAN
FCSGPCPYLRSADTTHSTVLGLYNTLNPEASASPSCVPQDLEPLTILYYVGRTPKVEQLSNMVVKSCKCS

DKTHTCPPCPAPEAAGGPSVFLFPPKPKDTLMISRTPEVTCVVVDVSHEDPEVKFNWYVDGVEVHNAKTKPREEQYNSTYRVVSVLTVLHQD
hIgG1 Fc (LALA), KiH chain B
10 20 30 40 50 60 70 80 90

WLNGKEYKCKVSNKALPAPIEKTISKAKGQPREPQVYTLPPSREEMTKNQVSLSCAVKGFYPSDIAVEWESNGQPENNYKTTPPVLDSDGSF
hIgG1 Fc (LALA), KiH chain B
100 110 120 130 140 150 160 170 180

FLVSKLTVDKSRWQQGNVFSCSVMHEALHNHYTQKSLSLSPGGGGGSGGGGSGGGGSQLCKFCNVRFSTCDNQKSCMSNCSITSICEKPQEV
hIgG1 Fc (LALA), KiH chain B | G4S | G4S | G4S | TBRII(delta25,D32N,D118A)
190 200 210 220 230 240 250 260 270

CVAVWRKNDENITLETVCHDPKLPYHDFILEDAASPKCIMKEKKKPGETFFMCSCSSAECNDNIIFSEEYNTSNPDGGGGSGGGGSGGGGSG
TBRII(delta25,D32N,D118A) | G4S | G4S | G4S
280 290 300 310 320 330 340 350 360

GGGSGGGGSALDTNYCFRNLEENCCVRPLYIDFRQDLGWKWVHEPKGYYANFCSGPCPYLRSADTTHSTVLGLYNTLNPEASASPSCVPQDL
G4S | G4S | hTGFbeta-3 (C77S)
370 380 390 400 410 420 430 440 450 460

EPLTILYYVGRTPKVEQLSNMVVKSCKCS
hTGFbeta-3 (C77S)
470 480 489

FIG. 7F (continued)

DKTHTCPPCPAPEAAGGPSVFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLWCLVKGFYPSDIAVEWESNGQPE
NNYKTTPPVLDSDGSFFLYSKLTVDKSRWQQGNVFSCSVMHEALHNHYTQKSLSLSPGGGGGSGGGGSGGGGSAPTSSSTKKT
QLQLEHLLLDLQMILNGINNYKNPKLTRMLTFKFYMPKKATELKHLQCLEEELKPLEEVLNLAQSKNFHLRPRDLISNINVIVLEL
KGSETTFMCEYADETATIVEFLNRWITFCQSIISTLT

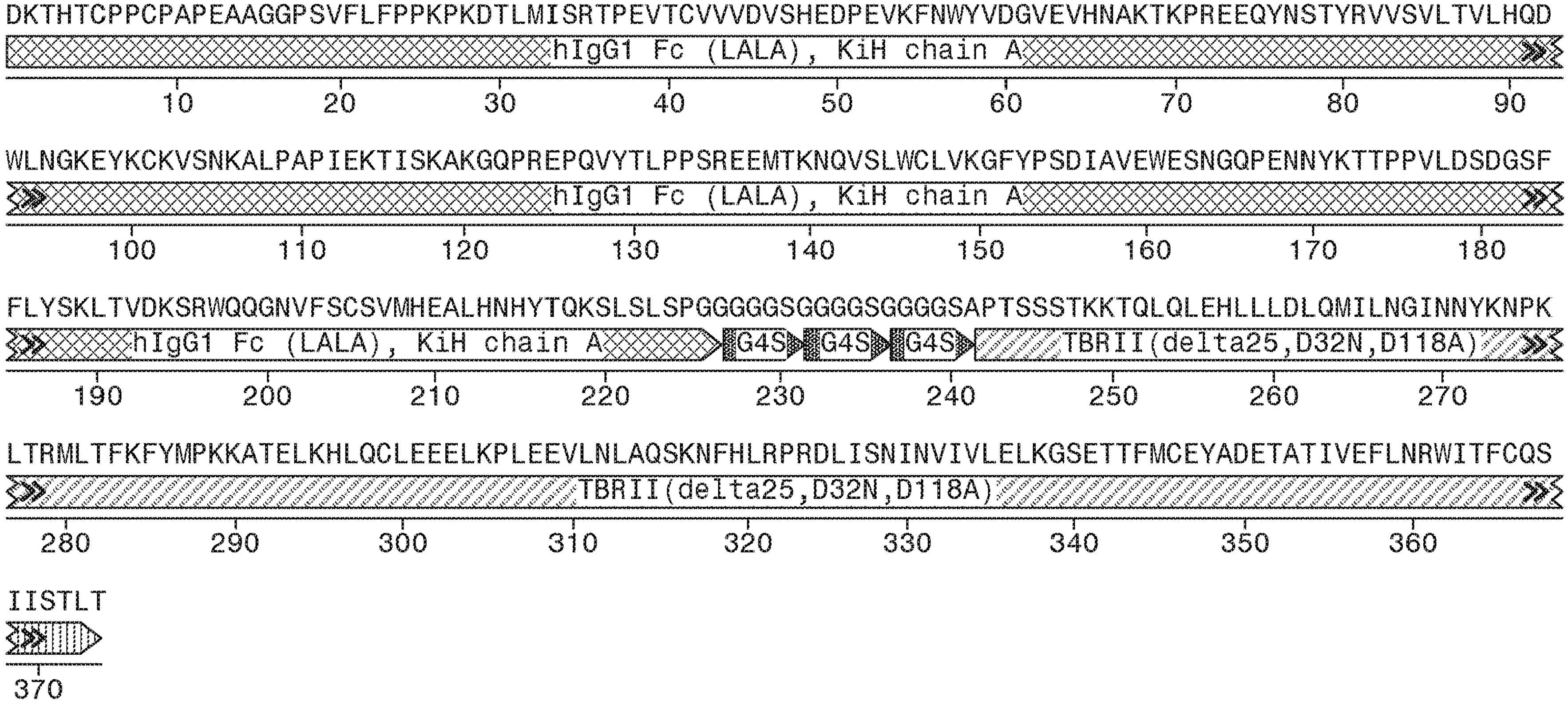

FIG. 7G

APTSSSTKKTQLQLEHLLLDLQMILNGINNYKNPKLTRMLTFKFYMPKKATELKHLQCLEEELKPLEEVLNLAQSKNFHLRPRDL
ISNINVIVLELKGSETTFMCEYADETATIVEFLNRWITFCQSIISTLTGGGGSGGGGSGGGGSAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISK
AKGQPREPQVYTKPPSREEMTKNQVSLSCLVKGFYPSDIAVEWESNGQPENNYKTTVPVLDSDGSFRLASYLTVDKSRWQQGN
VFSCSVMHEALHNHYTQKSLSLSPGGGGGSGGGGSGGGGSQLCKFCNVRFSTCDNQKSCMSNCSITSICEKPQEVCVAVWRKN
DENITLETVCHDPKLPYHDFILEDAASPKCIMKEKKKPGETFFMCSCSSAECNDNIIFSEEYNTSNPDGGGGSGGGGSGGGGSGGG
GSGGGGSALDTNYCFRNLEENCCVRPLYIDFRQDLGWKWVHEPKGYYANFCSGPCPYLRSADTTHSTVLGLYNTLNPEASASPS
CVPQDLEPLTILYYVGRTPKVEQLSNMVVKSCKCS

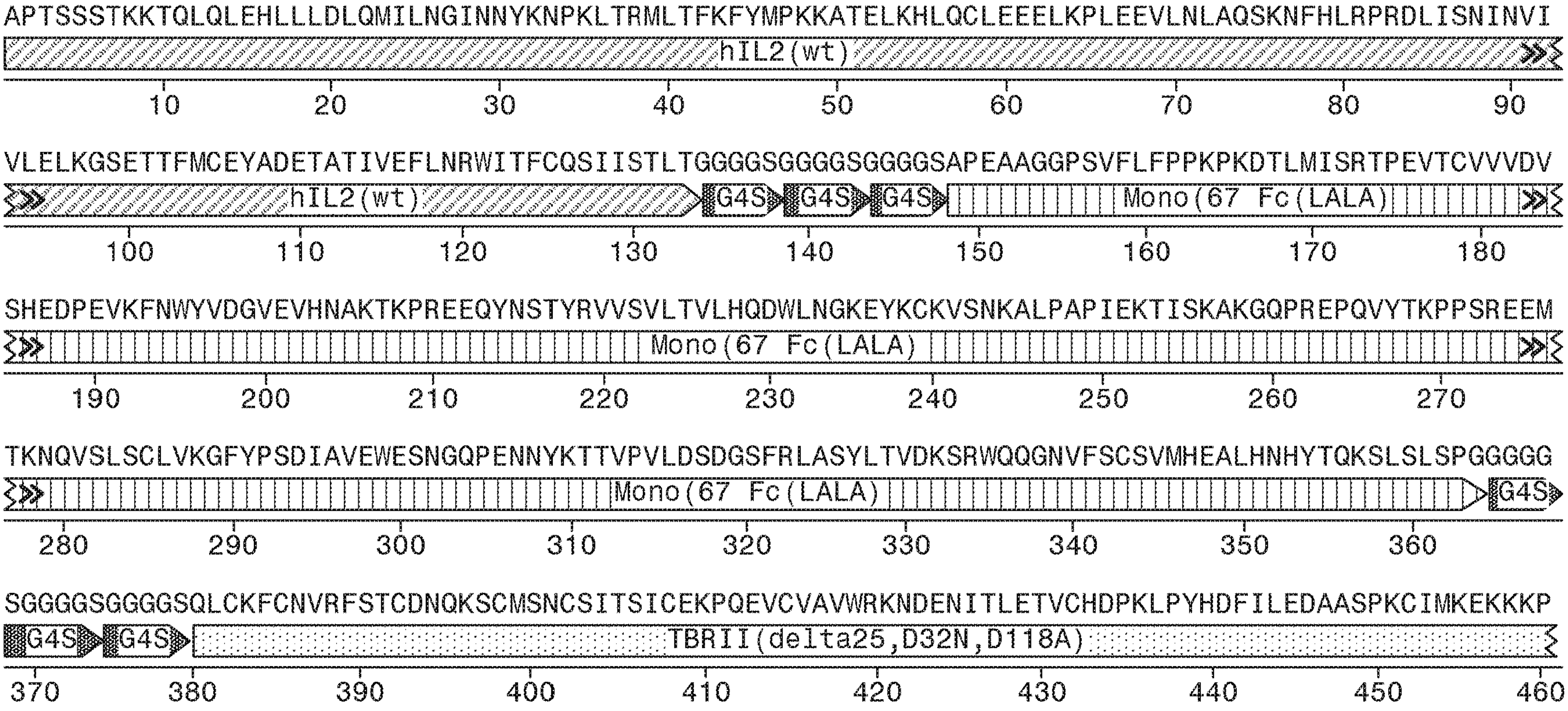

FIG. 7H

APTSSSTKKTQLQLETLLLDLQMILNGINNYKNPKLTRMLTAKFYMPKKATELKHLQCLEEELKPLEEVLNLAQSKNFHLRPRDL
ISNINVIVLELKGSETTFMCEYADETATIVEFLNRWITFCQSIISTLTGGGGSGGGGSGGGGSAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISK
AKGQPREPQVYTKPPSREEMTKNQVSLSCLVKGFYPSDIAVEWESNGQPENNYKTTVPVLDSDGSFRLASYLTVDKSRWQQGN
VFSCSVMHEALHNHYTQKSLSLSPGGGGGSGGGGSGGGGSQLCKFCDVRFSTCDNQKSCMSNCSITSICEKPQEVCVAVWRKN
DENITLETVCHDPKLPYHDFILEDAASPKCIMKEKKKPGETFFMCSCSSAECNDNIIFSEEYNTSNPDGGGGSGGGGSGGGGSGGG
GSGGGGSALDTNYCFRNLEENCCVRPLYIDFRQDLGWKWVHEPKGYYANFCSGPCPYLRSADTTHSTVLGLYNTLNPEASASPS
CVPQDLEPLTILYYVGRTPKVEQLSNMVVKSCKCS

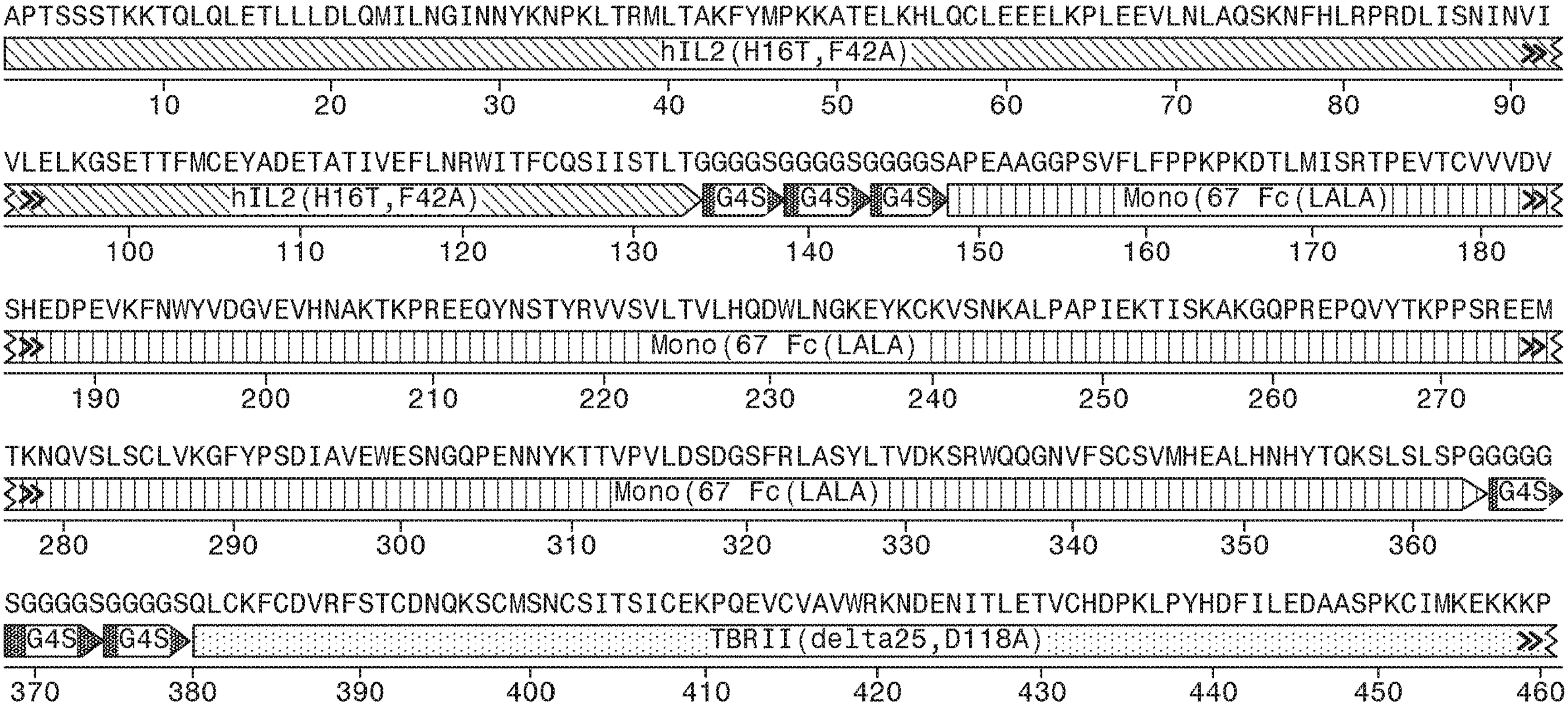

FIG. 7I

APTSSSTKKTQLQLETLLLDLQMILNGINNYKNPKLTRMLTAKFYMPKKATELKHLQCLEEELKPLEEVLNLAQSKNFHLRPRDL
ISNINVIVLELKGSETTFMCEYADETATIVEFLNRWITFCQSIISTLTGGGGSGGGGSGGGGSAPEAAGGPSVFLFPPKPKDTLMISR
TPEVTCVVVDVSHEDPEVKFNWYVDGVEVHNAKTKPREEQYNSTYRVVSVLTVLHQDWLNGKEYKCKVSNKALPAPIEKTISK
AKGQPREPQVYTKPPSREEMTKNQVSLSCLVKGFYPSDIAVEWESNGQPENNYKTTVPVLDSDGSFRLASYLTVDKSRWQQGN
VFSCSVMHEALHNHYTQKSLSLSPGGGGGSGGGGSGGGGSQLCKFCNVRFSTCDNQKSCMSNCSITSICEKPQEVCVAVWRKN
DENITLETVCHDPKLPYHDFILEDAASPKCIMKEKKKPGETFFMCSCSSAECNDNIIFSEEYNTSNPDGGGGSGGGGSGGGGSGGG
GSGGGGSALDTNYCFRNLEENCCVRPLYIDFRQDLGWKWVHEPKGYYANFCSGPCPYLRSADTTHSTVLGLYNTLNPEASASPS
CVPQDLEPLTILYYVGRTPKVEQLSNMVVKSCKCS

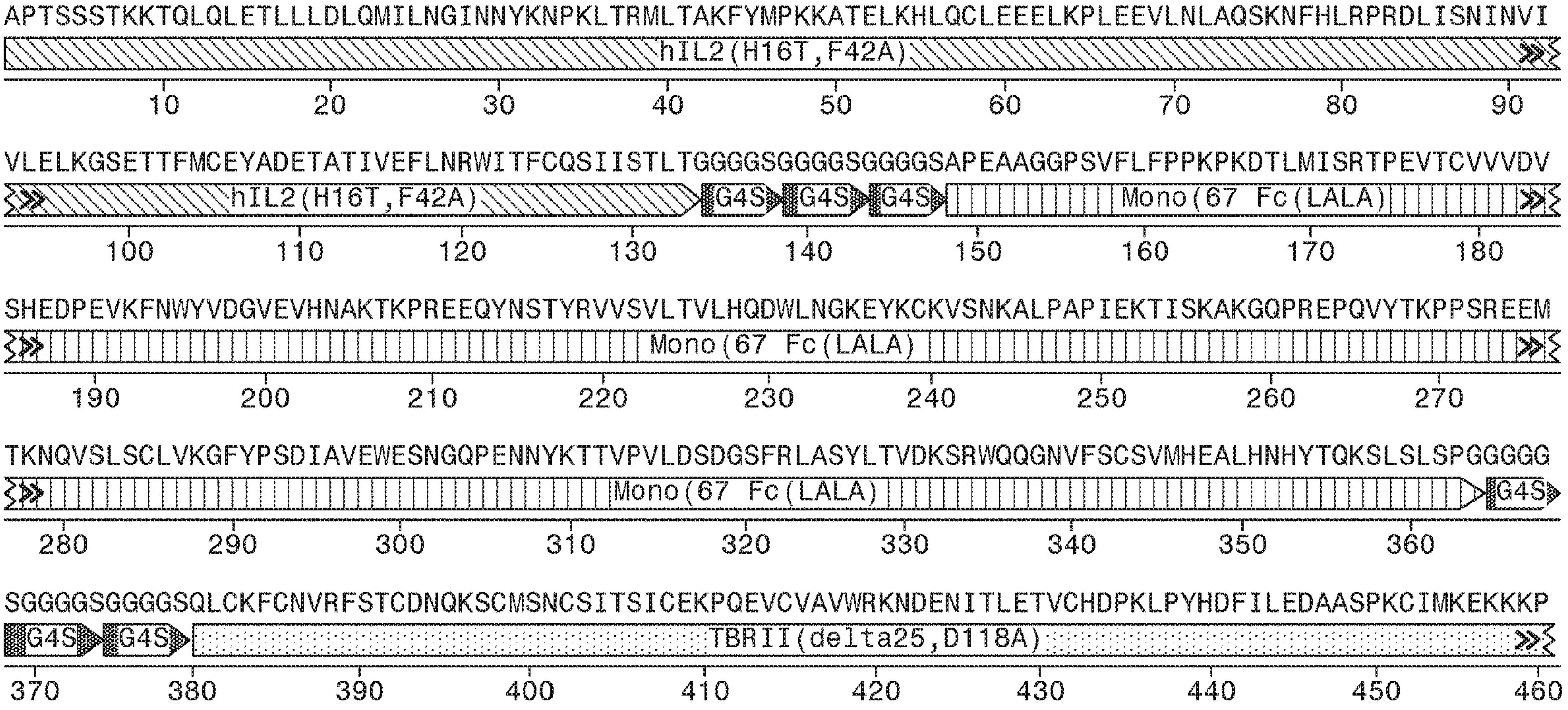

FIG. 7J

APTSSSTKKTQLQLEHLLLDLQMILNGINNYKNPKLTRMLTFKFYMPKKATELKHLQCLEEELKPLEEVLNLAQSKNFHLRPRDL
ISNINVIVLELKGSETTFMCEYADETATIVEFLNRWITFCQSIISTLTGGGGSGGGGSGGGGSDKTHTCPPCPAPEAAGGPSVFLFPP
KPKDTLMISRTPEVTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLSCAVKGFYPSDIAVEWESNGQPENNYKTTPPVLDSDGSFFLVSKLTV
DKSRWQQGNVFSCSVMHEALHNHYTQKSLSLSPGGGGGSGGGGSGGGGSQLCKFCNVRFSTCDNQKSCMSNCSITSICEKPQE
VCVAVWRKNDENITLETVCHDPKLPYHDFILEDAASPKCIMKEKKKPGETFFMCSCSSAECNDNIIFSEEYNTSNPD

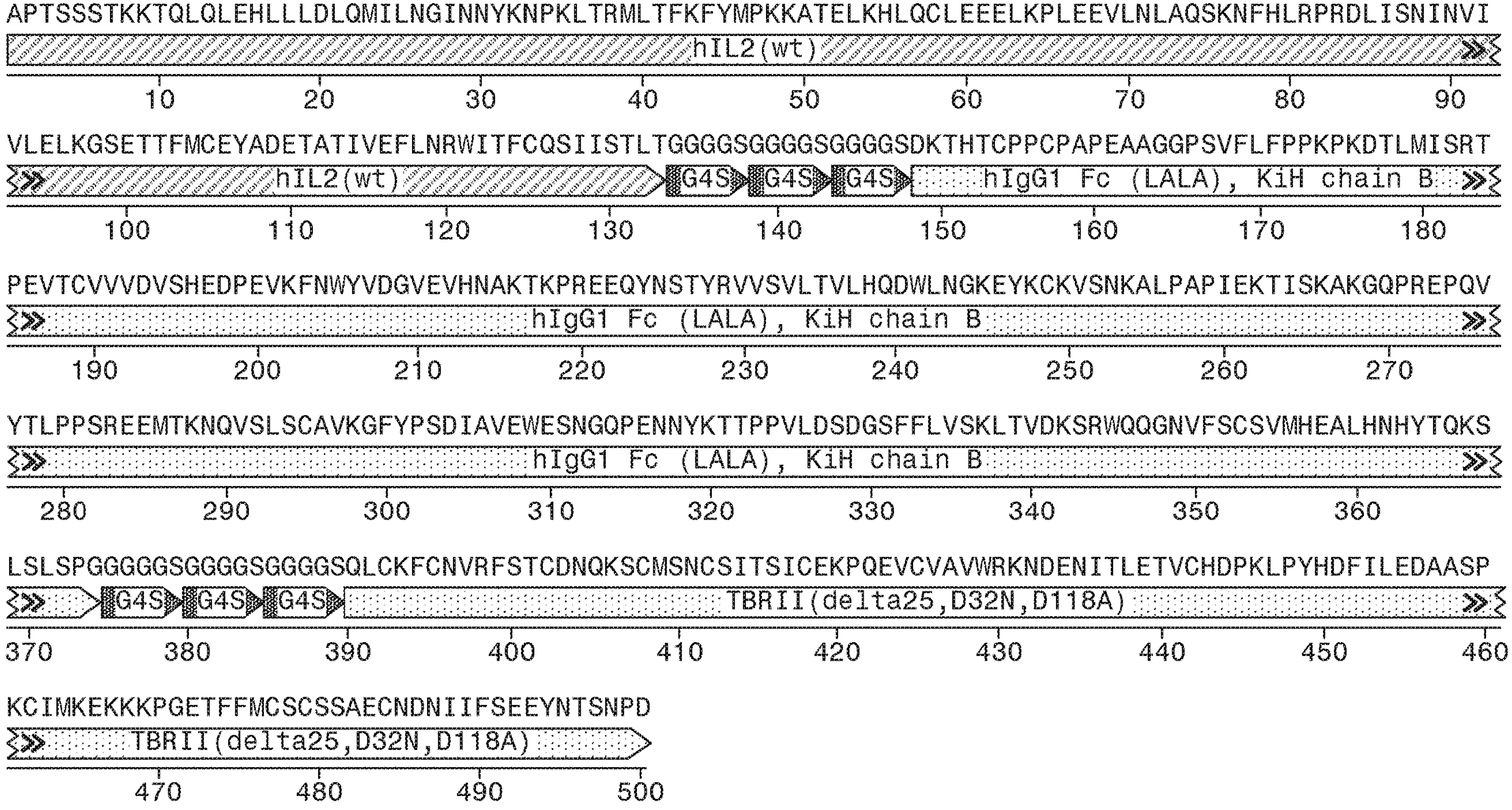

| Mutation | Kd (μM) TGF-β1 | Kd (μM) TGF-β3 |
|---|---|---|
| Δ14 | 0.32 | 0.68 |
| L27A | 7.97 | 14.8 |
| F30A | 44.0 | 104 |
| D32A | 3.52 | 8.87 |
| D32N | 5.90 | 19.9 |
| S49A | 0.79 | 1.18 |
| I50A | 7.96 | 16.7 |
| T51A | 2.97 | 8.75 |
| S52A | 0.60 | 0.98 |
| S52L | 154 | 620 |
| I53A | 2.49 | 6.87 |
| E55A | 2.99 | 5.30 |
| V77A | 0.69 | 1.37 |
| D118A | 1.51 | 2.69 |
| E119A | 3.35 | 8.47 |
| E119Q | 5.95 | 10.6 |

FIG. 10B

Construct 4033 (SEQ ID NO:191)

APTSSSTKKTQLQLEALLLDLQMILNGINNYKNPKLTRMLTAKFYMPKKATELKHLQCLE
EELKPLEEVLNLAQSKNFHLRPRDLISNINVIVLELKGSETTFMCEYADETATIVEFLNRWIT
FCQSIISTLTGGGGSGGGGSGGGGSDKTHTCPPCPAPEAAGGPSVFLFPPKPKDTLMISRTPE
VTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPCREEMTKNQVSLWCLVKGFYPSDI
AVEWESNGQPENNYKTTPPVLDSDGSFFLYSKLTVDKSRWQQGNVFSCSVMHEALHNHY
TQKSLSLSPGGGGGSGGGGSGGGGSGGGGSGGGGSALDTNYCFRNLEENCCVRPLYIDFR
QDLGWKWVHEPKGYYANFCSGPCPYLRSADTTHSTVLGLYNTLNPEASASPSCVPQDLEP
LTILYYVGRTPKVEQLSNMVVKSCKCS

FIG. 10C

Construct 4039 (SEQ ID NO:192)

DKTHTCPPCPAPEAAGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKG
QPREPQVCTLPPSREEMTKNQVSLSCAVKGFYPSDIAVEWESNGQPENNYKTTPPVLDSDG
SFFLVSKLTVDKSRWQQGNVFSCSVMHEALHNHYTQKSLSLSPGGGGGSGGGGSGGGGS
QLCKFCDVRFSTCDNQKSCMSNCSITSICEKPQEVCVAVWRKNDENITLETVCHDPKLPYH
DFILEDAASPKCIMKEKKKPGETFFMCSCSSAECNDNIIFSEEYNTSNPD

FIG. 11

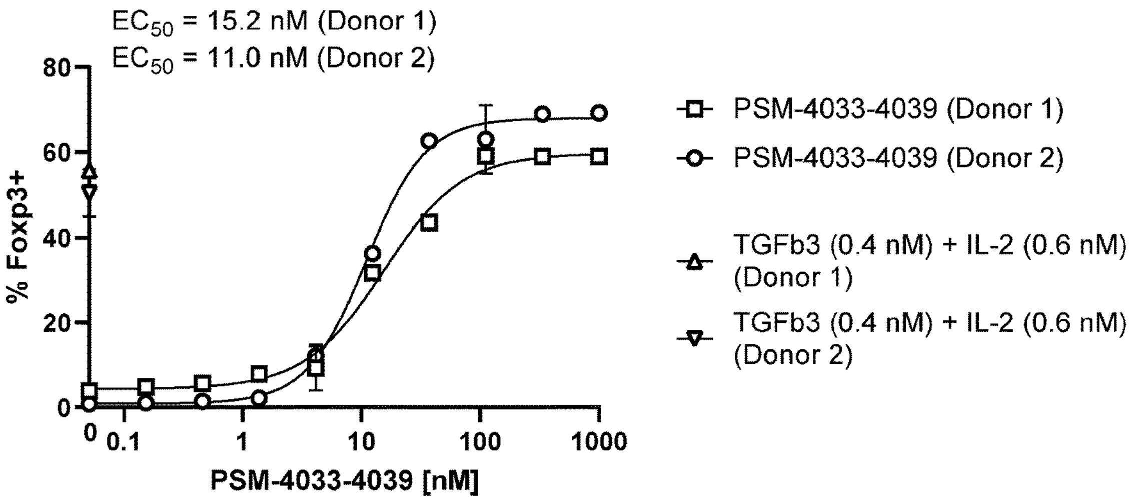

TGF-β POLYPEPTIDES

CROSS-REFERENCE TO RELATED APPLICATIONS

This application is a division of U.S. application Ser. No. 17/722,328 filed Apr. 16, 2022, which is a continuation of International Application No. PCT/US2020/056937 filed Oct. 22, 2020, which claims the benefit of U.S. Provisional Application No. 62/925,227, filed Oct. 23, 2019, which application is herein incorporated by reference in its entirety.

INCORPORATION BY REFERENCE OF SEQUENCE LISTING

This application contains a sequence listing submitted electronically, which serves as both the paper copy and the computer readable form (CRF) and consists of a file entitled "2910-12-PCT ST26.xml, which was created on Apr. 12, 2023, which is 434,759 bytes in size, and which is herein incorporated by reference in its entirety.

I. INTRODUCTION

A. TGF-β and its Actions

Transforming growth factor beta (TGF-β) is a cytokine belonging to the transforming growth factor superfamily that includes three mammalian (human) isoforms, TGF-β1, TGF-β2, and TGF-β3. TGF-βs are synthesized as precursor molecules containing a propeptide region in addition to the TGF-β sequences that homodimerize as an active form of TGF-β. TGF-β is secreted by macrophages and other cell types in a latent complex in which it is combined with two other polypeptides-latent TGF-β binding protein (LTBP) and latency-associated peptide (LAP). The latent TGF-β complex is stored in the extra cellular matrix (ECM), for example, bound to the surface of cells by CD36 via thrombospondin-1 (where it can be activated by plasmin) or to latent transforming growth factor beta binding proteins 1, 2, 3, and/or 4 (LTBP1-4).

The biological functions of TGF-β are seen after latent TGF-β activation, which is tightly regulated in response to ECM perturbations. TGF-β may be activated by a variety of cell or tissue specific pathways, or pathways observed in multiple cell or tissue types; however, the full mechanisms behind such activation pathways are not fully known. Activators include, but are not limited to, proteases, integrins, pH, and reactive oxygen species (ROS). In effect, the cell/tissue bound latent TGF-β complex functions, senses and responds to environmental perturbations releasing active TGF-β in a spatial and/or temporal manner. The released TGF-β acts to promote or inhibit cell proliferation depending on the context of its release. It also recruits stem/progenitor cells to participate in the tissue regeneration/remodeling process. Aberrations in TGF-β ligand expression, bioavailability, activation, receptor function, or post-transcriptional modifications disturb the normal function, and can lead to pathological consequences associated with many diseases, such as through the recruitment of excessive progenitors (e.g., in osteoarthritis or Camurati-Engelmann disease), or by the trans-differentiation of resident cells to unfavorable lineages (e.g., in epithelial to mesenchymal transition during cancer metastasis or tissue/organ fibrosis). Xu et al *Bone Research,* 6 (Article No. 2) (2018).

1 Integrin-Independent and Integrin-Dependent Activation a. Integrin-Independent Activation

Among the integrin-independent means of TGF-β activation are those that work through the action of, among other things, proteases and/or metalloproteases, reactive oxygen species (ROS), and thrombospondin-1.

Plasmin and several matrix metalloproteinases (MMPs) promote tumor invasion and tissue remodeling by proteolysis of extracellular matrix components. The TGF-β may become activated by the action of such proteases that release the latent complex from the matrix, which is followed by proteolysis of the LAP to release TGF-β to its receptors. Both matrix metalloprotease −9 and −2 are known to cleave latent TGF-β.

TGF-β has been shown to be rapidly activated in vivo following radiation exposure to induce ROS release. ROS are thought to alter the interaction between LAP and TGF-β, leading to its activation.

Thrombospondin-1 (TSP-1), a glycoprotein found in plasma of healthy individuals, is known to increase in response to injury. TSP-1 is believed to activate latent TGF-β by forming direct interactions with the latent TGF-β complex and preventing it from binding to the matured TGF-β. Thrombospondin mediated activation is believed to be involved in wound (e.g., dermal wound) healing.

b. Activation by Alpha(V) Containing Integrins

Integrins, and particularly β6, αV, and β8 containing integrins, are understood to contribute to latent TGF-β (e.g., TGF-β1) activation. Activation appears to occur by inducing conformational changes to the latent TGF-β1 complex and hence releasing the active TGF-β1 or by an integrin-protease-dependent mechanism. Conformational changes leading to TGF-β1 activation without proteolysis, particularly in epithelial cells, are understood to occur through integrin binding an Arginyl-Glycyl-Aspartic cell adhesion motif (RGD motif) present in LAP-β1 or LAP-β3. LAPs containing the RGD motif are recognized by a majority of αV containing integrins. For example, αVβ6 integrin can activate/release TGF-β1 by binding to the RGD motif present in LAP-β1 and LAP-β3. In addition, integrin-protease-dependent activation of TGF-β can occur by creating a connection between the latent TGF-β complex and MMPs, such as MMP-2 and MMP-9, that can activate TGF-β by proteolytic degradation of the latent TGF-β complex.

2 TGF-β Signaling and Actions

Activated TGF-β plays a crucial role in cell differentiation as well as T-cell regulation. See, e.g., *Cold Spring Harbor Perspect. Biol.* 2017; 9:a022236 and citations therein. TGF-β promotes the thymic development of several T-cell lineages by supporting the survival of thymus-derived Treg (tTreg), invariant natural killer T (iNKT), and CD8α+ T-cell precursors, and accordingly promoting development of T-cells inducible by strong agonist ligands. TGF-β supports conventional CD8+ T cells by promoting thymocyte expression of interleukin (IL)-7Ra. TGF-β also regulates peripheral T-cell homeostasis by promoting IL-7-dependent survival of low-affinity T cells, by controlling thymocyte IL-7Rα expression and by inhibiting T-cell receptor (TCR)-driven activation of autoreactive or high-affinity T cells. In early CD8+ T-cell differentiation, TGF-β inhibits cytotoxic T lymphocyte (CTL) formation and promotes the apoptosis of short-lived effector cells (SLECs) while promoting the differentiation of CD103-expressing tissue resident memory (TRM) cells. Although TGF-β inhibits T helper 1 and 2 (Th1 and Th2) cell differentiation, TGF-β acting with other factors promotes the development of various T-cells. TGF-β in conjunction with: IL-2 promotes production of peripheral Treg (pTreg), IL-6 promotes production of Th-17 cells, IL-4 promotes production of Th9 cells, and IL-21 and/or 23 promotes production of T follicular helper (Tfh) cells.

In addition to its action on T cells, a variety of other cells are regulated by TGF-β including B lymphocytes or "B cells," monocytes, and macrophages. TGF-β generally has inhibitory actions on B cells (Li et al., *Annual Review of Immunology.* 24 (1): 99-146 (2006) and Roes et al., *PNAS USA,* 100 (12): 7241-7246 (2003)); inhibiting B cell proliferation and inducing apoptosis of immature or resting B cells (Arsura, et al., *Immunity* 5(1): 31-40. (1996)). At least part of the action of TGF-β on B cells may be due to induction of IKBa, an inhibitor of NF-κB that regulates the production of cytokines including IL-1, TNF-a, and defensins. See, e.g., *Cold Spring Harbor Perspect. Biol.* 2017; 9:a022236 and citations therein.

In addition to its actions on B cells, TGF-β stimulates resting monocytes and inhibits activated macrophages. TGF-β displays inhibitory effects such as the proinflammatory response of macrophages that have been stimulated by Toll-Like-Receptor ("TLR") ligands. TGF-β stimulation, in the absence of TLR ligands or other cytokines, promotes production of several inflammatory cytokines by myeloid cells. TGF-β has been shown to induce peripheral blood monocytes and macrophages into tissues and enhance monocyte adherent properties. TGF-β can induce chemotaxis and enhance the adherent properties of mast cells. See, e.g., *Cold Spring Harbor Perspect. Biol.* 2017; 9:a022236 and citations therein.

Once TGF-β is activated, it is understood to act through cell surface signaling receptors. Signaling commences when an active TGF-β ligand binds to the transforming growth factor beta receptor II ("TβRII") on a cell surface. This interaction may result in the recruitment of transforming growth factor beta receptor I ("TβRI"). TβRII is capable of binding TGF-β1 alone, while TβRI can only bind the ligand in cooperation with TβRII. TβRI is phosphorylated and activated by TβRII, leading to signaling through the canonical signaling pathway via the recruitment and phosphorylation of the R-Smad proteins (Smad2 and Smad3). Those Smads subsequently bind to a co-Smad (Smad4), and together the complex drives the transcription of several genes. See Smith et al., *Clin. Cancer Res.;* 18(17): 4514-21 (2012). TGF-β can also signal through non-canonical (non-Smad) pathways that include various branches of MAP kinase pathways, Rho-like GTPase signaling pathways, and phosphatidylinositol-3-kinase/AKT pathways, that are activated by ligand-occupied receptors. Signaling through the non-canonical paths may reinforce, attenuate, or otherwise modulate downstream cellular responses. Zhang Ye, *Cell Res.* 19(1):128-39 (2009). In contrast to TβRI and TβRII, the transforming growth factor beta receptor III ("TβRIII" receptor or "beta glycan") does not participate in TGF-β signal transduction, but rather acts as a reservoir for TGF-β.

Perturbations of the activating factors, abnormal levels of activated TGF-β, and/or alterations in TGF-β signaling can lead to unregulated TGF-β signaling levels that can lead to several diseases or to complicated disease states. Indeed, TGF-β has been shown to have effects on conditions as diverse as inflammation, autoimmune disorders, fibrosis, cancer and cataracts.

TGF-β plays a pivotal role in maintaining hemostasis in the immune system as a factor involved in the induction of tolerance, and thereby affecting autoimmune responses. One mechanism by which TGF-β can bring about such effects is by driving T-cells (e.g., CD4+, CD8+, $CD4^-$ CD8+ and CD4 CD8 cells) to differentiate into T-regulatory cells or "T-Reg" cells (e.g., in the presence of IL-2). See, e.g., Bettini and Vagnali, *Ann. N.Y. Acad. Sci.,* 1183:1-12 (2010). T-Reg cells are essential for the maintenance of immune tolerance. Josefowicz et al. *Annu Rev Immunol,* 30: 531-564. (2012). TGF-β 's role in inducing tolerance to antigens, including self antigens, makes it a crucial factor in protecting against developing diseases such as arthritis (rheumatoid arthritis or "RA"), Type 1 diabetes mellitus ("T1D"), multiple sclerosis ("MS"), and systemic lupus erythematosus ("SLE"). For example, among TGF-β's key functions is regulation of autoimmune diseases and the related inflammatory processes. This is particularly true in the gut where it is believed to suppress macrophage cytokine production and mucosal inflammation in conditions such as inflammatory bowel disease or "IBD." Sanjab et al. *Cold Spring Harbor Perspect. Biol.* 2017; 9:a022236. Like IBD, RA is an autoimmune disorder with an inflammatory component directed at joints. RA results from aberrant responses in T and/or B cells. Systemic TGF-β appears to offer protection from RA development. See Schramm et al., *Arthritis Res. Ther.* 6:R114-R119 (2004) and Sanjab et al. *Cold Spring Harbor Perspect. Biol.* 2017; 9:a022236), and references cited therein.

A number of approaches to regulate TGF-β action at the level of the protein by sequestering it to effectively neutralize its action have been described in the literature. For example, monoclonal antibodies such as Metelimumab (CAT192) that is directed against TGF-β1, and Fresolimumab directed against multiple isoforms of TGF-β have been developed to bind, sequester, and neutralize TGF-β in vivo. In addition, receptor traps that tightly bind and sequester TGF-β thereby sequestering and neutralizing it have also been developed (see, e.g., Swaagrtra, et al., *Mol Cancer Ther;* 11(7): 1477-87 (2012) and U.S. Pat. Pub. No. 2018/0327477).

Unlike the molecules described above that are designed to bind and sequester the TGF-β and act as antagonists to TGF-β action, the masked TGF-β complexes described herein provide active TGF-β polypeptides (e.g., TGF-β signaling pathway agonists) and a masking polypeptide (e.g., a TGF-β receptor fragment) that interact with each other to reversibly mask the TGF-β polypeptide sequence. The masked TGF-β complexes may include sequence variations in the TGF-β and/or in the masking polypeptides that can reduce their mutual affinity and contribute to TGF-β's unmasking, permitting its binding signaling through heteromeric cell surface receptors (e.g., binding to TβRII followed by TβRI to form a heteromeric receptor). Once formed the heteromeric TβRI-TβRII polypeptide complex, which has high affinity for TGF-β, can effectively compete with the masking polypeptide. Sequence variations in TGF-β and/or its masking polypeptide can also permit avoidance of undesirable interactions between the unmasked TGF-β polypeptide and other molecules. Such sequence variations include deletions of portions of the N-terminus of TβRII that attenuate binding to TβRI, and/or TGF-β sequence variations preventing its dimerization (e.g., C77S substitutions) that limit off target binding to the reservoir of non-signaling TβRIII molecules. In addition to the foregoing, the masked TGF-β constructs and complexes may also comprise additional wild type (wt.) and/or variant immunomodulatory polypeptide sequences (MODs) that can substantively impact the outcome of TGF-β binding to a target cell, including in vitro effects and in vivo effects such as therapeutic outcomes.

II. SUMMARY

The present disclosure describes the preparation of constructs in which TGF-β is masked by another polypeptide ("masked TGF-β constructs," see, e.g., FIG. 1 structure A with a single polypeptide chain), and complexes in which TGF-β is masked by another polypeptide ("TGF-β polypeptide complexes," see, e.g., FIG. 1 structures B-F showing complexes comprising two polypeptide chains), which constructs and complexes, that also may comprise additional elements, are referred herein to collectively as "masked TGF-β constructs and complexes." The masked TGF-β constructs and complexes are built around a scaffold polypeptide (e.g., an immunoglobulin Fc region) and contain masking polypeptide sequences that bind to TGF-β (a "masking polypeptide sequence," "masking polypeptide," or "masking sequence"). The masked TGF-β constructs and complexes may also contain one or more independently selected immunomodulatory polypeptide sequences such as wild type or variant IL-2 polypeptide sequences.

The masked TGF-β constructs and complexes can be expressed in numerous mammalian cell types as the masked untargeted TGF-β activity does not adversely impact the cells to the extent observed with unmasked TGF-β.

Masked TGF-β constructs may comprise as a first polypeptide:

i) a scaffold polypeptide sequence;
ii) a TGF-β polypeptide sequence;
iii) a masking polypeptide sequence optionally comprising a TGF-β receptor polypeptide sequence or an anti-TGF-β polypeptide sequence;
iv) optionally, one or more independently selected MOD polypeptide sequences;
and
v) optionally one or more independently selected linker polypeptide sequences;

a construct comprising these elements being collectively referred to herein as a "masked TGF-β construct," wherein the masking polypeptide sequence and the TGF-β polypeptide sequence bind to each other. That masked TGF-β construct may be organized in order (from N-terminus to C-terminus) as, e.g.:

i) the scaffold polypeptide sequence, the masking polypeptide sequence, and the TGF-β polypeptide sequence; or
ii) a first MOD polypeptide sequence, the scaffold polypeptide sequence, the masking polypeptide sequence, and the TGF-β polypeptide sequence; or
iii) a first independently selected MOD polypeptide sequence, a second independently selected MOD polypeptide sequence, optionally one or more additional MOD polypeptide sequences, the scaffold polypeptide sequence, the masking polypeptide sequence, and the TGF-β polypeptide sequence;

wherein masked TGF-β construct optionally comprise one or more independently selected linker polypeptide sequences.

The scaffold polypeptide of the above-mentioned masked TGF-β constructs may comprises interspecific or non-interspecific dimerization sequences that cause formation of a homodimer where the scaffold polypeptide sequences optionally have one or more covalent attachments to each other.

The scaffold polypeptides of the above-mentioned masked TGF-β constructs may also comprise an interspecific dimerization sequence, and further comprise a second polypeptide that dimerizes with a first polypeptide (as described above) through a counterpart interspecific dimerization sequence to form a masked TGF-β complex heterodimer. The second polypeptide may comprise one of the following structures: (i) a scaffold polypeptide sequence comprising the counterpart interspecific dimerization sequence; (ii) one or two (or more) independently selected MOD sequences and a scaffold polypeptide sequence comprising the counterpart interspecific dimerization sequence; (iii) a scaffold polypeptide sequence comprising the counterpart interspecific dimerization sequence, and an independently selected MOD sequence; or (iv) one or two (or more) independently selected MOD sequences and a scaffold polypeptide sequence comprising the counterpart interspecific dimerization sequence wherein the first and/or second polypeptides optionally comprises one or more independently selected linker polypeptide sequences. The second polypeptide thus may comprise one of the following structures, from N-terminus to C-terminus: (i) a scaffold polypeptide sequence comprising the counterpart interspecific dimerization sequence; (ii) one or two (or more) independently selected MOD sequences and a scaffold polypeptide sequence comprising the counterpart interspecific dimerization sequence; (iii) a scaffold polypeptide sequence comprising the counterpart interspecific dimerization sequence, and one or two (or more) independently selected MOD sequences; or (iv) one or two (or more) independently selected MOD sequences and a scaffold polypeptide sequence comprising the counterpart interspecific dimerization sequence; wherein first and/or second polypeptide optionally comprise one or more independently selected linker polypeptide sequences. Alternatively, the masked TGF-β complex heterodimer may comprise in order from N-terminus to C-terminus: (i) the scaffold polypeptide sequence comprising the counterpart interspecific dimerization sequence, the masking polypeptide sequence, and the TGF-β polypeptide sequence; (ii) a first MOD polypeptide sequence, the scaffold polypeptide sequence comprising the counterpart interspecific dimerization sequence, the masking polypeptide sequence, and the TGF-β polypeptide sequence; or (iii) a first independently selected MOD polypeptide sequence, a second independently selected MOD polypeptide sequence, the scaffold polypeptide sequence comprising the counterpart interspecific dimerization sequence, the masking polypeptide sequence, and the TGF-β polypeptide sequence.

Masked TGF-β complexes may also comprise a first polypeptide and a second polypeptide as a masked TGF-β complex heterodimer, wherein:

(i) the first polypeptide comprises
  a) a scaffold polypeptide sequence comprising an interspecific dimerization sequence,
  b) a masking polypeptide sequence optionally comprising a TGF-β receptor polypeptide sequence or an anti-TGF-β polypeptide sequence,
  c) optionally, one or more independently selected MOD polypeptide sequences, and
  d) optionally one or more independently selected linker polypeptide sequences;

(ii) the second polypeptide comprises a) a scaffold polypeptide sequence comprising a counterpart interspecific dimerization sequence to the interspecific dimerization sequence in the first polypeptide, b) a TGF-β polypeptide sequence, c) optionally, one or more independently selected MOD polypeptide sequences, and d) optionally one or more independently selected linker polypeptide sequences;

a complex comprising these elements being collectively referred to a "masked TGF-β complex,"

wherein the masking polypeptide sequence and the TGF-β polypeptide sequence are provided on different polypeptide chains and bind to each other;

wherein the interspecific binding sequence and the counterpart interspecific binding sequence interact with each other in the heterodimer; and wherein masked TGF-β first polypeptide and/or the second polypeptide optionally comprise one or more independently selected linker polypeptide sequences.

The TGF-β polypeptide sequences may be derived from any of the TGF-β isoforms, and may comprise substitutions that limit the ability of the TGF-β sequences from dimerizing. The masking sequences may be, for example, anti-TGF-β antibody sequences or TGF-β receptor (TOR) ectodomain sequences. Where TβR ectodomains are used to mask the TGF-β sequences, they may be modified to avoid inadvertent signaling by the masked molecule (e.g., by deletion of all or part of the ectodomain not necessary for interaction with the TGF-β sequence).

This disclosure also describes and provides for methods of producing the masked TGF-β constructs and complexes, and methods of their use in effecting various cell types and in treating a variety of diseases/disorders including autoimmune and inflammatory diseases. The methods of treatment described herein may include co-administration of the masked TGF-β constructs and complexes with other molecules including, but not limited to: immunomodulators (e.g., interleukins, cytokines, chemokines and the like); antibodies and antibody fragments (e.g., scFv, nanobodies, etc.); small molecule therapeutics (e.g., vitamin D or retinoic acids); and combinations thereof that may be beneficial to achieve the desired laboratory or therapeutic outcome.

III. BRIEF DESCRIPTION OF THE DRAWINGS

FIG. 1 depicts some formats for masked TGF-β constructs and complexes in which a TGF-β receptor sequence is used to mask a TGF-β polypeptide. Structure A depicts a monomeric construct with a single location for one or more independently selected MODs (e.g., a set of tandem independently selected MODs). Structure B depicts a symmetrical homodimer where the polypeptides interact by way of their respective Ig Fc sequences, which can spontaneously form disulfide bonds that link the two polypeptides. Structures C-F depict heterodimeric structures where the TGF-β and TGF-β receptor sequences are in "cis" (on the same polypeptide) or "trans" (on different polypeptides) of the heterodimer. Locations where one or more independently selected MODs may be placed are shown by circles filled with diagonal or vertical lines or a checkered pattern. Interspecific binding pairs are represented by knob-in-hole sequences, but may be any of the others as discussed below. The constructs may include no MODs, or may include one, two or more independently selected MOD sequences, including MOD sequences in tandem, which MODs may be provided in the indicated locations. Exemplary MODs include, e.g., wild type or mutant (e.g., with reduced affinity and/or selective affinity for a particular receptor or receptors) PD-L1, FAS-L, IL-1, IL-2, IL-4, IL-6, IL-7, IL-10, IL-15, IL-21 and IL-23 MOD sequences. In each instance where a TGF-β receptor sequence is used to mask a TGF-β polypeptide, the receptor polypeptide may be replaced with another masking polypeptide such as an antibody polypeptide (e.g., scFV or a nanobody) with affinity for the TGF-β polypeptide. Scaffold sequences may be joined (e.g., by disulfide bonds) to form covalently linked homodimers or covalently linked heterodimers. Any of the constructs shown in the figures may have sequence variations in the TGF-β polypeptide that limit its ability to dimerize (e.g., C77S substitutions).

FIGS. 2A-2H provide amino acid sequences of immunoglobulin Fc polypeptides (SEQ ID NOs:68-83).

FIG. 2I provides the amino acid sequences of a human J-chain with the signal peptide aas 1-22 underlined (SEQ ID NO:84).

FIG. 2J provides a sequence of an IgG1 heavy chain constant region CH1 domain. The serine residues at positions 70 and 72, which may be substituted by glutamic acid and valine respectively (570E and S72V) for the formation of an MD13-like construct.

FIG. 2K provides a sequence of a light chain constant region "CL" domain from Ig κ and Ig λ chains. The serine at position 68 and the threonine at position 70 may be substituted by leucine and serine respectively (S68L and T705) for the formation of an MD13-like construct.

FIG. 3 provides the sequences of three different isoforms of TGF-β as preproproteins and the mature form of TGF-β3 along with the C77S mutant of the mature protein.

FIG. 4 provides an alignment of TGF-β isoforms 1-3 with the residues corresponding to the mature form of TGF-β2 bolded, except as residues Lys 25, Cys 77, Ile 92, and/or Lys 94 of TGF-β2 and their corresponding residues in the other forms of TGF-β isoforms 1 and 3 that are underlined and not bolded.

FIG. 5A provides the sequences of a type 1 TGF-β receptor (TβRI) and its ectodomain.

FIG. 5B provides the sequences of a type 2 TGF-β receptor (TβRII), its ectodomain, and fragments of the ectodomain. The locations indicated in bold and underlining in the isoform B are aas F30, D32, S52, E55 and D118 of the mature polypeptide, any of which may be substituted with an aa other than the naturally occurring aa.

FIG. 5C provides the sequences of a type 3 TGF-β receptor (TβRIII).

FIGS. 6A-6C show a plot showing the ability of different concentrations of various masked TGF-β constructs and complexes to stimulate the expression of FoxP3 on naïve CD4 T cells based on fluorescence cytometry analysis. FIG. 6A shows the induction of FoxP3 (as the percentage of CD4+ cells) based on the indicated concentrations of TGF-β3 or a masked TGF-133$_{WT}$ construct (see FIG. 1, structure A) in the absence and presence of 50 U/ml added IL-2 after 5 days in cell culture. FIG. 6B shows the distribution of FoxP3$^{+}$ cells (as the percentage of CD4 cells) in populations of naïve T cells treated for 5 days with various concentrations of TGF-β3 or one of three masked TGF-β3 constructs or a masked TGF-β3 complex bearing at least one N-terminal wt. or variant IL-2 MOD (see FIGS. 7G to 7I for the structures). FIG. 6C shows the induction of FoxP3$^{+}$ CD4$^{+}$ cells in the presence of a masked TGF-β3 polypeptide (structure (i) in FIG. 6B) at concentrations of 0.1 nM or 1000 nM.

FIG. 7A provides the aa sequence of a representative masked TGF-β (construct No.:3470) SEQ ID NO:146, having the overall structure of FIG. 1 structure A. The polypeptide comprising, from N-terminus to C-terminus, wt. human IL-2 (hIL2), three repeats of $G_4S$ linker (SEQ ID NO:203), human mono IgG Fc with LALA substitutions, three repeats of $G_4S$ linker (SEQ ID NO:203), a human TβRII $(hT\beta RII)_{\Delta 25}$ sequence with a D118A substitution, five repeats of $G_4S$ linker (SEQ ID NO:205), and human TGF-β3 (hTGF-β3) sequence with a C77S substitution.

FIG. 7B provides the aa sequence of a representative masked TGF-β (construct No.:3334) SEQ ID NO:147 having the overall structure of FIG. 1 structure B. The polypeptide, which forms a homodimer comprises, from N-terminus to C-terminus, hIL2 with H16T and F42A substitutions, three repeats of a $G_4S$ (SEQ ID NO:203), human IgG1 Fc with LALA substitutions, a $G_5S$ (SEQ ID NO:211) and two repeats of a $G_4S$ linker (SEQ ID NO:200), a $hT\beta RII_{\Delta 25}$, D118A, five repeats of $G_4S$ (SEQ ID NO:205), and hTGF-β3 sequence.

FIG. 7C provides the aa sequences of a representative masked TGF-β construct having the overall structure of FIG. 1 structure D which comprises a first and second polypeptide. The first polypeptide construct No.:3618 (SEQ ID NO:148) comprises from N-terminus to C-terminus, wt. hIL-2, three repeats of a $G_4S$ linker (SEQ ID NO:203), human IgG1 Fc knob-in-hole (KiH) polypeptide chain A with LALA substitutions, a five repeats of $G_4S$ linker sequence (SEQ ID NO:205), and hTGF-β3 sequence with a C77S substitution. The second polypeptide (construct No.: 3619), SEQ ID NO:149, comprises, from N-terminus to C-terminus, wt. hIL2, three repeats of $G_4S$ linker (SEQ ID NO:203), human IgG1 Fc KiH polypeptide chain B with LALA substitutions, a $G_5S$ linker (SEQ ID NO:211) and two repeats of $G_4S$ linker (SEQ ID NO:202), and a $hT\beta RII_{\Delta 25}$, D118A sequence.

FIG. 7D provides the aa sequences of a representative masked TGF-β construct having the overall structure of FIG. 1 structure E which comprises a first and second polypeptide. The first polypeptide (construct No.:3618), SEQ ID NO:150 described above, comprises, from N-terminus to C-terminus, wt. hIL-2, three repeats of a $G_4S$ linker (SEQ ID NO:203), human IgG1 Fc knob-in-hole (KiH) polypeptide chain A with LALA substitutions, a five repeats of $G_4S$ linker sequence (SEQ ID NO:205), and hTGF-β3 sequence with a C77S substitution. The second polypeptide (construct No.:3855), SEQ ID NO:151, comprises, from N-terminus to C-terminus, human IgG1 Fc KiH polypeptide chain B with LALA, T366S, L368A, and Y407V substitutions, three repeats of $G_4S$ linker (SEQ ID NO:203), and a $hT\beta RII_{\Delta 25}$, D118A sequence.

FIG. 7E provides the aa sequences of a representative masked TGF-β construct having the overall structure of FIG. 1 structure F which comprises a first and second polypeptide. The first polypeptide (construct No.:3891), SEQ ID NO:152, comprises, from N-terminus to C-terminus, hIL-2 with H16A, F42A, three repeats of $G_4S$ linker sequence (SEQ ID NO:203), human IgG1 Fc knob-in-hole (KiH) polypeptide chain A with LALA and T366W substitutions, a $G_5S$ (SEQ ID NO:211) and two repeats of $G_4S$ linker (SEQ ID NO:202), $hT\beta RII_{\Delta 25}$, D118A, five repeats of $G_4S$ linker (SEQ ID NO:205), and hTGF-β3 with a C77S substitution. The second polypeptide (construct No.:3664), SEQ ID NO:153, comprises, from N-terminus to C-terminus, human IgG1 Fc KiH polypeptide chain B with LALA substitutions.

FIG. 7F provides the aa sequences of a representative masked TGF-β construct having the overall structure of FIG. 1 structure F which comprises a first and second polypeptide. The first polypeptide (construct No.:3715), SEQ ID NO:155, comprises from N-terminus to C-terminus, human IgG1 Fc KiH polypeptide chain A with LALA substitutions, three repeats of $G_4S$ linker (SEQ ID NO:203), and human wt. IL2 sequences. The second polypeptide (construct No.: 3714), SEQ ID NO:156, comprises, from N-terminus to C-terminus, human IgG1 FcKiH polypeptide chain B with LALA substitutions, three repeats of a $G_4S$ linker (SEQ ID NO:203), a $hT\beta RII_{\Delta 25}$, with D32N and D118A substitutions, five repeats of $G_4S$ linker sequence (SEQ ID NO:205), and a hTGF-β3 sequence with a C77S substitution.

Any of the IL-2 sequence in FIGS. 7A to 7F may be substituted with a MOD or variant MOD other than IL-2, replaced by wt. IL-2, or replaced by an IL-2 sequence having substitutions at N88, H16 and/or F42, (e.g., a N88R, a substitution at H16 selected from H16A or H16T, and/or a substitution at F42 selected from F42A and F42T).

FIG. 7G provides the aa sequence of a representative masked TGF-β construct (construct No.:3472), SEQ ID NO:157, having the overall structure of FIG. 1 structure A. The polypeptide comprising, from N-terminus to C-terminus, wt. hIL2, three repeats of $G_4S$ linker (SEQ ID NO:203), human mono IgG Fc with LALA substitutions, three repeats of $G_4S$ linker (SEQ ID NO:203), a human TβRII $(hT\beta RII)_{\Delta 25}$ sequence with D32N and D118A substitutions, five repeats of $G_4S$ linker (SEQ ID NO:205), and human TGF-β3 (hTGF-β3) sequence with a C77S substitution.

FIG. 7H provides the aa sequence of a representative masked TGF-β construct (construct No.:3466), SEQ ID NO:158, having the overall structure of FIG. 1 structure A. The polypeptide comprising, from N-terminus to C-terminus, wt. hIL2, three repeats of $G_4S$ linker (SEQ ID NO:203), human mono IgG Fc with LALA substitutions, three repeats of $G_4S$ linker (SEQ ID NO:203), a human TβRII $(hT\beta RII)_{\Delta 25}$ sequence with a D118A substitution, five repeats of $G_4S$ linker (SEQ ID NO:205), and human TGF-β3 (hTGF-β3) sequence with a C77S substitution.

FIG. 7I provides the aa sequence of a representative masked TGF-β construct (construct No.:3468), SEQ ID NO:159, having the overall structure of FIG. 1 structure A. The polypeptide comprising, from N-terminus to C-terminus hIL2 with H16T F42A substitutions, three repeats of $G_4S$ linker (SEQ ID NO:203), human mono IgG Fc with LALA substitutions, three repeats of $G_4S$ linker (SEQ ID NO:203), a human TβRII $(hT\beta RII)_{\Delta 25}$ sequence with D32N and D118A substitutions, five repeats of $G_4S$ linker (SEQ ID NO:205), and human TGF-β3 (hTGF-β3) sequence with a C77S substitution.

FIG. 7J provides the aa sequences of a representative masked TGF-β construct having the overall structure of FIG. 1 structure D which comprises a first and second polypeptide. The first polypeptide (construct No.:3618), SEQ ID NO:148, comprises from N-terminus to C-terminus, wt. hIL-2, three repeats of a $G_4S$ linker (SEQ ID NO:203), human IgG1 Fc knob-in-hole (KiH) polypeptide chain A with LALA substitutions, a five repeats of $G_4S$ linker sequence (SEQ ID NO:205), and hTGF-133 sequence with a C77S substitution. The second polypeptide (construct No.:3621), SEQ ID NO:160, comprises, from N-terminus to C-terminus, wt. hIL2, three repeats of $G_4S$ linker (SEQ ID NO:203), human IgG1 Fc KiH polypeptide chain B with LALA substitutions, three repeats of $G_4S$ linker (SEQ ID NO:203), and a $hT\beta RII_{\Delta 25}$ sequence with D32N and D118A substitutions.

FIG. 8 shows a masked TGF-β construct (left) and two masked TGF-β complexes (center and right). Samples of the complexes were prepared by constructing nucleic acid vectors encoding the polypeptides, transfecting ExpiCHO cells and expressing the polypeptides. The polypeptides were purified by protein A chromatography followed by size exclusion chromatography. The purified proteins were subjected to SDS-PAGE and the resulting gels were stained with Coomassie blue. NR=not reducing or unreduced samples, and R=reduced samples (reduction with a disulfide reducing agent).

FIG. 9 shows the effect of various aa substitutions in mature TβRII polypeptide sequences (see FIG. 5B) on their affinity for TβRII and TGF-β3 or TGF-β1 (Table, top left). FIG. 9 also shows the effect of three of those substitutions, E55A, D32N, and S52L, on the binding interaction between a TβRII masked TGF-β construct and an immobilized TβRII-Fc receptor construct. The receptor construct is shown in a capture assay format with TGF-β3 in the top right of the figure where: mono-Fc is an Ig scaffold that does not form interspecific bonds to other scaffolds, and anti-IL-2 is an antibody against IL-2 labeled with biotin (B). Strep and HRP are streptavidin and horse radish peroxidase used for detection. The effect on binding was detected in a capture as binding curves developed for each of the four masked constructs (bottom). See Example 3.

FIGS. 10A-10C show the structure and amino acid sequences of the polypeptides that form the masked TGF-β3 complex PSM-4033-4039.

FIG. 11 shows the results of an experiment in which PSM-4033-4039 is used to induce Foxp3$^+$ iTregs from human peripheral naïve CD4$^+$ T cells. See Example 4.

IV. DETAILED DESCRIPTION

A. Definitions

Figure 1:
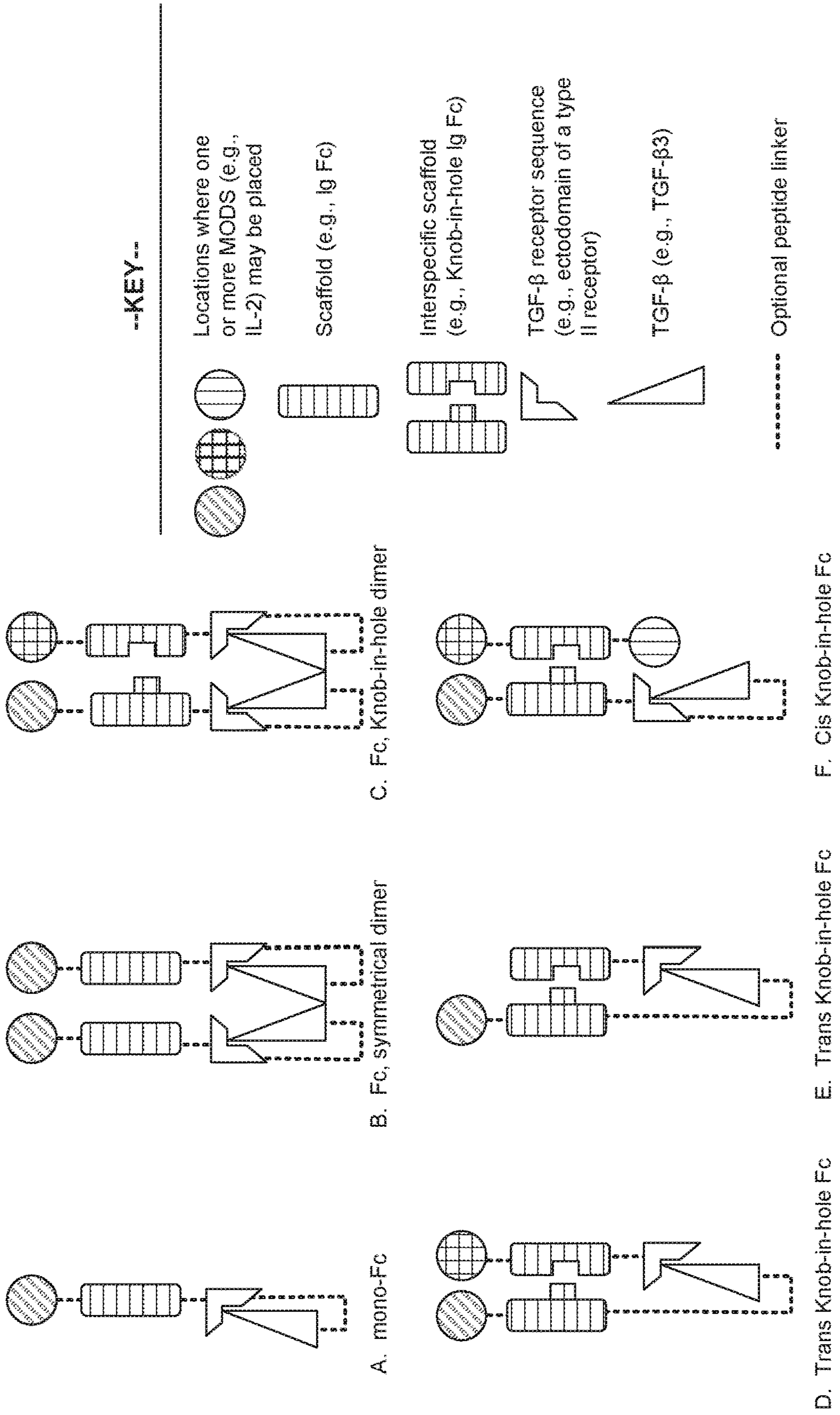

As used herein amino acid (abbreviated "aa" when singular unless the context dictates it can be plural, and as "aas" in the plural form) means the naturally occurring protogenic alpha amino acids incorporated into polypeptides and proteins in mammalian cell translation. Unless stated otherwise: L (Leu, leucine), A (Ala, alanine), G (Gly, glycine), S (Ser, serine), V (Val, valine), F (Phe, phenylalanine), Y (Tyr, tyrosine), H (His, histidine), R (Arg, arginine), N (Asn, asparagine), E (Glu, glutamic acid), D (Asp, asparagine), C (Cys, cysteine), Q (Gln, glutamine), I (Ile, isoleucine), M (Met, methionine), P (Pro, proline), T (Thr, threonine), K (Lys, lysine), and W (Trp, tryptophan) Amino acid also includes the amino acids hydroxyproline and selenocysteine, which appear in some proteins found in mammalian cells.

The terms "polypeptide," "polypeptide sequence," and "protein" as used herein are synonyms and mean a sequence of aas joined together by peptide bonds between their C-1 carboxyl group and their alpha amine to form the backbone of the polypeptide. Accordingly, each polypeptide (e.g., a first polypeptide) that comprises any one or more of: a MOD polypeptide sequence, a scaffold polypeptide sequence, a TGF-β polypeptide sequence, and/or a masking polypeptide sequence (e.g., a TGF-β receptor polypeptide sequence or anti-TGF-β polypeptide sequence) comprises any one or more of those polypeptide sequences as a polypeptide chain with a single contiguous backbone. Such polypeptides (e.g., first polypeptides) may be linked to other polypeptides by covalent bonds (e.g., such as disulfide bonds between the side chains of cysteine residues). Furthermore, as used herein, the terms "polypeptide", "polypeptide sequence" and "protein" include modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods.

Where an embodiment, claim, or aspect is directed to a specific type of mammal (e.g., human or non-human subjects), nucleic acid and polypeptide sequences may be limited to sequences from those subjects. Unless stated otherwise the polypeptide sequence of proteins (e.g., TGF-β, TβRs, immunoglobulins, and MODs) are human (*Homo Sapiens*) sequences.

As used herein "masked" means that a molecule (e.g., masked polypeptide or masked protein) is bound or otherwise engaged by a masking molecule (e.g., polypeptide, protein or protein fragment) that limits the availability of the masked molecule to other proteins (e.g., cell surface receptors) that also have affinity for the molecule.

As used herein the term masked TGF-β construct refers to a single polypeptide that comprises both a TGF-β (e.g., TGF-β1, TGF-β2, or TGF-β) polypeptide sequence and a masking polypeptide sequence that binds to or otherwise interacts with the TGF-β polypeptide. Unless stated otherwise a masked TGF-β construct comprises a scaffold polypeptide sequence and optionally comprises one or more independently selected immunomodulatory (MOD) polypeptide sequences.

As used herein the term masked TGF-β complex refers to two or more polypeptides (typically two polypeptides designated a first and a second polypeptide arranged as a homodimer or heterodimer, but which can be a higher order multimer). Masked TGF-β complexes comprise a TGF-β (e.g., TGF-β1, TGF-β2, or TGF-β) polypeptide sequence, a masking polypeptide sequence that binds to or otherwise interacts with the TGF-β polypeptide, and a scaffold polypeptide that comprises a dimerization or multimerization sequence through which the polypeptides of the TGF-β complex associate. Any one or more of the TGF-β complex polypeptides optionally comprises one or more independently selected MOD polypeptide sequences.

The phrase "masked TGF-β construct or complex" is an abbreviation for a masked TGF-β construct or masked TGF-β complex. The abbreviation may be used in its plural form "masked TGF-β constructs or complexes."

The phrase "masked TGF-β constructs and complexes" is an abbreviation for both "masked TGF-β constructs" and "masked TGF-β complexes."

Dimerization and multimerization sequences as used herein are polypeptide sequences that permit the association of polypeptide sequences (e.g., separate polypeptides) as dimers (e.g., heterodimers or homodimers), or multimers (homo- or hetero-multimers of three, four five or more polypeptide sequences). Dimerization and multimerization sequences permit the association of sequences in a non-covalent fashion that may be converted into a covalent complex under some circumstances (e.g., disulfide bond formation between the polypeptides).

Interspecific binding sequences are dimerization sequences that permit an asymmetric paring of polypeptides (heterodimer formation). Interspecific binding sequences favor formation of heterodimers with their counterpart interspecific binding sequence(s) (as opposed to forming homodimers), which is their cognate binding partner. Key-in-hole (or key-into-hole) Fc polypeptide pairs represent one example of an interspecific binding sequence and its counterpart interspecific binding sequence.

Nanobodies® or nanobody as used herein refers to an antibody fragment consisting of a single monomeric variable antibody domain that, like a whole antibody, is able to bind selectively to a specific antigen.

Wild type (abbreviated as "wt.") with regard to aa sequences means a naturally occurring aa sequence, or a contiguous portion of a naturally occurring aa sequence as understood from the context, that has not been altered (does not have any substitutions, deletions, or insertions therein) relative to a sequence found naturally in a living organism. A specific naturally occurring sequence may be designated as the wt. sequence for reference.

As used herein, "T cell" includes all types of immune cells expressing CD3, including T-helper cells (CD4+ cells), cytotoxic T cells (CD8+ cells), T-regulatory cells (Treg), and NK-T cells.

The term "binding," as used herein refers to a non-covalent interaction between two molecules, e.g., the non-covalent interaction between a MOD and its co-MOD. Non-covalent binding refers to a direct association between two molecules, due to, for example, electrostatic, hydrophobic, ionic, and/or hydrogen-bond interactions, including interactions such as salt bridges and water bridges. Non-covalent binding interactions are generally characterized by a dissociation constant ($K_D$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Specific binding" generally refers to binding with an affinity of at least about $10^{-7}$ M or greater, e.g., $5\times10^{-7}$ M, $10^{-8}$ M, $5\times10^{-8}$ M, $10^{-9}$ M, and greater. "Non-specific binding" generally refers to binding (e.g., the binding of a ligand to a moiety other than its designated binding site or receptor) with an affinity of less than about $10^{-7}$ M (e.g., binding with an affinity of $10^{-6}$ M, $10^{-5}$M, $10^{-4}$ M). "Covalent binding" or "covalent bond," as used herein, refers to the formation of one or more covalent chemical bonds between two different molecules.

"Affinity" refers to the strength of non-covalent binding, increased binding affinity being correlated with a lower $K_D$. As used herein, the term "affinity" refers to the equilibrium constant for the reversible binding of two agents (e.g., an antibody and an antigen) and is expressed as a dissociation constant ($K_D$).

The term "immunomodulatory polypeptide" or MOD, as used herein, includes a polypeptide on an antigen presenting cell (APC) (e.g., a dendritic cell, a B cell, and the like), or a portion of the polypeptide on an APC, that specifically binds a cognate co-immunomodulatory polypeptide ("co-MOD") on a T cell, thereby providing a signal. For example, the bonding of an interleukin such as IL-2 or a fragment thereof (a MOD) to a cell surface IL-2 receptor (a co-MOD) provides a signal to the cell. MODs include, but are not limited to, IL-1, IL-2, IL-4, IL-6, IL-7, IL-10, IL-15, IL-21 and IL-23, PD-L1 and Fas ligand (FAS-L). MODs also encompass, inter alia, an antibody or an antibody sequence (e.g., a nanobody) that specifically binds with a co-MOD molecule present on a T cell that results in signaling by the coMOD. As discussed herein, MODs also include variants of wt. MODs including, e.g., variant MODs that have a reduced binding affinity for a co-MOD. Such reduced affinity can take multiple forms. For example, a variant IL-2 MOD can have reduced affinity for one or more of the α, β, and/or γ chains of IL-2R. As discussed herein, variant IL-2 MODs comprising mutations at positions 16 and 42 can exhibit substantially no binding to the α chain of IL-2R and reduced affinity for the β chain of IL-2R. Additionally, for MODs that have more than one co-MOD (e.g., CD80 binds to both CD28 and CTLA-4), a variant MOD can have reduced affinity for one of the co-MODs such that it preferentially or selectively binds the other co-MOD. For the purpose of this disclosure, TGF-β (e.g., TGF-β1, TGF-β2, or TGF-β3), and fragments thereof, are not considered MODs.

Unless indicated otherwise, the term "substantially" is intended to encompass both "wholly" and "largely but not wholly". For example, a variant IL-2 MOD that exhibits substantially no binding to the α chain of IL-2R is an IL-2 variant MOD that does not bind to the α chain of IL-2R at all or largely does not bind to the α chain of IL-2R.

As used herein the term "in vivo" refers to any process or procedure occurring inside of the body, e.g., of an autoimmune patient.

As used herein, "in vitro" refers to any process or procedure occurring outside of the body, including procedures that may be referred to as ex vivo.

"Tandem," as used herein to describe the placement of MOD polypeptide sequences means having two or more MODs arranged adjacent to each other on a polypeptide separated, at most, by a linker (e.g., no scaffold, masking polypeptide or TGF-β sequences interposed).

As used herein the term "ectodomain" means the part (domain) of a membrane protein that extends into the extracellular space and that does not include a sufficient portion of the transmembrane domain to cause it to be anchored in the cell membrane.

"Sequence identity" as used herein is a measure of the as or nucleotide identity between two polynucleotide sequences or two polypeptide sequences. Stating that a protein or polynucleotide sequence has a certain percent "sequence identity" to another polynucleotide or polypeptide means that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), *J. Mol. Biol.* 215:403-10. Unless stated otherwise sequence identity is determined using alignments performed with NCBI BLAST algorithm version BLAST+ 2.9.0 released on Apr. 1, 2019 (for protein BLASTP 2.9.0+ and for nucleic acids BLASTN 2.9.0+).

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments, or from a series of synthetic oligonucleotides, to provide a synthetic nucleic acid which is capable of being expressed from a recombinant transcriptional unit contained in a cell or in a cell-free transcription and translation system. Recombinant used in reference to a peptide, polynucleotide, or protein indicates they have been prepared by expression from a recombinant nucleic acid.

As used herein, the term “about” used in connection with an amount indicates that the amount can vary by 10% of the stated amount. For example, “about 100” means an amount of from 90-110. Where about is used in the context of a range, the “about” used in reference to the lower amount of the range means that the lower amount includes an amount that is 10% lower than the lower amount of the range, and “about” used in reference to the higher amount of the range means that the higher amount includes an amount 10% higher than the higher amount of the range. For example, from about 100 to about 1000 means that the range extends from 90 to 1100.

The terms “treatment,” “treating,” and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. “Treatment” as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; and/or (c) relieving the disease, i.e., causing regression of the disease. The therapeutic agent (e.g., a masked TGF-β construct or complex) may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. Therapeutic treatment may be administered during the symptomatic stage of the disease, and in some cases after the symptomatic stage of the disease.

The terms “individual,” “subject,” “host,” and “patient,” are used interchangeably herein and refer to any mammalian subject for whom diagnosis, treatment, or therapy is desired. Mammals include, e.g., humans, non-human primates, rodents (e.g., rats; mice), lagomorphs (e.g., rabbits), ungulates (e.g., cows, rats, goats, sheep, horses, pigs and the like), canine (e.g., dogs), feline (e.g., cats) etc. (e.g., human, bovine, canine, feline, rodent, murine, caprine, simian, ovine, equine, lappine, porcine, etc.).

It must be noted that as used herein and in the appended aspects and claims, the singular forms “a,” “an,” and “the” include plural referents unless the context clearly dictates otherwise. Thus, for example, reference to “a Treg” includes a plurality of such Tregs and reference to “the TGF-β polypeptide” includes reference to one or more TGF-β polypeptides and equivalents thereof known to those skilled in the art, and so forth. It is further noted that the claims may be drafted to either include or exclude any optional element. As such, this statement is intended to serve as antecedent basis for either the use (inclusion) of such elements in claims (e.g., with terminology such as “solely,” “only” and the like), or their removal from claims or as a basis for a “negative” limitation excluding any specific optional element.

It is appreciated that certain features of the invention, which are, for clarity, described in the context of separate aspects or embodiments, may also be provided in combination in a single aspect or embodiment including those subsequently claimed. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

B. Description

1 Introduction

The TGF-β superfamily includes endogenous proteins with growth inhibiting functions. Increases in the expression of TGF-β or defects in cellular mechanisms that inhibit TGF-β action have been correlated with, among other things, the malignancy of many cancers due to TGF-β’s immunosuppressive actions. Dysregulation of TGF-β’s immunosuppressive functions are also implicated in autoimmune diseases. Because TGF-β is a key regulator of immune function, it has been the target of numerous studies and both TGF-β and its signaling pathway are considered therapeutic targets for the treatment of a variety of diseases including inflammatory processes and autoimmune disorders.

The ability to effectively prepare and deliver TGF-β as a therapeutic is complicated by the molecule’s toxicity and the complexity of TGF-β’s receptor system. Production of TGF-β in large quantities in mammalian cell expression systems is limited by the toxicity of the protein to many mammalian cells. Cells subject to the cytotoxicity of TGF-β include many of those used for the production of biological molecules, such as Chinese Hamster Ovary or “CHO” cells, which are one of the most robust and commonly employed cells for commercial protein production. Use of TGF-β as a therapeutic is also complicated by the high pI of TGF-β1 with pI of about 8.59 (as opposed to the pI of about 6.1 for TGF-β3), its limited stability/solubility under conditions that are not acidic (such acidic conditions are not generally amenable for therapeutic use). In addition, the large amount of high affinity TβRIII receptor (e.g., on the order of 5 nM for TGF-β2) present in mammalian systems relative to the affinity of TβRII for TGF-β (on the order of 1-2 μM) represents a significant pharmacodynamic sink, limiting access of TGF-β-based biologics to target tissues. Similarly, TβRIII’s role in recruiting TGF-β to TβRII/TβRI complexes may lead to significant off-target delivery of TGF-β, with unintended, undesirable and even toxic effects. Such off-target delivery may lead to non-specific activation, and could also lead to further production of active TGF-β, particularly where TGF-β signaling is under feed-forward control, thereby producing further unintended and undesirable effects. See, e.g., Jiang et al., *Redox Biol.* 2: 267-272 (2014).

The effective use of TGF-β as a therapeutic is further complicated by the need to provide additional stimuli to cells to direct the outcome of TGF-β stimulation. As noted above, cytokines such as, IL-1, IL-2, IL-4, IL-6, IL-7, IL-10, IL-15, IL-21 and IL-23, PD-L1 and Fas ligand (FAS-L) can have profound influences on the action of TGF-β. Accordingly, the ability to deliver TGF-β and additional stimuli in the form of cytokines etc. can be advantageous for achieving specific therapeutic or cell mediated outcomes (e.g., in vitro or in vivo) effects.

As discussed in more detail below, the current disclosure describes the use of a TGF-β polypeptide capable of interacting with and stimulating signaling on cells bearing TβRI and TβRII proteins. Advantageously, the TGF-β polypeptide is part of a masked TGF-β construct or complex, which is a fusion protein (a single polypeptide chain) or fusion protein complex (two or more polypeptide chains) that also contains a polypeptide that binds and masks the TGF-β polypeptide sequence (e.g., a TβRII sequence that functions as a masking sequence) built around a scaffold (e.g., one or two polypeptides such as immunoglobulin Fc polypeptides). Examples of such fusion proteins or fusion protein complexes are depicted in FIG. 1. In the event that the TGF-β polypeptide of the fusion protein interacts with, for example, a cellular TβRIII, the portion of the fusion protein that binds and masks TGF-β competes with the TβRIII, preventing the TGF-β from being sequestered in the TβRIII reservoir. In addition, the affinity of the masking polypeptide for the TGF-β polypeptide, which can be intentionally varied using aa substitutions, controls the overall potency of the masked polypeptide for its target receptor (e.g., TβRII) as demonstrated in FIG. 9. As TGF-β polypeptides principally bind TβRIII as a disulfide linked dimer, interactions with that receptor leading to sequestration can be attenuated by including aa substitutions that limit dimerization (e.g., C77S) or dimer stability as discussed below. Interaction of the TGF-β fusion protein or fusion protein complex with TβRII displaces the masking sequence, forming a cell surface bound TGF-β/TβRII complex. The subsequent recruitment of TβRI to form the heterodimeric TGF-β receptor provides a high affinity complex that binds TGF-β tightly (e.g., picomolar affinity) even in the presence of the masking polypeptide sequence. Accordingly, the masked TGF-β is still capable of binding to the heterodimeric TβRI/TβRII receptor complex and signaling through the canonical Smad protein pathway, the non-canonical Jun kinase pathway, and the p38 signaling path. In effect, the masking polypeptide delivers TGF-β to a cell and hands it off to a cell surface TβRII molecule that subsequently recruits the TβRI protein, forming a functional and active signaling complex that effectively holds the TGF-β polypeptide in place.

In addition to delivering TGF-β masked by a TGF-β binding protein (e.g., a fragment of a TGF-β receptor comprising all or part of its TGF-β binding ectodomain) in a form that avoids undesirable off target interactions, a masked TGF-β construct or complex may comprise one or more polypeptides that function as an immunomodulator (a "MOD" polypeptide) capable of affecting the result of TGF-β action on target cells. The ability to deliver both TGF-β and immunomodulators together not only allows the action of the TGF-β activating signal to be directed, but it reduces the amount of immunomodulator that would be required to produce the same effect on the target cells relative to administration of the immunomodulator alone. This is a result of the increased affinity (through avidity enhancement) obtained by having two polypeptide sequences with affinity for receptors on the same target cell. The increased avidity between masked TGF-β construct or complex bearing one or more MODs and target cells bearing receptors for both the TGF-β polypeptide and the one or more MODs (resulting from an increased free energy of binding, ΔG, due to MOD interactions with their receptors) provides for enhanced selectivity in the activation of target cells have both types of receptors, provided subsaturating amounts of the masked TGF-β construct or complex, are present. By way of example, a masked TGF-β construct, such as that in FIG. 1 structure A or FIG. 7G, having an IL-2 MOD is a more potent inducer of iTReg differentiation of naïve CD4+ cells than an otherwise identical masked TGF-β construct that lacks an IL-2 MOD even in the presence of an equivalent (equimolar) amount of the IL-2 MOD polypeptide. In addition, at subsaturating doses, and when similar numbers of cell types are present, a construct such as that in FIG. 1 structure A with an IL-2 MOD as shown in, for example, FIG. 7G, selectively binds to cells with both TGF-β and IL-2 receptors relative to the construct that lacks an IL-2 MOD.

The action of masked TGF-β constructs or complexes can be further specified by the incorporation of modifications that alter the actions of the individual polypeptide sequences. In some embodiments as substitutions that alter the ability of TGF-β to dimerize (e.g., a C77S substitution in TGF-β3) may be incorporated. As the monomeric form of TGF-β displays little if any affinity for TβRIII, incorporation of mutations that limit TGF-β's ability to dimerize limit off target binding to TβRIII that can drag the complex into the TGF-β "reservoir" and limit its ability to stimulate target cells.

Modifications (e.g., substitutions, deletions, insertions etc.) may also be made to polypeptide sequences other than the TGF-β polypeptide sequence, including the masking polypeptide sequence, and the immunomodulatory polypeptide sequences.

Figure 9:
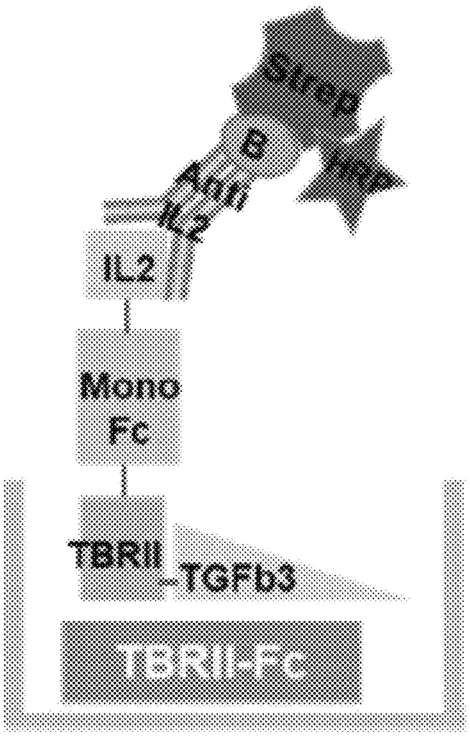

In addition to modifications of the TGF-β polypeptide sequence, modifications to the polypeptide that binds to TGF-β and masks it can be made. Such modifications can alter the availability of the TGF-β polypeptide sequence by changing the affinity of the masking polypeptide for TGF-β as well as the breathing rate (on and off rates) of the masking polypeptide and the TGF-β polypeptide. Although two different TGF-β polypeptide/masking polypeptide complexes may have the same binding association constant (ratio of kon to koff), the complex with a higher kon and koff can effectively be more available to cell surface TβRII binding depending on the rate constants, particularly the koff rate. FIG. 9 provides a list of some aa substitutions in TβRII that alter affinity for TGF-β1 and TGF-β3, along with a graph showing the affinity of otherwise identical TβRII masked TGF-β constructs either without or with one of three substitutions each having a different impact on TβRII binding to TGF-β3.

While it is possible to utilize various polypeptides to mask TGF-β including both single chain antibody sequences (e.g., humanized single chain antibody sequences), minimal TGF-β receptor sequences that bind TGF-β may be employed (e.g., the ectodomain of TβRI, TβRII, or TβRIII). TβRIII's ectodomain may be utilized as a masking polypeptide for dimeric TGF-β; however, its high affinity for TGF-β may cause it to antagonize the binding of TGF-β polypeptide sequences to TβRII. Nevertheless, TβRIII masking sequences could be effectively displaced by cell surface TβRI/TβRII complexes with higher affinity for TGF-β polypeptides, thereby permitting activation of those cell surface receptors.

TβRII's ectodomain may be utilized as a masking polypeptide. Deletion of N-terminal amino acids of TβRII (e.g., delta 14 or 25) can produce a protein (or polypeptide) suitable for masking TGF-β with a pI calculated to be about 4.5 to about 5.0 (e.g., about 4.7 to 4.85) in the presence or absence of D118A substitutions. The combination TGF-β1 polypeptides (which have high pI values) with TβRII masking polypeptides (e.g., including those with N-terminal deletions) can potentially neutralize the TGF-β1 polypeptide charge. The calculated pI of TβRII (delta25, D118A)/TGFβ1 is on the order of 6.23, where TGFβ1 has a pI of about 8.59. In contrast, complexes of delta 14 or delta 25 TβRII and TGF-β3 (with or without D118A and/or C77S substitutions) are calculated to have pI values of about 4.9 to about 5.3 (about pI of 5.06 to 5.17). In addition, although combining the TβRII ectodomain with an active TGF-β polypeptide could result in a complex capable of interacting with cell surface TβRI, thereby affecting TGF-β signaling (e.g., acting as an agonist, partial agonist, antagonist or partial antagonist) of TGF-β, the incorporation of aa substitutions limiting interactions with TβRI limits or blocks the masked complex's ability to participate in active signaling. Accordingly, as discussed below, incorporation TβRII ectodomain sequences with N-terminal deletions (e.g., deletion of 14 to 25 aas, Δ14 to Δ25) or substitutions (e.g., substitutions at D118 by an aa other than aspartic acid such as D118A, D118R, etc.) that that reduced or ablate binding to TβRI can be used to mask TGF-β and prevent stimulation of cells by the TβRII ectodomain masked TGF-β polypeptide where the N-terminus of the TβRII is intact. Consequently, masked TGF-β complexes, including those where TGF-β is masked by N-terminal deletion mutants of TβRII, can act by unmasking of the TGF-β (dissociation from the masking peptide or opening of the folded molecule), binding to a target cell's TβRII and TβRI to form an active heterodimeric TβRI/TβRII signaling complex.

Masking of TGF-β permits its expression at high levels in mammalian cells (e.g., CHO cells) without reduction in the cell viability. This is particularly true where the masked TGF-β polypeptide is blocked from engaging TβRI by N-terminal as deletions, substitutions, and/or other mutations. Blocking of TβRIII interactions (e.g., by blocking dimerization) can further reduce issues associated with cellular expression.

C. Masked TGF-β Constructs and Masked TGF-β Complexes

The present disclosure describes the preparation of masked TGF-β constructs (see, e.g., FIG. 1, structure A, with a single polypeptide chain) and masked TGF-β complexes (see, e.g., FIG. 1, structures B-F, having a complex of two polypeptide chains). The masked TGF-β constructs, and masked TGF-β complexes comprise as their components at least one TGF-β polypeptide sequence, at least one polypeptide that binds to and masks the TGF-β polypeptide(s), and optionally one or more (e.g., one, two or three) immunomodulatory polypeptides (MODs), all of which are assembled on a scaffold structure. Although masked TGF-β constructs, and masked TGF-β complexes, comprise portions of membrane bound proteins (e.g., TGF-β receptors), unless stated otherwise, they do not comprise portions of membrane anchoring domains (e.g., transmembrane domains sufficient to cause a majority of the expressed protein to become anchored in a cell membrane (e.g., expressed CHO cells).

Non-limiting examples of TGF-β constructs and complexes, including those of the forms shown in FIG. 1 are described below.

Components of the masked TGF-β constructs and complexes, including MODs, scaffolds, linkers, TGF-β polypeptides, and TGF-β masking polypeptides (e.g., a single chain antibody or a TGF-β receptor ectodomain) are each described in the sections that follow.

D. Immunomodulatory Polypeptide Sequences ("MODS")

1 the Incorporation of MODS into Masked TGF-β Constructs and Complexes

As discussed above, although immunomodulatory polypeptide (MODs) are not required for the delivery of masked TGF-β polypeptides or its ability to activate cells through the TβRI and TβRII heterodimeric receptor, MODs can substantially affect the outcome of TGF-β receptor activation. Accordingly, it can be desirable to incorporate wild type (wt.) or variant MODs (e.g., that display reduced affinity, increased affinity, or selectivity for specific receptors also referred to as "co-MODs," "co-immunomodulatory polypeptides" or cognate costimulatory receptors or their subtypes). Although TGF-β is an immunomodulatory polypeptide, because it is a central element in the masked TGF-β constructs and complexes described herein, the term "MOD(s)" as used herein does not include TGF-β or its polypeptides.

MODs that are suitable for inclusion into any of the masked TGF-β constructs and complexes (e.g., homodimer or heterodimer complexes) include, but are not limited to, as PD-L1, FAS-L, IL-1, IL-2, IL-4, IL-6, IL-7, IL-10, IL-15, IL-21 and IL-23.

In some cases, the MODs are selected independently from a mature PD-L1, FAS-L, IL-1, IL-2, IL-4, IL-6, IL-7, IL-10, IL-15, IL-21 and IL-23 polypeptides or a fragment of any thereof. The MOD polypeptide sequence(s) incorporated in masked TGF-β constructs and complexes can comprise only a portion of the secreted MOD polypeptide, or the extracellular portion of a full-length mature MOD protein if it is in a membrane anchored form. Thus, for example, the MOD polypeptide sequence in a masked TGF-β construct or complex can in some cases exclude one or more (e.g., each) of a signal peptide, a transmembrane domain, and/or an intracellular domain normally found in some naturally-occurring MODs.

In some cases, a MOD polypeptide sequence suitable for inclusion in masked TGF-β constructs and complexes of the present disclosure comprises all or a portion of (e.g., an extracellular portion of) the amino acid sequence of a naturally occurring MOD. In other instances, MODs suitable for inclusion in masked TGF-β constructs and complexes of the present disclosure include at least one (e.g., one, two, or three independently selected) variant MODs that comprises at least one amino acid insertion, substitution, and/or deletion compared to the amino acid sequence of a naturally-occurring MOD.

In some instances, a variant MOD exhibits a binding affinity for a co-MOD that is lower than the affinity of a corresponding naturally-occurring MOD (e.g., a MOD not comprising the amino acid substitution(s) present in the variant) for the co-MOD. Depending on the reduction in affinity, the use of MODs with reduced affinity for their co-MOD allows the TGF-β polypeptide to have more influence on, or even to dominate, the binding interactions. Where the binding affinity of the TGF-β polypeptide is higher than that of the MOD, it can drive the masked TGF-β construct or complex to associate with cells having a TGF-β receptor system (e.g., TGF-βR1 and TGF-βR2 that form a high affinity TGF-β binding heterodimer), while at the same time limiting off target binding to cells having even an abundance of co-MODs but lacking or having few TGF-β receptors. In essence, where the affinity (e.g., ΔG of binding) of the TGF-β polypeptide for its cellular receptor is greater than affinity of the MODs for their co-MODs (e.g., their ΔG of binding), the TGF-β drives the binding and specificity of the masked TGF-β construct or complex.

In an embodiment, any one or more MODs associated with masked TGF-β constructs and complexes are selected independently from the group consisting of wt. or variant: PD-L1; FAS-L; IL-1; IL-2; IL-4; IL-6; IL-7; IL-10; IL-15; IL-21; IL-23; and combinations thereof.

In some cases, such as where it is desirable to stimulate the production of Treg cells, at least one MOD polypeptide (e.g., one, two or three independently selected MODs) present in masked TGF-β constructs and complexes is an IL-2 polypeptide or an IL-2 variant polypeptide. Sequence variations in IL-2 may be selected to bias binding of the IL-2 polypeptide, and the masked TGF-β constructs or complexes, to target cells bearing different combinations of IL-2R receptor subunits. The IL-2 receptor is comprised of a common IL-2Rγ and two additional IL-2Rα and/or IL-2Rβ subunits to form trimeric $(IL\text{-}2R\alpha)_2$-IL-2Rγ, $(IL\text{-}2R\beta)_2$-IL-2Rγ, or high affinity (Kd about 10 picomolar) IL-2Rα-IL-2Rβ-IL-2Rγ receptors. The α chain (CD25) is unique to IL-2 whereas the β chain (CD122) is shared with the IL-15 receptor, and the γ chain (CD132), which is critical for signaling, can be partnered with other cytokine receptor chains. Substitutions at H16 (e.g., H16A or H16T) or F42 (e.g., F42A or F42T) can bias binding in favor of receptors with IL-2Rβ subunits; and accordingly, their incorporation biases binding to memory T cells and NK cells which display β-γ receptors ($(IL\text{-}2R\ \beta)_2$-IL-2Rγ), or activated T-cells and T regs displaying high affinity α-β-γ (IL-2Rα-IL-2Rβ-IL-2Rγ) receptors. In contrast, substitutions at N88 (e.g., N88R) decrease binding to IL-2Rβ and can bias binding in favor of receptors with IL-2Rα subunits; and accordingly, substitutions at N88 biases binding to cells with α-γ ($(IL\text{-}2R\alpha)_2$-IL-2R7)) and α-β-γ (IL-2Rα-IL-2Rβ-IL-2Rγ) receptors, while avoiding binding and activation of cells with β-γ receptors. See, e.g., Skrombolas and Frelinger, *Expert Rev Clin Immunol.,* 10(2): 207-217 (2014). Biasing, as used in the context of binding a substituted MOD (such as an IL-2 polypeptide with an as substitution) to its co-MOD or a cell displaying a co-MOD, means that the presence of a substitution changes the amount of interaction of the substituted MOD and co-MOD relative to the interaction between the wt. MOD and the same co-MOD. For example, IL-2 sequences with substitutions at N88 (e.g., N88R), which have a lower side effect profile (e.g., safer) and are better tolerated by human subjects, may be included with the above-mentioned substitutions at H16 and/or F42.

In some cases, such as where it is desirable to stimulate the production of iTreg cells (CD4+ FoxP3+ cells) (e.g., to induce peripheral tolerance to actively suppress effector T cells and/or inhibit immune-mediated tissue damage), at least one MOD polypeptide (e.g., one, two or three independently selected MODs) present in masked TGF-13 constructs or complexes is an independently selected wt. or variant PD-L1 MOD polypeptide. See, e.g., Francisco et al., *J. Exp. Med.,* 206(13): 3015-3029 (2009). In addition to the wt. or variant PD-L1 sequences, the masked TGF-13 constructs or complexes can comprise one or more independently selected wt. or variant IL-2 polypeptides. Sequence variations in IL-2 may be selected to bias binding of the IL-2 polypeptide, and the masked TGF-13 constructs, to target cells bearing different combinations IL-2R receptor subunits. As discussed above, the IL-2 variants include substitutions at H16 (e.g., H16A or H16T) and/or F42 (e.g., F42A or F42T) that can bias binding in favor of receptors with IL-2Rβ subunits; and/or IL-2 with substitutions at N88 (e.g., N88R) that decrease binding to IL-2Rβ are that better tolerated by human subjects. In an embodiment, masked TGF-β construct/-β complex comprise both H16T and F42A, or both H16A and F42 substitutions, either pair of which may be combined with an N88 (e.g., N88R) substitution.

In some cases, such as where it is desirable to stimulate the production of Th17 cells, at least one MOD polypeptide (e.g., one, two or three independently selected MODs) present in masked TGF-β constructs and complexes is an IL-6 polypeptide or an IL-6 variant polypeptide.

In some cases, such as where it is desirable to stimulate the production of Th9 cells, at least one MOD polypeptide (e.g., one, two or three independently selected MODs) present in masked TGF-β constructs and complexes is an IL-4 polypeptide or an IL-4 variant polypeptide. See, e.g., Elyaman et al., *Immunity.,* 36(4): 623-634*, Immunity.* (2012).

In some cases, such as where it is desirable to promote IL-7-dependent survival of low-affinity T cells, by control of thymocyte IL-7Ra expression, at least one MOD polypeptide (e.g., one, two or three independently selected MODs) present in masked TGF-β constructs and complexes is an IL-7 polypeptide or an IL-7 variant polypeptide.

In some cases, such as where it is desirable to stimulate the production of T follicular helper (Tfh) cells, at least one MOD polypeptide (e.g., one, two or three independently selected MODs) present in masked TGF-β construct masked TGF-β constructs and complexes is an IL-21 or an IL-23 polypeptide, or a variant of an IL-21 or an IL-23 polypeptide.

In some cases, such as where it is desirable to induce tolerance, at least one MOD polypeptide (e.g., one, two or three independently selected MODs) present in masked TGF-β constructs and, or a variant of a Fas ligand (FasL) polypeptide.

In some cases, such as where it is desirable to inhibit type II innate lymphoid cells (ILC2 cells) (e.g., to suppress asthma and allergic inflammation) at least one MOD polypeptide (e.g., one, two or three independently selected MODs) present in masked TGF-β constructs and complexes is an IL-10 polypeptide, or a variant of an IL-10 polypeptide. See, e.g., Rajas et al., *J Allergy Clin Immunol,* 139(5):1468 (2017); and Ogasawara et al., *J Allergy Clin Immunol,* 141(3): 1147-1151 (2018). Inhibition of ILC2 cells may be assessed by the reduction in their production of type-2 cytokines IL-5 and IL-13 in vivo (in a tissue or body fluid) or in vitro (in culture media). The IL-10 polypeptide may be a monomeric isomer such as the IL-10M1 molecule described by Josephson et al., *J. Biol. Chem.,* 275:13552-13557 (2000), or a variant thereof, both of which are discussed below. In contrast to wild type IL-10 whose biologically active form is an intertwined pair of IL-10 peptides that forms a complex consisting of 2 IL-10 molecules and 4 IL-10Ra receptor chains, IL-10M1 forms a 1:1 complex with the soluble IL-10Ra with a dissociation constant of 30 nm that is biologically active in cellular proliferation assays. Id.

2 MODs and Variant MODs with Reduced Affinity

Suitable MODS that exhibit reduced affinity for their co-MODs can have from 1 amino acid (aa) to 20 aa differences from a wild-type MOD sequence. For example, in some cases, a variant MOD polypeptide sequence present in a masked TGF-β construct complex may differ in amino acid sequence by 1 aa, 2 aa, 3 aa, 4 aa, 5 aa, 6 aa, 7 aa, 8 aa, 9 aa, or 10 aa from the corresponding wild-type MOD polypeptide sequence. As another example, in some cases, a variant MOD polypeptide present in a masked TGF-β construct or complex differs in amino acid sequence by 11 aa, 12 aa, 13 aa, 14 aa, 15 aa, 16 aa, 17 aa, 18 aa, 19 aa, or 20 aa from the corresponding wild-type MOD polypeptide. As an example, in some cases, a variant MOD polypeptide present in a masked TGF-β construct or complex includes 1, 2, 3, 4, 5, 6, 7, 8, 9, or 10 aa substitutions, compared to the corresponding reference (e.g., wild-type) MOD sequence. In some cases, a variant MOD present in a masked TGF-β construct or complex includes a single aa substitution compared to the corresponding reference (e.g., wild-type) MOD sequence. In some cases, a variant MOD present in a masked TGF-β construct or complex includes 2 aa substitutions (e.g., no more than 2 aa substitutions) compared to the corresponding reference (e.g., wild-type) MOD sequence. In some cases, a variant MOD present in a masked TGF-β construct or complex includes 3 aa substitutions (e.g., no more than 3 aa substitutions) compared to the corresponding reference (e.g., wild-type) MOD sequence. In some cases, a variant MOD present in a masked TGF-β construct or complex includes 4 aa or 5 aa substitutions compared to the corresponding reference (e.g., wild-type) MOD sequence. In some cases, a variant MOD present in a masked TGF-β construct or complex includes 6 aa or 7 aa substitutions compared to the corresponding reference (e.g., wild-type) MOD sequence. In some cases, a variant MOD present in a masked TGF-β construct or complex includes 8 aa or 9aa substitutions compared to the corresponding reference (e.g., wild-type) MOD sequence. In some cases, a variant MOD present in a masked TGF-β construct or complex includes 10 aa or 11 aa substitutions (e.g., no more than 10 aa substitutions) compared to the corresponding reference (e.g., wild-type) MOD sequence.

In some cases, a variant MOD present in a masked TGF-β construct or complex includes 11 aa or 12 aa substitutions compared to the corresponding reference (e.g., wild-type) MOD sequence. In some cases, a variant MOD present in a masked TGF-β construct or complex includes 13 aa or 14 aa substitutions compared to the corresponding reference (e.g., wild-type) MOD sequence. In some cases, a variant MOD present in a masked TGF-β construct or complex includes 15 aa or 16 aa substitutions compared to the corresponding reference (e.g., wild-type) MOD sequence. In some cases, a variant MOD present in a masked TGF-β construct or complex includes 17 aa or 18 aa substitutions compared to the corresponding reference (e.g., wild-type) MOD sequence. In some cases, a variant MOD present in a masked TGF-β construct or complex includes 19 aa or 20 aa substitutions compared to the corresponding reference (e.g., wild-type) MOD sequence.

As discussed above, variant MODs suitable for inclusion in a masked TGF-β construct or complex may exhibit reduced affinity for their cognate co-MOD, compared to the affinity of a corresponding wild-type MOD for the cognate co-MOD.

In some cases, a variant MOD polypeptide sequence present in a masked TGF-β construct or complex has a binding affinity for a cognate co-MOD that is from 1 nM to 100 μM. For example, in some cases, a variant MOD polypeptide present in a masked TGF-β construct or complex has a binding affinity for a cognate co-MOD that is from about 1 nM to about 5 nM, from about 5 nM to about 10 nM, from about 10 nM to about 50 nM, from about 50 nM to about 100 nM, from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

3 Determining Binding Affinity

Binding affinity between a MOD (e.g., a MOD polypeptide) and its cognate co-MOD can be determined by bio-layer interferometry (BLI) using purified MOD and purified cognate co-MOD. Binding affinity between masked TGF-β constructs or complexes that comprise a MOD and the MOD's cognate co-MOD can also be determined by BLI using purified masked TGF-β construct or complex and the MOD's cognate co-MOD. BLI methods are well known to those skilled in the art. See, e.g., Lad et al. (2015) *J. Biomol. Screen.* 20(4):498-507; and Shah and Duncan (2014) *J. Vis. Exp.* 18:e51383. The specific and relative binding affinities described in this disclosure between a MOD and its cognate co-MOD, or between a masked TGF-β construct or complex having a MOD and its cognate co-MOD, can be determined using the following procedures.

To determine binding affinity between a MOD-containing masked TGF-β construct or complex and the MOD's cognate co-MOD, a BLI assay can be carried out using an Octet RED 96 (Pal FortéBio) instrument, or a similar instrument, as follows. A control masked TGF-β construct or complex (e.g., a masked TGF-β construct or complex comprising a wild-type MOD) is immobilized onto an insoluble support (a "biosensor"). The immobilized masked TGF-β construct or complex is the "target." Immobilization can be effected by immobilizing a capture antibody onto the insoluble support, where the capture antibody immobilizes the masked TGF-β construct or complex. For example, where the masked TGF-β construct or complex comprises an Ig Fc scaffold, immobilization can be effected by immobilizing anti-Ig Fc (e.g., anti-human IgG Fc) antibodies onto the insoluble support, where the immobilized anti-Ig Fc antibodies bind to and immobilize the masked TGF-β construct or complex. A co-MOD is applied, at several different concentrations, to the immobilized masked TGF-β construct or complex, and the instrument's response is recorded. Assays are conducted in a liquid medium comprising 25 mM HEPES pH 6.8, 5% poly(ethylene glycol) 6000, 50 mM KCl, 0.1% bovine serum albumin, and 0.02% Tween 20 nonionic detergent. Binding of the co-MOD to the immobilized masked TGF-β construct or complex is conducted at 30° C.

As a positive control for binding and binding affinity, an antibody (e.g., a monoclonal antibody) can be used. The antibody may be selected based on the specific structure of the masked TGF-β construct or complex (see, e.g., FIG. 1). For example, a monoclonal antibody (mAb) directed against the TGF-β, TGF-β receptor, scaffold or MOD polypeptide sequences can be used as a positive control provided the antibody does not cause the masked TGF-β construct or complex to become dissociated from the support (biosensor). A standard curve can be generated using serial dilutions of the anti-MHC Class I or Class II monoclonal antibody. The co-MOD, or the anti-MHC mAb, is the "analyte." BLI analyzes the interference pattern of white light reflected from two surfaces: i) the immobilized polypeptide ("target"); and ii) an internal reference layer. A change in the number of molecules ("analyte"; e.g., co-MOD; anti-HLA antibody) bound to the biosensor tip causes a shift in the interference pattern; this shift in interference pattern can be measured in real time. The two kinetic terms that describe the affinity of the target/analyte interaction are the association constant ($k_a$) and dissociation constant ($k_d$). The ratio of these two terms ($k_d/_a$) gives rise to the affinity constant $K_D$.

As noted above, determining binding affinity between a MOD (e.g., IL-2 or an IL-2 variant) and its cognate co-MOD (e.g., IL-2R) also can be determined by BLI. The assay is similar to that described above for the masked TGF-β construct or complex. A BLI assay can be carried out using an Octet RED 96 (Pal FortéBio) instrument, or a similar instrument, as follows. A component MOD of a masked TGF-13 construct or complex (e.g., a variant IL-2 polypeptide of the present disclosure); and a control MOD (where a control MOD comprises a wild-type MOD, e.g., wild-type IL-2) are immobilized separately onto insoluble supports (a "biosensor"). Each MOD is the "target" Immobilization can be effected by immobilizing a capture antibody onto the insoluble support, where the capture antibody immobilizes the MOD. For example, if the target is fused to an immuno-affinity tag (e.g., FLAG, human IgG Fc, etc.), immobilization can be effected by immobilizing the appropriate antibody to the immuno-affinity tag (e.g., anti-human IgG Fc) on the insoluble support, where the immobilized antibodies bind to and immobilize the MOD (where the MOD comprises an IgFc polypeptide). A co-MOD (or polypeptide) is applied, at several different concentrations, to the immobilized MOD, and the instrument's response is recorded. Alternatively, a co-MOD (or polypeptide) is immobilized to the biosensor (e.g., for the IL-2 receptor heterotrimer, as a monomeric subunit, heterodimeric subcomplex, or the complete heterotrimer), the MOD is applied, at several different concentrations, to the immobilized co-MOD(s), and the instrument's response is recorded. Assays are conducted in a liquid medium comprising 25 mM HEPES pH 6.8, 5% poly(ethylene glycol) 6000, 50 mM KCl, 0.1% bovine serum albumin, and 0.02% Tween 20 nonionic detergent. Binding of the co-MOD to the immobilized MOD is conducted at 30° C. BLI analyzes the interference pattern of white light reflected from two surfaces: i) the immobilized polypeptide ("target"); and ii) an internal reference layer. A change in the number of molecules ("analyte"; e.g., co-MOD) bound to the biosensor tip causes a shift in the interference pattern; this shift in interference pattern can be measured in real time. The two kinetic terms that describe the affinity of the target/analyte interaction are the association constant ($k_a$) and dissociation constant ($k_d$). The ratio of these two terms ($k_d/_a$) gives rise to the affinity constant $K_D$. Determining the binding affinity of both a wild-type MOD (e.g., IL-2) for its co-MOD (e.g., its cognate binding partner or receptor; in the case of IL-2, the IL-2R), and a variant MOD (e.g., an IL-2 variant as disclosed herein) for its co-MOD (e.g., in the case of an IL-2 variant, the IL-2R), thus allows one to determine the relative binding affinity of the variant co-MOD, as compared to the wild-type co-MOD, for the co-MOD. That is, one can determine whether the binding affinity of a variant MOD for its co-MOD is reduced as compared to the binding affinity of the wild-type MOD for the same cognate co-MOD, and, if so, what is the percentage reduction from the binding affinity of the wild-type co-MOD.

The BLI assay is carried out in a multi-well plate. To run the assay, the plate layout is defined, the assay steps are defined, and biosensors are assigned in Octet Data Acquisition software. The biosensor assembly is hydrated. The hydrated biosensor assembly and the assay plate are equilibrated for 10 minutes on the Octet instrument. Once the data are acquired, the acquired data are loaded into the Octet Data Analysis software. The data are processed in the Processing window by specifying method for reference subtraction, y-axis alignment, inter-step correction, and Savitzky-Golay filtering. Data are analyzed in the Analysis window by specifying steps to analyze (Association and Dissociation), and selecting curve fit model (1:1), fitting method (global), and window of interest (in seconds). The quality of fit is evaluated. $K_D$ values for each data trace (analyte concentration) can be averaged if within a 3-fold range. $K_D$ error values should be within one order of magnitude of the affinity constant values; $R^2$ values should be above 0.95. See, e.g., Abdiche et al. (2008) *J. Anal. Biochem.* 377:209.

In some cases, the ratio of: i) the binding affinity of a control masked TGF-β construct or complex (where the control masked TGF-β construct or complex comprises a wild-type MOD) to a cognate co-MOD to ii) the binding affinity of a masked TGF-β construct or complex comprising a variant of the wild-type MOD to the cognate co-MOD, when measured by BLI (as described above), is at least 1.5:1, at least 2:1, at least 5:1, at least 10:1, at least 15:1, at least 20:1, at least 25:1, at least 50:1, at least 100:1, at least 500:1, at least $10^2$:1, at least $5\times10^2$:1, at least $10^3$:1, at least $5\times10^3$:1, at least $10^4$:1, at least $10^5$:1, or at least $10^6$:1. In some cases, the ratio of: i) the binding affinity of a control masked TGF-β construct or complex (where the control masked TGF-β construct or complex comprises a wild-type MOD) to a cognate co-MOD to ii) the binding affinity of a masked TGF-β construct or complex comprising a variant of the wild-type MOD to the cognate co-MOD, when measured by BLI, is in a range of from 1.5:1 to $10^6$:1, e.g., from 1.5:1 to 10:1, from 10:1 to 50:1, from 50:1 to $10^2$:1, from $10^2$:1 to $10^3$:1, from $10^3$:1 to $10^4$:1, from $10^4$:1 to $10^5$:1, or from $10^5$:1 to $10^6$:1.

In some cases, a variant MOD present in a masked TGF-β construct or complex has a binding affinity for a cognate co-MOD that is from 1 nM to 100 nM, or from 100 nM to 100 μM. For example, in some cases, a variant MOD present in a masked TGF-β construct or complex has a binding affinity for a cognate co-MOD that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM. In some cases, a variant MOD present in a masked TGF-β construct or complex has a binding affinity for a cognate co-MOD that is from about 1 nM to about 5 nM, from about 5 nM to about 10 nM, from about 10 nM to about 50 nM, or from about 50 nM to about 100 nM.

4 PD-L1 and its Variants

As one non-limiting example, a MOD or variant MOD present in a masked TGF-β construct or complex is a PD-L1 or variant PD-L1 polypeptide. Wild-type PD-L1 binds to PD1.

A wild-type human PD-L1 polypeptide can comprise the following amino acid sequence: MRIFAVFIFM TYWHLLNAFT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKICLT LSPST (SEQ ID NO:1); where aas 1-18 form the signal sequence, aas 19-127 form the Ig-like V-type or IgV domain, and 133-225 for the Ig-like C2 type domain.

A wild-type human PD-L1 ectodomain can comprise the following amino acid sequence: FT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPGNI LNVSIKI (SEQ ID NO:2); where aas 1-109 form the Ig-like V-type or "IgV" domain, and aas 115-207 for the Ig-like C2 type domain.

A wild-type PD-L1 IgV domain, suitable for use as a MOD may comprise aa 18, aas IgV aas 19-127 of SEQ D No. 1, and a carboxyl terminal stabilization sequences, such as for instance the last seven amino acids (bolded and italicized) of the sequence: A FTVTVPKDLY VVEYGSNMTI ECKFPVEKQL DLAALIVYWE MEDKNIIQFV HGEEDLKTQH SSYRQRARLL KDQLSLGNAA LQITDVKLQD AGVYRCMISY GGADYKRITV KVNAPYAAAL HEH SEQ ID NO:138. Where the carboxyl stabilizing sequence comprises a histidine (e.g., a histidine approximately 5 residues to the C-terminal side of the Tyr (Y) appearing as aa 117 of SEQ ID NO:138) at about aa 122, the histidine may form a stabilizing electrostatic bond with the backbone amide at aas 82 and 83 (bolded and italicized in SEQ ID NO:138 (Q107 and L106 of SEQ ID NO:1). As an alternative, a stabilizing disulfide bond may be formed by substituting one of aas 82 or 83) (Q107 and L106 of SEQ ID NO:1) and one of aa residues 121, 122, or 123 (equivalent to as positions 139-141 of SEQ ID NO:1).

A wild-type PD-1 polypeptide can comprise the following amino acid sequence:

```
                                            (SEQ ID NO: 3)
PGWFLDSPDR PWNPPTFSPA LLVVTEGDNA TFTCSFSNTS

ESFVLNWYRM SPSNQTDKLA AFPEDRSQPG QDCRFRVTQL

PNGRDFHMSV VRARRNDSGT YLCGAISLAP KAQIKESLRA

ELRVTERRAE VPTAHPSPSP RPAGQFQTLV VGVVGGLLGS

LVLLVWVLAV ICSRAARGTI GARRTGQPLK EDPSAVPVFS
```

-continued

```
VDYGELDFQW REKTPEPPVP CVPEQTEYAT IVFPSGMGTS

SPARRGSADG PRSAQPLRPE DGHCSWPL.
```

In some cases, a variant PD-L1 polypeptide (e.g., a variant of SEQ ID NO:2 or PD-L1's IgV domain) exhibits reduced binding affinity to PD-1 (e.g., a PD-1 polypeptide comprising the amino acid sequence set forth in SEQ ID NO:3), compared to the binding affinity of a PD-L1 polypeptide comprising the amino acid sequence set forth in SEQ ID NO:1 or SEQ ID NO:2. For example, in some cases, a variant PD-L1 polypeptide binds PD-1 (e.g., a PD-1 polypeptide comprising the amino acid sequence set forth in SEQ ID NO:3) with a binding affinity that is at least 10% less, at least 20% less, at least 30% less, at least 40% less, at least 50% less, at least 60% less, at least 70% less, at least 80% less, at least 90% less, at least 95% less, or more than 95% less than the binding affinity of a PD-L1 polypeptide comprising the amino acid sequence set forth in SEQ ID NO:1 or SEQ ID NO:2.

In some cases, a variant PD-L1 polypeptide (e.g., a variant of SEQ ID NO:2 or its IgV domain) has a binding affinity to PD-1 (e.g., of SEQ ID NO:3) that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM). As another example, in some cases, a variant PD-L1 polypeptide (e.g. a variant of SEQ ID NO:2) has a binding affinity for PD1 (e.g., a PD1 polypeptide comprising the amino acid sequence set forth in SEQ ID NO:3) that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

A number of aa substitutions may be made in the PD-L1 ectodomain sequences used as MODs, including substitutions to sequences having greater than 90% (95%, 98% or 99%) sequence identity to at least 85 contiguous aas (e.g., at least 90, at least 95, at least 100, or at least 105 contiguous aas) of any one of SEQ ID NO:1, SEQ ID NO:2, aas 19-127 (the IgV domain) of SEQ ID NO:1, and SEQ ID NO:138. The substitutions may include (a) disulfide bond substitution pairs D103C and G33C, or V104 and S34C; (b) salt bridge forming substitution pairs Q107D and K62R or Q107D and S80R; and/or (c) Pi stacking substitutions M36Y or M36F (based on SEQ ID NO:1). A PD-L1 MOD sequence may comprise a sequence having at least 85 contiguous aas (e.g., at least 90, at least 95, at least 100, or at least 105 contiguous aas) of SEQ ID NO:2, and at least one disulfide, salt bridge, or Pi stacking substitution. A PD-L1 MOD sequence may comprise a sequence having at least 85 contiguous aas (e.g., at least 90, at least 95, at least 100, or at least 105 contiguous aas) of aas 19-127 (the IgV domain) of SEQ ID NO:1, and at least one disulfide, salt bridge, or Pi stacking substitution. A PD-L1 MOD sequence may comprise a sequence having at least 85 contiguous aas (e.g., at least 90, at least 95, at least 100, or at least 105 contiguous aas) of aas SEQ ID NO:138, and at least one disulfide, salt bridge, or Pi stacking substitution.

In some cases, a variant PD-L1 polypeptide has a single aa substitution compared to the PD-L1 amino acid sequence set forth in SEQ ID NO:1, SEQ ID NO:2 or PD-L1's IgV domain. In some cases, a variant PD-L1 polypeptide has from 2 aa to 10 aa substitutions compared to the PD-L1 amino acid sequence set forth in SEQ ID NO:1, SEQ ID NO:2 or PD-L1's IgV domain. In some cases, a variant PD-L1 polypeptide has 2 aa substitutions compared to the PD-L1 amino acid sequence set forth in SEQ ID NO:1, SEQ ID NO:2 or PD-L1's IgV domain. In some cases, a variant PD-L1 polypeptide has 3 aa or 4 aa substitutions compared to the PD-L1 amino acid sequence set forth in SEQ ID NO:1, SEQ ID NO:2 or PD-L1's IgV domain. In some cases, a variant PD-L1 polypeptide has 5 aa or 6 aa substitutions compared to the PD-L1 amino acid sequence set forth in SEQ ID NO:1, SEQ ID NO:2 or PD-L1's IgV domain. In some cases, a variant PD-L1 polypeptide has 7 aa or 8 aa substitutions compared to the PD-L1 amino acid sequence set forth in SEQ ID NO:1, SEQ ID NO:2 or PD-L1's IgV domain. In some cases, a variant PD-L1 polypeptide has 9 aa or 10 aa substitutions compared to the PD-L1 amino acid sequence set forth in SEQ ID NO:1, SEQ ID NO:2 or PD-L1's IgV domain.

Suitable variant PD-L1 polypeptide sequences include polypeptide sequences having at least 80%, at least 85%, at least 90%, at least 95%, at least 98%, or at least 99% aa sequence identity to at least 170 contiguous aa (e.g., at least 180, 190 or 200 contiguous aa) of SEQ ID NO:2 (e.g. which have at least one aa insertion, deletion or substitution). Suitable variant PD-L1 IgV polypeptide sequences include polypeptide sequences having at least 80%, at least 85%, at least 90%, at least 95%, at least 98%, or at least 99% aa sequence identity to at least 70 contiguous aa (e.g., at least 80, 90, 100 or 105 contiguous aas) of aas 1-109 of SEQ ID NO:2 (e.g. which have at least one aa insertion, deletion or substitution).

In an instance, variant PD-L1 polypeptide sequences include polypeptide sequences having at least 90% (e.g., at least 95%, 98%, or 99%), or 100%, aa sequence identity to SEQ ID NO:2, wherein the residue at position 8 is an aa other than D; in one such instance that residue is an A, and in another, R. Variant PD-L1 polypeptide sequences include polypeptide sequences having at least 90% (e.g., at least 95%, 98%, or 99%), or 100%, aa sequence identity to SEQ ID NO:2, wherein the residue at position 36 is an aa other than I; in one such instance that residue is an A, and in another, D. Variant PD-L1 polypeptide sequences also include polypeptide sequences having at least 90% (e.g., at least 95%, 98%, or 99%), or 100%, aa sequence identity to SEQ ID NO:2, wherein the residue at position 54 is an aa other than E; in one such instance that residue is an A, and in another, R.

5 IL-1 and its Variants

As one non-limiting example, a MOD or variant MOD present in a masked TGF-β construct or complex is an IL-1 or variant IL-1 polypeptide. Wild-type IL-1 has two isoforms, IL-1α and IL-1β, both of which bind to the IL-1 receptor.

A wild-type human IL-1α precursor polypeptide can comprise the following amino acid sequence: MAKVPDMFEDL KNCYSENEEDS SSIDHLSLNQK SFYHVSYGPLH EGCMDQSVSLS ISETSKTSKLT FKESMVVVATN GKVLKKRRLSL SQSITDDDLEA IANDSEEEIIK PRSAPFSFLSN VKYNFMRIIKY EFILNDALNQS IIRANDQYLTA AALHNLDEAVK FDMGAYKSSKD DAKITVILRIS KTQLYVTAQDE DQPVLLKEMPE IPKTITGSETN LLFFWETHGTK NYFTSVAHPNL FIATKQDYWVC LAGGPPSITDF QILENQA (SEQ ID NO:4) UniProtKB-P01583, NCBI Ref. Seq. NP_000566.3, that can have one or more of the following naturally occurring variations R85Q, A1145, N125D, D138N, and D176H.

A mature wild-type human IL-1α polypeptide can comprise the following amino acid sequence:

```
                                          (SEQ ID NO: 5)
PRSAPFSFLS NVKYNFMRII KYEFILNDAL NQSIIRANDQ

YLTAAALHNL DEAVKFDMGA YKSSKDDAKI TVILRISKTQ

LYVTAQDEDQ PVLLKEMPEI PKTITGSETN LLFFWETHGT

KNYFTSVAHP NLFIATKQDY WVCLAGGPPS ITDFQILENQ A.
```

A wild-type human IL-1β precursor polypeptide can comprise the following amino acid sequence: MAEVPELASE MMAYYSGNED DLFFEADGPK QMKCSFQDLD LCPLDGGIQL RISDHHYSKG FRQAASVVVA MDKLRKMLVP CPQTFQENDL STFFPFIFEE EPIFFDTWDN EAYVHDAPVR SLNCTLRDSQ QKSLVMSGPY ELKALHLQGQ DMEQQVVFSM SFVQGEESND KIPVALGLKE KNLYLSCVLK DDKPTLQLES VDPKNYPKKK MEKRFVFNKI EINNKLEFES AQFPNWYIST SQAENMPVFL GGTKGGQDIT DFTMQFVSS (SEQ ID NO:6) UniProtKB-P0158, NCBI Ref. Seq. NP_000567.1.

A mature wild-type human IL-1β polypeptide can comprise the following amino acid sequence

```
                                          (SEQ ID NO: 7)
APVRSLNCTLRDSQQKSLVMSGPYELKALHLQGQDMEQQVVFSMSFVQGE

ESNDKIPVALGLKEKNLYLSCVLKDDKPTLQLESVDPKNYPKKKMEKRFV

FNKIEINNKLEFESAQFPNWYISTSQAENMPVFLGGTKGGQDITDFTMQF

VSS.
```

Both IL-1α and IL-1β bind to the IL-1 receptor, which can have the sequence: MKVLLRLICF IALLISSLEA DKCKEREEKI ILVSSANEID VRPCPLNPNE HKGTITWYKD DSKTPVSTEQ ASRIHQHKEK LWFVPAKVED SGHYYCVVRN SSYCLRIKIS AKFVENEPNL CYNAQAIFKQ KLPVAGDGGL VCPYMEFFKN ENNELPKLQW YKDCKPLLLD NIHFSGVKDR LIVMNVAEKH RGNYTCHASY TYLGKQYPIT RVIEFITLEE NKPTRPVIVS PANETMEVDL GSQIQLICNV TGQLSDIAYW KWNGSVIDED DPVLGEDYYS VENPANKRRS TLITVLNISE IESRFYKHPF TCFAKNTHGI DAAYIQLIYP VTNFQKHMIG ICVTLTVIIV CSVFIYKIFK IDIVLWYRDS CYDFLPIKAS DGKTYDAYIL YPKTVGEGST SDCDIFVFKV LPEVLEKQCG YKLFIYGRDD YVGEDIVEVI NENVKKSRRL IIILVRETSG FSWLGGSSEE QIAMYNALVQ DGIKVVLLEL EKIQDYEKMP ESIKFIKQKH GAIRWSGDFT QGPQSAKTRF WKNVRYHMPV QRRSPSSKHQ LLSPATKEKL QREAHVPLG, (SEQ ID NO:8), NCBI Ref. Seq. NP_000868.1, with aas 21 to 569 forming the mature polypeptide, the ectodomain of which can be used to determine binding affinity to IL-1α and IL-1β.

In some cases, a variant IL-1α and IL-1β polypeptide exhibits reduced binding affinity to an IL-1 receptor having the sequence set forth in SEQ ID NO:8 or its ectodomain, compared to the binding affinity of an IL-1 polypeptide comprising the amino acid sequence set forth in SEQ ID NO:5 or SEQ ID NO:7. For example, in some cases, a variant IL-1α and IL-1β polypeptide binds the IL-1 receptor set forth in SEQ ID NO:8 or the mature proteins of the ectodomain) with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of a IL-1α or IL-1β polypeptide comprising the amino acid sequence set forth in SEQ ID NO:5 or SEQ ID NO:7.

In some cases, a variant IL-1α or IL-1β polypeptide (e.g., a variant of SEQ ID NOs:5 or 7) has a binding affinity to an IL-1 receptor having the sequence set forth in SEQ ID NO:8 that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM). As another example, in some cases, a variant IL-1α or IL-1β polypeptide (e.g., a variant of SEQ ID NOs:5 or 7) has a binding affinity for the IL-1 receptor set forth in SEQ ID NO:8 or its ectodomain that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-1α or IL-1β polypeptide has a single aa substitution compared to the IL-1α or IL-1β amino acid sequence set forth in SEQ ID NO:5 or SEQ ID NO:7. In some cases, a variant IL-1α or IL-1β polypeptide has from 2 aa to 10 aa substitutions compared to the IL-1α or IL-1β amino acid sequence set forth in SEQ ID NO:5 or SEQ ID NO:7. In some cases, a variant IL-1α or IL-113 polypeptide has 2 aa substitutions compared to the IL-1α or IL-1β amino acid sequence set forth in SEQ ID NO:5 or SEQ ID NO:7. In some cases, a variant IL-1α or IL-1β polypeptide has 3 aa or 4 aa substitutions compared to the IL-1α or IL-1β amino acid sequence set forth in SEQ ID NO:5 or SEQ ID NO:7. In some cases, a variant IL-1α or IL-1β polypeptide has 5 aa or 6 aa substitutions compared to the IL-1α or IL-1β amino acid sequence set forth in SEQ ID NO:5 or SEQ ID NO:7. In some cases, a variant IL-1α or IL-1β polypeptide has 7 aa or 8 aa substitutions compared to the IL-1α or IL-1β amino acid sequence set forth in SEQ ID NO:5 or SEQ ID NO:7. In some cases, a variant IL-1α or IL-1β polypeptide has 9 aa or 10 aa substitutions compared to the IL-1α or IL-1β amino acid sequence set forth in SEQ ID NO:5 or SEQ ID NO:7.

Suitable variant IL-1α or IL-1βpolypeptide sequences include polypeptide sequences having at least 80%, at least 85%, at least 90%, at least 95%, at least 98%, or at least 99% aa sequence identity to at least 100 contiguous aa of the amino acid sequence set forth in SEQ ID NO:5 or SEQ ID NO:7 (e.g., which have at least one aa substitution, deletion or insertion).

6 IL-2 and its Variants

As one non-limiting example, a MOD or variant MOD present in a masked TGF-β construct or complex is an IL-2 or variant IL-2 polypeptide. In some cases, a variant MOD present in a masked TGF-β construct or complex is a variant IL-2 polypeptide. Wild-type IL-2 binds to an IL-2 receptor (IL-2R). A wild-type IL-2 amino acid sequence can be as follows: APTSSSTKKTQLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (aa 21-153 of UniProt P60568, SEQ ID NO:9).

Wild-type IL-2 binds to an IL-2 receptor (IL-2R) on the surface of a cell. An IL-2 receptor is in some cases a heterotrimeric polypeptide comprising an alpha chain (IL-2Rα; also referred to as CD25), a beta chain (IL-2Rβ; also referred to as CD122) and a gamma chain (IL-2Rγ; also referred to as CD132). Amino acid sequences of human IL-2Rα, IL-2Rβ, and IL-2Rγ can be as follows.

```
Human IL-2Rα:
                                        (SEQ ID NO: 10)
ELCDDDPPE IPHATFKAMA YKEGTMLNCE CKRGFRRIKS
GSLYMLCTGN SSHSSWDNQC QCTSSATRNT TKQVTPQPEE
QKERKTTEMQ SPMQPVDQAS LPGHCREPPP WENEATERIY
HFVVGQMVYY QCVQGYRALH RGPAESVCKM THGKTRWTQP
QLICTGEMET SQFPGEEKPQ ASPEGRPESE TSCLVTTTDF
QIQTEMAATM ETSIFTTEYQ VAVAGCVFLL ISVLLLSGLT
WQRRQRKSRR TI.
```

```
Human IL-2Rβ:
                                        (SEQ ID NO: 11)
VNG TSQFTCFYNS RANISCVWSQ DGALQDTSCQ VHAWPDRRRW
NQTCELLPVS QASWACNLIL GAPDSQKLTT VDIVTLRVLC
REGVRWRVMA IQDFKPFENL RLMAPISLQV VHVETHRCNI
SWEISQASHY FERHLEFEAR TLSPGHTWEE APLLTLKQKQ
EWICLETLTP DTQYEFQVRV KPLQGEFTTW SPWSQPLAFR
TKPAALGKDT IPWLGHLLVG LSGAFGFIIL VYLLINCRNT
GPWLKKVLKC NTPDPSKFFS QLSSEHGGDV QKWLSSPFPS
SSFSPGGLAP EISPLEVLER DKVTQLLLQQ DKVPEPASLS
SNHSLTSCFT NQGYFFFHLP DALEIEACQV YFTYDPYSEE
DPDEGVAGAP TGSSPQPLQP LSGEDDAYCT FPSRDDLLLF
SPSLLGGPSP PSTAPGGSGA GEERMPPSLQ ERVPRDWDPQ
PLGPPTPGVP DLVDFQPPPE LVLREAGEEV PDAGPREGVS
FPWSRPPGQG EFRALNARLP LNTDAYLSLQ ELQGQDPTHL V.
```

```
Human IL-2Rγ:
                                        (SEQ ID NO: 12)
LNTTILTP NGNEDTTADF FLTTMPTDSL SVSTLPLPEV
QCFVFNVEYM NCTWNSSSEP QPTNLTLHYW YKNSDNDKVQ
KCSHYLFSEE ITSGCQLQKK EIHLYQTFVV QLQDPREPRR
QATQMLKLQN LVIPWAPENL TLHKLSESQL ELNWNNRFLN
HCLEHLVQYR TDWDHSWTEQ SVDYRHKFSL PSVDGQKRYT
FRVRSRFNPL CGSAQHWSEW SHPIHWGSNT SKENPFLFAL
EAVVISVGSM GLIISLLCVY FWLERTMPRI PTLKNLEDLV
TEYHGNFSAW SGVSKGLAES LQPDYSERLC LVSEIPPKGG
ALGEGPGASP CNQHSPYWAP PCYTLKPET.
```

In some cases, where a masked TGF-β construct or complex comprises a variant IL-2 polypeptide, a cognate co-MOD is an IL-2R comprising polypeptides comprising the amino acid sequences of any one of SEQ ID NO:10, SEQ ID NO:11, and SEQ ID NO:12.

In some cases, a variant IL-2 polypeptide exhibits reduced binding affinity to IL-2R, compared to the binding affinity of an IL-2 polypeptide comprising the amino acid sequence set forth in SEQ ID NO:9. For example, in some cases, a variant IL-2 polypeptide binds IL-2R with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of an IL-2 polypeptide comprising the amino acid sequence set forth in SEQ ID NO:9 for an IL-2R (e.g., an IL-2R comprising polypeptides comprising the amino acid sequence set forth in SEQ ID NOs:10-12), when assayed under the same conditions.

In some cases, a variant IL-2 polypeptide (e.g., a variant of SEQ ID NO:9) has a binding affinity to IL-2R (e.g., of SEQ ID NOs:10-12) that is from 100 nM to 100 μM. As another example, in some cases, a variant IL-2 polypeptide (e.g., a variant of SEQ ID NO:9) has a binding affinity for IL-2R (e.g., an IL-2R comprising polypeptides comprising the amino acid sequence set forth in SEQ ID NOs: 10-12) that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-2 polypeptide has a single aa substitution compared to the IL-2 amino acid sequence set forth in SEQ ID NO:9. In some cases, a variant IL-2 polypeptide has from 2 to 10 aa substitutions compared to the IL-2 amino acid sequence set forth in SEQ ID NO:9. In some cases, a variant IL-2 polypeptide has 2 aa substitutions compared to the IL-2 amino acid sequence set forth in SEQ ID NO:9. In some cases, a variant IL-2 polypeptide has 3 aa substitutions compared to the IL-2 amino acid sequence set forth in SEQ ID NO:9. In some cases, a variant IL-2 polypeptide has 4 aa substitutions compared to the IL-2 amino acid sequence set forth in SEQ ID NO:9. In some cases, a variant IL-2 polypeptide has 5 aa substitutions compared to the IL-2 amino acid sequence set forth in SEQ ID NO:9. In some cases, a variant IL-2 polypeptide has 6 aa substitutions compared to the IL-2 amino acid sequence set forth in SEQ ID NO:9. In some cases, a variant IL-2 polypeptide has 7 aa substitutions compared to the IL-2 amino acid sequence set forth in SEQ ID NO:9. In some cases, a variant IL-2 polypeptide has 8 aa substitutions compared to the IL-2 amino acid sequence set forth in SEQ ID NO:9. In some cases, a variant IL-2 polypeptide has 9 aa substitutions compared to the IL-2 amino acid sequence set forth in SEQ ID NO:9. In some cases, a variant IL-2 polypeptide has 10 aa substitutions compared to the IL-2 amino acid sequence set forth in SEQ ID NO:9.

Suitable variant IL-2 polypeptide sequences include polypeptide sequences comprising an aa sequence having at least 80%, at least 85%, at least 90%, at least 95%, at least 98%, at least 99%, or 100%, aa sequence identity to at least 80 (e.g., 90, 100, 110, 120, 130 or 133) contiguous aas of SEQ ID NO:9. In addition, IL-2 variants include polypeptides that comprises an aa sequence having at least 80%, at least 85%, at least 90%, at least 95%, at least 98%, at least 99%, or 100%, aa sequence identity to at least 80 (e.g., 90, 100, 110, 120, 130 or 133) contiguous aas of any one of the variant IL-2 aa sequences that follow (see SEQ ID NOs: 13-27).

APTSSSTKKT QLQLXHLLLDLQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:13), where X is any amino acid other than Glu. In some cases, X is Ala.

APTSSSTKKT QLQLEHLLLXLQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:14), where X is any amino acid other than Asp. In some cases, X is Ala.

APTSSSTKKT QLQLEXLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:15), where X (H16) is any amino acid other than His. In some cases, X is Ala (H16A). In some cases, X is Arg. In some cases, X is Asn. In some cases, X is Asp. In some cases, X is Cys. In some cases, X is Glu. In some cases, X is Gln. In some cases, X is Gly. In some cases, X is Ile. In some cases, X is Lys. In some cases, X is Leu. In some cases, X is Met. In some cases, X is Phe. In some cases, X is Pro. In some cases, X is Ser. In some cases, X is Thr (H16T). In some cases, X is Tyr. In some cases, X is Trp. In some cases, X is Val.

APTSSSTKKT QLQLEHLLLD LQMILNGINN YKNPKLTRML TXKFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:16), where X (F42) is any amino acid other than Phe. In some cases, X is Ala (F42A). In some cases, X is Thr (F42T).

APTSSSTKKT QLQLEHLLLD LQMILNGINN YKNPKLTRML TFKFXMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:17), where X is any amino acid other than Tyr. In some cases, X is Ala;

APTSSSTKKT QLQLEHLLLD LQMILNGINN YKNPKLTRML TFKFYMPKKA TELKHLQCLE EELKPLEEVL NLAQSKNFHL RPRDLISXIN VIVLELKGSE TTFMCEYADE TATIVEFLNR WITFCQSIIS TLT (SEQ ID NO:18), where X (N88) is any amino acid other than Asn. In some cases, X is Ala; in some cases, X is Arg. APTSSSTKKT QLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCXSIIS TLT (SEQ ID NO:19), where X is any amino acid other than Gln. In some cases, X is Ala.

APTSSSTKKT QLQLE$X_1$LLLD LQMILNGINN YKNPKLTRML T$X_2$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:20), where $X_1$ (H16) is any amino acid other than His, and where $X_2$ (F42) is any amino acid other than Phe. In some cases, $X_1$ is Ala. In some cases, $X_2$ is Ala. In some cases, $X_1$ is Ala; and $X_2$ is Ala (H16A, F42A). In some cases, $X_1$ is Thr; and $X_2$ is Ala (H16T, F42A). In some cases, $X_1$ is Ala; and $X_2$ is Thr (H16A, F42T). In some cases, $X_1$ is Thr; and $X_2$ is Thr (H16T, F42T).

APTSSSTKKT QLQLE$X_1$LLLD LQMILNGINN YKNPKLTRML T$X_2$KFYMPKKA TELKHLQCLE EELKPLEEVL NLAQSKNFHL RPRDLISRIN VIVLELKGSE TTFMCEYADE TATIVEFLNR WITFCQSIIS TLT (SEQ ID NO:21), which comprises an N88R substitution, and where $X_1$ (H16) is any amino acid other than His, and where $X_2$ (F42) is any amino acid other than Phe. In some cases, $X_1$ is Ala. In some cases, $X_2$ is Ala. In some cases, $X_1$ is Ala; and $X_2$ is Ala. In some cases, $X_1$ is Thr; and $X_2$ is Ala. In some cases, $X_1$ is Ala; and $X_2$ is Thr. In some cases, $X_1$ is Thr; and $X_2$ is Thr.

APTSSSTKKT QLQLEHLLL$X_1$ LQMILNGINN YKNPKLTRML T$X_2$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:22), where $X_1$ is any amino acid other than Asp; and where $X_2$ is any amino acid other than Phe. In some cases, $X_1$ is Ala. In some cases, $X_2$ is Ala. In some cases, $X_1$ is Ala; and $X_2$ is Ala.

APTSSSTKKT QLQL$X_1$HLLL$X_2$ LQMILNGINN YKNPKLTRML T$X_3$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:23), where $X_1$ is any amino acid other than Glu; where $X_2$ is any amino acid other than Asp; and where $X_3$ is any amino acid other than Phe. In some cases, $X_1$ is Ala. In some cases, $X_2$ is Ala. In some cases, $X_3$ is Ala. In some cases, any two or all three of $X_1$ is Ala; $X_2$ is Ala; and $X_3$ is Ala.

APTSSSTKKT QLQLE$X_1$LLL$X_2$ LQMILNGINN YKNPKLTRML T$X_3$KFYMPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:24), where $X_1$ is any amino acid other than His; where $X_2$ is any amino acid other than Asp; and where $X_3$ is any amino acid other than Phe. In some cases, $X_1$ is Ala. In some cases, $X_2$ is Ala. In some cases, $X_3$ is Ala. In some cases, $X_1$ is Ala; $X_2$ is Ala; and $X_3$ is Ala.

APTSSSTKKT QLQLEHLLL$X_1$ LQMILNGINN YKNPKLTRML T$X_2$KFYMPKKA TELKHLQCLE EELKPLEEVL NLAQSKNFHL RPRDLISNIN VIVLELKGSE TTFMCEYADE TATIVEFLNR WITFCXS$X_3$IIS TLT (SEQ ID NO:25), where $X_1$ is any amino acid other than Asp; where $X_2$ is any amino acid other than Phe; and where $X_3$ is any amino acid other than Gln. In some cases, $X_1$ is Ala. In some cases, $X_2$ is Ala. In some cases, $X_3$ is Ala. In some cases, $X_1$ is Ala; $X_2$ is Ala; and $X_3$ is Ala.

APTSSSTKKT QLQLEHLLL$X_1$ LQMILNGINN YKNPKLTRML T$X_2$KF$X_3$MPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:26), where $X_1$ is any amino acid other than Asp; where $X_2$ is any amino acid other than Phe; and where $X_3$ is any amino acid other than Tyr. In some cases, $X_1$ is Ala. In some cases, $X_2$ is Ala. In some cases, $X_3$ is Ala. In some cases, $X_1$ is Ala; $X_2$ is Ala; and $X_3$ is Ala.

APTSSSTKKT QLQLE$X_1$LLL$X_2$ LQMILNGINN YKNPKLTRML T$X_3$KF$X_4$MPKKA TELKHLQCLE EELKPLEEVL NLAQSKNFHL RPRDLISNIN VIVLELKGSE TTFMCEYADE TATIVEFLNR WITFCQSIIS TLT (SEQ ID NO:27), where $X_1$ is any amino acid other than His; where $X_2$ is any amino acid other than Asp; where $X_3$ is any amino acid other than Phe; and where $X_4$ is any amino acid other than Tyr. In some cases, $X_1$ is Ala. In some cases, $X_2$ is Ala. In some cases, $X_3$ is Ala. In some cases, $X_4$ is Ala. In some cases, $X_1$ is Ala; $X_2$ is Ala; $X_3$ is Ala; and $X_4$ is Ala.

APTSSSTKKT QLQLEHLLL$X_1$ LQMILNGINN YKNPKLTRML T$X_2$KF$X_3$MPKKA TELKHLQCLE EELKPLEEVL NLAQSKNFHL RPRDLISNIN VIVLELKGSE TTFMCEYADE TATIVEFLNR WITFC$X_4$SIIS TLT (SEQ ID NO:139), where $X_1$ is any amino acid other than Asp; where $X_2$ is any amino acid other than Phe; where $X_3$ is any amino acid other than Tyr; and where $X_4$ is any amino acid other than Gln. In some cases, $X_1$ is Ala. In some cases, $X_2$ is Ala. In some cases, $X_3$ is Ala. In some cases, $X_4$ is Ala. In some cases, $X_1$ is Ala; $X_2$ is Ala; $X_3$ is Ala; and $X_4$ is Ala.

APTSSSTKKT QLQLE$X_1$LLL$X_2$ LQMILNGINN YKNPKLTRML T$X_3$KF$X_4$MPKKA TELKHLQCLE EELKPLEEVL NLAQSKNFHL RPRDLISNIN VIVLELKGSE TTFMCEYADE TATIVEFLNR WITFC$X_5$SIIS TLT (SEQ ID NO:140), where $X_1$ is any amino acid other than His; where $X_2$ is any amino acid other than Asp; where $X_3$ is any amino acid other than Phe; where $X_4$ is any amino acid other than Tyr; and where $X_5$ is any amino acid other than Gln. In some cases, $X_1$ is Ala. In some cases, $X_2$ is Ala. In some cases, $X_3$ is Ala. In some cases, $X_4$ is Ala. In some cases, $X_5$ is Ala. In some cases, any two, three, four, or all five of $X_1$ is Ala; $X_2$ is Ala; $X_3$ is Ala; $X_4$ is Ala; and/or $X_5$ is Ala.

APTSSSTKKT QLQLE$X_1$LLLD LQMILNGINN YKNPKLTRML T$X_2$KFYMPKKA TELKHLQCLE EELKPLEEVL NLAQSKNFHL RPRDLISNIN VIVLELKGSE TTFMCEYADE TATIVEFLNR WITFC$X_3$SIIS TLT (SEQ ID NO:141), where $X_1$ is any amino acid other than His; where $X_2$ is any amino acid other than Phe; and where $X_3$ is any amino acid other than Gln. In some cases, $X_1$ is Ala. In some cases, $X_2$ is Ala. In some cases, $X_3$ is Ala. In some cases, any two or all three of $X_1$ is Ala; $X_2$ is Ala; and/or $X_3$ is Ala.

7 IL-4 and its Variants

As one non-limiting example, a MOD or variant MOD present in a masked TGF-β construct or complex is an IL-4 or variant IL-4 polypeptide. Wild-type IL-4 has two isoforms, IL-4a and IL-413, both of which bind to the membrane bound IL-4 receptor (isoform 1) or its soluble counterpart (isoform 2).

A wild-type human IL-4 isoform 1 precursor polypeptide can comprise the following amino acid sequence: MGLTSQLLPP LFFLLACAGN FVHGHKCDIT LQEIIKTLNS LTEQKTLCTE LTVTDIFAAS KNTTEKETFC RAATVLRQFY SHHEKDTRCL GATAQQFHRH KQLIRFLKRL DRNLWGLAGL NSCPVKEANQ STLENFLERL KTIMREKYSK CSS (SEQ ID NO:28) NCBI Ref. Seq. NP_000580.1.

A mature wild-type human IL-4 isoform 1 polypeptide can comprise the following amino acid sequence: KCDIT LQEIIKTLNS LTEQKTLCTE LTVTDIFAAS KNTTEKETFC RAATVLRQFY SHHEKDTRCL GATAQQFHRH KQLIRFLKRL DRNLWGLAGL NSCPVKEANQ STLENFLERL KTIMREKYSK CSS (SEQ ID NO:29).

A wild-type human IL-4 isoform 2 precursor polypeptide can comprise the following amino acid sequence: MGLTSQLLPP LFFLLACAGN FVHGHKCDIT LQEIIKTLNS LTEQKNTTEK ETFCRAATVL RQFYSHHEKD TRCLGATAQQ FHRHKQLIRF LKRLDRNLWG LAGLNSCPVK EANQSTLENF LERLKTIMRE KYSKCSS, NCBI Ref. Seq: NP_758858.1, (SEQ ID NO:30).

A mature wild-type human IL-4 isoform 2 polypeptide can comprise the following amino acid sequence KCDIT LQEIIKTLNS LTEQKNTTEK ETFCRAATVL RQFYSHHEKD TRCLGATAQQ FHRHKQLIRF LKRLDRNLWG LAGLNSCPVK EANQSTLENF LERLKTIMRE KYSKCSS (SEQ ID NO:31).

Both IL-4 isoform 1 and isoform 2 bind to the membrane bound IL-4 receptor (IL-4R) and/or its soluble isoform 2. Membrane bound IL-4 receptor can have the sequence MGWLCSGLLF PVSCLVLLQV ASSGNMKVLQ EPTCVSDYMS ISTCEWKMNG PTNCSTELRL LYQLVFLLSE AHTCIPENNG GAGCVCHLLM DDVVSADNYT LDLWAGQQLL WKGSFKPSEH VKPRAPGNLT VHTNVSDTLL LTWSNPYPPD NYLYNHLTYA VNIWSENDPA DFRIYNVTYL EPSLRIAAST LKSGISYRAR VRAWAQCYNT TWSEWSPSTK WHNSYREPFE QHLLLGVSVS CIVILAVCLL CYVSIT- KIKK EWWDQIPNPA RSRLVAIIIQ DAQGSQWEKR SRGQEPAKCP HWKNCLTKLL PCFLEHNMKR DEDPHKAAKE MPFQGSGKSA WCPVEISKTV LWPE-SISVVR CVELFEAPVE CEEEEEVEEE KGSFCASPES SRDDFQEGRE GIVARLTESL FLDLLGEENG GFCQQDMGES CLLPPSGSTS AHMPWDEFPS AGPKE-APPWG KEQPLHLEPS PPASPTQSPD NLTCTETPLV IAGNPAYRSF SNSLSQSPCP RELGPDPLLA RHLEEVE-PEM PCVPQLSEPT TVPQPEPETW EQILRRNVLQ HGAAAAPVSA PTSGYQEFVH AVEQGGTQAS AVVGLGPPGE AGYKAFSSLL ASSAVSPEKC GFGASSGEEG YKPFQDLIPG CPGDPAPVPV PLFTGFLDRE PPRSPQSSHL PSSSPEHLGL EPGEKVEDMP KPPLPQEQAT DPLVDSLGSG IVY-SALTCHL CGHLKQCHGQ EDGGQTPVMA SPCCGCCCGD RSSPPTTPLR APDPSPGGVP LEA-SLCPASL APSGISEKSK SSSSFHPAPG NAQSSSQTPK IVNFVSVGPT YMRVS, (SEQ ID NO:32), NCBI Ref. Seq. NP_000409.1, with aas 26 to 825 forming the mature polypeptide, and aas 233-256 the transmembrane region; the ectodomain of the protein can be used to determine binding affinity to IL-4 isoform 1 or 2.

The soluble isoform 2, having the sequence MGWLCSGLLF PVSCLVLLQV ASSGNMKVLQ EPTCVSDYMS ISTCEWKMNG PTNCSTELRL LYQLVFLLSE AHTCIPENNG GAGCVCHLLM DDVVSADNYT LDLWAGQQLL WKGSFKPSEH VKPRAPGNLT VHTNVSDTLL LTWSNPYPPDN YLYNHLTYAVN IWSENDPADF RIYNVTYLEP SLRI-AASTLK SGISYRARVRA WAQCYNTTWSE WSP-STKWHNS NIC, (SEQ ID NO:33), UniProtKB-P24394, can also be used for determining binding affinity of both IL-4 isoforms.

In some cases, a variant IL-4 isoform 1 or 2 polypeptide (e.g., a variant of SEQ ID NOs:29 or 31) exhibits reduced binding affinity to a mature IL-4 receptor sequence set forth in SEQ ID NO:32 or its ectodomain, or the soluble IL-4 receptor set forth in SEQ ID NO:33, compared to the binding affinity of an IL-4 polypeptide comprising the amino acid sequence set forth in SEQ ID NO:29 or SEQ ID NO:31. For example, in some cases, a variant IL-4 isoform 1 or 2 polypeptide binds the mature IL-4 receptor set forth in SEQ ID NO:32 (or its ectodomain) or in SEQ ID NO:33 with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of a IL-4 isoform 1 or 2 polypeptide comprising the amino acid sequence set forth in SEQ ID NO:29 or SEQ ID NO:31.

In some cases, a variant IL-4 isoform 1 or 2 polypeptide (e.g., a variant of SEQ ID NOs:29 or 31) has a binding affinity that is from 1 nM to 1 mM to a mature IL-4 receptor set forth in SEQ ID NO:32 (or its ectodomain) or in SEQ ID NO:33 (e.g., from 1 nM to 10 nM, from 10 nM to 100 nM, from 100 nM to 1 μM, from 1 μM to 10 μM, from 10 μM to 100 μM, or from 100 μM to 1 mM). As another example, in some cases, a variant IL-4 isoform 1 or 2 polypeptide (e.g., a variant of SEQ ID NOs:29 or 31) has a binding affinity for the mature IL-4 receptor set forth in SEQ ID NO:32 (or its ectodomain) or in SEQ ID NO:33 that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-4 isoform 1 or 2 polypeptide has a single aa substitution compared to the IL-4 isoform 1 or 2 amino acid sequence set forth in SEQ ID NO:29 or SEQ ID NO:31. In some cases, a variant IL-4 isoform 1 or 2 polypeptide has from 2 aa to 10 aa substitutions compared to the IL-4 isoform 1 or 2 amino acid sequence set forth in SEQ ID NO:29 or SEQ ID NO:31. In some cases, a variant IL-4 isoform 1 or 2 polypeptide has 2 aa substitutions compared to the IL-4 isoform 1 or 2 amino acid sequence set forth in SEQ ID NO:29 or SEQ ID NO:31. In some cases, a variant IL-4 isoform 1 or 2 polypeptide has 3 aa or 4 aa substitutions compared to the IL-4 isoform 1 or 2 amino acid sequence set forth in SEQ ID NO:29 or SEQ ID NO:31. In some cases, a variant IL-4 polypeptide has 5 aa or 6 aa substitutions compared to the IL-4 isoform 1 or 2 amino acid sequence set forth in SEQ ID NO:29 or SEQ ID NO:31. In some cases, a variant IL-4 isoform 1 or 2 polypeptide has 7 aa or 8 aa substitutions compared to the IL-4 isoform 1 or 2 amino acid sequence set forth in SEQ ID NO:29 or SEQ ID NO:31. In some cases, a variant IL-4 isoform 1 or 2 polypeptide has 9 aa or 10 aa substitutions compared to the IL-4 isoform 1 or 2 amino acid sequence set forth in SEQ ID NO:29 or SEQ ID NO:31.

Suitable variant IL-4 isoform 1 or 2 polypeptide sequences include polypeptide sequences having at least 80%, at least 85%, at least 90%, at least 95%, at least 98%, or at least 99% aa sequence identity to at least 80 contiguous aa (e.g., at least 100, or 110 contiguous aa) of SEQ ID NO:29 or SEQ ID NO:31 (e.g., which have at least one aa substitution, deletion or insertion).

8 IL-6 and its Variants

As one non-limiting example, a MOD or variant MOD present in a masked TGF-β construct or complex is an IL-6 or variant IL-6 polypeptide. Wild-type IL-6 binds to the IL-6 receptor that is comprised of an alpha and beta (gp130) subunit, which forms a signaling hexamer of two trimers having an IL-6 molecule and each subunit. See, e.g., Lacroix et al., *J. Biol. Chem.*, 290(45)26943-953 (2015).

A wild-type human IL-6 precursor polypeptide can comprise the following amino acid sequence: MNSFSTSAFG PVAFSLGLLL VLPAAFPAPV PPGEDSKDVA APHRQPLTSS ERIDKQIRYI LDGISALRKE TCNKSNMCES SKEALAENNL NLPKMAEKDG CFQSGFNEET CLVKIITGLL EFEVYLEYLQ NRFESSE-EQA RAVQMSTKVL IQFLQKKAKN LDAITTPDPT TNASLLTKLQ AQNQWLQDMT THLILRSFKE FLQSSLRALR QM (SEQ ID NO:34) NCBI Ref. Seq. NP_0005911.

A mature wild-type human IL-6 polypeptide can comprise the following amino acid sequence:

```
                                        (SEQ ID NO: 35)
VPPGEDSKDVA APHRQPLTSS ERIDKQIRYI LDGISALRKE

TCNKSNMCES SKEALAENNL NLPKMAEKDG CFQSGFNEET

CLVKIITGLL EFEVYLEYLQ NRFESSEEQA RAVQMSTKVL

IQFLQKKAKN LDAITTPDPT TNASLLTKLQ AQNQWLQDMT

THLILRSFKE FLQSSLRALR QM.
```

IL-6 binds to the membrane bound IL-6 receptor, which is comprised of an alpha and beta subunit. The human IL-6R alpha subunit can have the sequence MLAVGCALLA ALLAAPGAAL APRRCPAQEV ARGVLTSLPG DSVTLTCPGV EPEDNATVHW VLRKPAAGSH PSRWAGMGRR LLLRSVQLHD SGNYSCYRAG RPAGTVHLLV DVPPEEPQLS CFRKSPLSNV VCEWGPRSTP SLTTKAVLLV RKFQNSPAED FQEPCQYSQE SQKFSCQLAV PEGDSSFYIV SMCVASSVGS KFSKTQTFQG CGILQPDPPA NITVTAVARN PRWLSVTWQD PHSWNSSFYR LRFELRYRAE RSKTFTTWMV KDLQHHCVIH DAWSGLRHVV QLRAQEEFGQ GEWSEWSPEA MGTPWTESRS PPAENEVSTP MQALTTNKDD DNILFRDSAN ATSLPVQDSS SVPLPTFLVA GGSLAFGTLL CIAIVLRFKK TWKLRALKEG KTSMHPPYSL GQLVPERPRP TPVLVPLISP PVSPSSLGSD NTSSHNRPDA RDPRSPYDIS NTDYFFPR, (SEQ ID NO:36), NCBI Ref. Seq: NP_000556.1, with aas 26 to 825 forming the mature polypeptide, and aas 233-256 the transmembrane region. After binding IL-6, the IL6 alpha subunit binds the IL-6 beta subunit.

The human IL-6R beta subunit can have the sequence (SEQ ID NO: 37)

```
MLTLQTWLVQ ALFIFLTTES TGELLDPCGY ISPESPVVQL
HSNFTAVCVL KEKCMDYFHV NANYIVWKTN HFTIPKEQYT
IINRTASSVT FTDIASLNIQ LTCNILTGFQ LEQNVYGITI
ISGLPPEKPK NLSCIVNEGK KMRCEWDGGR ETHLETNFTL
KSEWATHKFA DCKAKRDTPT SCTVDYSTVY FVNIEVWVEA
ENALGKVTSD HINFDPVYKV KPNPPHNLSV INSEELSSIL
KLTWTNPSIK SVIILKYNIQ YRTKDASTWS QIPPEDTAST
RSSFTVQDLK PFTEYVFRIR CMKEDGKGYW SDWSEEASGI
TYEDRPSKAP SFWYKIDPSH TQGYRTVQLV WKTLPPFEAN
GKILDYEVTL TRWKSHLQNY TVNATKLTVN LTNDRYLATL
TVRNLVGKSD AAVLTIPACD FQATHPVMDL KAFPKDNMLW
VEWTTPRESV KKYILEWCVL SDKAPCITDW QQEDGTVHRT
YLRGNLAESK CYLITVTPVY ADGPGSPESI KAYLKQAPPS
KGPTVRTKKV GKNEAVLEWD QLPVDVQNGF IRNYTIFYRT
IIGNETAVNV DSSHTEYTLS SLTSDTLYMV RMAAYTDEGG
KDGPEFTFTT PKFAQGEIEA IVVPVCLAFL LTTLLGVLFC
FNKRDLIKKH IWPNVPDPSK SHIAQWSPHT PPRHNFNSKD
QMYSDGNFTD VSVVEIEAND KKPFPEDLKS LDLFKKEKIN
TEGHSSGIGG SSCMSSSRPS ISSSDENESS QNTSSTVQYS
TVVHSGYRHQ VPSVQVFSRS ESTQPLLDSE ERPEDLQLVD
HVDGGDGILP RQQYFKQNCS QHESSPDISH FERSKQVSSV
NEEDFVRLKQ QISDHISQSC GSGQMKMFQE VSAADAFGPG
TEGQVERFET VGMEAATDEG MPKSYLPQTV RQGGYMPQ,,
```

UniProtKB-P40189, with aas 23 to 918 forming the mature polypeptide, and aas 620-641 the transmembrane region.

As an alternative to IL-6 binding to the membrane bound IL-6R alpha subunit, it can bind the mature soluble form of the IL-6R alpha subunit having the sequence MLAVGCALLA ALLAAPGAAL APRRCPAQEV ARGVLTSLPG DSVTLTCPGV EPEDNATVHW VLRKPAAGSH PSRWAGMGRR LLLRSVQLHD SGNYSCYRAG RPAGTVHLLV DVPPEEPQLS CFRKSPLSNV VCEWGPRSTP SLTTKAVLLV RKFQNSPAED FQEPCQYSQE SQKFSCQLAV PEGDSSFYIV SMCVASSVGS KFSKTQTFQG CGILQPDPPA NITVTAVARN PRWLSVTWQD PHSWNSSFYR LRFELRYRAE RSKTFTTWMV KDLQHHCVIH DAWSGLRHVV QLRAQEEFGQ GEWSEWSPEA MGTPWTESRS PPAENEVSTP MQALTTNKDD DNILFRDSAN ATSLPVQDSS SVPLPTFLVA GGSLAFGTLL CIAIVLRFKK TWKLRALKEG KTSMHPPYSL GQLVPERPRP TPVLVPLISP PVSPSSLGSD NTSSHNRPDA RDPRSPYDIS NTDYFFPR, (SEQ ID NO:38) with the mature peptide comprising aas 20 to 468, UniProtKB-P08887.1. The soluble subunit can take the place of the membrane bound IL-6R alpha subunit and can be used in binding affinity assays.

In some cases, a variant IL-6 polypeptide (e.g., a variant of SEQ ID NO:35) exhibits reduced binding affinity to a mature IL-6 receptor set forth in SEQ ID NOs:36 and 37, or SEQ ID NOs:37 and 38, compared to the binding affinity of an IL-6 polypeptide comprising the amino acid sequence set forth in SEQ ID NO:35. For example, in some cases, a variant IL-6 polypeptide binds a mature IL-6 receptor set forth in SEQ ID NOs:36 and 37, or SEQ ID NOs:37 and 38, with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of an IL-6 polypeptide comprising the amino acid sequence set forth in SEQ ID NO:35.

In some cases, a variant IL-6 polypeptide (e.g., a variant of SEQ ID NO:35) has a binding affinity that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM) to a mature IL-6 receptor set forth in SEQ ID NOs:36 and 37 or SEQ ID NOs:37 and 38. As another example, in some cases, a variant IL-6 polypeptide (e.g., a variant of SEQ ID NO:35) has an affinity to a mature IL-6 receptor set forth in SEQ ID NOs:36 and 37, or SEQ ID NOs:37 and 38, that is from 100 nM to 100 μM (e.g., from 100 nM to 1 μM, from 1 μM to 10 μM, or from 10 μM to 100 μM). As another example, in some cases, a variant IL-6 polypeptide (e.g., a variant of SEQ ID NO:35) has a binding affinity for the mature IL-6 receptor set forth in SEQ ID NOs:36 and 37, or SEQ ID NOs:37 and 38, that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-6 polypeptide has a single aa substitution compared to the IL-6 amino acid sequence set forth in SEQ ID NO:35. In some cases, a variant IL-6 polypeptide has from 2 aa to 10 aa substitutions compared to the IL-6 amino acid sequence set forth in SEQ ID NO:35. In some cases, a variant IL-6 polypeptide has 2 aa substitutions compared to the IL-6 amino acid sequence set forth in SEQ ID NO:35. In some cases, a variant IL-6 polypeptide has 3 aa or 4 aa substitutions compared to the IL-6 amino acid sequence set forth in SEQ ID NO:35. In some cases, a variant IL-6 polypeptide has 5 aa or 6 aa substitutions compared to the IL-6 amino acid sequence set forth in SEQ ID NO:35. In some cases, a variant IL-6 polypeptide has 7 aa or 8 aa substitutions compared to the IL-6 amino acid sequence set forth in SEQ ID NO:35. In some cases, a variant IL-6 polypeptide has 9 aa or 10 aa substitutions compared to the IL-6 amino acid sequence set forth in SEQ ID NO:35.

Suitable variant IL-6 polypeptide sequences include polypeptide sequences having at least 80%, at least 85%, at least 90%, at least 95%, at least 98%, or at least 99% aa sequence identity to at least 80 contiguous aa (e.g., at least 100, or 110 contiguous aa) of SEQ ID NO:35 (e.g., which have at least one aa substitution, deletion or insertion).

9 IL-7 and its Variants

As one non-limiting example, a MOD or variant MOD present in a masked TGF-β construct or complex is an IL-7 or variant IL-7 polypeptide. Wild-type IL-7 has four isoforms all of which bind to the membrane bound IL-7 receptor, which has two subunits, alpha (α) and the common gamma (common-γ) chain.

A wild-type human IL-7 isoform 1 precursor polypeptide can comprise the following amino acid sequence: MFHVSFRYIF GLPPLILVLL PVASSDCDIE GKDGKQYESV LMVSIDQLLD SMKEIGSNCL NNEFNFFKRH ICDANKEGMF LFRAARKLRQ FLKMNSTGDF DLHLLKVSEG TTILLNCTGQ VKGRKPAALG EAQPTKSLEE NKSLKEQKKL NDLCFLKRLL QEIKTCWNKI LMGTKEH (SEQ ID NO:39) UniProtKB-P13232, NCBI Ref Seq. NP_000871.1.

A mature wild-type human IL-7 isoform 1 polypeptide can comprise the following amino acid sequence: DCDIE GKDGKQYESV LMVSIDQLLD SMKEIGSNCL NNEFNFFKRH ICDANKEGMF LFRAARKLRQ FLKMNSTGDF DLHLLKVSEG TTILLNCTGQ VKGRKPAALG EAQPTKSLEE NKSLKEQKKL NDLCFLKRLL QEIKTCWNKI LMGTKEH (SEQ ID NO:40).

A wild-type human IL-7 isoform 2 precursor polypeptide can comprise the following amino acid sequence: MFHVSFRYIF GLPPLILVLL PVASSDCDIE GKDGKQYESV LMVSIDQLLD SMKEIGSNCL NNEFNFFKRH ICDANKVKGR KPAALGEAQP TKSLEENKSL KEQKKLNDLC FLKRLLQEIK TCWNKILMGT KEH, (SEQ ID NO:41) NCBI Ref. Seq: NP_001186815.1.

A mature wild-type human IL-7 isoform 2 polypeptide can comprise the following amino acid sequence: SDCDIE GKDGKQYESV LMVSIDQLLD SMKEIGSNCL NNEFNFFKRH ICDANKVKGR KPAALGEAQP TKSLEENKSL KEQKKLNDLC FLKRLLQEIK TCWNKILMGT KEH (SEQ ID NO:42).

A wild-type human IL-7 isoform 3 precursor polypeptide can comprise the following amino acid sequence: MFHVSFRYIF GLPPLILVLL PVASSDCDIE GKDGKQYESV LMVSIDQLLD SMKEIGSNCL NNEFNFFKRH ICDANKEGMF LFRAARKLRQ FLKMNSTGDF DLHLLKVSEG TTILLNCTGQ EENKSLKEQK KLNDLCFLKR LLQEIKTCWN KILMGTKEH, (SEQ ID NO:43) NCBI Ref. Seq: NP_001186816.1.

A mature wild-type human IL-7 isoform 3 polypeptide can comprise the following amino acid sequence: CDIE GKDGKQYESV LMVSIDQLLD SMKEIGSNCL NNEFNFFKRH ICDANKEGMF LFRAARKLRQ FLKMNSTGDF DLHLLKVSEG TTILLNCTGQ EENKSLKEQK KLNDLCFLKR LLQEIKTCWN KILMGTKEH (SEQ ID NO:44).

A wild-type human IL-7 isoform 4 precursor polypeptide can comprise the following amino acid sequence: MFHVSFRYIF GLPPLILVLL PVASSDCDIE GKDGKQYESV LMVSIDQLLD SMKEIGSNCL NNEFNFFKRH ICDANKEENK SLKEQKKLND LCFLKRLLQE IKTCWNKILM GTKEH, NCBI Ref. Seq: NP_001186817.1 (SEQ ID NO:45).

A mature wild-type human IL-7 isoform 4 polypeptide can comprise the following amino acid sequence: SDCDIE GKDGKQYESV LMVSIDQLLD SMKEIGSNCL NNEFNFFKRH ICDANKEENK SLKEQKKLND LCFLKRLLQE IKTCWNKILM GTKEH (SEQ ID NO:46).

The IL-7 receptor alpha subunit can have the sequence: MTILGTTGFM VFSLLQVVSG ESGYAQNGDL EDAELDDYSF SCYSQLEVNG SQHSLTCAFE DPDVNITNLE FEICGALVEV KCLNFRKLQE IYFIETKKFL LIGKSNICVK VGEKSLTCKK IDLTTIVKPE APFDLSVVYR EGANDFVVTF NTSHLQKKYV KVLMHDVAYR QEKDENKWTH VNLSSTKLTL LQRKLQPAAM YEIKVRSIPD HYFKGFWSEW SPSYYFRTPE INNSSGEMDP ILLTISILSF FSVALLVILA CVLWKKRIKP IVWPSLPDHK KTLEHLCKKP RKNLNVSFNP ESFLDCQIHR VDDIQARDEV EGFLQDTFPQ QLEESEKQRL GGDVQSPNCP SEDVVITPES FGRDSSLTCL AGNVSACDAP ILSSSRSLDC RESGKNGPHV YQDLLLSLGT TNSTLPPPFS LQSGILTLNP VAQGQPILTS LGSNQEEAYV TMSSFYQNQ (SEQ ID NO:47), NCBI Ref. Seq. NP_002176.2, with aas 21 to 459 forming the mature polypeptide, and aas 240-264 the transmembrane region. All or part of the receptor subunit (e.g., the ectodomain (aas 21-239) of the protein can be used to determine binding affinity to IL-7 isoforms along with IL-7 receptor gamma subunit.

The common-γ subunit (IL-7RG or IL-R7γ) can have the sequence MLKPSLPFTS LLFLQLPLLG VGLNTTILTP NGNEDTTADF FLTTMPTDSL SVSTLPLPEV QCFVFNVEYM NCTWNSSSEP QPTNLTLHYW YKNSDNDKVQ KCSHYLFSEE ITSGCQLQKK EIHLYQTFVV QLQDPREPRR QATQMLKLQN LVIPWAPENL TLHKLSESQL ELNWNNRFLN HCLEHLVQYR TDWDHSWTEQ SVDYRHKFSL PSVDGQKRYT FRVRSRFNPL CGSAQHWSEW SHPIHWGSNT SKENPFLFAL EAVVISVGSM GLIISLLCVY FWLERTMPRI PTLKNLEDLV TEYHGNFSAW SGVSKGLAES LQPDYSERLC LVSEIPPKGG ALGEGPGASP CNQHSPYWAP PCYTLKPET, NCBI Ref. Seq. NP_000197.1, (SEQ ID NO:48) with aas 23 to 369 forming the mature polypeptide, and aas 263-283 the transmembrane region. All or part of the receptor subunit (e.g., the ectodomain (aas 23-262) of the protein can be used to determine binding affinity to IL-7 along with the alpha subunit.

In some cases, a variant IL-7 isoform 1, 2, 3, or 4 polypeptide (e.g. of SEQ ID NOs:40, 42, 44, or 46) exhibits reduced binding affinity to a mature IL-7 receptor sequence (e.g., an IL-7 receptor comprising all or part of the polypeptides set forth in SEQ ID NOs: 47 and 48, such as their ectodomains), compared to the binding affinity of an IL-7 polypeptide comprising the amino acid sequence set forth in SEQ ID NOs:40, 42, 44, or 46. For example, in some cases, a variant IL-7 isoform 1, 2, 3, or 4 polypeptide binds an IL-7 receptor comprising all or part of the polypeptides set forth in SEQ ID NOs: 47 and 48, such as their ectodomains, with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of an IL-7 isoform 1, 2, 3, or 4 polypeptide comprising the amino acid sequence set forth in SEQ ID NOs:40, 42, 44, or 46.

In some cases, a variant of IL-7 isoform 1, 2, 3, or 4 polypeptide (e.g. a variant of SEQ ID NOs:40, 42, 44, or 46) has a binding affinity for an IL-7 receptor comprising all or part of the polypeptides set forth in SEQ ID NOs: 47 and 48, such as their ectodomains, that is from 1 nM to 1 mM. In some cases, a variant IL-7 isoform 1, 2, 3, or 4 polypeptide (e.g. a variant of SEQ ID NOs:40, 42, 44, or 46) has a binding affinity to a mature IL-7 receptor comprising all or part of the polypeptides set forth in SEQ ID NOs: 47 and 48, such as their ectodomains, that is from 100 nM to 100 μM (e.g., from 100 nM to 1 μM, from 1 μM to 10 μM, or from 10 μM to 100 μM). As another example, in some cases, a variant IL-7 isoform 1, 2, 3, or 4 polypeptide has a binding affinity for a mature IL-7 receptor comprising all or part of the polypeptides set forth in SEQ ID NOs:47 and 48, such as their ectodomains, that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-7 isoform 1, 2, 3, or 4 polypeptide has a single aa substitution compared to the IL-7 isoform 1, 2, 3, or 4 amino acid sequence set forth in SEQ ID NOs:40, 42, 44, or 46. In some cases, a variant IL-7 isoform 1, 2, 3, or 4 polypeptide has from 2 aa to 10 aa substitutions compared to the IL-7 isoform 1, 2, 3, or 4 amino acid sequence set forth in SEQ ID NOs:40, 42, 44, or 46. In some cases, a variant IL-7 isoform 1, 2, 3, or 4 polypeptide has 2 aa substitutions compared to the IL-7 isoform 1, 2, 3, or 4 amino acid sequence set forth in SEQ ID NOs:40, 42, 44, or 46. In some cases, a variant IL-7 isoform 1, 2, 3, or 4 polypeptide has 3 aa or 4 aa substitutions compared to the IL-7 isoform 1, 2, 3, or 4 amino acid sequence set forth in SEQ ID NOs:40, 42, 44, or 46. In some cases, a variant IL-7 polypeptide has 5 aa or 6 aa substitutions compared to the IL-7 isoform 1, 2, 3, or 4 amino acid sequence set forth in SEQ ID NOs:40, 42, 44, or 46. In some cases, a variant IL-7 isoform 1, 2, 3, or 4 polypeptide has 7 aa or 8 aa substitutions compared to the IL-7 isoform 1, 2, 3, or 4 amino acid sequence set forth in SEQ ID NOs:40, 42, 44, or 46. In some cases, a variant IL-7 isoform 1, 2, 3, or 4 polypeptide has 9 aa or 10 aa substitutions compared to the IL-7 isoform 1, 2, 3, or 4 amino acid sequence set forth in SEQ ID NOs:40, 42, 44, or 46.

Suitable variant IL-7 isoform 1, 2, 3, or 4 polypeptide sequences include polypeptide sequences having at least 80%, at least 85%, at least 90%, at least 95%, at least 98%, or at least 99% aa sequence identity to at least 50 contiguous aa (e.g., at least 60, at least 70, at least 80, at least 90, at least 100, or at least 110 contiguous aa) of SEQ ID NOs:40, 42, 44, or 46 (e.g., which have at least one aa substitution, deletion or insertion).

10 IL-10 and its Variants

As one non-limiting example, a MOD or variant MOD present in a masked TGF-β construct or complex is an IL-10 or variant IL-10 polypeptide, such as monomeric IL-10 variants having an insertion in the hinge region between the D and E helices described by Josephson et al., *J. Biol. Chem.* 275:13552-13557 (2000). Wild-type IL-10 has isoforms, all of which bind to the membrane bound IL-10 receptor, which has both alpha (α) IL-10RA and beta (β) IL-10RB subunits. The receptor exists as a tetramer on the surface of cells (e.g., B cells, T cells, NK cells, mast cells, and dendritic cells).

A wild-type human IL-10 isoform 1 precursor polypeptide can comprise the following amino acid sequence: MHS-SALLCCL VLLTGVRASP GQGTQSENSC THFPGNLPNM LRDLRDAFSR VKTFFQMKDQ LDNLLLKESL LEDFKGYLGC QALSEMIQFY LEEVMPQAEN QDPDIKAHVN SLGENLKTLR LRLRRCHRFL PCENKSKAVE QVKNAFNKLQ EKGIYKAMSE FDIFINYIEA YMTMKIRN (SEQ ID NO:49) UniProtKB-P22301, NCBI Ref Seq. NP_000563.1, which may have an H227L sequence variation.

A mature wild-type human IL-10 polypeptide can comprise the following amino acid sequence SP GQGTQSENSC THFPGNLPNM LRDLRDAFSR VKTFFQMKDQ LDNLLLKESL LEDFKGYLGC QALSEMIQFY LEEVMPQAEN QDPDIKAHVN SLGENLKTLR LRLRRCHRFL PCENKSKAVE QVKNAFNKLQ EKGIYKAMSE FDIFINYIEA YMTMKIRN (SEQ ID NO:50).

A human IL-10 polypeptide can comprise the following amino acid sequence MIQFYLEEVM PQAENQDPDI KAHVNSLGEN LKTLRLRLRR CHRFLPCENK SKAVEQVKNA FNKLQEKGIY KAMS, UniProtKB-A0A286YEX3 1 (SEQ ID NO:51).

An IL-10 polypeptide can comprise an insertion in the hinge region between the D and E helices of the IL-10 polypeptide (e.g., a 5-7 aa insertion adjacent to any of E48, N49, K50, or S51 of SEQ ID NO:51, or the equivalent location of in SEQ ID NOs:49 or 50) that render it a monomeric form. A monomeric IL-10 polypeptide can comprise a 5-7 aa insertion between N49 and K50 of SEQ ID NO:51 (or the equivalent location of in SEQ ID NOs:49 or 50). In an instance the 5-7 amino acids comprise Ala, Gly and/or Ser. In an instance the 5-7 amino acids are selected from Ala or Ser. In an instance the 5-7 aas are selected from Gly and Ser. In one instance the insertion comprises the IL-10M1 aa insertion (GGGGSGGG SEQ ID NO:142) between N49 and K50 of SEQ ID NO:51 (or the equivalent location in SEQ ID NOs:49 or 50). In one instance the IL-10 variant consists of the IL-10M1 (SEQ ID NO:189) GGGSGG inserted into SEQ ID NO:51 between aa 49 and 50. See, e.g., Josephson et al., *J. Biol. Chem.* 275:13552-13557 (2000).

The IL-10 receptor alpha subunit can have the sequence: MLPCLVVLLA ALLSLRLGSD AHGTELPSPP SVWFEAEFFH HILHWTPIPN QSESTCYEVA LLRY-GIESWN SISNCSQTLS YDLTAVTLDL YHSNGYRARV RAVDGSRHSN WTVTNTRFSV DEVTLTVGSV NLEIHNGFIL GKIQLPRPKM APANDTYESI FSHFREYEIA IRKVPGNFTF THKKVKHENF SLLTS-GEVGE FCVQVKPSVA SRSNKGMWSK EECISLTRQY FTVTNVIIFF AFVLLLSGAL AYCLALQLYV RRRKKLPSVL LFKKPSPFIF ISQRPSPETQ DTIHPLDEEA FLKVSPELKN LDLHGSTDSG FGSTKPSLQT EEPQFLLPDP HPQADRTLGN REPPVLGDSC SSGSSNSTDS GICLQEPSLS PSTGPTWEQQ VGSNSRGQDD SGIDLVQNSE GRAGDTQGGS ALGHHSPPEP EVPGEEDPAA VAFQGYLRQT RCAEEKATKT GCLEEESPLT DGLGPKFGRC LVDEAGLHPP ALAKGYLKQD PLEMTLASSG APTGQWNQPT EEWSLLALSS CSDLGISDWS FAHDLAPLGC VAAPGGLLGS FNSDLVTLPL ISSLQSSE, (SEQ ID NO:52), NCBI Ref. Seq. NP_001549.2, with aas 21 to 587 forming the mature polypeptide, and aas 236-256 the transmembrane region. All or part of the receptor subunit (e.g., the ectodomain (aas 21-235) of the protein can be used to determine binding affinity to IL-10 isoforms along with IL-10 receptor beta subunit.

The IL-10 receptor beta subunit can have the sequence MAWSLGSWLG GCLLVSALGM VPPPENVRMN SVNFKNILQW ESPAFAKGNL TFTAQYLSYR IFQDKCMNTT LTECDFSSLS KYGDHTLRVR AEFADEHSDW VNITFCPVDD TIIGPPGMQV EVLADSLHMR FLAPKIENEY ETWTMKNVYN SWTYNVQYWK NGTDEKFQIT PQYDFEVLRN LEPWTTYCVQ VRGFLPDRNK AGEWSEPVCE QTTHDETVPS WMVAVILMAS VFMVCLALLG CFALLWCVYK KTKYAFSPRN SLPQHLKEFL GHPHHNTLLF FSFPLSDEND VFDKLSVIAE DSESGKQNPG DSCSLGTPPG QGPQS, NCBI Ref. Seq. NP_000619.3, (SEQ ID NO:53) with aas 20 to 325 forming the mature polypeptide, and aas 221-242 the transmembrane region. All or part of the receptor subunit (e.g., the ectodomain (aas 20-220) of the protein can be used to determine binding affinity to IL-10 along with the alpha subunit.

In some cases, a variant IL-10 isoform polypeptide (e.g., a variant of SEQ ID NOs: 50, 51, or an monomeric IL-10 variant of those sequences bearing a 5-7 aa insertion into the hinge between the D and E helices described above) exhibits reduced binding affinity to a mature IL-10 receptor sequence (e.g., an IL-10 receptor comprising all or part of the polypeptides set forth in SEQ ID NOs: 52 or 53, such as their ectodomains), compared to the binding affinity of an IL-10 polypeptide comprising the amino acid sequence set forth in SEQ ID NOs: 50 or 51. For example, in some cases, a variant of an IL-10 polypeptide (e.g., a variant of SEQ ID NOs: 50 or 51) binds an IL-10 receptor comprising all or part of the polypeptides set forth in SEQ ID NOs: 52 and 53, such as their ectodomains, with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of an IL-10 isoform (e.g., of SEQ ID NOs: 50 or 51) to an IL-10 receptor comprising all or part of the polypeptides set forth in SEQ ID NOs: 52 or 53 (such as their ectodomains).

In some cases, a variant IL-10 polypeptide (e.g., a variant of SEQ ID NOs: 50 or 51 which may comprise one of the above-mentioned insertions in the hinge region between the D and E helices) has a binding affinity for an IL-10 receptor (e.g., comprising all or part of the polypeptides set forth in SEQ ID NOs: 52 and 53, such as their ectodomains), that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM). In some cases, a variant IL-10 polypeptide (e.g., a variant of SEQ ID NOs: 50 or 51) has a binding affinity to a mature IL-10 receptor (e.g., comprising all or part of the polypeptides set forth in SEQ ID NOs:52 and 53, such as their ectodomains), that is from 100 nM to 100 μM (e.g., from 100 nM to 1 μM, from 1 μM to 10 μM, or from 10 μM to 100 μM). As another example, in some cases, a variant IL-10 polypeptide (e.g., a variant of SEQ ID NOs:50 or 51) has a binding affinity for a mature IL-10 receptor (e.g., comprising all or part of the polypeptides set forth in SEQ ID NOs:52 and 53, such as their ectodomains), that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-10 polypeptide has a single aa substitution compared to an IL-10 polypeptide sequence set forth in SEQ ID NOs:50 or 51. In some cases, a variant IL-10 polypeptide has from 2 aa to 10 aa substitutions compared to an IL-10 polypeptide sequence set forth in SEQ ID NOs:50 or 51. In some cases, a variant IL-10 polypeptide has 2 aa substitutions compared to an IL-10 polypeptide sequence set forth in SEQ ID NOs:50 or 51. In some cases, a variant IL-10 polypeptide has 3 aa or 4 aa substitutions compared to an IL-10 polypeptide sequence set forth in SEQ ID NOs:50 or 51. In some cases, a variant IL-10 polypeptide has 5 aa or 6 aa substitutions compared to an IL-10 polypeptide sequence set forth in SEQ ID NOs:50 or 51. In some cases, a variant IL-10 polypeptide has 7 aa or 8 aa substitutions compared to an IL-10 polypeptide sequence set forth in SEQ ID NOs:50 or 51. In some cases, a variant IL-10 polypeptide has 9 aa or 10 aa substitutions compared to an IL-10 polypeptide sequence set forth in SEQ ID NOs:50 or 51. In some cases, a variant IL-10 polypeptide has 1-10 aa substitutions, and comprises a 5-7 aa substitution in hinge region between the D and E helices (e.g., K49 and N50 of SEQ ID NO:50) compared to an IL-10 polypeptide sequence set forth in SEQ ID NOs:50 or 51.

Suitable variant IL-10 polypeptide sequences include polypeptide sequences with at least 80%, at least 85%, at least 90%, at least 95%, at least 98%, or at least 99% aa sequence identity to at least 50 contiguous aa (e.g., at least 60, at least 70, at least 80, at least 90, at least 100, at least 110, at least 120, at least 130, at least 140, at least 150, or at least 160) contiguous aa of SEQ ID NOs: 50 or 51 (e.g. which have at least one aa substitution, deletion or insertion).

11 IL-15 and its Variants

In some cases, the MOD present in a masked TGF-β construct or complex of the present disclosure is an IL-15 polypeptide. The sequences of IL-15 polypeptides, including two isoforms formed by alternative splicing giving rise to different precursor proteins, are known in the art. In an embodiment, a wt. IL-15 polypeptide has the sequence: MRISKPHLRS ISIQCYLCLL LNSHFLTEAG IHVFILGCFS AGLPKTEANW VNVISDLKKI EDLIQSMHID ATLYTESDVH PSCKVTAMKC FLLELQVISL ESGDASIHDT VENLIILANN SLSSNGNVTE SGCKECEELE EKNIKEFLQS FVHIVQMFIN TS, (SEQ ID NO. 54), UniProtKB-P40933, NCBI Ref. NP_000576.1, IL-15 preprotein with aa 1 to 29 as the signal peptide, and 30-48 as the propeptide.

A mature IL-15 polypeptide, denoted as isoform 1 for the purpose of this disclosure, can have the form NW VNVISDLKKI EDLIQSMHID ATLYTESDVH PSCKVTAMKC FLLELQVISL ESGDASIHDT VENLIILANN SLSSNG-NVTE SGCKECEELE EKNIKEFLQS FVHIVQMFIN TS, (SEQ ID NO:55).

IL-15 is structurally similar to IL-2 and signals through a cell surface trimeric receptor having the same beta and gamma chains as the IL-2 receptor but having distinct IL-15 receptor alpha (IL-15Ra) subunit. An amino acid sequence of human an IL-15Rα isoform 1 precursor protein can be MAPRRARGCR TLGLPALLLL LLLRPPATRG ITCPPPMSVE HADIWVKSYS LYSRERYICN SGFKRK-AGTS SLTECVLNKA TNVAHWTTPS LKCIRDPALV HQRPAPPSTV TTAGVTPQPE SLSPSGKEPA ASSPSSNNTA ATTAAIVPGS QLMPSKSPST GTTEIS-SHES SHGTPSQTTA KNWELTASAS HQPPGVYPQG HSDTTVAIST STVLLCGLSA VSLLACYLKS RQTP-PLASVE MEAMEALPVT WGTSSRDEDL ENCSHHL (SEQ ID NO:56) NCBI Ref NP_002180, with aas 1-30 forming the signal sequence, and aas peptide 31-267 the mature polypeptide. The sequences of the IL-2Rβ, and IL-2Rγ are provided as SEQ ID NOs: 11 and 12.

In some cases, a variant IL-15 isoform 1 polypeptide (e.g., a variant of SEQ ID NO:55) exhibits reduced binding affinity to a mature IL-15 receptor sequence (e.g., an IL-15 receptor comprising all or part of the polypeptides set forth in SEQ ID NOs:11, 12, and 56, such as their ectodomains), compared to the binding affinity of an IL-15 polypeptide comprising the amino acid sequence set forth in SEQ ID NO:55. For example, in some cases, a variant of an IL-15 polypeptide (e.g., a variant of SEQ ID NO:55) binds an IL-15 receptor comprising all or part of the polypeptides set forth in SEQ ID NOs:11, 12, and 56, such as their ectodomains, with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of a IL-15 polypeptide comprising the amino acid sequence set forth in SEQ ID NO:55.

In some cases, a variant IL-15 polypeptide (e.g., a variant of SEQ ID NO:55) has a binding affinity for an IL-15 receptor comprising all or part of the polypeptides set forth in SEQ ID NOs:11, 12, and 56, such as their ectodomains, that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM). As another example, in some cases, a variant IL-15 polypeptide (e.g., a variant of SEQ ID NO:55) has a binding affinity for a mature IL-15 receptor comprising all or part of the polypeptides set forth in SEQ ID NOs:11, 12, and 56, such as their ectodomains, that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-15 polypeptide (e.g., a variant of SEQ ID NO:55) has a single aa substitution compared to the IL-15 polypeptide sequence set forth in SEQ ID NO:55. In some cases, a variant IL-15 polypeptide (e.g., a variant of SEQ ID NO:55) has from 2 aa to 10 aa substitutions compared to the IL-15 polypeptide sequence set forth in SEQ ID NO:55. In some cases, a variant IL-15 polypeptide has 2 aa substitutions compared to the IL-15 polypeptide sequence set forth in SEQ ID NO:55. In some cases, a variant IL-15 polypeptide has 3 aa or 4 aa substitutions compared to the IL-15 polypeptide sequence set forth in SEQ ID NO:55. In some cases, a variant IL-15 polypeptide has 5 aa or 6 aa substitutions compared to the IL-15 polypeptide sequence set forth in SEQ ID NO:55. In some cases, a variant IL-15 polypeptide has 7 aa or 8 aa substitutions compared to the IL-15 polypeptide sequence set forth in SEQ ID NO:55. In some cases, a variant IL-15 polypeptide has 9 aa or 10 aa substitutions compared to the IL-15 polypeptide sequence set forth in SEQ ID NO:55.

Suitable variant IL-15 polypeptide sequences include polypeptide sequences with at least 80%, at least 85%, at least 90%, at least 95%, at least 98%, or at least 99% aa sequence identity to at least 50 contiguous aa (e.g., at least 60, at least 70, at least 80, at least 90, at least 100, or at least 110 contiguous aa) of SEQ ID NO:55, and which have at least one aa substitution, deletion or insertion.

12 IL-21 and its Variants

In some cases, the MOD present in a masked TGF-β construct or complex of the present disclosure is an IL-21 polypeptide. The sequences of IL-21 polypeptides, including two isoforms formed by alternative splicing giving rise to different precursor proteins, are known in the art.

In an embodiment, a wild type (wt.) IL-21 isoform 1 polypeptide has the sequence MRSSPGNMER IVI-CLMVIFL GTLVHKSSSQ GQDRHMIRMR QLIDI-VDQLK NYVNDLVPEF LPAPEDVETN CEWSAFSCFQ KAQLKSANTG NNERIINVSI KKLKRKPPST NAGRRQKHRL TCPSCDSYEK KPPKEFLERF KSLLQKMIHQ HLSSRTHGSE DS, (SEQ ID NO:57), UniProtKB-Q9HBE4, NCBI Ref. NP_068575.1, IL-21 protein with aa 1 to 29 as the signal peptide.

A mature IL-21 isoform 1 polypeptide can have the aa sequence Q GQDRHMIRMR QLIDIVDQLK NYVNDLVPEF LPAPEDVETN CEWSAFSCFQ KAQLKSANTG NNERIINVSI KKLKRKPPST NAGRRQKHRL TCPSCDSYEK KPPKEFLERF KSLLQKMIHQ HLSSRTHGSE DS, (SEQ ID NO:58).

In an embodiment, a wild type (wt.) IL-21 isoform 2 polypeptide has the sequence

```
                                        (SEQ ID NO: 59)
MRSSPGNMER IVICLMVIFL GTLVHKSSSQ GQDRHMIRMR

QLIDIVDQLK NYVNDLVPEF LPAPEDVETN CEWSAFSCFQ

KAQLKSANTG NNERIINVSI KKLKRKPPST NAGRRQKHRL

TCPSCDSYEK KPPKEFLERF KSLLQKMIHQ HLSSRTHGSE DS,,
```

NP_001193935.1, IL-21 protein with aa 1 to 29 as the signal peptide.

A mature IL-21 isoform 2 polypeptide can have the aa sequence MRSSPGNMER IVICLMVIFL GTLVHKSSSQ GQDRHMIRMR QLIDIVDQLK NYVNDLVPEF LPAPE-DVETN CEWSAFSCFQ KAQLKSANTG NNERIINVSI KKLKRKPPST NAGRRQKHRL TCPSCDSYEK KPPKE-FLERF KSLLQKVSTL SFI, (SEQ ID NO:60).

IL-21 signals through a dimeric cell surface receptor having the same gamma chains as the IL-2 receptor but having distinct IL-21R receptor subunit. An aa sequence of a human IL-21R isoform 1 precursor protein can be MPRG-WAAPLL LLLLQGGWGC PDLVCYTDYL QTVICILEMW NLHPSTLTLT WQDQYEELKD EATSCSLHRS AHNATHATYT CHMDVFHFMA DDIFSVNITD QSGNYSQECG SFLLAESIKP APPFNVTVTF SGQYNISWRS DYEDPAFYML KGKLQYELQY RNRGDPWAVS PRRKLISVDS RSVSLLPLEF RKDSSYELQV RAGPMPGSSY QGTWSEWSDP VIFQTQSEEL KEGWNPHLLL LLLL-VIVFIP AFWSLKTHPL WRLWKKIWAV PSPERFFMPL YKGCSGDFKK WVGAPFTGSS LELGPWSPEV PSTLEVYSCH PPRSPAKRLQ LTELQEPAEL VESDGVPKPS FWPTAQNSGG SAYSEERDRP YGLVSIDTVT VLDAEGPCTW PCSCEDDGYP ALD-LDAGLEP SPGLEDPLLD AGTTVLSCGC VSAGSPGLGG PLGSLLDRLK PPLADGEDWA GGLPWGGRSP GGVSESEAGS PLAGLDMDTF DSGFVGSDCS SPVECDFTSP GDEGPPRSYL RQWV-VIPPPL SSPGPQAS (SEQ ID NO:61) NCBI Ref Seq. NP_068570.1, with aas 1-19 forming the signal sequence, aas 20-538 the mature polypeptide, aas 233 . . . 253 the transmembrane domain, and aas 20-232 the ectodomain.

In some cases, a variant IL-21 polypeptide exhibits reduced binding affinity to a mature IL-21 receptor sequence (e.g., an IL-21 receptor comprising all or part of the polypeptides set forth in SEQ ID NOs:12 and 61, such as their ectodomains), compared to the binding affinity of a wt. IL-21 polypeptide comprising the amino acid sequence set forth in SEQ ID NO:58 or 60. For example, in some cases, a variant of an IL-21 polypeptide comprising SEQ ID NO:58 or 60 binds an IL-21 receptor comprising all or part of the polypeptides set forth in SEQ ID NOs:12 and 61, such as their ectodomains, with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of a wt. IL-21 polypeptide comprising the amino acid sequence set forth in SEQ ID NO:58 or 60.

In some cases, a variant IL-21 polypeptide (e.g., a variant of SEQ ID NO:58 or 60) has a binding affinity for an IL-21 receptor (e.g., comprising all or part of the polypeptides set forth in SEQ ID NOs:12 and 61, such as their ectodomains) that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM). In some cases, a variant IL-21 polypeptide (e.g., a variant of SEQ ID NO:58 or 60) has a binding affinity to all or part of a mature IL-21 receptor (e.g., comprising all or part of the polypeptides set forth in SEQ ID NOs:12 and 61, such as their ectodomains), that is from 100 nM to 100 μM (e.g., from 100 nM to 1 μM, from 1 μM to 10 μM, or from 10 μM to 100 μM). As another example, in some cases, a variant IL-21 polypeptide (e.g., a variant of SEQ ID NO:58 or 60) has a binding affinity for all or part of an IL-21 receptor (e.g., comprising all or part of the polypeptides set forth in SEQ ID NOs:12 and 61, such as their ectodomains) that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-21 polypeptide (e.g., a variant of SEQ ID NO:58 or 60) has a single aa substitution compared to the IL-21 polypeptide sequence set forth in SEQ ID NO:58 or 60. In some cases, a variant IL-21 polypeptide (e.g., a variant of SEQ ID NO:58 or 60) has from 2 aa to 10 aa substitutions compared to the IL-21 polypeptide sequence set forth in SEQ ID NO:58 or 60. In some cases, a variant IL-21 polypeptide has 2 aa substitutions compared to the IL-21 polypeptide sequence set forth in SEQ ID NO:58 or 60. In some cases, a variant IL-21 polypeptide has 3 aa or 4 aa substitutions compared to the IL-21 polypeptide sequence set forth in SEQ ID NO:58 or 60. In some cases, a variant IL-21 polypeptide has 5 aa or 6 aa substitutions compared to the IL-21 polypeptide sequence set forth in SEQ ID NO:58 or 60. In some cases, a variant IL-21 polypeptide has 7 aa or 8 aa substitutions compared to the IL-21 polypeptide sequence set forth in SEQ ID NO:58 or 60. In some cases, a variant IL-21 polypeptide has 9 aa or 10 aa substitutions compared to the IL-21 polypeptide sequence set forth in SEQ ID NO:58 or 60.

Suitable IL-21 polypeptide sequences include polypeptide sequences with at least 80%, at least 85%, at least 90%, at least 95%, at least 98%, or at least 99% aa sequence identity to at least 50 contiguous aa (e.g., at least 60, at least 70, at least 80, at least 90, at least 100, or at least 110 contiguous aa) of SEQ ID NO:58 or 60, and which have at least one aa substitution, deletion or insertion.

13 IL-23 and its Variants

In some cases, the MOD present in a masked TGF-β construct or complex of the present disclosure is an IL-23 polypeptide. IL-23 is a heterodimeric cytokine composed of an IL-23A (IL-23p19) subunit and an IL-12B (IL-12p40) subunit (that is shared with IL-12).

In an embodiment, a wild type (wt.) IL-23A polypeptide has the sequence: MLGSRAVMLL LLLPWTAQGR AVPGGSSPAW TQCQQLSQKL CTLAWSAHPL VGHMDLREEG DEETTNDVPH IQCGDGCDPQ GLRDNSQFCL QRIHQGLIFY EKLLGSDIFT GEPSLLPDSP VGQLHASLLG LSQLLQPEGH HWETQQIPSL SPSQPWQRLL LRFKILRSLQ AFVA-VAARVF AHGAATLSP, (SEQ ID NO:62), NCBI Ref. Seq. NP_057668.1 protein with aa 1 to 19 as the signal peptide, and 20-189 as the mature peptide.

A mature IL-23A polypeptide can have the aa sequence: R AVPGGSSPAW TQCQQLSQKL CTLAWSAHPL VGHMDLREEG DEETTNDVPH IQCGDGCDPQ GLRDNSQFCL QRIHQGLIFY EKLLGSDIFT GEPSLLPDSP VGQLHASLLG LSQLLQPEGH HWETQQIPSL SPSQPWQRLL LRFKILRSLQ AFVA-VAARVF AHGAATLSP, (SEQ ID NO:63).

In an embodiment, a wild type (wt) IL-12B polypeptide has the sequence: MCHQQLVISW FSLVFLASPL VAI-WELKKDV YVVELDWYPD APGEMVVLTC DTPEED-GITW TLDQSSEVLG SGKTLTIQVK EFGDAGQYTC HKGGEVLSHS LLLLHKKEDG IWSTDILKDQ KEPKNKTFLR CEAKNYSGRF TCWWLTTIST DLTFSVKSSR GSSDPQGVTC GAATLSAERV RGDN-KEYEYS VECQEDSACP AAEESLPIEV MVDAVHKLKY ENYTSSFFIR DIIKPDPPKN LQLKPLKNSR QVEVSWEYPD TWSTPHSYFS LTFCVQVQGK SKREKKDRVF TDKTSATVIC RKNA-SISVRA QDRYYSSSWS EWASVPCS, (SEQ ID NO:64), UniProtKB—P29460 protein with aa 1 to 22 as the signal peptide, and 23 o 328 as the mature peptide.

A mature IL-12B polypeptide can have the aa sequence: IWELKKDV YVVELDWYPD APGEMVVLTC DTPEED-GITW TLDQSSEVLG SGKTLTIQVK EFGDAGQYTC HKGGEVLSHS LLLLHKKEDG IWSTDILKDQ KEPKNKTFLR CEAKNYSGRF TCWWLTTIST DLTFSVKSSR GSSDPQGVTC GAATLSAERV RGDNKEYEYS VECQEDSACP AAEESLPIEV MVDAVHKLKY ENYTSSFFIR DIIKPDPPKN LQLKPLKNSR QVEVSWEYPD TWSTPHSYFS LTFCVQVQGK SKREKKDRVF TDKTSATVIC RKNASISVRA QDRYYSSSWS EWASVPCS, (SEQ ID NO:65).

IL-23 signals through a dimeric cell surface receptor comprised of an IL-23 receptor polypeptide (IL-23R) and a subunit it has in common with the IL-12 receptor, denoted 12RB1 or 12Rβ1.

An IL-23R isoform 1 precursor protein sequence can be: MNQVTIQWDA VIALYILFSW CHGGITNINC SGHIWVEPAT IFKMGMNISI YCQAAIKNCQ PRKLHFYKNG IKERFQITRI NKTTARLWYK NFLEPHASMY CTAECPKHFQ ETLICGKDIS SGYPPDIPDE VTCVIYEYSG NMTCTWNAGK LTYIDTKYVV HVKSLETEEE QQYLTSSYIN ISTDSLQGGK KYLVWVQAAN ALGMEESKQL QIHLDDIVIP SAAVISRAET INATVPKTII YWDSQTTIEK VSCEMRYKAT TNQTWNVKEF DTNFTYVQQS EFYLEPNIKY VFQVRCQETG KRYWQPWSSL FFHKTPETVP QVTSKAFQHD TWNSGLTVAS ISTGHLTSDN RGDIGLLLGM IVFAVMLSIL SLIGIFNRSF RTGIKRRILL LIPKWLYEDI PNMKNSNVVK MLQENSELMN NNSSEQVLYV DPMITEIKEI FIPEHKPTDY KKENTGPLET RDYPQNSLFD NTTVVYIPDL NTGYKPQISN FLPEGSHLSN NNEITSLTLK PPVDSLDSGN NPRLQKHPNF AFSVSSVNSL SNTIFLGELS LILNQGECSS PDIQNSVEEE TTMLLENDSP SETIPEQTLL PDEFVSCLGI VNEELPSINT YFPQNILESH FNRISLLEK, (SEQ ID NO:66) NCBI Ref. Seq. NP_653302.2, with aas 1-23 forming the signal sequence, aas 24-629 the mature polypeptide, aas 356 to 376 the transmembrane domain, and aas 24-355 the ectodomain.

An 12RB1 isoform 1 precursor protein as sequence can be: MEPLVTWVVP LLFLFLLSRQ GAACRTSECC FQDPPYPDAD SGSASGPRDL RCYRISSDRY ECSWQYEGPT AGVSHFLRCC LSSGRCCYFA AGSATRLQFS DQAGVSVLYT VTLWVESWAR NQTEKSPEVT LQLYNSVKYE PPLGDIKVSK LAGQLRMEWE TPDNQVGAEV QFRHRTPSSP WKLGDCGPQD DDTESCLCPL EMNVAQEFQL RRRQLGSQGS SWSKWSSPVC VPPENPPQPQ VRFSVEQLGQ DGRRRLTLKE QPTQLELPEG CQGLAPGTEV TYRLQLHMLS CPCKAKATRT LHLGKMPYLS GAAYNVAVIS SNQFGPGLNQ TWHIPADTHT EPVALNISVG TNGTTMYWPA RAQSMTYCIE WQPVGQDGGL ATCSLTAPQD PDPAGMATYS WSRESGAMGQ EKCYYITIFA SAHPEKLTLW STVLSTYHFG GNASAAGTPH HVSVKNHSLD SVSVDWAPSL LSTCPGVLKE YVVRCRDEDS KQVSEHPVQP TETQVTLSGL RAGVAYTVQV RADTAWLRGV WSQPQRFSIE VQVSDWLIFF ASLGSFLSIL LVGVLGYLGL NRAARHLCPP LPTPCASSAI EFPGGKETWQ WINPVDFQEE ASLQEALVVE MSWDKGERTE PLEKTELPEG APELALDTEL SLEDGDRCKA KM, (SEQ ID NO:67) NCBI Ref Seq. NP_005526.1 with aas 1-23 forming the signal sequence, aas 24-662 the mature polypeptide, aas 546 to 570 the transmembrane domain, and aas 24-545 the ectodomain.

In some cases, a variant IL-23 (e.g., comprising a variant of SEQ ID NO:63 and/or 65) polypeptide exhibits reduced binding affinity to a mature IL-23 receptor sequence (e.g., an IL-23 receptor comprising all or part of the polypeptides set forth in SEQ ID NOs:66 and 67, such as their ectodomains), compared to the binding affinity of an IL-23 polypeptide comprising the amino acid sequence set forth in SEQ ID NO:63 or 65. For example, in some cases, a variant of an IL-23 polypeptide (e.g., comprising a variant of SEQ ID NO:63 and/or 65) binds an IL-23 receptor (e.g., comprising all or part of the polypeptides set forth in SEQ ID NOs:66 and 67, such as their ectodomains), with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of an IL-23 polypeptide comprising the amino acid sequence set forth in SEQ ID NO:63 or 65.

In some cases, a variant IL-23 polypeptide (e.g., comprising a variant of SEQ ID NO:63 and/or 65) has a binding affinity for an IL-23 receptor (e.g., comprising all or part of the polypeptides set forth in SEQ ID NOs:66 and 67, such as their ectodomains), that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM). As another example, in some cases, a variant IL-23 polypeptide (e.g., comprising a variant of SEQ ID NO:63 and/or 65) has a binding affinity for a mature IL-23 receptor (e.g., comprising all or part of the polypeptides set forth in SEQ ID NOs:66 and 67, such as their ectodomains) that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant IL-23 polypeptide (e.g., comprising a variant of SEQ ID NO:63 and/or 65) has a single aa substitution compared to the IL-23 polypeptide sequence set forth in SEQ ID NO:63 and/or 65. In some cases, a variant IL-23 polypeptide (e.g., comprising a variant of SEQ ID NO:63 and/or 65) has from 2 aa to 10 aa substitutions compared to the IL-23 polypeptide sequence set forth in SEQ ID NO:63 and/or 65. In some cases, a variant IL-23 polypeptide has 2 aa substitutions compared to the IL-23 polypeptide sequence set forth in SEQ ID NO:63 and/or 65. In some cases, a variant IL-23 polypeptide has 3 aa or 4 aa substitutions compared to the IL-23 polypeptide sequence set forth in SEQ ID NO:63 and/or 65. In some cases, a variant IL-23 polypeptide has 5 aa or 6 aa substitutions compared to the IL-23 polypeptide sequence set forth in SEQ ID NO:63 and/or 65. In some cases, a variant IL-23 polypeptide has 7 aa or 8 aa substitutions compared to the IL-23 polypeptide sequence set forth in SEQ ID NO:63 and/or 65. In some cases, a variant IL-23 polypeptide has 9 aa or 10 aa substitutions compared to the IL-23 polypeptide sequence set forth in SEQ ID NO:63 and/or 65.

Suitable variant IL-23 polypeptide sequences include polypeptide sequences with at least 80%, at least 85%, at least 90%, at least 95%, at least 98%, or at least 99% aa sequence identity to at least 50 contiguous aa (e.g., at least 60, at least 70, at least 80, at least 90, at least 100, at least 110, at least 120, at least 140, at least 160, at least 180, at least 200, at least 220, at least 240, at least 260, at least 280, at least 300, at least 320, or at least 340 contiguous aas) of SEQ ID NO:63 and/or 65, and which have at least one aa substitution, deletion or insertion.

14 Fas Ligand (FasL) and its Variants

In some cases, the MOD present in a masked TGF-β construct or complex of the present disclosure is a Fas Ligand (FasL). FasL is a homomeric type-II transmembrane protein in the tumor necrosis factor (TNF) family. FasL signals by trimerization of the Fas receptor in a target cell, which forms a death-inducing complex leading to apoptosis of the target cell. Soluble FasL results from matrix metalloproteinase-7 (MMP-7) cleavage of membrane-bound FasL at a conserved site.

In an embodiment, a wt. *Homo sapiens* FasL protein has the sequence MQQPFNYPYP QIYWVDSSAS SPWAPPGTVL PCPTSVPRRP GQRRPPPPPP PPPLPPPPPP PPLPPLPLPP LKKRGNHSTG LCLLVMFFMV LVALVGLGLG MFQLFHLQKE LAELRESTSQ MHTASSLEKQ IGHPSPPPEK KELRKVAHLT GKSNSRSMPL EWEDTYGIVL LSGVKYKKGG LVINETGLYF VYSKVYFRGQ SCNNLPLSHK VYMRNSKYPQ DLVMMEGKMM SYCTTGQMWA RSSYLGAVFN LTSADHLYVN VSELSLVNFE ESQTFFGLYK L, (SEQ ID NO:143), NCBI Ref. Seq. NP_000630.1, UniProtKB-P48023 where residues 1-80 are cytoplasmic, 81-102 are the transmembrane domain and aas 103-281 are extracellular (ectodomain).

A suitable FasL polypeptide comprises all or part of the ectodomain of FasL QLFHLQKE LAELRESTSQ MHTASSLEKQ IGHPSPPPEK KELRKVAHLT GKSNSRSMPL EWEDTYGIVL LSGVKYKKGG LVINETGLYF VYSKVYFRGQ SCNNLPLSHK VYMRNSKYPQ DLVMMEGKMM SYCTTGQMWA RSSYLGAVFN LTSADHLYVN VSELSLVNFE ESQTFFGLYK L. (SEQ ID NO:144).

A Fas receptor can have the sequence MLGIWTLLPL VLTSVARLSS KSVNAQVTDI NSKGLELRKT VTTVETQNLE GLHHDGQFCH KPCPPGERKA RDCTVNGDEP DCVPCQEGKE YTDKAHFSSK CRRCRLCDEG HGLEVEINCT RTQNTKCRCK PNFFCNSTVC EHCDPCTKCE HGIIKECTLT SNTKCKEEGS RSNLGWLCLL LLPIPLIVWV KRKEVQKTCR KHRKENQGSH ESPTLNPETV AINLSDVDLS KYITTIAGVM TLSQVKGFVR KNGVNEAKID EIKNDNVQDT AEQKVQLLRN WHQLHGKKEA YDTLIKDLKK ANLCTLAEKI QTIILKDITS DSENSNFRNE IQSLV, (SEQ ID NO:145) NCBI Reference Sequence: NP_000034.1, UniProtKB-P25445, where aas 26-173 form the ectodomain (extracellular domain), aas 174-190 form the transmembrane domain, and 191-335 the cytoplasmic domain. The ectodomain may be used to determine binding affinity with FasL.

In some cases, a variant FasL polypeptide (e.g., comprising a variant of SEQ ID NO144) exhibits reduced binding affinity to a mature Fas receptor sequence (e.g., a FasL receptor comprising all or part of the polypeptides set forth in SEQ ID NO:145, such as its ectodomain), compared to the binding affinity of an FasL polypeptide comprising the amino acid sequence set forth in SEQ ID NO:144. For example, in some cases, a variant FasL polypeptide (e.g., comprising a variant of SEQ ID NO:144) binds an Fas receptor (e.g., comprising all or part of the polypeptides set forth in SEQ ID NO:145, such as its ectodomains), with a binding affinity that is at least 10% less, at least 20% less, at least 30% less, at least 40% less, at least 50% less, at least 60% less, at least 70% less, at least 80% less, at least 90% less, at least 95% less, or more than 95% less, than the binding affinity of an FasL polypeptide comprising the amino acid sequence set forth in SEQ ID NO:144.

In some cases, a variant FasL polypeptide (e.g., comprising a variant of SEQ ID NO:144) has a binding affinity for an Fas receptor (e.g., comprising all or part of the polypeptides set forth in SEQ ID NO:145, such as its ectodomain), that is from 1 nM to 1 mM (e.g., from 1 nM to 10 nM, from 10 nM to 100 nM, from 100 nM to 1 μM, from 1 μM to 10 μM, from 10 μM to 100 μM, or from 100 μM to 1 mM). As another example, in some cases, a variant FasL polypeptide (e.g., comprising a variant of SEQ ID NO:144) has a binding affinity for a mature Fas receptor (e.g., comprising all or part of the polypeptides set forth in SEQ ID NO:145, such as its ectodomains), that is from about 100 nM to about 200 nM, from about 200 nM to about 300 nM, from about 300 nM to about 400 nM, from about 400 nM to about 500 nM, from about 500 nM to about 600 nM, from about 600 nM to about 700 nM, from about 700 nM to about 800 nM, from about 800 nM to about 900 nM, from about 900 nM to about 1 μM, from about 1 μM to about 5 μM, from about 5 μM to about 10 μM, from about 10 μM to about 20 μM, from about 20 μM to about 30 μM, from about 30 μM to about 50 μM, from about 50 μM to about 75 μM, or from about 75 μM to about 100 μM.

In some cases, a variant FasL polypeptide (e.g., comprising a variant of SEQ ID NO:144) has a single aa substitution compared to the FasL polypeptide sequence set forth in SEQ ID NO:144. In some cases, a variant FasL polypeptide (e.g., comprising a variant of SEQ ID NO:144) has from 2 aa to 10 aa substitutions compared to the FasL polypeptide sequence set forth in SEQ ID NO:144. In some cases, a variant FasL polypeptide has 2 aa substitutions compared to the FasL polypeptide sequence set forth in SEQ ID NO:144. In some cases, a variant FasL polypeptide has 3 aa or 4 aa substitutions compared to the FasL polypeptide sequence set forth in SEQ ID NO:144. In some cases, a variant FasL polypeptide has 5 aa or 6 aa substitutions compared to the FasL polypeptide sequence set forth in SEQ ID NO:144. In some cases, a variant FasL polypeptide has 7 aa or 8 aa substitutions compared to the FasL polypeptide sequence set forth in SEQ ID NO:144. In some cases, a variant FasL polypeptide has 9 aa or 10 aa substitutions compared to the FasL polypeptide sequence set forth in SEQ ID NO:144.

Suitable variant FasL polypeptide sequences include polypeptide sequences with at least 80%, at least 85%, at least 90%, at least 95%, at least 98%, or at least 99% aa sequence identity to at least 50 contiguous aa (e.g., at least 60, at least 70, at least 80, at least 90, at least 100, at least 110, at least 120, at least 140, at least 160, or at least 180 contiguous aa) of SEQ ID NO:144 (e.g., which have at least one aa substitution, deletion or insertion).

E. Scaffolds

Scaffold polypeptides serve, among other things, as structural elements providing a framework upon which other components of a masked TGF-β construct or complex are organized (see, e.g., FIG. 1, structure A, with an IgFc scaffold). Where the polypeptide sequence that masks a TGF-β polypeptide and the TGF-β polypeptide are located in trans (on a different polypeptides of the complex), scaffolds sequences that form interspecific and non-interspecific duplexes (or higher order structures) can keep the masking polypeptide sequence associated with the TGF-β polypeptide even during periods where the complex is in an open form with TGF-β polypeptide sequence is available to interact with other molecules (not in direct contact with the masking sequence). Depending on the nature of the scaffold, it can also act as an organizational element providing higher order structure in terms of protein folding and dimerization or multimerization (e.g., homodimerization or heterodimerization accomplished through dimerization sequences). The scaffold can also contribute to serum stability, particularly where it is an immunoglobulin heavy chain constant region (e.g., an Ig Fc). Suitable scaffold polypeptides will, in some cases, be half-life extending polypeptides. In some cases, a suitable scaffold polypeptide increases the in vivo half-life (e.g., the serum half-life) of a masked TGF-β construct or complex, compared to a control masked TGF-β construct or complex having a scaffold polypeptide with a different, non-immunoglobulin sequence, by at least about 10%, at least about 15%, at least about 25%, at least about 50%, at least about 2-fold, at least about 5-fold, at least about 10-fold, at least about 25-fold, at least about 50-fold, at least about 100-fold, or more than 100-fold. As an example, in some cases an Ig Fc polypeptide sequence (e.g., including interspecific Ig sequence such as a knob-in-hole sequence pairs) increases the stability and/or in vivo half-life (e.g., the serum half-life) of a masked TGF-β construct or complex, compared to a control masked TGF-β construct or complex having the Ig Fc polypeptide sequence replaced by a linker (e.g., a GGGS, SEQ ID NO:127, aa repeat of equal sequence length). The increase in in vivo half-life can be by at least about 10%, at least about 15%, at least about 25%, at least about 50%, at least about 2-fold, at least about 2.5-fold, at least about 5-fold, at least about 10-fold, at least about 25-fold, at least about 50-fold, at least about 100-fold, or more than 100-fold. Where an Ig Fc polypeptide is employed in the masked TGF-β construct, the Ig Fc can contain mutations that will prevent the spontaneous formation of dimers of the masked TGF-β construct (see, e.g., Tianlei Ying et al., *J. Biol. Chem.*, 287 (23), pp 19399-19408 (Jun. 1, 2012)), and additionally may include mutations (e.g., the LALA mutations discussed below) that substantially reduce or eliminate the ability of the Ig polypeptide to induce cell lysis, e.g., though complement-dependent cytotoxicity (CDC) and/or antibody-dependent cellular cytotoxicity (ADCC).

Where scaffold polypeptide sequences of a masked TGF-β construct comprise one or more sequences that permit scaffolds to interact (specifically bind) with other scaffold molecules, the masked TGF-β constructs can form homodimer complexes (see, e.g., FIG. 1, structure B) or heterodimer complexes (see, e.g., FIG. 1, structures C-F). Masked TGF-β constructs may also comprise one or more aa sequences that permit scaffolds to interact (specifically bind) with other scaffold molecules forming higher order structures. Sequences that form higher order multimer structures permit the formation of masked TGF-β construct or complexes of higher order (e.g., trimers, tetramers, pentamers etc.). By way of example, scaffold polypeptides comprising IgM Fc regions (e.g., SEQ ID NO:83) permit formation of pentameric (particularly when j-chain sequences are also expressed e.g., SEQ ID NO:84) or hexameric masked TGF-β construct or complexes. Petrušić et al., *Med Hypotheses.* 77(6):959-61 (2011). Masked TGF-β constructs in the form of homo- and hetero-dimers, trimers, tetramers, pentamers etc. are referred to as masked TGF-β complexes.

Where it is desirable to bring together a masked TGF-β with one or more other polypeptide sequences (such as one or more specific MODs or copies of MODs), scaffold polypeptide sequences may comprise interspecific dimerization sequences that tend to form a heterodimer with their counterpart interspecific binding (dimerization) sequence. Interspecific binding sequences may in some instance form homodimers, but preferentially dimerize (bind more strongly) with their counterpart interspecific binding sequence. Accordingly, specific heterodimers may be (tend to be) formed when an interspecific dimerization sequence and its counterpart interspecific binding sequence are incorporated into a pair of polypeptides. By way of example, where an interspecific dimerization sequence and its counterpart are incorporated into a pair of polypeptides to selectively form heterodimers, greater than 60%, 70%, 80%, 90%, 95%, 98% or 99% of an equimolar mixture of the peptides are engaged in heterodimer formation, with the remainder of the peptides present as monomers or homodimers.

A variety of aa sequences that specifically bind to each other or themselves with sufficient affinity may be utilized as dimerization sequences in a masked TGF-β construct or complex (see, e.g., U.S. Patent Publication No. 2003/0138440). The sequences may be of relatively compact size (e.g., such as less than about 300, 250, 225, 200, 175, 150, 125, 100, 75, or 50 aa). Dimerization/multimerization sequences include, but are not limited to: immunoglobulin heavy chain constant region (Ig Fc) polypeptide sequences (sequences comprising CH2-CH3 regions of immunoglobulins; see, e.g., FIGS. 2A-2H and SEQ ID NOs: 68 to 83); Fc knob-in-hole sequences (e.g., SEQ ID NOs:77 and 78); polypeptides of the collectin family (e.g., ACRP30 or ACRP30-like proteins) that contain collagen domains consisting of collagen repeats Gly-Xaa-Yaa; coiled-coil domains; leucine-zipper domains; Fos/Jun binding pairs; Ig heavy chain region 1 (CH1) and light chain constant region CL sequences (CH1/CL pairs such as a CH1 sequence paired with a κ or λ Ig light chain constant region sequence).

In some embodiments, the scaffold polypeptide sequence comprises an immunoglobulin heavy chain constant region (CH2-CH3) polypeptide sequence that functions as a dimerization or multimerization sequence (see, e.g., FIGS. 2A-2H and SEQ ID NOs: 68 to 83). In embodiments, the Ig polypeptide substantially will not induce cell lysis, e.g., through activation of complement-dependent cytotoxicity (CDC) and/or antibody-dependent cellular cytotoxicity (ADCC), and thus may include mutations that substantially reduce or eliminate the ability of the Ig polypeptide to induce cell lysis. In some cases, the Fc sequence has at least about 70%, at least about 80%, at least about 90%, at least about 95%, at least about 98%, at least about 99%, or 100% aa sequence identity to an aa sequence of an Fc region depicted in FIGS. 2A-2H. Such immunoglobulin sequences can covalently link the polypeptides of a masked TGF-β complex together by forming one or two interchain disulfide bonds. As discussed below, an additional disulfide bond can be introduced to stabilize dimers, particularly where a pair of interspecific Ig sequence such knob-in-hole polypeptide pairs are employed.

In an embodiment, the scaffold polypeptide sequence of a masked TGF-β complex comprises a sequence that has at least about 70%, at least about 80%, at least about 90%, at least about 95%, at least about 98%, at least about 99%, or 100% aa sequence identity to at least 150 contiguous aas (at least 175, at least 200, at least 225, at least 250, at least 275, at least 300, at least 325, or at least 350 contiguous aas), or all aas, of the IgA Fc sequence depicted in FIG. 2A (SEQ ID NO:68). In an embodiment, the scaffold polypeptide sequence comprises a sequence that has at least about 70%, at least about 80%, at least about 90%, at least about 95%, at least about 98%, at least about 99%, or 100% aa sequence identity to at least 150 contiguous aas (at least 175, at least 200, at least 225, at least 250, at least 275, at least 300, at least 325, or at least 350 contiguous aas), or all aas, of the IgD Fc sequence depicted in FIG. 2B (SEQ ID NO:69). In an embodiment, the scaffold polypeptide sequence comprises a sequence that has at least about 70%, at least about 80%, at least about 90%, at least about 95%, at least about 98%, at least about 99%, or 100% aa sequence identity to least 125 contiguous aas (at least 150, at least 175, or at least 200 contiguous aas), or all aas, of the IgE Fc sequence depicted in FIG. 2C (SEQ ID NO:70). In an embodiment, the scaffold polypeptide sequence comprises a sequence that has at least about 70%, at least about 80%, at least about 90%, at least about 95%, at least about 98%, at least about 99%, or 100% aa sequence identity to least 125 contiguous aas (at least 150, at least 175, or at least 200 contiguous aas), or all aas, of the wt. IgG Fc polypeptide sequence, such as the IgG1 Fc sequence depicted in FIG. 2D (SEQ ID NOs: 71-78). In an embodiment, the scaffold polypeptide sequence comprises a sequence that has at least about 70%, at least about 80%, at least about 90%, at least about 95%, at least about 98%, at least about 99%, or 100% aa sequence identity to at least 125 contiguous aas (at least 150, at least 175, at least 200, at least 225, at least 250, at least 275, or at least 300), or all aas, of the IgG2 Fc polypeptide sequence depicted in FIG. 2E (SEQ ID NO:79). In an embodiment, the scaffold polypeptide sequence comprises a sequence that has at least about 70%, at least about 80%, at least about 90%, at least about 95%, at least about 98%, at least about 99%, or 100% aa sequence identity to at least 125 contiguous aas (at least 150, at least 175, at least 200, or at least 225), or all aas, of the IgG3 Fc sequence depicted in FIG. 2F (SEQ ID NO:80). In an embodiment, the scaffold polypeptide sequence comprises a sequence that has at least about 70%, at least about 80%, at least about 90%, at least about 95%, at least about 98%, at least about 99%, or 100% aa sequence identity to at least 125 contiguous aas (at least 150, at least 175, at least 200, at least 225, or at least 250,), or all aas, of the IgG4 Fc sequence depicted in FIG. 2G (SEQ ID NO:81 or 82). In an embodiment, the scaffold polypeptide sequence comprises a sequence that has at least about 70%, at least about 80%, at least about 90%, at least about 95%, at least about 98%, at least about 99%, or 100% aa sequence identity to at least 125 contiguous aas (at least 150, at least 175, at least 200, at least 225, or at least 250), or all aas, of the IgM Fc polypeptide sequence depicted in FIG. 2H (SEQ ID NO:83). The above-recited polypeptides of a masked TGF-β complex comprising immunoglobulin scaffold polypeptide sequences (e.g., depicted in FIGS. 2A-2H) can be covalently linked together by formation of one or two interchain disulfide bonds between cysteines adjacent to their hinge regions.

In some cases, the dimerization sequence of a scaffold polypeptide present in a masked TGF-β construct or complex has at least about 70% (e.g., at least about 80%, 90%, 95%, 98%, 99% or 100%) aa sequence identity to the human IgG1 Fc polypeptide depicted in FIG. 2D, and comprises a substitution of N297 with an alanine (N297A substitution, or N77 as numbered in FIG. 2D, SEQ ID NO:74) substitution. In some cases, the dimerization sequence of a scaffold polypeptide present in masked TGF-β construct or complex comprises an aa sequence depicted in FIG. 2D (human IgG1 Fc), except for a substitution of N297 (N77 of the aa sequence depicted in FIG. 2D) with an aa other than asparagine. Substitutions at N297 lead to the removal of carbohydrate modifications and result antibody sequences with reduced complement component 1q ("C1q") binding compared to the wt. protein, and accordingly a reduction in complement-dependent cytotoxicity.

In some cases, the dimerization sequence of a scaffold polypeptide present in a masked TGF-β construct or complex comprises an aa sequence depicted in FIG. 2D (human IgG1 Fc), except for a substitution of L234 (L14 of the aa sequence depicted in FIG. 2D) with an aa other than leucine. L234 and other aas in the lower hinge region (e.g., aas 234-LLGGPS-239, which correspond to aas 14-19 of SEQ ID NO:71) of IgG are involved in binding to the Fc lambda receptor (FcλR), and accordingly, mutations at that location reduce binding to the receptor (relative to the wt. protein). In some cases, the dimerization sequence of a scaffold polypeptide present in a masked TGF-β construct or complex comprises an aa sequence depicted in FIG. 2D (human IgG1 Fc), except for a substitution of L235 (L15 of the aa sequence depicted in FIG. 2D) with an aa other than leucine. In some cases, the dimerization sequence of a scaffold polypeptide present in a masked TGF-β construct or complex comprises an aa sequence depicted in FIG. 2D (e.g., the wt. human IgG1 sequence) with L234A and L235A ("LALA") substitutions (the positions corresponding to positions 14 and 15 of the wt. aa sequence depicted in FIG. 2D; see, e.g., SEQ ID NO:75).

In some cases, the dimerization sequence of a scaffold polypeptide present in a masked TGF-β construct or complex comprises an aa sequence depicted in FIG. 2D (human IgG1 Fc), having a substitution of P331 (P111 of the aa sequence depicted in FIG. 2D) with an aa other than proline; in some cases, the substitution is a P331S substitution. Substitutions at P331, like those at N297, lead to reduced binding to C1q relative to the wt. protein, and thus a reduction in complement-dependent cytotoxicity. Substitutions of D270, K322, and/or P329 (corresponding to D50, K122, and P119 of SEQ ID NO:71 in FIG. 2D), for example with alanine, may be utilized alone or in place of a P331 substitution to reduce binding to C1q. In some cases, the dimerization sequence of a scaffold polypeptide present in a masked TGF-β construct or complex is an IgG1 Fc polypeptide that comprises L234A and/or L235A substitutions (substitutions of leucines at L14 and/or L15 of the aa sequences depicted in FIG. 2D with Ala). In some cases, the dimerization sequence of a scaffold polypeptide present in a masked TGF-β construct or complex comprises the aa sequence depicted in FIG. 2D (wt. human IgG1 Fc), except for substitutions at L234 and/or L235 (L14 and/or L15 of the aa sequence depicted in FIG. 2D) with aas other than leucine, and a substitution of P331 (P111 of the aa sequence depicted in FIG. 2D) with an aa other than proline. In some cases, the dimerization sequence of a scaffold polypeptide present in a masked TGF-β construct or complex comprises the "Triple Mutant" aa sequence (SEQ ID NO:73) depicted in FIG. 2D (human IgG1 Fc) comprising L234F, L235E, and P331S substitutions (corresponding to aa positions 14, 15, and 111 of the aa sequence depicted in FIG. 2D).

Where an asymmetric pairing between two polypeptides of a masked TGF-β complex is desired, the dimerization sequence of a scaffold polypeptide present in a masked TGF-β construct or complex comprises, consist essentially of, or consist of an interspecific binding sequence. Interspecific binding sequences favor formation of heterodimers with their cognate polypeptide sequence (i.e., the interspecific sequence and its counterpart interspecific sequence), particularly those based on immunoglobulin Fc sequence variants. Such interspecific polypeptide sequences include knob-in-hole without (KiH) or with (KiH)s-s a stabilizing disulfide bond, HA-TF, ZW-1, 7.8.60, DD-KK, EW-RVT, EW-RVTs-s, and A107 sequences. One interspecific binding pair comprises a T366Y and Y407T mutant pair in the CH3 domain interface of IgG1, or the corresponding residues of other immunoglobulins. See Ridgway et al., *Protein Engineering,* 9:7, 617-621 (1996), (substitutions are denoted by EU numbering scheme of Kabat et al. (1991)). A second interspecific binding pair involves the formation of a knob by a T366W substitution, and a hole by the triple substitutions T366S, L368A and Y407V on the complementary Fc sequence. See Xu et al. mAbs 7:1, 231-242 (2015). Another interspecific binding pair has a first Fc polypeptide with Y349C, T366S, L368A, and Y407V substitutions and a second Fc polypeptide with S354C, and T366W substitutions (disulfide bonds can form between the Y349C and the S354C). Brinkmann and Konthermann, mAbs, 9:2, 182-212 (2015). Fc polypeptide sequences, either with or without knob-in-hole modifications, can be stabilized by the formation of disulfide bonds between the Fc polypeptides (e.g., the hinge region disulfide bonds). Several interspecific polypeptide binding sequences are summarized in Table 1, with cross reference to the numbering of the as positions as they appear in the wt. IgG1 sequence (SEQ ID NO:71) set forth in FIG. 2D shown in brackets "I".

99%, or 100% sequence identity to at least 170, at least 180, at least 190, at least 200, at least 210, at least 220, or all 227 contiguous aas of the IgG1 of SEQ ID NO:71. One or both scaffold aa sequences optionally comprising substitutions at one of more of L234 and L235 (e.g., L234A/L235A "LALA" or L234F/L235E), N297 (e.g., N297A), P331 (e.g. P331S), L351 (e.g., L351K), T366 (e.g., T366S), P395 (e.g., P395V), F405 (e.g., F405R), Y407 (e.g., Y407A), and K409 (e.g., K409Y) using Kabat numbering. Those substitutions appear at L14 and L15 (e.g., L14A/L15A "LALA" or L14F/L15E), N77 (e.g., N77A), P111 (e.g. P111S), L131 (e.g., L131K), T146 (e.g., T146S), P175 (e.g., P175V), F185 (e.g., F185R), Y187 (e.g., Y187A), and K189 (e.g., K189Y) in the IgG1 sequence of SEQ ID NO:71.

In an embodiment, a masked TGF-β complex comprises a first polypeptide comprising an IgG1 scaffold with a

TABLE 1

Interspecific Sequences and their cognate counterpart interspecific sequences

| Interspecific Pair Name | Substitutions in the first interspecific polypeptide sequence | Substitutions in the second (counterpart) interspecific polypeptide sequence | Comments |
|---|---|---|---|
| KiH | T366W {T146W} | T366S/L368A/Y407V {T146S/L148A/Y187V} | Hydrophobic/steric complementarity |
| KiHs-s | T366W/S354C* {T146W/S134C*} | T366S/L368A/Y407V/Y349C {T146S/L148A/Y187V/Y129C} | KiH + inter-CH3 domain S—S bond |
| HA-TF | S364H/F405A {S144H/F185A} | Y349T/T394F {Y129T/T174F} | Hydrophobic/steric complementarity |
| ZW1 | T350V/L351Y/F405A/Y407V {T130V/L131Y/F185A/Y187V} | T350V/T366L/K392L/T394W {T130V/T146L/K172L/T174W} | Hydrophobic/steric complementarity |
| 7.8.60 | K360D/D399M/Y407A {K140D/D179M/Y187A} | E345R/Q347R/T366V/K409V {E125R/Q127R/T146V/K189V} | Hydrophobic/steric complementarity + electrostatic complementarity |
| DD-KK | K409D/K392D {K189D/K172D} | D399K/E356K {D179K/E136K} | Electrostatic complementarity |
| EW-RVT | K360E/K409W {K140E/K189W} | Q347R/D399V/F405T {Q127R/D179V/F185T} | Hydrophobic/steric complementarity & long-range electrostatic interaction |
| EW-RVTs-s | K360E/K409W/Y349C* {K140E/K189W/Y129C*} | Q347R/D399V/F405T/S354C {Q127R/D179V/F185T/S134C} | EW-RVT + inter-CH3 domain S—S bond |
| A107 | K370E/K409W {K150E/K189W} | E357N/D399V/F405T {E137N/D179V/F185T} | Hydrophobic/steric complementarity + hydrogen bonding complementarity |

Table 1 modified from Ha et al., Frontiers in Immunol. 7:1-16 (2016).
*aa forms a stabilizing disulfide bond.

In addition to the interspecific pairs of sequences in Table 1, interspecific "SEED" sequences having 45 residues derived from IgA in an IgG1 CH3 domain of the interspecific sequence and 57 residues derived from IgG1 in the IgA CH3 on the counterpart interspecific sequence. See Ha et al., *Frontiers in Immunol.,* 7:1-16 (2016).

In an embodiment, the scaffold sequences found in a masked TGF-β construct or complex comprise an interspecific binding sequence or its counterpart interspecific binding sequence selected from the group consisting of: knob-in-hole (KiH); knob-in-hole with a stabilizing disulfide (KiHs-s); HA-TF; ZW-1; 7.8.60; DD-KK; EW-RVT; EW-RVTs-s; A107; or SEED sequences.

In an embodiment, a masked TGF-β complex comprises a first polypeptide comprising an IgG1 scaffold with a T146W KiH sequence substitution, and a second polypeptide comprising an IgG1 scaffold with T146W, L148A, and Y187V KiH sequence substitutions, where the scaffolds comprises a sequence having at least 80%, 90%, 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering). See, e.g., FIG. 2D, SEQ ID NOs:77 and 78.

In an embodiment, the first and second polypeptide of a masked TGF-β complex comprise in the first scaffold sequence T146W and S134C KiHs-s substitutions, and in the second scaffold sequence T146S, L148A, Y187V and Y129C KiHs-s substitutions, where the scaffolds comprise a sequence having at least 80%, 90%, 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

In an embodiment, the first and second polypeptide of a masked TGF-β complex comprise in the first scaffold sequence S144H and F185A HA-TF substitutions, and in the second scaffold sequence Y129T and T174F HA-TF substitutions, where the scaffolds comprise a sequence having at least 80%, 90%, 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

In an embodiment, the first and second polypeptides of a masked TGF-β complex comprise in the first scaffold sequence T130V, L131Y, F185A, and Y187V ZW1 substitutions, and in the second scaffold sequence T130V, T146L, K172L, and T174W ZW1 substitutions, where the scaffolds comprise a sequence having at least 80%, 90%, 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

In an embodiment, the first and second polypeptides of a masked TGF-β complex comprise in the first scaffold sequence K140D, D179M, and Y187A 7.8.60 substitutions, and in the second scaffold sequence E125R, Q127R, T146V, and K189V 7.8.60 substitutions, where the scaffolds comprise a sequence having at least 80%, 90%, 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

In an embodiment, the first and second β polypeptides of a masked TGF-β complex comprise in the first scaffold sequence K189D, and K172D DD-KK substitutions, and in the second scaffold sequence D179K and E136K DD-KK substitutions, where the scaffolds comprise a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering), In an embodiment, the first and second polypeptides of a masked TGF-β complex comprise in the first scaffold sequence K140E and K189W EW-RVT substitutions, and in the second scaffold sequence Q127R, D179V, and F185T EW-RVT substitutions, where the scaffolds comprise a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

In an embodiment, the first and second polypeptides of a masked TGF-β complex comprise in the first scaffold sequence K140E, K189W, and Y129C EW-RVTs-s substitutions, and in the second scaffold sequence Q127R, D179V, F185T, and S134C EW-RVTs-s substitutions, where the scaffolds comprise a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

In an embodiment, the first and second polypeptides of a masked TGF-β complex comprise in the first scaffold sequence K150E and K189W A107 substitutions, and in the second scaffold sequence E137N, D179V, and F185T A107 substitutions, where the scaffolds comprise a sequence having at least 80%, 90%. 95%, 98%, 99%, or 100% sequence identity to at least 170, at least 180, at least 190, at least 200, at least 210, at least 220, or all 227 contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering).

As an alternative to the use of immunoglobulin heavy chain constant regions as scaffolds, immunoglobulin light chain constant regions can be paired with heavy chain CH1 sequences as dimerization sequences that form, or are a part of, scaffold polypeptide sequences. In an embodiment, the first and second polypeptides of a masked TGF-β complex comprise in the first scaffold sequence an Ig CH1 domain (e.g., the polypeptide of SEQ ID NO:85), and in the second scaffold sequence Ig κ chain constant region sequence SEQ ID NO:86), where the scaffolds comprise a sequence having at least 80%, 85%, 90%. 95%, 98%, 99%, or 100% sequence identity to at least 70, at least 80, at least 90, at least 100, or at least 110 contiguous aas of SEQ ID NOs: 85 and/or 86 respectively). See FIGS. 2J and 2K. The CH1 and Ig κ sequences may be modified to increase their affinity for each other, and accordingly the stability of any heterodimer formed utilizing them as a dimerization sequences. Among the substitutions that increase the stability of CH1-Ig κ heterodimers are those identified as the MD13 combination in Chen et al., MAbs, 8(4):761-774 (2016). In MD13 two substitutions are introduced into to each of the CH1 and Ig κ sequences. The CH1 sequence is modified to contain S64E and S66V substitutions (570E and S72V in SEQ ID NO:85 shown in FIG. 2J). The Ig κ sequence is modified to contain S69L and T71S substitutions (S68L and T70S in SEQ ID NO:86 shown in FIG. 2K).

In another embodiment, the first and second polypeptide of a masked TGF-β complex comprise in the first scaffold sequence an Ig CH1 domain (e.g., the polypeptide of SEQ ID NO:85), and in the second scaffold sequence Ig λ chain constant region sequence SEQ ID NO:87), where the scaffolds comprise a sequence having at least 80%, 85%, 90%. 95%, 98%, 99%, or 100% sequence identity to at least 70, at least 80, at least 90, at least 100, or at least 110 contiguous aas of SEQ ID NOs:85 and/or 87 respectively. See FIGS. 2J and 2K.

In some cases, the scaffold polypeptide sequence of a first and a second polypeptide of a masked TGF-β complex each comprise a leucine zipper polypeptide as a dimerization sequence. The leucine zipper polypeptides bind to one another to form dimer (e.g., homodimer). Non-limiting examples of leucine-zipper polypeptides include, for example, a peptide of any one of the following aa sequences: RMKQIEDKIEEILSKIYHIENEIARIKKLIGER (SEQ ID NO:88); LSSIEKKQEEQTSW LIWISNELTLIRNELAQS (SEQ ID NO:89); LSSIEKKLEEITSQLIQISNELTLIRNELAQ (SEQ ID NO:90; LSSIEKKLEEITSQLIQIRNELTLIRNELAQ (SEQ ID NO:91); LSSIEKKLEEITSQLQQIR NELTLIRNELAQ (SEQ ID NO:92); LSSLEKKLEELTSQLIQLRNELTLLRNELAQ (SEQ ID NO:93); ISSLEKKIEELTSQIQQLRNEITLLRNEIAQ (SEQ ID NO:94). In some cases, a leucine zipper polypeptide comprises the following aa sequence: LEIEAAFLERENTALETRVAELRQRVQR LRNRVSQYRTRYGPLGGGK (SEQ ID NO:95). Additional leucine-zipper polypeptides are known in the art, any of which is suitable for use as scaffold or incorporation into a scaffold as a dimerization sequence.

In some cases, the scaffold polypeptide sequence of a first and a second polypeptide of a masked TGF-β complex each comprise a coiled-coil peptide that forms a dimer (e.g., homodimer). Non-limiting examples of coiled-coil polypeptides include, for example, a peptide of any one of the following aa sequences: LKSVENRLAVVENQLKTVIEELKTVKDLLSN (SEQ ID NO:96); LARIEEKLKTIKA QLSEIASTLNMIREQLAQ (SEQ ID NO:97); VSRLEEKVKTLKSQVTELASTVSLLREQ VAQ (SEQ ID NO:98); IQSEKKIEDISSLIGQIQSEITLIRNEIAQ (SEQ ID NO:99); LMSLEKKLEELTQTLMQL QNELSMLKNELAQ (SEQ ID NO:100).

In some cases, a scaffold polypeptide sequence that permits dimerization (homodimerization) of a first and a second polypeptide of a masked TGF-β complex each comprise a polypeptide sequence having at least one cysteine residue that can form a disulfide bond. Examples of such polypeptide sequences include: a human FasL polypeptide VDLEGSTSNGRQCAGIRL (SEQ ID NO:101); EDDVTTTEELAPALVPPPKGTCAGWMA (SEQ ID NO:102); and GHDQETTTQGPGVLLPLP KGACTGQMA (SEQ ID NO:103).

Peptides suitable as multimerization (oligomerization) sequences permit formation of masked TGF-β complexes greater than dimers (e.g., trimers tetramers, pentamers, hexamers, etc.) include, but are not limited to, IgM constant regions (see, e.g., FIG. 2H) which forms hexamer, or pentamers (particularly when combined with a mature j-chain peptide lacking a signal sequence such as that provided in FIG. 2I). Collagen domains, which form trimers, can also be employed. Collagen domains can comprise (Gly-Xaa-Xaa) n, where Xaa is any aa, or and where n is an integer (e.g., from 10 to 40); where Xaa and Yaa are independently any aa and n is an integer from 10 to 40. In Gly-Xaa-Yaa sequences, Xaa and Yaa are frequently proline and hydroxyproline respectively in greater than 25%, 50%, 75%, 80% 90% or 95% of the Gly-Xaa-Yaa occurrences, or in each of the Gly-Xaa-Yaa occurrences. In some cases, a collagen domain comprises the sequence (Gly-Xaa-Pro)n, where n is an integer (e.g., from 10 to 40). A collagen oligomerization peptide can comprise the following aa sequence: VTAFSNMDDMLQKAHLVIEGTFIYLRDSTEFFIRVRDGWKKLQLGELIPIPADSPPP PALSSNP (SEQ ID NO:104).

F. TGF-β Polypeptides

As noted above, a masked TGF-β construct or complex comprises at least one TGF-β polypeptide (e.g., one or more independently selected TGF-β polypeptides) Amino acid sequences of TGF-β polypeptides are known in the art. In some cases, the TGF-β polypeptide present in a masked TGF-β construct or complex is a TGF-β1 polypeptide. In some cases, the TGF-β polypeptide present in a masked TGF-β construct or complex is a TGF-β2 polypeptide. In some cases, the TGF-β polypeptide present in a masked TGF-β construct or complex is a TGF-β3 polypeptide.

While TGF-β1, TGF-β2, or TGF-β3 polypeptide sequences may be incorporated into a masked TGF-β construct or complex, a variety of factors may influence the choice of the specific TGF-β polypeptide, and the specific sequence and aa substitutions that will be employed. For example, TGF-β1 and TGF-β3 are subject to “clipping” of their amino acid sequences when expressed in a number of mammalian cell systems (e.g., CHO cell). In addition, dimerized TGF-β (e.g., TGF-β2) has a higher affinity for the TβR3 (beta glycan receptor) than for the TβR2 receptor, which could lead to off target binding and loss of biological active masked protein to the large in vivo pool of non-signaling TβR3 molecules. In order to minimize high-affinity off target binding to TβR3, it may be desirable to substitute the residues leading to dimeric TGF-β molecules, which are joined by a disulfide bond. Accordingly, cysteine 77 (C77) may be substituted by an amino acid other than cysteine (e.g., a serine forming a C77S substitution).

A suitable TGF-β polypeptide can have a length from about 70 aas to about 125 aas; for example, a suitable TGF-β polypeptide can have a length from about 70 aas to about 80 aas from about 80 aas to about 90 aas; from about 90 aas to about 100 aas; from about 100 aas to about 105 aas, from about 105 aas to about 110 aas, from about 110 aas to about 112 aas, from about 113 aas to about 120 aas, or from about 120 aas to about 125 aas. A suitable TGF-β polypeptide can comprise an amino acid sequence having at least 60%, at least 70%, at least 80%, at least 80%, at least 85%, at least 90%, at least 95%, at least 98%, at least 99%, or 100%, aa sequence identity to at least 80, at least 90, at least 100, or at least 110 contiguous aas of the mature form of a human TGF-β1 polypeptide, a human TGF-132 polypeptide, or a human TGF-β3 polypeptide.

1 TGF-β1 Polypeptides

A suitable TGF-β1 polypeptide can comprise an amino acid sequence having at least 60%, at least 70%, at least 80%, at least 90%, at least 95%, at least 98%, at least 99%, or 100%, aa sequence identity to at least 70, at least 80, at least 90, at least 100, at least 110, or 112 aas of the following TGF-131 amino acid sequence: AL DTNYCFSSTE KNCCVRQLYI DFRKDLGWKW IHEPKGYHAN FCLGPCPYIW SLDTQYSKVL ALYNQHNPGA SAAPCCVPQA LEPLPIVYYV GRKPKVEQLS NMIVRSCKCS (SEQ ID NO:105, 112 aas in length); where the TGF-β1 polypeptide has a length of about 112 aas. A TGF-β1 preproprotein is provided in FIG. 3 as SEQ ID NO:106 Amino acids R25, C77, V92 and R94 are bolded and italicized see FIG. 4.

In some cases, a suitable TGF-β1 polypeptide comprises a C77S substitution. Thus, in some cases, a suitable TGF-β1 polypeptide comprises an amino acid sequence having at least 60%, at least 70%, at least 80%, at least 90%, at least 95%, at least 98%, at least 99%, or 100%, aa sequence identity to at least 70, at least 80, at least 90, at least 100, at least 110, or 112 aas of the following TGF-β1 amino acid sequence: AL DTNYCFSSTE KNCCVRQLYI DFRKDLGWKW IHEPKGYHAN FCLGPCPYIW SLDTQYSKVL ALYNQHNPGA SAAPSCVPQA LEPLPIVYYV GRKPKVEQLS NMIVRSCKCS (SEQ ID NO:107), where amino acid 77 is Ser. Positions 25, 77, 92 and 94 are bolded and italicized.

2 TGF-β2 Polypeptides

A suitable TGF-β2 polypeptide can comprise an amino acid sequence having at least 60%, at least 70%, at least 80%, at least 90%, at least 95%, at least 98%, at least 99%, or 100%, aa sequence identity to at least 70, at least 80, at least 90, at least 100, at least 110, or 112 aas of the following TGF-132 amino acid sequence: ALDAAYCFR NVQDNCCLRP LYIDFKRDLG WKWIHEPKGY NANFCAGACP YLWSSDTQHS RVLSLYNTIN PEASASPCCV SQDLEPLTIL YYIGKTPKIE QLSNMIVKSC KCS (SEQ ID NO:108), where the TGF-β2 polypeptide has a length of about 112 aas. A TGF-β2 preproprotein is provided in FIG. 3 as SEQ ID NO:109. Residues Lys 25, Ile 92, and/or Lys 94 are bolded and italicized.

In some cases, a suitable TGF-β2 polypeptide comprises a C77S substitution. Thus, in some cases, a suitable TGF-β2 polypeptide comprises an amino acid sequence having at least 60%, at least 70%, at least 80%, at least 90%, at least 95%, at least 98%, at least 99%, or 100%, aa sequence identity to at least 70, at least 80, at least 90, at least 100, at least 110, or 112 aas of the following TGF-β2 amino acid sequence: ALDAAYCFR NVQDNCCLRP LYIDFKRDLG WKWIHEPKGY NANFCAGACP YLWSSDTQHS RVLSLYNTIN PEASASPSCV SQDLEPLTIL YYIGKTPKIE QLSNMIVKSC KCS (SEQ ID NO:110), where amino acid 77 is Ser.

3 TGF-β3 Polypeptides

A suitable TGF-β3 polypeptide can comprise an amino acid sequence having at least 60%, at least 70%, at least 80%, at least 90%, at least 95%, at least 98%, at least 99%, or 100%, aa sequence identity to at least 70, at least 80, at least 90, at least 100, at least 110, or 112 aas of the following TGF-133 amino acid sequence: ALDTNYCFRN LEENCCVRPL YIDFRQDLGW KWVHEPKGYY ANFCSGPCPY LRSADTTHST VLGLYNTLNP EASASPCCVP QDLEPLTILY YVGRTPKVEQ LSNMVVKSCK CS (SEQ ID NO:111), where the TGF-β3 polypeptide has a length of about 112 aas. A TGF-β3 isoform 1 preproprotein is provided in FIG. 3 as SEQ ID NO:112. Positions 25, 92 and 94 are bolded and italicized.

In some cases, a suitable TGF-β3 polypeptide comprises a C77S substitution. In some cases, a suitable TGF-β3 polypeptide comprises an amino acid sequence having at least 60%, at least 70%, at least 80%, at least 90%, at least 95%, at least 98%, at least 99%, or 100%, aa sequence identity to at least 70, at least 80, at least 90, at least 100, at least 110, or 112 aas of the following TGF-β3 amino acid sequence: ALDTNYCFRN LEENCCVRPL YIDFRQDLGW KWVHEPKGYY ANFCSGPCPY LRSADTTHST VLGLYNTLNP EASASPSCVP QDLEPLTILY YVGRTPKVEQ LSNMVVKSCK CS (SEQ ID NO:113), where amino acid 77 is Ser. Positions 25, 92 and 94 are bolded and italicized.

4 Additional TGF-β Polypeptide Sequence Variations

In addition to sequence variations that alter TGF-β molecule dimerization (e.g., cysteine 77 substitutions such as C77S), TGF-β1-3 polypeptides having sequence variations that affect affinity and other properties may be incorporated into a masked TGF-β construct or complex. When a masked TGF-β construct or complex comprises a TGF-β variant with reduced affinity for the masking polypeptide (e.g., TβR polypeptide such as a TβRII polypeptide) those components dissociate more readily, making the masked TGF-β polypeptide more available to cellular TβR proteins. Because the TβRII protein is generally the first peptide of the heteromeric TβR signaling complex to interact with TGF-β, interactions with TβRII effectively controls entry of TGF-β into active signaling complexes. Accordingly, variants controlling the affinity of TGF-β for TβRII effectively control entry of masked TGF-β constructs and complexes into active signaling complexes.

The present disclosure includes and provides for masked TGF-β constructs and complexes comprising a variant masking TβR (e.g., TβRII) polypeptide sequence and/or a variant TGF-β polypeptide having altered (e.g., reduced) affinity for each other (relative to an otherwise identical masked TGF-β construct or complex without the sequence variation(s)). Affinity between a TGF-β polypeptide and a TβR (e.g., TβRII) polypeptide may be determined using (BLI) as described above for MODs and their co-MODs.

a. Additional TGF-β2 Sequence Variants

The present disclosure includes and provides for masked TGF-β2 constructs and complexes comprising a masking TβR (e.g., TβRII) polypeptide sequence and either a wt. or a variant TGF-β2 polypeptide; where the variant polypeptide has a reduced affinity for the masking TβR (relative to an otherwise identical wt. TGF-β polypeptide sequence without the sequence variations).

The disclosure provides for a masked TGF-β construct or complex comprises a masking TβRII receptor sequence and a variant TGF-β2 polypeptide having greater than 85% (e.g., greater than 90%, 95%, 98% or 99%) sequence identity to at least 100 contiguous aa of SEQ ID NO:108, and comprising a substitution reducing the affinity of the variant TGF-β2 polypeptide for the TβRII receptor sequence.

In some cases, a masked TGF-β construct or complex comprises a masking TβRII polypeptide and a variant TGF-β (e.g., TGF-β2) polypeptide comprising a substitution at one or more, two or more, or all three of Lys 25, Ile 92, and/or Lys 94 (see SEQ ID NO:108 for the location of the residues, and FIG. 4 for the corresponding residues in TGF-β1 and TGF-β3). Those aa residues have been shown to affect the affinity of TGF-β2 for TβRII polypeptides (see Crescenzo et al., *J. Mol. Biol.,* 355: 47-62 (2006)). The masked TGF-β construct or complex optionally comprises one or more independently selected MODs such as IL-2 or a variant thereof. In one instance, the masked TGF-β construct or complex comprises a masking TβRII polypeptide and a TGF-β2 polypeptide having an aa other than Lys or Arg at position 25 of SEQ ID NO:108; and optionally comprises one or more independently selected MODs (e.g., one or more IL-2 MOD polypeptide or reduced affinity variant thereof). A masked TGF-β construct or complex with a masking TβRII polypeptide may comprises a TGF-β2 polypeptide having an aa other than Ile or Val at position 92 of SEQ ID NO:108 (or an aa other than Ile, Val, or Leu at position 92); and optionally comprises one or more independently selected MODs (e.g., one or more IL-2 MOD polypeptide or reduced affinity variant thereof). A masked TGF-β construct or complex with a masking TβRII polypeptide may comprise a TGF-β2 polypeptide having an aa other than Lys or Arg at position 94 of SEQ ID NO:108; and optionally comprises one or more independently selected MODs (e.g., one or more IL-2 MOD polypeptide or reduced affinity variant thereof). A masked TGF-β construct or complex with a masking TβRII polypeptide may comprise a TGF-β2 polypeptide comprising a substitution at one or more, two or more or all three of Lys 25, Ile 92, and/or Lys 94, and further comprises one or more independently selected MODs. A masked TGF-β construct or complex with a masking TβRII polypeptide may comprise a TGF-β2 polypeptide comprising a substitution at one or more, two or more or all three of Lys 25, Ile 92, and/or Lys 94, and further comprises one or more independently selected IL-2 MODs or reduced affinity variants thereof b. Additional TGF-β1 and TGF-β3 Sequence Variants In some cases, a masked TGF-β construct or complex comprises a masking TβRII polypeptide and a variant TGF-β1 or TGF-β3 polypeptide comprising a substitution at one or more, two or more or all three aa positions corresponding to Lys 25, Ile 92, and/or Lys 94 in TGF-β2 SEQ ID NO:108. In TGF-β1 or TGF-β3, the aa that corresponds to: Lys 25 is an Arg 25, Ile 92 is Val 92, and Lys 94 is Arg 94, each of which is a conservative substitution. See, e.g., SEQ ID NOs:106 and 107 for TGF-β1 and SEQ ID NOs:112 and 113 for TGF-β3.

As noted above, the masked TGF-β construct or complex optionally comprises one or more independently selected MODs such as IL-2 or a variant thereof. In one instance, the masked TGF-β construct or complex with a masking TβRII polypeptide comprises a TGF-β1 or 133 polypeptide having an aa other than Arg or Lys at position 25; and optionally comprises one or more independently selected MODs (e.g., one or more IL-2 MOD polypeptide or reduced affinity variant thereof). In one instance, the masked TGF-β construct or complex with a masking TβRII polypeptide comprises a TGF-β1 or 133 polypeptide having an aa other than Val or Ile at position 92 (or an aa other than Ile, Val, or Leu at position 92); and optionally comprises one or more independently selected MODs (e.g., one or more IL-2 MOD polypeptide or reduced affinity variant thereof). In another instance, the masked TGF-β construct or complex with a masking TβRII polypeptide comprises a TGF-β2 polypeptide having an aa other than Arg or Lys; and optionally comprises one or more independently selected MODs (e.g., one or more IL-2 MOD polypeptide or reduced affinity variant thereof). In one specific instance, a masked TGF-β construct or complex with a masking TβRII polypeptide comprises a TGF-β1 or 133 polypeptide comprising a substitution at one or more, two or more or all three of Arg 25, Val 92, and/or Arg 94, and further comprises one or more independently selected MODs. In another specific instance, a masked TGF-β construct or complex with a masking TβRII polypeptide comprises a TGF-β1 or 133 polypeptide comprising a substitution at one or more, two or more or all three of Arg 25, Val 92, and/or Arg 94, and further comprises one or more independently selected IL-2 MODs, or reduced affinity variants thereof.

G. TGF-β Receptor Polypeptides and Other Polypeptides that Bind and Mask TGF-β

In any of the above-mentioned TGF-β polypeptides or polypeptide complexes the polypeptide that binds to and masks the TGF-β polypeptide (a "masking polypeptide") can take a variety of forms, including fragments of TβRI, TβRII, TβRIII and anti TGF-β antibodies or fragments thereof (e.g., Fab., single chain antibodies, etc.).

1 TGF-β Receptor Polypeptides

The masking of TGF-β in masked TGF-β constructs and complexes may be accomplished by utilizing a TGF-β receptor fragment (e.g., the ectodomain sequences of TβRI, TβRII or TβRIII) that comprises polypeptide sequences sufficient to bind a TGF-β polypeptide (e.g., TGF-β1, TGF-β2 or TGF-β3). In an embodiment, the masking sequence comprises all or part of the TβRI, TβRII, or TβRIII ectodomain.

a. TGF-β Receptor I (TβRI)

In an embodiment the polypeptide sequence masking TGF-β in a masked TGF-β construct or complexes may be derived from a TβRI (e.g., isoform 1 SEQ ID NO:114) and may comprises all or part of the TβRI ectodomain (aas 34-126). In some cases, a suitable TβRI polypeptide for masking TGF-β comprises an amino acid sequence having at least 60%, at least 70%, at least 80%, at least 90%, at least 95%, at least 98%, at least 99%, or 100%, aa sequence identity to at least 70, at least 80, at least 90, at least 100, or 103 aas of the following TβRI ectodomain aa sequence: LQCFCHL CTKDNFTCVT DGLCFVSVTE TTDKVIHNSM CIAEIDLIPR DRPFVCAPSS KTGSVTT-TYC CNQDHCNKIE LPTTVKSSPG LGPVEL (SEQ ID NO:115).

b. TGF-β Receptor II (TβRII)

In embodiments, the polypeptide sequence masking TGF-β in a masked TGF-β construct or complex may be derived from a TβRII (e.g., isoform A SEQ ID NO:116), and may comprises all or part of the TβRII ectodomain sequence (aas 24 to 177). In an embodiment, a suitable TβRII isoform A polypeptide for masking TGF-β may comprise an amino acid sequence having at least 60%, at least 70%, at least 80%, at least 90%, at least 95%, at least 98%, at least 99%, or 100%, aa sequence identity to at least 70, at least 80, at least 90, at least 100, at least 110, at least 120, at least 130, at least 140, at least 150 or at least 154 aas of the following TβRII isoform A ectodomain aa sequence: IPPHVQK SDVEMEAQKD EIICPSCNRT AHPLRHINND MIVTDNNGAV KFPQLCKFCD VRFSTCDNQK SCMSNCSITS ICEKPQEVCV AVWRKNDENI TLETVCHDPK LPYHDFILED AASPKCIMKE KKKPGETFFM CSCSSDECND NIIFSEE (SEQ ID NO:117). The location of the aspartic acid residue corresponding to D118 in the B isoform is bolded, underlined, and italicized.

In an embodiment, the polypeptide sequence masking TGF-β in a masked TGF-β construct or complex may be derived from TβRII isoform B SEQ ID NO:118) and may comprises all or part of the TβRII ectodomain sequence (aas 24 to 166). In embodiment, a suitable TβRII isoform B polypeptide for masking TGF-β comprises an amino acid sequence having at least 60%, at least 70%, at least 80%, at least 90%, at least 95%, at least 98%, at least 99%, or 100%, aa sequence identity to at least 70, at least 80, at least 90, at least 100, or 103 aas of the TβRII isoform B ectodomain aa sequence: IPPHVQKSVN NDMIVTDNNG AVKFPQLCKF CDVRFSTCDN QKSCMSNCSI TSICEKPQEV CVAVWRKNDE NITLETVCHD PKLPYHDFIL EDAASPKCIM KEKKKPGETF FMCSCSSDEC NDNIIFSEEY NTSNPDLLLV IFQ (SEQ ID NO:119). As discussed below, any one or more of F30, D32, S52, E55, or D118 (italicized and bolded) may be substituted by an amino acid other than the naturally occurring aa at those positions (e.g., alanine). A polypeptide sequence masking TGF-β may comprise the polypeptide of SEQ ID NO:119 bearing a D118A or D118R substitution. A sequence masking TGF-β may comprise the peptide of SEQ ID NO:119 bearing a D118A or D118R substitution and one or more of a F30A, D32N, S52L and/or E55A substitution.

Although TβRII's ectodomain may be utilized as a masking polypeptide, that region of the protein has charged and hydrophobic patches that can lead to an unfavorable pI nd can be toxic to cell expressing the polypeptide. In addition, combining a TβRII ectodomain with the an active TGF-β polypeptide can result in a complex that could combine with cell surface TβRI and cause activation of that signaling receptor (e.g., signaling through the Smad pathway). Modifying TβRII ectodomain sequences used to mask TGF-β by removing or altering sequences involved in TβRI association can avoid the unintentional stimulation of cells by the masked TGF-β except through their own cell surface heterodimeric TβRI/TβRII complex. Modifications of TβRII may also alter (e.g., reduce) the affinity of the TβRII for TGF-β (e.g., TGF-β3), thereby permitting control of TGF-β unmasking and its availability as a signaling molecule. Masked TGF-β construct or complexes comprising TβR (e.g., TβRII) peptides with the highest affinity for TGF-β (e.g., TGF-β3) most tightly mask the TGF-β sequence and require higher doses to achieve the same effect. In contrast, aa substitutions in TβRII that lower the affinity unmask the TGF-β polypeptide and are biologically effective at lower doses. See, e.g., Example 3.

Accordingly, where it is desirable to block/limit signaling by the masked TGF-β polypeptide through TβRI and/or modify (e.g., reduce) the affinity of a masking TβRII polypeptide for TGF-β a number of alterations to TβRII may be incorporated into the TβRII polypeptide sequence. Modifications that can be made include the above-mentioned deletions of N-terminal 25 amino acids from 1 to 25 aa in length (e.g., Δ14, Δ25) and/or substitutions at one or more of L27, F30, D32, S49, 150, T51, S52, I53, E55, V77, D118, and/or E119. Some specific modifications resulting in a reduction in TβRI association with TβRII and reduced affinity for TGF-β include any one or more of L27A, F30A, D32A, D32N, 549A, I50A, T51A, S52A, 552L, I53A, E55A, V77A, D118A, D118R, E119A, and/or E119Q based on SEQ ID NO:119. See, e.g., J. Groppe et al., *Mol Cell,* 29, 157-168, (2008) and De Crescenzo et al., *JMB,* 355, 47-62 (2006). See FIG. 9 for the effects of those substitutions on TGF-β3-TβRII and TβRI-TβRII complexes. Modifications of TβRII the including an N-terminal Δ25 deletion and/or substitutions at F24 (e.g., an F24A substitution) substantially or completely block signal through the canonical SMAD signaling pathway). In one aspect, the aspartic acid at position 118 (D118) of the mature TβRII B isoform (SEQ ID NO:119) is replaced by an amino acid other than Asp or Glu, such as Ala giving rise to a "D118A" substitution or by an Arg giving rise to a D118R substitution. The Asp residues corresponding to D118 are indicated in SEQ ID NOs:117-123 (with bold and underlining in FIG. 5B). N-terminal deletions of from 1 to 25 aa in length (e.g., a Δ25 deletions) and/or substitutions at F24 (e.g., an F24A substitution) may be combined with D118 substitutions (e.g., D118A or D118R). N-terminal deletions of from 1 to 25 aa in length (e.g., a Δ25 deletions) and/or substitutions at F24 (e.g., an F24A substitution) may also be combined with substitutions at any of L27, F30, D32, S49, 150, T51, S52, I53, E55, V77, D118, and/or E119 (e.g., D118A) substitutions, and particularly any of the specific substitutions recited for those locations in SEQ ID NO:119 described above to alter the affinity.

Deletions of the N-terminus of the TβRII polypeptides may also result in loss of TβRI interactions and prevent masked TGF-β constructs and complexes comprising a TβRII polypeptide from acting as a constitutively active complex that engages and activates TβRI signaling. A 14 aa deletion (Δ14) of the TβRII polypeptide substantively reduces the interaction of the protein with TβRI, and a Δ25 aa deletion of TβRII appears to completely abrogate the interaction with TβRI. N-terminal deletions also substantially alter the pI of the protein, with the Δ14 TβRII ectodomain mutant displaying a pI of about 4.5-5.0 (e.g., about 4.74). Accordingly, TGF-β constructs or complexes may comprise TβRII ectodomain polypeptides (e.g., polypeptides of SEQ ID NOs:117 or 118) with N-terminal deletions, such as from 14 to 25 aas (e.g., 14, 15, 16, 17, 18, 19, 20, 21, 22, 23, 24, or 25 aa). Modified ectodomain sequences, including those that limit interactions with TβRI, that may be utilized to mask TGF-β polypeptides in a masked TGF-β construct or complex are described in the paragraphs that follow.

In an embodiment, the sequence masking TGF-β in a masked TGF-β construct or complex comprises sequence having at least 60%, at least 70%, at least 80%, at least 90%, at least 95%, at least 98%, at least 99%, or 100%, aa sequence identity to at least 70, at least 80, at least 90, at least 100, or 103 aas of the TβRII isoform B ectodomain sequence: IPPHVQKSVN NDMIVTDNNG AVKFPQLCKF CDVRFSTCDN QKSCMSNCSI TSICEKPQEV CVAVWRKNDE NITLETVCHD PKLPYHDFIL EDAASPKCIM KEKKKPGETF FMCSCSSDEC NDNIIFSEE (SEQ ID NO:120). Any one or more of F30, D32, S52, E55, or D118 (italicized and bolded) may be substituted by an amino acid other than the naturally occurring aa at those positions (e.g., alanine). In an embodiment, the sequence masking TGF-β comprises the peptide of SEQ ID NO:120 bearing a D118A substitution. In an embodiment, the sequence masking TGF-β comprises the polypeptide of SEQ ID NO:120 bearing a D118A substitution and one or more of a F30A, D32N, S52L and/or E55A substitution.

Combinations of N-terminal deletions of TβRII, such as from 14 to 25 aas (e.g., 14, 15, 16, 17, 18, 19, 20, 21, 22, 23, 24, or 25 aa), that block inadvertent cell signaling due to the masked TGF-13/TβRII complex interacting with TβRI may be combined with other TβRII ectodomain substitutions, including those at any one or more of F30, D32, S52, E55, and/or D118. The combination of deletions and substitutions ensures the masked TGF-β construct or complex does not cause cell signaling except through the cell's membrane bound TβRI & TβRII receptors.

In an embodiment, the sequence masking TGF-β in a masked TGF-β construct or complex comprises sequence having at least 60%, at least 70%, at least 80%, at least 90%, at least 95%, at least 98%, at least 99%, or 100%, aa sequence identity to at least 70, at least 80, at least 90, at least 100, or 103 aas of the TβRII isoform B ectodomain sequence: VTDNNG AVKFPQLCKF CDVRFSTCDN QKSCMSNCSI TSICEKPQEV CVAVWRKNDE NITLETVCHD PKLPYHDFIL EDAASPKCIM KEKKKPGETF FMCSCSSDEC NDNIIFSEE (SEQ ID NO:121), which has aas 1-14 (Δ14) deleted. Any one or more of F30, D32, S52, E55, or D118 (italicized and bolded) may be substituted by an amino acid other than the naturally occurring aa at those positions (e.g., alanine). In an embodiment, the sequence masking TGF-β comprises the peptide of SEQ ID NO:121 bearing a D118A substitution. In an embodiment, the sequence masking TGF-β comprises the polypeptide of SEQ ID NO:121 bearing a D118A substitution and one or more of a F30A, D32N, S52L and/or E55A substitution.

In an embodiment, the sequence masking TGF-β in a masked TGF-β construct or complex comprises sequence having at least 60%, at least 70%, at least 80%, at least 90%, at least 95%, at least 98%, at least 99%, or 100%, aa sequence identity to at least 70, at least 80, at least 90, at least 100, or 103 aas of the sequence: QLCKF CDVRFSTCDN QKSCMSNCSI TSICEKPQEV CVAVWRKNDE NITLETVCHD PKLPYHDFIL EDAASPKCIM KEKKKPGETF FMCSCSSDEC NDNIIFSEE (SEQ ID NO:122), which has aas 1-25 (Δ25) deleted. Any one or more of F30, D32, S52, E55, or D118 (italicized and bolded) may be substituted by an amino acid other than the naturally occurring aa at those positions (e.g., alanine). In an embodiment, the sequence masking TGF-β comprises the polypeptide of SEQ ID NO:122 bearing a D118A substitution (shown as SEQ ID NO:123 in FIG. 5B). In an embodiment, the sequence masking TGF-β in a masked TGF-β construct or complex comprises the peptide of SEQ ID NO:122 bearing a D118A substitution and one or more of a F30A, D32N, S52L and/or E55A substitution. In an embodiment, the sequence masking TGF-β in a masked TGF-β construct or complex comprises the peptide of SEQ ID NO:122 (see FIG. 5B) bearing D118A and F30A substitutions. In an embodiment, the sequence masking TGF-β in a masked TGF-β construct or complex comprises the peptide of SEQ ID NO:122 (see FIG. 5B) bearing D118A and D32N substitutions. In an embodiment, the sequence masking TGF-β in a masked TGF-β construct or complex comprises the peptide of SEQ ID NO:122 (see FIG. 5B) bearing D118A and S52L substitutions. In an embodiment, the sequence masking TGF-β in a masked TGF-β construct or complex comprises the peptide of SEQ ID NO:122 (see FIG. 5B) bearing D118A and E55A.

c. TGF-β Receptor III (TβRIII)

In an embodiment, the polypeptide sequence masking TGF-β in a masked TGF-β construct or complexes may be derived from a TβRIII (e.g., isoform A SEQ ID NO:124 and isoform B 125), and may comprise all or part of a TβRIII ectodomain (aas 27-787 of the A isoform or 27-786 of the B isoform). In some cases, a suitable TβRIII polypeptide for masking TGF-β comprises an amino acid sequence having at least 60%, at least 70%, at least 80%, at least 90%, at least 95%, at least 98%, at least 99%, or 100%, aa sequence identity to at least 70, at least 80, at least 90, at least 100, or 120 aas of a TβRIII A isoform or B isoform ectodomain sequences (e.g., provided in FIG. 5C as SEQ ID NO:124 or SEQ ID NO:125).

2 Antibodies

Although TGF-β receptor polypeptides (e.g., ectodomain sequences) can function to bind and mask TGF-β polypeptides in masked TGF-β constructs or complexes, other polypeptide sequences (protein sequences) that bind to TGF-β sequences can also be employed as masking polypeptides. Among the suitable polypeptide or protein sequences that can be used to mask TGF-β are antibodies with affinity for TGF-β (e.g., antibodies specific for an one or more of TGF-β1, TGF-β2, or TGF-β3) or their fragments, nanobodies with affinity for TGF-β polypeptides, and particularly single chain anti-TGF-β antibodies (e.g., any of which may be humanized). Some antibodies, including scFV antibodies, that bind and neutralize TGF-β have been described. See, e.g., U.S. Pat. No. 9,090,685. Throughout the embodiments and/or aspects of the invention described in this disclosure, TβR (e.g., TβRII) sequences used to mask TGF-β polypeptides may be replaced with masking antibody sequences (e.g., a scFV or a nanobody) with affinity for the TGF-β polypeptide. For instance, in each of the masked TGF-β constructs or complexes in FIG. 1 where a TGF-β receptor sequence is used to mask a TGF-β polypeptide, the receptor polypeptide may be replaced with a masking antibody polypeptide (e.g., scFV or a nanobody) with affinity for the TGF-β polypeptide.

One potential advantage of using an antibody (e.g., a single chain antibody) as a masking polypeptide is the ability to limit it to the isoform of the TGF-β polypeptide(s) to be masked. By way of example, single chain antibody sequences based on Metelimumab (CAT192) directed against TGF-β1 (e.g., Lord et al., mAbs 10(3): 444-452 (2018)) can be used to mask that TGF-β isoform when present in TGF-β constructs or complexes. In another embodiment, a single chain antibody sequence specific for TGF-β2 is used to mask that TGF-β isoform when present in TGF-β constructs or complexes. In another embodiment, a single chain antibody sequence specific for TGF-β3 is used to mask that TGF-β isoform when present in TGF-β constructs or complexes. Single chain antibodies can also be specific for a combination of TGF-β isoforms (e.g., ectodomain sequences appearing in masked TGF-β constructs or complexes selected from the group consisting of: TGF-β1 & TGF-β2; TGF-β1 & TGF-β3; and TGF-β2 & TGF-β3. The single chain antibodies may also be pan-specific for TGF-β1, TGF-β2, and TGF-β3 ectodomain sequences appearing in masked TGF-β constructs or complexes. See, e.g., WO 2014/164709. Antibodies and single chain antibodies that have the desired specificity and affinity for TGF-β isoforms can be prepared by a variety of methods, including screening hybridomas and/or modification (e.g., combinatorial modification) to the variable region sequence of antibodies that have affinity for a target TGF-β polypeptide sequence.

In an embodiment, a masked TGF-β construct or complex comprises a single chain antibody to mask a TGF-β sequence (e.g., a TGF-β3 sequence). In one such embodiment the single chain amino acid sequence is specific for the TGF-β3 set forth in SEQ ID NO:111 comprising a C77S substitution (see SEQ ID NO:112).

H. Linkers

As noted above, a masked TGF-β construct or complex can include a linker peptide/polypeptide sequence interposed between any two elements of a masked TGF-β construct or complex. Although the term "linker" is employed, the same sequences described below as linkers may also be placed at the N- and/or C-terminus of a polypeptide of a masked TGF-β construct or complex for example as protection against proteolytic degradation.

Suitable linkers (also referred to as "spacers") can be readily selected and can be any of a number of suitable lengths, such as from 1 aa to 25 aa, from 3 aa to 20 aa, from 2 aa to 15 aa, from 3 aa to 12 aa, from 4 aa to 10 aa, from 5 aa to 9 aa, from 6 aa to 8 aa, or from 7 aa to 8 aa. A suitable linker can be 1, 2, 3, 4, 5, 6, 7, 8, 9, 10, 11, 12, 13, 14, 15, 16, 17, 18, 19, 20, 21, 22, 23, 24, or 25 aa in length. A suitable linker can be from 25 to 35 aa in length. A suitable linker can be 25, 26, 27, 28, 29, 30, 31, 32, 33, 34, or 35 aa in length. A suitable linker can also be from 35 to 45 aa in length. A suitable linker can be 35, 36, 37, 38, 39, 40, 41, 42, 43, 44, or 45 aa in length. A suitable linker can be from 45 to 50 aa in length. A suitable linker can be 45, 46, 47, 48, 49, or 50 aa in length.

Exemplary linkers include those comprising glycine, or a polyglycine containing sequence from about 2 to about 50 (e.g., 2-4, 4-7, 7-10, 10-20, 20-35, or 35-50) contiguous glycine residues (SEQ ID NO:193); glycine-serine polymers (including, for example, $(GS)_n$ (SEQ ID NO:194), $(GSGGS)_n$ (SEQ ID NOs:126 and 195) and $(GGGS)_n$ (SEQ ID NOs:127 and 196), where n is an integer of at least one (e.g., 1-10, 10-20, or 20-30); glycine-alanine polymers or alanine-serine polymers (e.g., having a length of 1-10, 10-20, or 20-30 aa); and other flexible linkers known in the art. Glycine and glycine-serine polymers can be used; both Gly and Ser are relatively unstructured, and therefore can serve as a neutral tether between components. Glycine polymers can be used; glycine assesses significantly more phi-psi space than even alanine, and is much less restricted than residues with longer side chains (see Scheraga, *Rev. Computational Chem.,* 11173-142 (1992)). Exemplary linkers can comprise amino acid sequences including, but not limited to, GGSG (SEQ ID NO:128), GGSGG (SEQ ID NO:129), GSGSG (SEQ ID NO:130), GSGGG (SEQ ID NO:131), GGGSG (SEQ ID NO:132), GSSSG (SEQ ID NO:133), and the like. Exemplary linkers can comprise, e.g., GGSG (SEQ ID NO:134) which may be repeated 2, 3, 4, 5, 6, 7, 8, 9, or 10 (SEQ ID NO:197) times. In some cases, a linker comprises the amino acid sequence (GSSSS) (SEQ ID NO:135) that may be repeated 2, 3, or 4 times (SEQ ID NOs:198-200). In some cases, a linker comprises the amino acid sequence (GSSSS) repeated four (SEQ ID NO:200) or five (SEQ ID NO:201) times. Exemplary linkers can include, e.g., (GGGGS) (SEQ ID NO:136), which can be repeated 2, 3, 4, 5, 6, 7, 8, 9, or 10 times (SEQ ID NOs:202-210 respectively). In some cases, a linker comprises the amino acid sequence (GGGGS) (SEQ ID NO:136) once or repeated 2 times (SEQ ID NO:202). In some cases, a linker comprises the amino acid sequence (GGGGS) (SEQ ID NO:136) repeated 3 or 4 times (SEQ ID NOs:203-204, respectively). In some cases, a linker comprises the amino acid sequence (GGGGS) (SEQ ID NO:136) repeated 5, 6, or 7 times (SEQ ID NOs:205-207, respectively). In some cases, a linker comprises the amino acid sequence (GGGGS) (SEQ ID NO:136) repeated 8, 9, or 10 times (SEQ ID NOs:208-210, respectively).

In some cases, a linker polypeptide present in a first polypeptide of a masked TGF-β complex includes a cysteine residue that can form a disulfide bond with a cysteine residue present in a second polypeptide of the masked TGF-β construct or complex. In some cases, for example, a suitable linker comprises the amino acid sequence G<u>C</u>GASGGGGSGGGGS (SEQ ID NO:137).

I. Exemplary Masked TGF-β Constructs and Complexes

As discussed above, in any of the masked TGF-β constructs and complexes described in the present disclosure, the masking polypeptide that binds to and masks the TGF-β polypeptide sequences can take a variety of forms. The masking peptide may be an antibody, binding fragment of an antibody, a single chain antibody or portion thereof that binds TGF-β (e.g., an scFv), or nanobody; any of which may be humanized. The masking polypeptide may also be a TGF-β receptor fragment (e.g., the ectodomain sequences of TβRI, TβRII or TβRIII) that comprises polypeptide sequences sufficient to bind a TGF-β polypeptide (e.g., TGF-β1, TGF-β2 or TGF-β3).

In any of the above-mentioned masked TGF-β constructs and complexes, the TGF-β polypeptide sequence employed may be based upon TGF-β1, TGF-β2 or TGF-β3. In an embodiment the TGF-β polypeptide comprises a TGF-β3 sequence. Full length mature TGF-β protein sequence is not required in the masked TGF-β constructs and complexes, only the portion of TGF-β needed to interact with cell surface TβRII and permit the masked TGF-β complexes with cell surface TβRII to recruit TβRI and thereby initiate signaling (e.g., signaling through the Smad and non-Smad pathways).

Although immunomodulatory polypeptide (MODs) are not required for the delivery of masked TGF-β or its ability to activate cells bearing TβRI and TβRII, as noted above, the presence of MODs can substantially affect the outcome of TGF-β cell activation. Consequently, the incorporation of MODs in any of the above-mentioned masked TGF-β constructs and complexes can be used to drive various outcomes, including therapeutic outcomes, from the use of the masked TGF-β constructs and complexes described herein. In an embodiment, the MODs present in a masked TGF-β construct or complex are selected from the group consisting of PD-L1, Fas-L, IL-2, IL-4, IL-6, IL-7, IL-21, IL-23, and variants of any thereof including those with reduced affinity for their co-MOD.

While it may be desirable to incorporate MODs into masked TGF-β constructs and complexes, their presence is not necessary in all cases, particularly where the masked TGF-β constructs and complexes are administered along with other materials, including cytokines (e.g., one or more independently selected interleukin, lymphokine, interferon, chemokine, and/or tumor necrosis factor). For example, where it is desirable to support the development of conventional CD8+ T cells (or the survival of low affinity CD8+ T cells) by promoting thymocyte expression of the interleukin 7 receptor (e.g., IL-7Ra), masked TGF-β constructs and complexes without a MOD polypeptide ("MOD-less") may be employed. Similarly, where it is desirable to promote the development of T-cell populations that are induced by strong agonist ligands, MOD-containing or MOD-less masked TGF-β constructs and complexes may be employed to support the survival of thymus-derived Treg (tTreg), invariant natural killer T (iNKT), and CD8αα+ T-cell precursors.

The following are non-limiting examples of masked TGF-β constructs and complexes.

1 Masked TGF-β Constructs

In the case of masked TGF-β constructs, all of the components (e.g., TGF-β, scaffold, a masking polypeptide such as a TβRII sequence, and optionally one or more MODs) are part of a single polypeptide chain (see, e.g., FIG. 1, structure A). In such an embodiment, the scaffold polypeptide does not form a dimer or higher order structure with other scaffold polypeptides, and accordingly the masked TGF-β constructs are not in the form of homodimers, heterodimers or higher order multimer structures (trimers etc.).

In the case of the masked TGF-β construct in FIG. 1, Structure A the polypeptide may comprise, from N-terminus to C-terminus: optionally one or more MODs; a scaffold polypeptide (without an interspecific binding sequence); a polypeptide that binds to and masks the TGF-β polypeptide; and a TGF-β polypeptide sequence. Such masked TGF-β constructs include those where:

(i) the polypeptide comprises from N-terminus to C-terminus: optionally one or more independently selected wt. or reduced affinity variant MODs; a scaffold polypeptide (without an interspecific binding sequence); a TβR polypeptide that binds to and masks the TGF-β polypeptide; and a TGF-β polypeptide sequence;

(ii) the polypeptide comprises from N-terminus to C-terminus: optionally one or more independently selected wt. or reduced affinity variant MODs; a scaffold polypeptide (without an interspecific binding sequence); a TβRII polypeptide that binds to and masks the TGF-β polypeptide; and a TGF-β polypeptide sequence;

(iii) the polypeptide comprises from N-terminus to C-terminus: one or more independently selected wt. or reduced affinity variant MODs; a scaffold polypeptide (without an interspecific binding sequence); a TβR polypeptide that binds to and masks the TGF-β polypeptide; and a TGF-β polypeptide sequence;

(iv) the polypeptide comprises from N-terminus to C-terminus: one or more independently selected wt. or reduced affinity variant IL-2 MODs; a scaffold polypeptide (without an interspecific binding sequence); a TβR polypeptide that binds to and masks the TGF-β polypeptide; and a TGF-β polypeptide sequence;

(v) the polypeptide comprises from N-terminus to C-terminus: one or more independently selected wt. or reduced affinity variant MODs; a scaffold polypeptide (without an interspecific binding sequence); a TβR polypeptide that binds to and masks a TGF-β3 polypeptide; and a TGF-β3 polypeptide sequence;

(vi) the polypeptide comprises from N-terminus to C-terminus: one or more independently selected wt. or reduced affinity variant MODs; a scaffold polypeptide (without an interspecific binding sequence); a TβRII polypeptide that binds to and masks a TGF-β3 polypeptide; and a TGF-β3 polypeptide sequence; and (vii) the polypeptide comprises from N-terminus to C-terminus: one or more independently selected wt. or reduced affinity variant IL-2 MODs; a scaffold polypeptide (without an interspecific binding sequence); a TβRII polypeptide that binds to and masks a TGF-β3 polypeptide; and a TGF-β3 polypeptide sequence.

In any instance of the masked TGF-β constructs described herein, C77 of the TGF-β polypeptide sequence may be substituted to prevent dimerization (e.g., a C77S substitution), and the TGF-β polypeptide may further comprise variations to reduce their affinity for the masking TβR polypeptide (e.g., at one, two or all three of aas 25, 92 and/or 94), along with modifications in the MODs and the TOR polypeptide sequences. Exemplary TβR polypeptide sequences that may be incorporated into masked TGF-β constructs include Δ14 or Δ25 TβRII polypeptides optionally having a D118A or D118R substitution to attenuate TβRI engagement. MODs variants are described along with their polypeptide sequences and additional modifications of TβRI, TβRII, and TβRIII are described above.

Figure 7A:
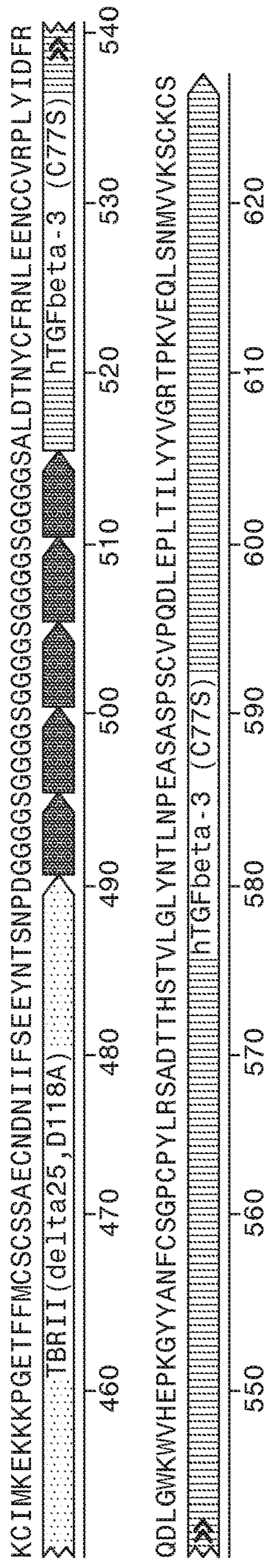
Figure 7B:
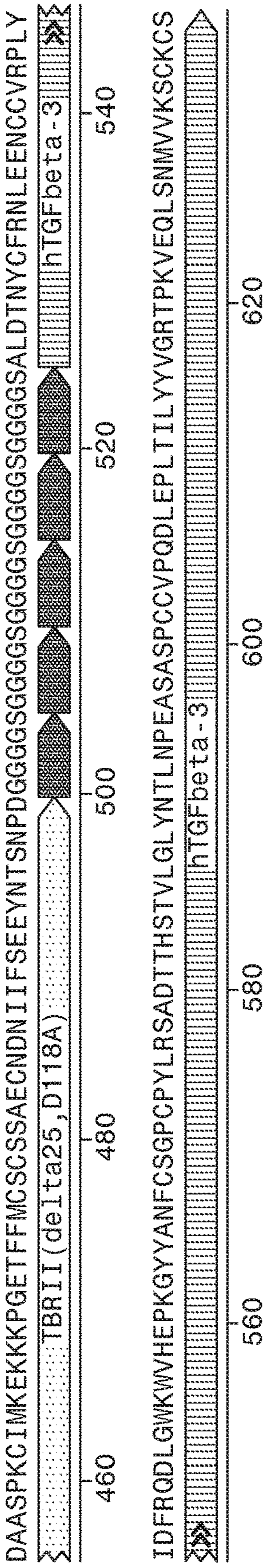

In an embodiment, a masked TGF-β construct has the sequence set forth in SEQ ID NO:146 (see FIG. 7A). In an embodiment, a masked TGF-β construct has the sequence set forth in SEQ ID NO:147 (see FIG. 7B). In an embodiment, a masked TGF-β construct has the sequence set forth in SEQ ID NO157 (see FIG. 7G). In an embodiment, a masked TGF-β construct has the sequence set forth in SEQ ID NO:158 (see FIG. 7H). In an embodiment, a masked TGF-β construct has the sequence set forth in SEQ ID NO:159 (see FIG. 7I).

2 Masked TGF-β Complexes

Masked TGF-β complexes comprise at least two polypeptides, a first and a second polypeptide, each of which contains a scaffold polypeptide that associates with another scaffold polypeptide, bringing the first and second polypeptides together into a complex. Consequently, TGF-β polypeptide complexes form homodimers, heterodimers, or higher order multimeric structures:

(i) in a first instance, the masked TGF-β complex comprises at least one TGF-β polypeptide sequence, at least one polypeptide that binds to and masks the one or more TGF-β polypeptides (e.g., a masking sequence for each TGF-β polypeptide sequence), and optionally one or more immunomodulatory polypeptides (MODs) assembled on a scaffold structure that can dimerize to form a homodimer (e.g., a symmetrical dimer) as in FIG. 1, structure B. In such homodimers, the Ig Fc polypeptides can permit the spontaneous formation of disulfide bonds between the Ig Fc polypeptides in the scaffold of each construct, and may include mutations (e.g., the LALA mutations discussed herein) that substantially reduce or eliminate the ability of the Ig polypeptide to induce cell lysis, e.g., though complement-dependent cytotoxicity (CDC) and antibody-dependent cellular cytotoxicity (ADCC).

(ii) in a second instance, a masked TGF-β complex comprises
   (a) a first polypeptide comprising at least one TGF-β polypeptide sequence, at least one polypeptide that binds to and masks the one or more TGF-β polypeptides (e.g., a masking sequence for each TGF-β polypeptide sequence), and optionally one or more immunomodulatory polypeptides (MODs) assembled on a scaffold structure comprising an interspecific dimerization sequence, and
   (b) a second polypeptide comprising at least one TGF-β polypeptide sequence, at least one polypeptide that binds to and masks the at least one TGF-β polypeptide, and optionally one or more immunomodulatory polypeptides (MODs) assembled on a scaffold structure comprising a counterpart to the interspecific dimerization sequence of the first polypeptide;
   where the first and second polypeptides form a heterodimer through interaction of the interspecific dimerization sequences as in FIG. 1, structure C.

(iii) in a third instance, a masked TGF-β complex comprises
   (a) a first polypeptide comprising at least one TGF-β polypeptide sequence, at least one polypeptide that binds to and masks the at least one or more TGF-β polypeptides (e.g., a masking sequence for each TGF-β polypeptide sequence), and optionally one or more immunomodulatory polypeptides (MODs) assembled on a scaffold structure comprising an interspecific dimerization sequence, and (b) a second polypeptide comprising a scaffold structure comprising a counterpart to the interspecific dimerization sequence of the first polypeptide, and optionally one or more immunomodulatory polypeptides (MODs);

where the first and second polypeptides form a heterodimer through interaction of the interspecific dimerization sequences as in FIG. 1, structure F, and (iv) in a fourth instance, a masked TGF-β complex comprises (a) a first polypeptide comprising at least one TGF-β polypeptide sequence, and optionally one or more immunomodulatory polypeptides (MODs) assembled on a scaffold structure comprising an interspecific dimerization sequence, and (b) a second polypeptide comprising at least one polypeptide that binds to and masks the at least one or more TGF-β polypeptides, and optionally one or more immunomodulatory polypeptides (MODs) assembled on a scaffold structure comprising a counterpart to the interspecific dimerization sequence of the first polypeptide;

where the first and second polypeptides form a heterodimer through interaction of the interspecific dimerization sequences as in FIG. 1, structures D and E.

In some instances, the masked TGF-β complexes (FIG. 1, structures B, C and F), the sequence comprising the TGF-β polypeptide (the first polypeptide) may comprise, from N-terminus to C-terminus: optionally one or more MODs; a scaffold polypeptide (with or without an interspecific binding sequence); a polypeptide that binds to and masks the TGF-β polypeptide; and a TGF-β polypeptide sequence. The polypeptide not containing a TGF-β sequence in FIG. 1, structure F, (the second polypeptide) comprises a scaffold polypeptide with an interspecific binding sequence and optionally comprises a MOD on the N-terminus, C-terminus, or both the N- and C-termini.

In some instances, the masked TGF-β complexes in FIG. 1, structures D and E, the TGF-β polypeptide sequence-containing polypeptide (the first polypeptide) may comprise, from N-terminus to C-terminus: one or more optional MODs; a scaffold polypeptide (with interspecific binding sequence); and a TGF-β polypeptide sequence. The polypeptide not containing a TGF-β sequence in FIG. 1, structures D and E, (the second polypeptide) may comprise, from N-terminus to C-terminus: optionally one or more MODs, a scaffold polypeptide with an interspecific binding sequence, and a polypeptide that binds to and masks the TGF-β polypeptide. Although not illustrated in FIG. 1, the first polypeptide comprising the TGF-β polypeptide sequence may not comprise one or more MODs and the second polypeptide comprising the masking sequence may comprise one or more MODs.

The above-described instances of masked TGF-β complexes include those where the first polypeptide comprises, from N-terminus to C-terminus:

(i) optionally one or more MODs; a scaffold polypeptide (with an interspecific binding sequence); and a TGF-β polypeptide sequence;

(ii) optionally one or more independently selected wt. or reduced affinity variant MODs; a scaffold polypeptide (with an interspecific binding sequence); and a TGF-β polypeptide sequence;

(iii) one or more independently selected wt. or reduced affinity variant MODs; a scaffold polypeptide (with an interspecific binding sequence); and a TGF-β1 or 2 polypeptide sequence;

(iv) one or more independently selected wt. or reduced affinity variant IL-2 MODs; a scaffold polypeptide (without an interspecific binding sequence); and a TGF-β polypeptide sequence;

(v) one or more independently selected wt. or reduced affinity variant MODs; a scaffold polypeptide (with an interspecific binding sequence); and a TGF-β3 polypeptide sequence;

(vi) one or more independently selected wt. or reduced affinity variant MODs; a scaffold polypeptide (with an interspecific binding sequence); and a TGF-β3 polypeptide sequence; or (vii) one or more independently selected wt. or reduced affinity variant IL-2 MODs; a scaffold polypeptide (with an interspecific binding sequence); and a TGF-β3 polypeptide sequence. In each instance, the second polypeptide comprises from N-terminus to C-terminus a scaffold polypeptide comprising the counterpart to the interspecific binding (dimerization sequence) of the first polypeptide followed by a TβR (e.g., a TβRII) polypeptide that binds to and masks the TGF-β polypeptide of the first polypeptide. In the case of a masked TGF-β complex as in FIG. 1, structure F, a TβR (e.g., a TβRII) polypeptide may be interposed between the N-terminal MOD (if present) and the scaffold of the first polypeptide and the second polypeptide comprises the counterpart to the interspecific binding (dimerization sequence) of the first polypeptide to which one or more independently selected wt. or reduced affinity variant MODs (e.g., wt. or variant IL-2 MODs) may be attached at the N- or C-termini.

In any instance of the masked TGF-β complexes described herein, C77 of the TGF-β polypeptide sequence may be substituted to prevent dimerization (e.g., a C77S substitution), and the TGF-β polypeptide may further comprise variations to reduce their affinity for the masking TβR polypeptide (e.g., at one, two or all three of aas 25, 92 and/or 94), along with modifications in the MODs and the TβR polypeptide sequences. Exemplary TβR polypeptide sequences that may be incorporated into masked TGF-β constructs include Δ14 or Δ25 TβRII polypeptides optionally having a D118A substitution. MODs variants are described along with their polypeptide sequences and additional modifications of TβRI, TβRII, and TβRIII are described above.

In an embodiment, a masked TGF-β complex comprise polypeptides having the sequences set forth in SEQ ID NOs:148 and 149 (see FIG. 7C). In an embodiment, a masked TGF-β complex comprise polypeptides having the sequences set forth in SEQ ID NOs:150 and 151 (see FIG. 7D). In an embodiment, a masked TGF-β complex comprise polypeptides having the sequences set forth in SEQ ID NOs:152 and 153 (see FIG. 7E). In an embodiment, a masked TGF-β complex comprise polypeptides having the sequences set forth in SEQ ID NOs:155 and 156 (see FIG. 7F). In an embodiment, a masked TGF-β complex comprise polypeptides having the sequences set forth in SEQ ID NOs:148 and 160 (see FIG. 7J).

J. Nucleic Acids

The present disclosure provides a nucleic acid comprising a nucleotide sequence encoding masked TGF-β constructs and complexes. In some cases, the nucleic acid is a recombinant expression vector; thus, the present disclosure provides a recombinant expression vector comprising a nucleotide sequence encoding a masked TGF-β construct or complex. In some cases, the nucleic acid is a recombinant expression vector; thus, the present disclosure provides a recombinant expression vector comprising a nucleotide sequence encoding masked TGF-β constructs and complexes. The discussion, of nucleic acids that follows refers to nucleic acids encoding masked TGF-β constructs and complexes of the present disclosure.

1 Nucleic Acids Encoding Single-Chain Antigen-Presenting Polypeptides

As described above, a masked TGF-β construct comprises a single polypeptide chain. Thus, the present disclosure provides a nucleic acid comprising a nucleotide sequence encoding a single-chain masked TGF-β construct. A nucleic acid comprising a nucleotide sequence encoding a single-chain masked TGF-β construct can be operably linked to a transcription control element(s), e.g., a promoter.

2 Nucleic Acid(s) Encoding Masked TGF-β Complexes

As noted above, in some cases, a masked TGF-β complex comprises at least two separate polypeptide chains (a first polypeptide chain and a second polypeptide chain). The present disclosure provides nucleic acids comprising nucleotide sequences encoding a masked TGF-β complex. In some cases, the individual polypeptide chains of a masked TGF-β complex are encoded in separate nucleic acids. In some cases, all polypeptide chains of a masked TGF-β construct or complex are encoded in a single nucleic acid. In some cases, a first nucleic acid comprises a nucleotide sequence encoding the first polypeptide of a masked TGF-β complex; and a second nucleic acid comprises a nucleotide sequence encoding the second polypeptide of a masked TGF-β complex. In some cases, single nucleic acid comprises a nucleotide sequence encoding the first and the second polypeptide of a masked TGF-β complex, which may be operably linked and under the transcriptional control of a single promoter or two independently selected promoters.

3 Separate Nucleic Acids Encoding Individual Polypeptide Chains of a Masked TGF-β Construct or Complex As noted above, in some cases, the individual polypeptide chains of a masked TGF-β complex are encoded by separate nucleic acids. In some cases, nucleotide sequences encoding the separate polypeptide chains of a masked TGF-β complex are operably linked to transcriptional control elements, e.g., promoters, such as promoters that are functional in a eukaryotic cell, where the promoter can be a constitutive promoter or an inducible promoter.

For example, the present disclosure provides a first nucleic acid and a second nucleic acid, where the first nucleic acid comprises a nucleotide sequence encoding the first polypeptide of a masked TGF-β complex, and where the second nucleic acid comprises a nucleotide sequence encoding the second polypeptide of the masked TGF-β complex. In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

In some cases, the nucleotide sequences encoding the first and the second polypeptides are operably linked to transcriptional control elements. In some cases, the transcriptional control element is a promoter that is functional in a eukaryotic cell. In some cases, the nucleic acids are present in separate expression vectors.

4 Nucleic Acid Encoding Two or More Polypeptides Present in a Masked TGF-β Complex The present disclosure provides a nucleic acid comprising nucleotide sequences encoding at least the first polypeptide and the second polypeptide of a masked TGF-β complex. In some cases, where a masked TGF-β complex includes a first, second, and third polypeptide, the nucleic acid includes a nucleotide sequence encoding the first, second, and third polypeptides. In some cases, the nucleotide sequences encoding the first polypeptide and the second polypeptide of a masked TGF-β complex encode a proteolytically cleavable site or linker interposed between the encoded first polypeptide and second polypeptide. In some cases, the nucleotide sequences encoding the first polypeptide and the second polypeptide of a masked TGF-β complex includes a nucleotide encoding an internal ribosome entry site (IRES) interposed between the encoded the first polypeptide and second polypeptides. In some cases, the nucleotide sequences encoding the first polypeptide and the second polypeptide of a masked TGF-β complex includes a sequence encoding a ribosome skipping signal (or cis-acting hydrolase element, CHYSEL) interposed between the nucleotide sequence encoding the first polypeptide and the nucleotide sequence encoding the second polypeptide.

In some cases, the first nucleic acid (e.g., a recombinant expression vector, an mRNA, a viral RNA, etc.) comprises a nucleotide sequence encoding a first polypeptide chain of a masked TGF-β complex; and a second nucleic acid (e.g., a recombinant expression vector, an mRNA, a viral RNA, etc.) comprises a nucleotide sequence encoding a second polypeptide chain of a masked TGF-β complex. In some cases, the nucleotide sequence encoding the first polypeptide, and the second nucleotide sequence encoding the second polypeptide, are each operably linked to independently selected transcriptional control elements, e.g., promoters, such as promoters that are functional in a eukaryotic cell, where the promoter can be a constitutive promoter or an inducible promoter.

5 Recombinant Expression Vectors

The present disclosure provides recombinant expression vectors comprising nucleic acids. In some cases, the recombinant expression vector is a non-viral vector. In some cases, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, a non-integrating viral vector, etc.

Suitable expression vectors include, but are not limited to, viral vectors (e.g., viral vectors based on vaccinia virus; poliovirus; adenovirus (see, e.g., Li et al., *Invest Opthalmol Vis Sci,* 35:2543 2549, 1994; Borras et al., *Gene Ther,* 6:515 524, 1999*; Li and Davidson, PNAS,* 92:7700 7704, 1995; Sakamoto et al., *H Gene Ther,* 5:1088 1097, 1999; WO 94/12649, WO 93/03769; WO 93/19191; WO 94/28938; WO 95/11984 and WO 95/00655); adeno-associated virus (see, e.g., Ali et al., *Hum Gene Ther,* 9:81 86, 1998, Flannery et al., *PNAS,* 94:6916 6921, 1997; Bennett et al., *Invest Opthalmol Vis Sci,* 38:2857 2863, 1997; Jomary et al., *Gene Ther,* 4:683 690, 1997, Rolling et al., *Hum Gene Ther,* 10:641 648, 1999; Ali et al., *Hum Mol Genet,* 5:591 594, 1996; Srivastava in WO 93/09239, Samulski et al., *J. Vir.* (1989) 63:3822-3828; Mendelson et al., *Virol.* (1988) 166: 154-165; and Flotte et al., *PNAS* (1993) 90:10613-10617); SV40; herpes simplex virus; human immunodeficiency virus (see, e.g., Miyoshi et al., *PNAS,* 94:10319 23, 1997; Takahashi et al., *J Virol,* 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. Numerous suitable expression vectors are known to those of skill in the art, and many are commercially available.

Depending on the host/vector system utilized, any of a number of suitable transcription and translation control elements, including constitutive and inducible promoters, transcription enhancer elements, transcription terminators, etc. may be used in the expression vector (see, e.g., Bitter et al., (1987) *Methods in Enzymology,* 153:516-544).

In some cases, a nucleotide sequence encoding the polypeptides of masked TGF-β constructs and complexes are operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some cases, a nucleotide sequence encoding a DNA-targeting RNA and/or a site-directed modifying polypeptide is operably linked to multiple control elements that allow expression of the nucleotide sequence encoding a DNA-targeting RNA and/or a site-directed modifying polypeptide in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

6 Preparation of Genetically Modified Host Cells Expressing Masked TGF-β Constructs and Complexes and Purification of Masked TGF-β Constructs and Complexes The present disclosure provides a genetically modified host cell, where the host cell is genetically modified with one or more nucleic acid(s) encoding a masked TGF-β construct or complex.

Suitable host cells include eukaryotic cells, such as yeast cells, insect cells, and mammalian cells. In some cases, the host cell is a cell of a mammalian cell line. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Genetically modified host cells can be used to produce a masked TGF-β construct or complex. For example, a genetically modified host cell can be used to produce a masked TGF-β complex, or a single-chain masked TGF-β construct by introducing expression vector(s), such as those described above, comprising nucleotide sequences encoding the polypeptide(s) into a host cell, generating thereby producing a genetically modified host cell. The host cell may constitutively express the masked TGF-β construct or complex, or express it in response to exposure to an inducer where the promoters driving expression are inducible (e.g., a CMV promoter and a tetracycline resistance operon induced by exposure to tetracycline).

The masked TGF-β construct or complex is obtained from the cells, or if the polypeptide(s) are targeted to the secretory pathway by incorporation of signal sequences, from the cell culture media. The protein may be purified by any means known in the art including, for example, one or more of precipitation (e.g., ammonium sulfate or ethanol), isoelectric focusing, and one or more types of chromatography. Suitable chromatographic methods include, but are not limited to, size-based chromatographic separation (e.g., size exclusion or gel permeation), hydrophobic interaction chromatography, ion-exchange chromatography, and affinity chromatography. Where the masked TGF-β construct or complex comprises an immunoglobulin polypeptide sequence (e.g., as a scaffold) the protein A or protein G may be used to affinity purify the masked TGF-β construct or complex. In the absence of an immunoglobulin polypeptide, the complex may be affinity purified using an antibody directed a polypeptide present in the masked TGF-β construct or complex; or alternatively, by incorporation of an affinity tag such as a myc epitope (CEQKLISEEDL SEQ ID NO:154), "HIS" tag (for divalent metal ion resin binding), or a "FLAG" tag. A purification and/or concentration step that may be combined with any of the foregoing methods employs size limited semipermeable membrane (e.g., a dialysis membrane or pressure cell), which may be used to remove contaminants having a substantially different molecular weight and/or to concentrate the purified protein.

In an embodiment, a masked TGF-β construct or complex is expressed from a nucleic acid sequence introduced into a mammalian cell (e.g., a CHO cell) and targeted to the secretory pathway such that it is excreted from the cell into its culture media (e.g., a serum free media). The masked TGF-β construct or complex is purified from the cell culture media using affinity chromatography alone or in combination with sized-based separation (e.g., size-based chromatographic or membrane separation). In a specific example of such an embodiment, the masked TGF-β construct or complex comprises an immunoglobulin scaffold (e.g., an IgG polypeptide sequence), and purification is accomplished by affinity chromatography (e.g., protein A or G) alone or in combination with sized based separation (size-based chromatography).

K. Compositions

The present disclosure provides compositions, including pharmaceutical compositions, comprising a masked TGF-β construct or complex. The present disclosure also provides compositions, including pharmaceutical compositions, comprising a nucleic acid or a recombinant expression vector.

1 Compositions Comprising a Masked TGF-β Construct or Complex

A composition of the present disclosure can comprise, in addition to a masked TGF-β construct or complex, one or more of: a salt, e.g., NaCl, $MgCl_2$, KCl, $MgSO_4$, etc.; a buffering agent, e.g., a Tris buffer, N-(2-hydroxyethyl)piperazine-N'-(2-ethanesulfonic acid) (HEPES), 2-(N-morpholino) ethanesulfonic acid (MES), 2-(N-Morpholino)ethanesulfonic acid sodium salt (MES), 3-(N-morpholino) propanesulfonic acid (MOPS), N-tris[hydroxymethyl] methyl-3-aminopropanesulfonic acid (TAPS), etc.; a solubilizing agent; a detergent, e.g., a non-ionic detergent such as Tween-20, etc.; a protease inhibitor; glycerol; and the like.

The composition may comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", $19^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A pharmaceutical composition can comprise: i) a masked TGF-β construct or complex; and ii) a pharmaceutically acceptable excipient. In some cases, a subject pharmaceutical composition will be suitable for administration to a subject, e.g., will be sterile. For example, in some embodiments, a subject pharmaceutical composition will be suitable for administration to a human subject, e.g., where the composition is sterile and is substantially free of detectable pyrogens and/or other toxins, or where such detectable pyrogens and/or other toxins are present at a level within acceptable limits set by an applicable regulatory agency, e.g., the USF&DA.

The protein compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

For example, compositions may include aqueous solution, powder form, granules, tablets, pills, suppositories, capsules, suspensions, sprays, and the like. The composition may be formulated according to the various routes of administration described below.

Where a masked TGF-β construct or complex is utilized (e.g., introduced into a cell culture system) or administered (e.g., subcutaneously, intraperitoneally, intramuscularly, intralymphatically, and/or intravenously) as an injectable directly into a tissue, a formulation can be provided as a ready-to-use dosage form, or as non-aqueous form (e.g., a storage-stable powder that can be reconstituted) or aqueous form, such as liquid composed of pharmaceutically acceptable carriers and excipients. The protein-containing formulations may also be provided in a form that enhances serum half-life of the subject protein following administration. For example, the protein may be provided in a liposome formulation, prepared as a colloid, or other conventional techniques for extending serum half-life. A variety of methods are available for preparing liposomes, as described in, e.g., Szoka et al. 1980 *Ann. Rev. Biophys. Bioeng.* 9:467, U.S. Pat. Nos. 4,235,871, 4,501,728 and 4,837,028. The preparations may also be provided in controlled release or slow-release forms.

In some cases, a composition comprises: a) a masked TGF-β construct or complex; and b) saline (e.g., 0.9% NaCl). In some cases, the composition is sterile. In some cases, the composition is suitable for administration to a human subject, e.g., where the composition is sterile and is substantially free of detectable pyrogens and/or other toxins, or where such detectable pyrogens and/or other toxins are present in an amount within acceptable limits. Thus, the present disclosure provides a composition comprising: a) a masked TGF-β construct or complex; and b) saline (e.g., 0.9% NaCl), where the composition is sterile and is substantially free of detectable pyrogens and/or other toxins, or where such detectable pyrogens and/or other toxins are present in an amount within acceptable limits.

Other examples of formulations suitable for parenteral administration include isotonic sterile injection solutions, anti-oxidants, bacteriostats, and solutes that render the formulation isotonic with the blood of the intended recipient, suspending agents, solubilizers, thickening agents, stabilizers, and preservatives. For example, a subject pharmaceutical composition can be present in a container, e.g., a sterile container, such as a syringe. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The concentration of a masked TGF-β construct or complex in a formulation can vary widely such as from less than about 0.1% (usually at or at least about 2%) to as much as 20% to 50% or more by weight (e.g., from 0.1% to 1%, 1% to 5%. 5% to 10%, 10% to 20%, or 20% to 50% by weight) and will usually be selected primarily based on fluid volumes, viscosities, and patient-based factors in accordance with the particular mode of administration selected and the patient's needs.

The present disclosure provides a container comprising a composition, e.g., a liquid composition. The container can be, e.g., a syringe, an ampoule, and the like. In some cases, the container is sterile. In some cases, both the container and the composition are sterile.

2 Compositions Comprising a Nucleic Acid or a Recombinant Expression Vector

The present disclosure provides compositions, e.g., pharmaceutical compositions, comprising a nucleic acid or a recombinant expression vector of the present disclosure. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

A composition of the present disclosure can include: a) one or more nucleic acids or one or more recombinant expression vectors comprising nucleotide sequences encoding a masked TGF-β construct or complex; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl)amino-tris(hydroxymethyl)methane (BIS-Tris), N-(2-hydroxyethyl)piperazine-N'3-propanesulfonic acid (EPPS or HEPPS), glycylglycine, N-2-hydroxyethylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethane-sulfonic acid (TES), N-tris(hydroxymethyl)methyl-glycine (Tricine), tris(hydroxymethyl)-aminomethane (Tris), etc.). Suitable salts include, e.g., NaCl, MgCl2, KCl, MgSO4, etc.

A pharmaceutical formulation can include a nucleic acid or recombinant expression vector in an amount of from about 0.001% to about 99% (w/w) (e.g., 0.001-0.1, 0.1-1.0, 1.0-10, 10-20, 20-40, 40-80, or 80-100 percent w/w). In the description of formulations, below, "subject nucleic acid or recombinant expression vector" will be understood to include a nucleic acid or recombinant expression vector. For example, in some cases, a subject formulation comprises a nucleic acid or recombinant expression vector.

A subject nucleic acid or recombinant expression vector can be admixed, encapsulated, conjugated or otherwise associated with other compounds or mixtures of compounds; such compounds can include, e.g., liposomes or receptor-targeted molecules. A subject nucleic acid or recombinant expression vector can be combined in a formulation with one or more components that assist in uptake, distribution and/or absorption.

A subject nucleic acid or recombinant expression vector composition can be formulated into any of many possible dosage forms such as, but not limited to, tablets, capsules, gel capsules, liquid syrups, soft gels, suppositories, and enemas. A subject nucleic acid or recombinant expression vector composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A formulation comprising a subject nucleic acid or recombinant expression vector can be a liposomal formulation. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and non-cationic liposomes can be used to deliver a subject nucleic acid or recombinant expression vector.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions may also include surfactants. The use of surfactants in drug products, formulations and in emulsions is well known in the art. Surfactants and their uses are further described in U.S. Pat. No. 6,287,860.

In one embodiment, various penetration enhancers are included, to effect the efficient delivery of nucleic acids. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which a subject antisense nucleic acid is administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanolamine, N,N-dimethylacetamide, N,N-dimethylformamide, 2-pyrrolidone and derivatives thereof, tetrahydrofurfuryl alcohol, and AZONE™.

L. Formulations

Suitable formulations are described above, where the compositions are of pharmaceutically acceptable grade (e.g., the compositions include a pharmaceutically acceptable excipient(s) and active molecules). In some cases, a suitable formulation comprises: a) a masked TGF-β construct or complex; and b) a pharmaceutically acceptable excipient. In some cases, a suitable formulation comprises: a) a nucleic acid comprising a nucleotide sequence encoding a masked TGF-β construct or complex; and b) a pharmaceutically acceptable excipient; in some instances, the nucleic acid is an mRNA. In some cases, a suitable formulation comprises: a) a first nucleic acid comprising a nucleotide sequence encoding the first polypeptide of a masked TGF-β construct or complex; b) a second nucleic acid comprising a nucleotide sequence encoding the second polypeptide of a masked TGF-β construct or complex; and c) a pharmaceutically acceptable excipient. In some cases, a suitable formulation comprises: a) a recombinant expression vector comprising a nucleotide sequence encoding a masked TGF-β construct or complex; and b) a pharmaceutically acceptable excipient. In some cases, a suitable formulation comprises: a) a first recombinant expression vector comprising a nucleotide sequence encoding the first polypeptide of a masked TGF-β construct or complex; b) a second recombinant expression vector comprising a nucleotide sequence encoding the second polypeptide of a masked TGF-β construct or complex; and c) a pharmaceutically acceptable excipient.

Suitable pharmaceutically acceptable excipients are described above.

M. Methods

A masked TGF-β construct or complex is useful for modulating an activity of a T cell. Thus, the present disclosure provides methods of modulating an activity of a T cell, the methods generally involving contacting a target T cell with a masked TGF-β construct or complex.

1 Methods of Modulating Immune Cell Activity Including Generating, Stimulating or Inhibiting Specific Immune Cell Types The present disclosure provides a method of selectively modulating the activity of cells that express TβRI and TβRII, the method comprising contacting the cell (e.g., T cells, B cells, and innate cells, including natural killer (NK) cells, macrophages, dendritic cells, and granulocytes) with a masked TGF-β construct or complex, where contacting the T cell with a masked TGF-β construct or complex selectively modulates the activity of the epitope-specific T cell. In some cases, the contacting occurs in vitro. In some cases, the contacting occurs in vivo. Wherein the activity of the cells (e.g., signaling through canonical pathway, non-canonical pathways, and/or downstream gene expression) subject to a masked TGF-β construct or complex may be assessed relative to treatment groups (e.g., cells subjects) that have not been exposed to TGF-β or a masked TGF-β construct or complex.

The present disclosure provides a method of reducing the number and/or activity of T cells or B cells (e.g., pathogenic autoreactive T cells and/or pathogenic autoreactive B cells); the method comprising administering (e.g., to a subject in need thereof) one or more masked TGF-β constructs or complexes. In some cases, the method increases the number and/or activity of a regulatory T cell (Treg), resulting in reduced number and/or activity of T cells or B cells (e.g., one or more autoreactive T cells and/or one or more autoreactive B cells), wherein the reduction in the number and/or activity of T cells or B cells subjected to one or more masked TGF-β constructs or complexes is assessed relative to treatment groups (e.g., cells subjects) that have not been exposed to TGF-β or one or more masked TGF-β constructs or complexes.

Administration of one or more masked TGF-β constructs or complexes, optionally comprising one or more (e.g., one, two or more or three or more) independently selected wildtype or variant MODs may directly or indirectly effect various cell populations. By way of example, administration of masked TGF-β constructs or complexes, optionally comprising one or more wild type or variant IL-2 MODs may directly stimulate the development and/or survival of FoxP3+ Treg cells (in vivo or in vitro). In addition to any direct action that a TGF-β/IL-2 complex has on various immune cells, the resultant Treg cells can suppress immune responses by, for example, blocking induction of T cell activation and/or the effector phase of T cell responses, suppressing B cell activation, and/or inhibiting the differentiation and/or proliferation of natural killer cells.

a. Tregs

(i) tTregs, pTregs, iTregs and TGF-β Constructs or Complexes Comprising IL-2

The present disclosure provides a method of promoting the development (e.g., expansion) and/or survival of thymus-derived Treg (tTreg) and/or peripheral Treg (pTreg) (Tregs are $CD4^{+}$, $FoxP3^{+}$, and $CD25^{+}$ cells that can suppress autoreactive T cells and B cells); the method comprising administering (e.g., to one or more subjects in need thereof), or contacting CD4+ T cells (e.g., naïve CD4+ T cells) with, one or more masked TGF-β constructs or complexes; (e.g., in tissue culture, blood, or in a specific tissue location such as a wound). The one or more masked TGF-β constructs or complexes administered or contacted in the method may comprise one or more (e.g., one, two or three) independently selected IL-2 MOD polypeptide sequences and/or variant IL-2 MOD polypeptide sequences. Administration or contacting may be conducted in conjunction with the administration or contacting of the cells with vitamin D (e.g., Vitamin D3 or an analog thereof), retinoic acid (e.g., all trans retinoic acid), and/or an inhibitor of the mammalian target of rapamycin (mTOR) (e.g., rapamycin or a functional analog thereof such as sirolimus, everolimus or temsirolimus). Accordingly, the present disclosure provides a method of promoting the development and/or survival of induced regulatory T cells (iTregs), which are FoxpP3+, FoxP3+ thymus derived Treg (tTreg) and/or FoxP3+ peripheral Treg (pTreg), the method comprising administering (e.g., to a subject in need thereof), or contacting CD4+ T cells (e.g., naïve CD4+ T cells) with, one or more masked TGF-β constructs or complexes that comprises one or more IL-2 MOD polypeptide sequences and/or variant IL-2 MOD polypeptide sequences, optionally in the presence of vitamin D or an analog thereof, retinoic acid (e.g., all trans retinoic acid) or an analog thereof, and/or rapamycin or an analog thereof. The effects of administration or treatment with one or more masked TGF-β constructs or complexes may be assessed relative the baseline value (e.g., number of cells prior to treatment) or relative to a treatment group (e.g., cells or subjects) that are matched with a test group (e.g., otherwise identical to), but that have not been exposed to TGF-β or one or more masked TGF-β constructs or complexes.

The present disclosure provides a method of increasing the induction/proliferation of Tregs, maintaining Tregs and/or sustaining their function, the method comprising contacting T cells (e.g., CD4+ T cell in vivo or in vitro) with one or more masked TGF-β constructs or complexes comprising one or more (e.g., one, two or three) independently selected IL-2 MOD polypeptide sequences and/or variant IL-2 MOD polypeptide sequences. The contacting increases the induction/proliferation of Tregs, maintains the Tregs, and/or sustains their function either relative to a baseline value determined prior to the contacting or relative to a control group of otherwise identical cells that have not been contacted with the one or more masked TGF-β constructs or complexes. The disclosure includes and provides for masked TGF-β constructs or complexes comprising one or more (e.g., one, two or three) independently selected IL-2 MOD polypeptide sequences and/or variant IL-2 MOD polypeptide sequences for use in the method. In an embodiment, the masked TGF-β constructs or complexes comprising one or more (e.g., one, two or three) independently selected IL-2 MOD polypeptide sequences and/or variant IL-2 MOD polypeptide sequences has the structural organization described in FIG. 1 structures A, B or C. In an embodiment, the masked TGF-β constructs or complexes comprising one or more (e.g., one, two or three) independently selected IL-2 MOD polypeptide sequences and/or variant IL-2 MOD polypeptide sequences has the structural organization described in FIG. 1 structures D or E. In an embodiment, the masked TGF-β constructs or complexes comprising one or more (e.g., one, two or three) independently selected IL-2 MOD polypeptide sequences and/or variant IL-2 MOD polypeptide sequences has the structural organization described in FIG. 1 structure F.

The present disclosure provides a method of increasing the induction/proliferation of Tregs, maintaining Tregs and/or sustaining their function, the method comprising contacting T cells (e.g., CD4+ T cell in vivo or in vitro) with one or more masked TGF-β constructs or complexes comprising one or more (e.g., one, two or three) independently selected PD-L1 or PD-L2 MOD polypeptide sequences and/or variant PD-L1 or PD-L2 MOD polypeptide sequences. The contacting increases the induction/proliferation of Tregs, maintains the Tregs, and/or sustains their function either relative to a baseline value determined prior to the contacting or relative to a control group of otherwise identical cells that have not been contacted with the one or more masked TGF-β constructs or complexes. The disclosure includes and provides for masked TGF-β constructs or complexes comprising one or more (e.g., one, two or three) independently selected PD-L1 or PD-L2 MOD polypeptide sequences and/or variant PD-L1 or PD-L2 MOD polypeptide sequences for use in the method. In an embodiment, the masked TGF-β constructs or complexes comprising one or more (e.g., one, two or three) independently selected PD-L1 or PD-L2 MOD polypeptide sequences and/or variant PD-L1 or PD-L2 MOD polypeptide sequences has the structural organization described in FIG. 1 structures A, B or C. In an embodiment, the masked TGF-β constructs or complexes comprising one or more (e.g., one, two or three) independently selected PD-L1 MOD polypeptide sequences and/or variant PD-L1 or PD-L2 MOD polypeptide sequences has the structural organization described in FIG. 1 structures D or E. In an embodiment, the masked TGF-β constructs or complexes comprising one or more (e.g., one, two or three) independently selected PD-L1 or PD-L2 MOD polypeptide sequences and/or variant PD-L1 or PD-L2 MOD polypeptide sequences has the structural organization described in FIG. 1 structure F. Masked TGF-β constructs or complexes comprising one or more (e.g., one, two or three) independently selected PD-L1 or PD-L2 MOD polypeptide sequences and/or variant PD-L1 or PD-L2 MOD polypeptide sequences may be administered with IL-2 (e.g., recombinant IL-2 such as Proleukin (aldesleukin)) for the induction/proliferation of Tregs (e.g., Tbet+ FoxP3+ iTreg cells), maintaining Tregs, and/or sustaining their function.

The present disclosure provides a method for increasing the induction/proliferation of Tregs, maintaining Tregs (e.g., Treg numbers), and/or sustaining their function, the method comprising contacting T cells (e.g., CD4+ cells in vivo or in vitro) with one or more masked TGF-β constructs or complexes comprising one or more (e.g., one, two or three) independently selected IL-2 and/or variant IL-2 MOD polypeptide sequences, and one or more independently selected wt. or variant PD-L1 and/or PD-L2 MOD polypeptide sequences. The contacting increases the induction/proliferation of Tregs, maintains the Tregs, and/or sustains their function either relative to a baseline value determined prior to the contacting or relative to a control group of otherwise identical cells that have not been contacted with the one or more masked TGF-β constructs or complexes. The disclosure includes and provides for masked TGF-β constructs or complexes comprising one or more (e.g., one, two or three) independently selected IL-2 MOD and/or variant IL-2 MOD polypeptide sequences and one or more independently selected wt. or variant PD-L1 and/or PD-L2 polypeptide sequences for use in the method. In an embodiment, the masked TGF-β constructs or complexes comprising one or more (e.g., one, two or three) independently selected IL-2 MOD and/or variant IL-2 MOD polypeptide sequences and one or more independently selected wt. or variant PD-L1 and/or PD-L2 polypeptide sequences has the structural organization described in FIG. 1 structures A, B or C. In an embodiment, the masked TGF-β constructs or complexes comprising one or more (e.g., one, two or three) independently selected IL-2 MOD and/or variant IL-2 MOD polypeptide sequences and one or more independently selected wt. or variant PD-L1 and/or PD-L2 polypeptide sequences has the structural organization described in FIG. 1 structures D or E. In an embodiment, the masked TGF-β constructs or complexes comprising one or more (e.g., one, two or three) independently selected IL-2 MOD and/or variant IL-2 MOD polypeptide sequences and one or more independently selected wt. or variant PD-L1 and/or PD-L2 polypeptide sequences has the structural organization described in FIG. 1 structure F.

Contacting T cells (e.g., naïve CD4+ cells) with masked TGF-β constructs or complexes (e.g., in vivo or in vitro) comprising one or more (e.g., one, two or three) independently selected IL-2 MOD and/or variant IL-2 MOD polypeptide sequences, alone or in combination with one or more independently selected wt. or variant PD-L1 and/or PD-L2 MOD polypeptide sequences can increase the expression of FoxP3 and Treg cell induction (e.g., Tbet+ FoxP3+ iTreg cells). Similarly, contacting T cells (e.g., naïve CD4+ cells) with masked TGF-β constructs or complexes (e.g., in vitro or in vivo) comprising one or more (e.g., one, two or three) independently selected PD-L1 or PD-L2 and/or variant PD-L1 or PD-L2 MOD polypeptide sequences, alone or in combination with IL-2 (e.g., recombinant human IL-2) can increase the expression of FoxP3 and Treg cell induction (e.g., Tbet+ FoxP3+ iTreg cells). Where both IL-2 and either PD-L1 or PD-L2 are provided to the cells the contacting may reduce T reg endolysosomal asparaginyl endopeptidase. Reduction in endolysosomal asparaginyl endopeptidase, which is responsible for destabilizing Foxp3 in Tregs, results in maintenance of Tregs (e.g., iTregs) and sustains their function. See, e.g., Francsisco et al., J Exp. Med., 206(13) 3015-3029 (2018) and Stathopoulou et al. Immunity 49(2): 247-263 (2018). Accordingly, where the masked TGF-β constructs or complexes comprise both IL-2 and either PD-L1 or PD-L2, contacting the T-cells may result not only in increased numbers of Treg, but also increased stability and function of those cells.

Where contacting of masked TGF-β constructs or complexes comprising IL-2 MOD (wt. and/or variant) and/or PD-L1 and/or PD-L2 (wt. and/or variant) polypeptide sequences occurs in vivo (or in vitro with the treated cells administered to patient), the contacting may constitute treatment. Such treatments result in increased Treg cell levels (e.g., total number of iTregs or their fraction in a tissue or circulating in blood) in an individual or population of individuals. The treatment may also result in elevated levels of FoxP3 in Tregs.

Where the masked TGF-β constructs or complexes comprise wt. and/or variant IL-2 MOD polypeptide sequence(s) in combination with wt. or variant PD-L1 and/or PD-L2 MOD polypeptide sequence(s) the increased Treg cell levels (e.g., total number of iTregs or their fraction in a tissue or circulating in blood) in an individual or population of individuals persists for a longer period of time than is observed when treating an individual or population of individuals (e.g., matched for age, gender, weight, and/or disease status) with an otherwise identical masked TGF-β construct or complex lacking the PD-L1 sequence(s). Treatment with masked TGF-β constructs or complexes comprising wt. and/or variant IL-2 MOD polypeptide sequences in combination with wt. or variant PD-L1 and/or PD-L2 MOD polypeptide sequences may also result in persistently elevated levels of FoxP3 in Tregs relative to the levels observed when the treatment is conducted with an otherwise identical masked TGF-β construct or complex that lacks PD-L1 polypeptide sequences. Treatment with masked TGF-β constructs or complexes comprising wt. and/or variant IL-2 MOD polypeptide sequences in combination with wt. or variant PD-L1 and/or PD-L2 MOD polypeptide sequences may also result in reduced activity of endolysosomal asparaginyl endopeptidase in Treg cells relative to the activity of that enzyme in T-cells of an individual (or group of individuals on average) that have been treated with an otherwise identical masked TGF-β construct or complex that lacks PD-L1 MOD polypeptide sequences.

The process of contacting T-cells, with masked TGF-β constructs or complexes comprising wt. and/or variant IL-2 MOD polypeptide sequences alone or in combination with wt. or variant PD-L1 and/or PD-L2 MOD polypeptide sequences (e.g., in vitro, ex vivo or in vivo such as in a process of treating an individual), may further comprise contacting the T cells presence of vitamin D or an analog thereof, retinoic acid (e.g., all trans retinoic acid) or an analog thereof, and/or an mTOR inhibitor such as rapamycin or an analog thereof). Contacting in the presences of those agents may increase level of Tregs (e.g., number or relative number of Tregs in an individual or tissue due to proliferation or maintenance of cells with the Treg phenotype) either relative to a baseline value determined prior to the contacting or relative to a the value determine in a control group (e.g., a group of individuals) that have not been contacted with the one or more masked TGF-β constructs or complexes. Where control groups of individuals are employed the individual may be matched for one or more of age, sex, and weight. The individuals may also be matched for ethnicity, alcohol consumption, and/or smoking status.

The present disclosure provides a method of increasing the number of Tregs in one or more subjects (e.g., individuals or patients), the method comprising administering to the one or more subjects one or more masked TGF-β constructs or complexes comprising one or more (e.g., one, two or three) independently selected IL-2 MOD polypeptide sequences and/or variant IL-2 MOD polypeptide sequences and optionally comprising one or more independently selected wt. or variant PD-L1 or PD-L2 MOD polypeptide sequences, where the administering results in an increase in the number of Tregs in the one or more subjects. For example, the average number of Tregs (e.g., in blood or a tissue or a location such as a wound) can be increased by at least 5%, at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, at least 10-fold, or more than 10-fold relative to the number of Tregs in the individual prior to administration of the one or more masked TGF-β constructs or complexes or relative to a control group that did not receive the one or more masked TGF-β constructs or complexes.

The present disclosure provides a method of increasing the number of Tregs in one or more subjects (e.g., individuals or patients), the method comprising administering to the one or more subjects one or more masked TGF-β constructs or complexes comprising one or more (e.g., one, two or three) independently selected wt. or variant PD-L1 and/or PD-L2 polypeptide sequences optionally in combination with IL-2 (e.g., recombinant IL-2 such as Proleukin (aldesleukin)), where the administering results in an increase in the number of Tregs in the one or more subjects. For example, the average number of Tregs (e.g., in blood or a tissue or a location such as a wound) can be increased by at least 5%, at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, at least 10-fold, or more than 10-fold relative to the number of Tregs in the individual prior to administration of the one or more masked TGF-β constructs or complexes or relative to a control group that did not receive the one or more masked TGF-β constructs or complexes b. T Helper Cells (i) Th9 Cells and Masked TGF-β Constructs or Complexes Comprising IL-4

The present disclosure provides a method of promoting the development and/or survival of thymus-derived Th9 cells (CD4+ cells characterized by expression of CD4 and CCR6 and the lack of CCR4); the method comprising administering (e.g., to a subject in need thereof), or contacting CD4+ T cells (e.g., naïve CD4+ T cells or Th2 cells) with, one or more masked TGF-β constructs or complexes. The one or more masked TGF-β constructs or complexes administered or contacted in the method may comprise one or more (e.g., one, two or three) independently selected IL-4 MOD polypeptide sequences and/or variant IL-4 MOD polypeptide sequences. Accordingly, the present disclosure provides a method of promoting the development and/or survival of Th9 cells comprising administering (e.g., to a subject in need thereof), or contacting naïve T cells with, one or more masked TGF-β constructs or complexes that comprises one or more IL-4 MOD polypeptide sequences and/or variant IL-4 MOD polypeptide sequences, where the administering results in an increase in the number of Th9 cells in the individual. For example, the number of Th9 cells (e.g., in tissue culture, blood, or in a specific tissue location) can be increased by at least 5%, at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, at least 10-fold, or more than 10-fold.

(ii) Th17 Cells and TGF-β Constructs or Complexes Comprising IL-17

The present disclosure provides a method of stimulating the production of Th17 cells (T cells defined by their production of IL-17), the method comprising administering (e.g., to a subject in need thereof), or contacting CD4+ T cells (e.g., naïve CD4+ T cells) with one or more masked TGF-β constructs or complexes comprising at least one IL-6 or variant IL-6 MOD polypeptide (e.g., one, two or three IL-6 and/or variant IL-6 MOD polypeptides). For example, the number of Th17 cells (e.g., in tissue culture, blood, or in a specific tissue location) can be increased by at least 5%, at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, at least 10-fold, or more than 10-fold relative to either the number present prior to administration of the one or more masked TGF-β constructs or complexes, or relative to a control group that did not receive the one or more masked TGF-β constructs or complexes. The method may be useful for maintaining the gut mucosal barrier function and may be needed for protection against pathogenic bacteria (e.g., against *Citrobacter*) and for recruiting neutrophils and monocytes and neutrophils to attack and destroy extracellular fungi (e.g., mucocutaneous *Candida*).

(iii) Tfh Cells and Masked TGF-β Constructs or Complexes Comprising IL-21 and IL-23

The present disclosure provides a method of stimulating the production of T follicular helper (Tfh) cells (T cells which are defined by CXCR5 expression), the method comprising administering (e.g., to a subject in need thereof), or contacting macrophages with, one or more masked TGF-β constructs or complexes comprising at least one MOD polypeptide (e.g., one, two or three) independently selected from an IL-21 MOD polypeptide, an IL-23 MOD polypeptide, a variant of an IL-21 or a variant of an IL-23 MOD polypeptide. For example, the number of Tfh cells (e.g., in tissue culture, blood, or in a specific tissue location such as a lymphoid follicle) can be increased by at least 5%, at least 10%, at least 15%, at least 20%, at least 25%, at least 30%, at least 40%, at least 50%, at least 60%, at least 70%, at least 80%, at least 90%, at least 2-fold, at least 2.5-fold, at least 5-fold, at least 10-fold, or more than 10-fold relative to either the number present prior to administration of the one or more masked TGF-β constructs or complexes, or relative to a control group that did not receive the one or more masked TGF-β constructs or complexes. The method may be useful in supporting the development of antigen-specific antibody responses.

c. T Effector Cells and Masked TGF-β Constructs or Complexes Comprising IL-7

(i) IL-7 and CD8+ T Cells

The present disclosure provides a method of promoting the development (lineage commitment) and/or survival of CD4+ and/or CD8+ T-cell (e.g., by promoting thymocyte expression of the IL-7R (e.g., IL-7Ra); the method comprising administering (e.g., to a subject in need thereof), or contacting precursor CD4+CD8+ T-cells with, one or more masked TGF-β constructs or complexes. The one or more masked TGF-β constructs or complexes administered or contacted in the method may comprise one or more (e.g., one, two or three) independently selected IL-7 MOD polypeptide sequences and/or variant IL-7 MOD polypeptide sequences. Accordingly, the present disclosure provides a method of promoting the development of cells committed to CD4+ or CD8+ lineages (e.g., by promoting thymocyte expression of interleukin (IL)-7Ra), the method comprising administering (e.g., to a subject in need thereof), or contacting CD 4+ and or CD8+ cell precursors (e.g., CD4+8+ T-cells) with one or more masked TGF-β constructs or complexes comprising one or more (e.g., one, two or three) independently selected IL-7 MOD polypeptide sequences and/or variant IL-7 MOD polypeptide sequences; wherein the development and/or survival of CD4+ and/or CD8+ cells is assessed by monitor peripheral blood or specific tissue (e.g., thymus) CD4+ and/or CD8+ cell numbers.

(i) IL-7 and Low Affinity T-Cells

The present disclosure provides a method of regulating peripheral T-cell homeostasis by promoting IL-7-dependent survival of CD4+ T cells and CD8+ T cells with T-cell receptors having low affinity for peptides being presented by MHC proteins. See, e.g., *Cold Spring Harbor Perspect. Biol.* 2017; 9:a022236 and citations therein. The method may operate by controlling thymocyte IL-7Rα expression. The method promoting IL-7-dependent survival comprises administering (e.g., to a subject in need thereof) one or more masked TGF-β constructs or complexes. The one or more masked TGF-β constructs or complexes administered may comprise one or more (e.g., one, two or three) independently selected IL-7 MOD polypeptide sequences and/or variant IL-7 MOD polypeptide sequences. Accordingly, the present disclosure provides a method of regulating peripheral T-cell homeostasis; the method comprising administering (e.g., to a subject in need thereof) one or more masked TGF-β constructs or complexes comprising one or more (e.g., one, two or three) independently selected IL-7 MOD polypeptide sequences and/or variant IL-7 MOD polypeptide sequences, wherein administration of the TGF-β construct or complex increases the number of peripheral CD4+ T cells and CD8+ T cells in a subject, or group of subjects, relative to the number of those cells prior to administration.

d. Masked TGF-β Constructs or Complexes and IL-10

The present disclosure provides a method of inhibiting type 2 innate lymphoid cells (ILC2 cells) (e.g., to suppress asthma and allergic inflammation, see, e.g., Rajas et al., *J Allergy Clin Immunol,* 139(5):1468 (2017); and Ogasawara et al., *J Allergy Clin Immunol,* 141(3): 1147-1151 (2018)), using one or more masked TGF-β constructs or complexes comprising at least one (e.g., at least two) independently selected wild type or variant IL-10 MOD polypeptide (e.g., one, two or three independently selected MODs). Variant IL-10 MOD polypeptides may include all or part of a monomeric IL-10 polypeptide (e.g., all or part of SEQ ID NO:50 or 51 substituted with a 5-7 as insertion in the hinge region between helices D and E mentioned above). See, e.g., Josephson et al., *J. Biol. Chem.* 275:13552-13557 (2000). The method of inhibiting type II innate lymphoid cells comprising administering (e.g., to a subject in need thereof), or contacting type II innate lymphoid cells with, one or more masked TGF-β constructs or complexes optionally comprising one or more (e.g., one, two or more or three or more) independently selected wild type or variant IL-10 MODs. The inhibition of ILC2 cells is assessed by suppression of type 2 cytokine (e.g., IL-3 and/or IL-13) expression by ILC2 cells relative to either the amount if type 2 cytokines prior to administration of the one or more masked TGF-β constructs or complexes, or relative to the amount of type 2 cytokines in a control group (e.g., in cells, tissue, or bodily fluid from a subject) that have not been exposed to TGF-β or the one or more masked TGF-β constructs or complexes.

TGF-β and IL-10 have nonredundant roles in maintaining gastrointestinal homeostasis, with IL-10 functioning both upstream and downstream of TGF-β. For example, IL-10 can induce TGF-β expression and secretion by lamina propria T cells and it acts cooperatively with TGF-β to promote differentiation of Treg cells. Accordingly, the present disclosure provides methods of maintaining intestinal homeostasis and differentiation of Treg cells in a subject comprising administering one or more masked TGF-β constructs or complexes comprising a wt. or variant IL-10 sequence or both an IL-2 and IL-10 aa sequence, either or both of which may be an independently selected wt. or a variant sequence. See, e.g., *Cold Spring Harbor Perspect. Biol.* 2017; 9:a022236 and citations therein.

In some case, such as where it is desirable to induce tolerance, at least one MOD polypeptide (e.g., one, two or three independently selected MODs) present in one or more masked TGF-β constructs or complexes comprising at least one (e.g., at least two) independently selected wild type or variant IL-10 MOD polypeptides. See, e.g., *Am J Physiol Gastrointest Liver Physiol* 306: G575-G581 (2014), and Levings et al. *Int Arch Allergy Immunol.* 129(4):263-76 (2002). The variant IL-10 MOD polypeptides may include all or part of a monomeric IL-10 polypeptide (e.g., all or part of SEQ ID NO:50 or 51 substituted with a 5-7 aa insertion in the hinge region between helices D and E to form an active monomeric IL-10 as mentioned above. Accordingly, the present disclosure provides methods of inducing tolerance in a subject comprising administering one or more masked TGF-β constructs or complexes comprising a wt. or variant IL-10 sequence or both an IL-2 and IL-10 polypeptide sequence. Alternatively, one or more masked TGF-β constructs or complexes comprising a wt. or variant IL-10 (e.g., monomeric IL-10) sequence may be administered with (concurrently or combined) one or more masked TGF-β constructs or complexes comprising a wt. or variant IL-2 polypeptide sequence.

e. Masked TGF-β Constructs or Complexes and FasL

In some case, such as where it is desirable to induce tolerance or suppress T-effector cells, at least one MOD polypeptide (e.g., one, two or three independently selected MODs) present in one or more masked TGF-β constructs or complexes may comprise a Fas ligand (FasL) polypeptide, or a variant of a Fas ligand polypeptide. (see, e.g., Qiu et. al. *J Surg Res.* 218:180-193 (2017). As discussed above, IL-10 or variant IL-10 polypeptides may also be utilized to induce tolerance.

Accordingly, the present disclosure provides methods of inducing tolerance or suppressing T-effector cells in a subject comprising administering one or more masked TGF-β constructs or complexes comprising a wt. or variant FasL polypeptide sequence or both an IL-2 and a FasL polypeptide sequence. The present disclosure also provides for induction of tolerance. Alternatively, one or more masked TGF-β constructs or complexes comprising a wt. or variant FasL sequence may be administered with (concurrently or combined) one or more masked TGF-β constructs or complexes comprising a wt. or variant IL-2 polypeptide sequence.

f. Methods of Modulating Other Cells

The present disclosure provides a method of supporting the development and/or survival of invariant natural killer T (iNKT) cells; the method comprising administering (e.g., to a subject in need thereof), or contacting iNKT cell precursor cells with a masked TGF-β construct or complex, optionally comprising one or more (e.g., one, two or more or three or more) independently selected wild type or variant MODs. Where the development and/or survival is assessed relative to treatment groups (e.g., cells or subjects) that have not been exposed to TGF-β or a masked TGF-β construct or complex.

The present disclosure provides a method of inhibiting macrophages (e.g., macrophages activated by a Toll Like Receptor Ligand or cytokine stimulation); the method comprising administering (e.g., to a subject in need thereof), or contacting macrophages with, one or more masked TGF-β constructs or complexes optionally comprising one or more (e.g., one, two or more or three or more) independently selected wildtype or variant MODs; wherein the inhibition is assessed relative to treatment groups (e.g., cells or subjects) that have not been exposed to TGF-β and/or a one or more masked TGF-β constructs or complexes. Activation, and inhibition of macrophage activation is assessed by methods known in the art, such as nitric oxide production by activated macrophages.

TGF-β inhibits $H_2O_2$ production by monocytes, and is a chemoattractant for monocytes that inhibits fibronectin adherence. See, e.g., Warwick Davies and Cole, *J Immunol.* 155(6): 3186-3193 (1995). Accordingly, the present disclosure provides a method of stimulating monocytes (e.g., resting monocytes) to undergo migration; the method comprising administering (e.g., to a subject in need thereof), or contacting monocytes with one or more masked TGF-β constructs or complexes optionally comprising one or more (e.g., one, two or more or three or more) independently selected wildtype or variant MODs; wherein the stimulation is assessed relative to treatment groups (e.g., cells or subjects) that have not been exposed to TGF-β and/or one or more masked TGF-β constructs or complexes. Activation, and inhibition of monocytes activation is assessed by methods known in the art, including measurement of $H_2O_2$ production and fibronectin adherence. $H_2O_2$ production (e.g., in response to a monocyte stimulus) may be decreased by at least 5% (e.g., at least 10%, at least 15%, at least 20%, at least 25%, at least 30%, at least 40%, at least 50%, at least 60%, at least 70%, at least 80%, at least 90%, 10-fold, 20-fold, 30-fold, or more).

The present disclosure provides a method of altering peripheral blood monocyte and/or macrophage migration (e.g., assessed by time-lapse microscopy or Boyden chamber assay) into tissues (e.g., injured or inflamed tissue), and/or to enhance macrophage and/or monocyte adherent properties; the method comprising administering (e.g., to a subject in need thereof), or contacting myeloid cells with a masked TGF-β construct or complex, optionally comprising one or more (e.g., one, two or more or three or more) independently selected wildtype or variant MODs; wherein the migration and/or adherent properties are assessed relative to treatment groups (e.g., cells or subjects) that have not been exposed to TGF-β or a masked TGF-β construct or complex. For example, some instances short term interaction of cells or tissue with TGF-β (e.g., TGF-β1) stimulated the migration of macrophages or monocytes, whereas long-term exposure decreased their migration. See, e.g., Kim et al., Blood 108:1821-1829 (2006), and Xu et al Bone Research, 6 (Article No. 2) (2018).

The present disclosure provides a method of inducing chemotaxis (e.g., assessed by time-lapse microscopy or Boyden chamber assay) and/or enhancing the adherent properties of mast cells; the method comprising administering (e.g., to a subject in need thereof), or contacting mast cells with, a masked TGF-β construct or complex, optionally comprising one or more (e.g., one, two or more or three or more) independently selected wildtype or variant MODs; wherein the chemotaxis and/or adherent properties are assessed relative to treatment groups (e.g., cells or subjects) that have not been exposed to TGF-β or a masked TGF-β construct or complex.

The present disclosure includes and provides methods of modulating auto reactive and/or inflammatory T cells (e.g., Th1, Th2, Th17 and/or Th22 cells). The methods comprise administering (e.g., to a subject in need thereof), or contacting the T cells (e.g., in vivo or in vitro) with, one or more masked TGF-β constructs or complexes, optionally comprising one or more (e.g., one, two or more or three or more) independently selected wildtype and/or variant MODs. The TGF-β constructs or complexes that optionally comprise one or more wildtype and/or variant MODs may directly interact with such inflammatory T cells, and/or indirectly affect such cells through released molecules (e.g., cytokines/interleukins) or through other cell populations. By way of example, administration of masked TGF-β constructs or complexes optionally comprising one or more wild type and/or variant IL-2 MODs (a TGF-β/IL-2 complex) may directly stimulate the development and/or survival of FoxP3+ T reg cells (in vitro or in vivo). In addition to the direct interactions of a TGF-β/IL-2 complexes with cells resulting in $FoxP3^{+}$ T reg cells, the resultant T regs may influence other cells such as by, for example, blocking induction of T cell activation and/or the effector phase of T cell responses, suppressing B cell activation, and inhibiting the differentiation and/or proliferation of natural killer cells. Such actions by T regs may be carried out through various means including, but not limited to, production of IL-10, TGF-β, and/or the binding of CTLA-4 on the T reg to B7 (B7-1 or CD80/B7-2 or CD86) on antigen presenting cells thereby competing with CD28 costimulation of those cells. Accordingly, this disclosure includes and provides for methods of modulating autoreactive T cells and inflammatory T cells belonging to lineages such as Th1, Th2, Th17, Th22 etc. The autoreactive cells may be a population of bystander T cells (e.g., bystander Th1, Th2, and/or Th17 cells). For example, in celiac disease the T cells that are modulated may include Th17 cells found in the intestinal mucosa resulting in reduced expression, secretion, and/or mucosal tissue levels of IL-17A, IL-17F, IL-21, and/or IL-22.

The present disclosure includes and provides a method of inhibiting the action of CD4+ Th1 cells (e.g., reduce their secretion of interferon γ and/or TNF) and thereby activation of macrophages (e.g., phagocytosis and the macrophage involvement in delayed type hypersensitivity or "DTH" that is a component of inflammatory disease including granulomatous inflammation). The method comprising administering (e.g., to a subject in need thereof), or contacting CD4+ Th1 cells with, a one or more masked TGF-β constructs or complexes, optionally comprising one or more (e.g., one, two or more or three or more) independently selected wildtype or variant MODs; wherein the inhibition of Th1 cell action is assessed by the production of interferon γ and/or TNF relative to a treatment group (e.g., cells or subjects) that have not been exposed to TGF-β and/or one or more masked TGF-β constructs or complexes.

The present disclosure includes and provides a method of inhibiting the action (activation) of CD4+ Th2 cells (e.g., reduced IgE, mast cell, and eosinophil mediated reactions); the method comprising administering (e.g., to a subject in need thereof), or contacting CD4+ Th2 cells with, one or more masked TGF-β constructs or complexes, optionally comprising one or more (e.g., one, two or more or three or more) independently selected wildtype or variant MODs; wherein the inhibition of Th2 cell action (the degree of Th2 cell activation) is assessed by the production of IL-4, IL-5, and/or IL-13 relative to a treatment group (e.g., cells or subjects) that have not been exposed to TGF-β and/or one or more masked TGF-β constructs or complexes.

2 Methods of Selectively Delivering a Costimulatory Polypeptide

The present disclosure provides a method of delivering TGF-β in a masked form along with one or more (e.g., one, two or more, three or more, or four or more) independently selected MODs and/or variant MODs using one or more masked TGF-β constructs or complexes. Delivery of MODs to cells comprising TβRs can be complicated due to the interact actions of MODs with their receptors (co-MODs) on cells that contain or do not contain TβRs. Masked TGF-β constructs or complexes may be targeted to cells by varying the number MODs and the affinity for their corresponding co-MODs relative to the effective affinity of the masked TGF-β polypeptide for the TβR. Incorporating variant MODs with reduced affinity into masked TGF-β constructs or complexes allows the TGF-β polypeptide to more strongly influence, or even dominate, the binding interactions. Incorporating a combination of variant MODs with reduced affinity (provided they can still stimulate their co-MODs) and TGF-β polypeptides with relatively strong affinity for the TβR permits the masked TGF-β constructs and complexes comprising one or more MOD(s) to be biased (or even selective) in their binding to cells with both TβRs and the corresponding co-MOD(s). Such a combination also avoids the off-target stimulation of cell bearing the co-MODs without TβR.

The present disclosure provides for the selective delivery of both a TGF-β polypeptide and at least one variant MOD selectively to target cells (e.g., in vitro or in vivo) expressing on their surface membrane a TβR (e.g., TβRII and/or TβRI) and co-MODs corresponding to the at least one variant MOD. When used in this context, "selective delivery" means that the MOD of the masked TGF-β construct or complex is delivered to a co-MOD on a higher number of cells that express a TβR (e.g., TβRII and/or TβRI), i.e., the "target cells", than to cells that do not comprise a TβR, i.e., "non-target cells."

In view of the foregoing, the present disclosure provides for the delivery of both a TGF-β polypeptide and at least one variant MOD selectively to target cells (e.g., in vitro or in vivo) expressing on their surface membrane a TβR (e.g., TβRII and/or TβRI) and co-MODs corresponding to the at least one variant MOD; the method comprising: contacting a population of cells with an amount of a masked TGF-β construct or complex comprising at least one reduced affinity variant MOD that is insufficient to saturate the TβRS present on the cells (e.g., occupy less than 70%, 60%, 50%, 40% or 30% of the TβRS present on the cells); and permitting the masked TGF-β construct or complex comprising at least one reduced affinity variant MOD to interact with the cells (e.g., for a time sufficient to bind). In such a method the ratio of (i) number of cells expressing both the TβR and a co-MOD bound by the masked TGF-β construct or complex comprising at least one reduced affinity variant MOD divided by the number of cells expressing the co-MOD bound by the masked TGF-β construct or complex comprising at least one reduced affinity variant MOD is greater than (ii) the ratio of number of cells expressing both the TβR and a co-MOD bound by the masked TGF-β construct or complex comprising the wt. MOD divided by the number of cells expressing the co-MOD bound by the masked TGF-β construct or complex comprising the wt. MOD.

The present disclosure provides for the delivery to target cells (e.g., in vitro or in vivo) of both a masked TGF-β polypeptide and at least one wt. and/or variant IL-2 MOD polypeptide, comprising contacting the target cell with a masked TGF-β construct or complex comprising at least one wt. and/or variant IL-2 MOD polypeptide optionally in the presence of vitamin D, retinoic acid (e.g., all trans retinoic acid), and/or rapamycin. In one case masked TGF-β polypeptide comprising at least one wt. or variant IL-2 MOD polypeptide are delivered in the presence of any one, any two, or all three of vitamin D, retinoic acid (e.g., all trans retinoic acid), and/or rapamycin.

The present disclosure provides for the delivery and optionally the selective delivery to target cells (e.g., in vitro or in vivo) of a masked TGF-β construct or complex comprising at least one wild type and/or variant IL-6 MOD polypeptide.

The present disclosure provides for the delivery and optionally the selective delivery to target cells (e.g., in vitro or in vivo) of both a masked TGF-β construct or complex comprising at least one wild type and/or variant IL-7 MOD polypeptide.

The present disclosure provides for the delivery and optionally the selective delivery to target cells (e.g., in vitro or in vivo) of both a masked TGF-β construct or complex comprising at least one wild type and/or variant IL-10 MOD polypeptide.

The present disclosure provides for the delivery and optionally the selective delivery to target cells (e.g., in vitro or in vivo) of both a masked TGF-β construct or complex comprising at least one wild type and/or variant IL-15 MOD polypeptide.

The present disclosure provides for the delivery and optionally the selective delivery to target cells (e.g., in vitro or in vivo) of both a masked TGF-β construct or complex comprising at least one wild type and/or variant IL-21 MOD polypeptide.

The present disclosure provides for the delivery and optionally the selective delivery to target cells (e.g., in vitro or in vivo) of both a masked TGF-β construct or complex comprising at least one wild type and/or variant IL-23 MOD polypeptide.

The present disclosure provides for the delivery and optionally the selective delivery to target cells (e.g., in vitro or in vivo) of both a masked TGF-β construct or complex comprising at least one wild type and/variant PD-L1 MOD polypeptide.

The present disclosure provides for the delivery and optionally the selective delivery to target cells (e.g., in vitro or in vivo) of both a masked TGF-β construct or complex comprising at least one wild type and/or variant FasL MOD polypeptide.

3 Methods of Treatment or Prophylaxis

The present disclosure provides treatment and prophylaxis methods, the methods may comprise contacting a target population of cells from an individual (e.g., in vitro or in vivo) and/or administering to the individual, an effective amount of a masked TGF-β construct or complex (e.g., PSM-4033-4039), or one or more nucleic acids or expression vectors encoding the masked TGF-β construct or complex, effective to selectively modulate the activity of the target cell population of cells and/or to treat the individual. Where target cells are treated separately from the individual (i.e., in vitro), all or a portion of the cells or their progeny may be administered to individual. In some cases, a method of treatment or prophylaxis comprises administering to an individual in need thereof an effective amount of one or more recombinant expression vectors comprising nucleotide sequences encoding a masked TGF-β construct or complex. In some cases, a method of treatment or prophylaxis comprises administering to an individual in need thereof one or more mRNA molecules comprising nucleotide sequences encoding a masked TGF-β construct or complex. In some cases, a method of treatment or prophylaxis comprises contacting a target population of cells from an individual (i.e., in vitro) in need thereof with an effective amount of a masked TGF-β construct or complex (e.g., PSM-4033-4039) and thereby forming a contacted target population of cells, the method further comprising administering all or part of the contacted target population of cells (and/or their progeny) to the individual. In some cases, a method of treatment or prophylaxis comprises administering to an individual in need thereof an effective amount of a masked TGF-β construct or complex (e.g., PSM-4033-4039), or a pharmaceutically acceptable composition comprising an effective amount of a masked TGF-β construct or complex (e.g., PSM-4033-4039). Conditions that can be treated (e.g., to cure and/or ameliorate symptoms) with a composition comprising an effective amount of a masked TGF-β construct or complex (e.g., PSM-4033-4039) include: conditions associated with an insufficient number of Treg cells or insufficiently active Treg cells, autoimmune diseases or disorders, allergic reaction(s), wounds (e.g., dermal and/or mucosal wounds), and/or burns. In addition, individuals undergoing organ transplantation may also benefit from treatment.

A method of treatment or prophylaxis comprising administering to an individual with an insufficient number of FoxP3+ Treg cells or insufficiently active FoxP3+ Treg cells an effective amount of a masked TGF-β construct or complex (e.g., PSM-4033-4039) and/or one or more nucleic acids (e.g., recombinant expression vectors) encoding the masked TGF-β construct or complex. In one instance, the masked TGF-β construct or complex comprises PSM-4033-4039. In one instance, the masked TGF-β construct or complex comprises one or more (e.g., one, two or three) independently selected IL-2 or variant IL-2 MOD polypeptide sequences. The masked TGF-β construct or complex and/or one or more nucleic acids (e.g., recombinant expression vectors) encoding the masked TGF-β construct or complex, with or without an IL-2 or variant IL-2 MOD, may be administered before, during (concurrent or combined administration) or after administration of any one or more of vitamin D (e.g., 1α,25-dihydroxyvitamin D3 or 1α,25-

Dihydroxycholecalciferol) or a vitamin D analog, rapamycin, and/or a retinoic acid (e.g., all trans retinoic acid).

A method of treatment or prophylaxis may comprise administering to an individual with an autoimmune disease or disorder which is in need thereof an effective amount of a masked TGF-β construct or complex and/or one or more nucleic acids (e.g., recombinant expression vectors) comprising nucleotide sequences encoding a masked TGF-β construct or complex. In one instance, the masked TGF-β construct or complex comprise one or more (e.g., one, two or three) independently selected IL-2 or variant IL-2 MOD polypeptide sequences (e.g., PSM-4033-4039). In a second instance, the masked TGF-β construct or complex comprise one or more (e.g., one, two or three) independently selected IL-10 or variant IL-10 MOD polypeptide sequences. In one instance, the masked TGF-β construct or complex comprises at least one independently selected IL-2 or variant IL-2 MOD polypeptide sequence and at least one independently selected IL-10 or variant IL-10 MOD polypeptide sequence. In a second instance, the masked TGF-β construct or complex comprise one or more (e.g., one, two or three) independently selected IL-10 or variant IL-10 MOD polypeptide sequences. Autoimmune diseases that can be treated with a method of the present disclosure include, but are not limited to, Addison's disease, alopecia areata, ankylosing spondylitis, autoimmune encephalomyelitis, autoimmune hemolytic anemia, autoimmune hepatitis, autoimmune-associated infertility, autoimmune thrombocytopenic purpura, bullous pemphigoid, Crohn's disease, Goodpasture's syndrome, glomerulonephritis (e.g., crescentic glomerulonephritis, proliferative glomerulonephritis), Grave's disease, Hashimoto's thyroiditis, mixed connective tissue disease, multiple sclerosis, myasthenia gravis (MG), pemphigus (e.g., pemphigus vulgaris), pernicious anemia, polymyositis, psoriasis, psoriatic arthritis, rheumatoid arthritis, scleroderma, Sjögren's syndrome, systemic lupus erythematosus (SLE), vasculitis, and vitiligo. In an embodiment, the autoimmune disease that can be treated with a method of the present disclosure is T1D. In an embodiment, the autoimmune disease that can be treated with a method of the present disclosure is celiac disease. T1D and/or celiac disease also may be excluded from the autoimmune diseases subject to treatment with a method of the present disclosure.

A method of treatment or prophylaxis comprising administering to an individual with a deficiency in Th17 cells (e.g., individuals unable to sufficiently respond to bacterial and/or fungal infections in the gut) an effective amount of a masked TGF-β construct or complex and/or one or more nucleic acids (e.g., recombinant expression vectors) encoding the masked TGF-β construct or complex. In one instance, the masked TGF-β construct or complex comprises one or more (e.g., one, two or three) independently selected IL-6 or variant IL-6 MOD polypeptide sequences. A method of treatment or prophylaxis may comprise administering to an individual unable to sufficiently respond to bacterial and/or fungal infections in the gut an effective amount of a masked TGF-β construct or complex comprising one or more independently selected IL-6 and/or variant IL-6 polypeptides, or one or more nucleic acids (e.g., recombinant expression vectors) encoding the masked TGF-β construct or complex comprising one or more independently selected IL-6 and/or variant IL-6 polypeptides.

A method of treatment or prophylaxis comprising administering to an individual with a deficiency in Th9 cells (e.g., individuals unable to sufficiently respond to helminth infections) an effective amount of a masked TGF-β construct or complex and/or one or more nucleic acids (e.g., recombinant expression vectors) encoding the masked TGF-β construct or complex sufficient to respond to helminth infection. In one instance, the masked TGF-β construct or complex comprise one or more (e.g., one, two or three) independently selected IL-4 or variant IL-4 MOD polypeptide sequences. A method of treatment or prophylaxis may comprise administering to an individual unable to sufficiently respond to sufficiently respond to helminth infections an effective amount of a masked TGF-β construct or complex comprising one or more independently selected IL-4 and/or variant IL-4 polypeptides, or one or more nucleic acids (e.g., recombinant expression vectors) encoding the masked TGF-β construct or complex comprising one or more independently selected IL-4 and/or variant IL-4 polypeptides.

A method of treatment or prophylaxis comprising administering to an individual with a deficiency in Tfh cells (e.g., individuals unable to produce high affinity antibodies or sufficient amounts of high affinity antibodies) an effective amount of a masked TGF-β construct or complex and/or one or more nucleic acids (e.g., recombinant expression vectors) encoding the masked TGF-β construct or complex sufficient to increase the production of high affinity antibodies. In one instance, the masked TGF-β construct or complex comprises one or more (e.g., one, two or three) independently selected IL-21, IL-23, variant IL-21 or variant IL-23 MOD polypeptide sequences. A method of treatment or prophylaxis may comprise administering to an individual unable to produce high affinity antibodies or insufficient amounts of high affinity antibodies an effective amount of a masked TGF-β construct or complex comprising one or more independently selected IL-21, IL-23, variant IL-21 or variant IL-23 MOD polypeptide sequences, or one or more nucleic acids (e.g., recombinant expression vectors) encoding the masked TGF-β construct or complex comprising one or more independently selected IL-21, IL-23, variant IL-21 or variant IL-23 MOD polypeptide sequences.

A method of treatment or prophylaxis comprising administering to an individual having excess Th1 cell activity relative to a control group (e.g., and individual with elevated levels of activated macrophages and/or elevated levels of interferon gamma "IFN-γ" in a target tissue or circulating) an effective amount of a masked TGF-β construct or complex and/or one or more nucleic acids (e.g., recombinant expression vectors) encoding the masked TGF-β construct or complex. A method of treatment or prophylaxis may comprise administering to an individual with elevated levels of activated macrophages and/or elevated levels of interferon gamma "IFN-γ" (e.g., circulating or in a target tissue) an effective amount of a masked TGF-β construct or complex, or one or more nucleic acids (e.g., recombinant expression vectors) encoding the masked TGF-β construct or complex.

A method of treatment or prophylaxis comprising administering to an individual having excess Th2 cell activity relative to a control group (e.g., an individual with elevated levels of activated MAST cells and/or with elevated levels of IgE that circulating or tissue localize) an effective amount of a masked TGF-β construct or complex and/or one or more nucleic acids (e.g., recombinant expression vectors) encoding the masked TGF-β construct or complex. A method of treatment or prophylaxis may comprise administering to an individual with elevated levels of activated MAST cells and/or with elevated levels of IgE (circulating or tissue localize) an effective amount of a masked TGF-β construct or complex, or one or more nucleic acids (e.g., recombinant expression vectors) encoding the masked TGF-β construct or complex.

A method of treatment or prophylaxis comprising administering to an individual having T-cell receptor-driven activation of autoreactive T cells (or high affinity T-cells) an effective amount of a masked TGF-β construct or complex (e.g., PSM-4033-4039) and/or one or more nucleic acids (e.g., recombinant expression vectors) encoding the masked TGF-β construct or complex. A method of treatment or prophylaxis may comprise administering to an individual with autoreactive T-cells an effective amount of a masked TGF-β construct or complex (e.g., PSM-4033-4039), or one or more nucleic acids (e.g., recombinant expression vectors) encoding the masked TGF-β construct or complex.

A method of treatment or prophylaxis comprising administering to an individual in which it is desirable to promote IL-7-dependent survival of low-affinity CD4+ and/or CD8+ T cells (e.g., by control of thymocyte IL-7Ra expression) an effective amount of a masked TGF-β construct or complex and/or one or more nucleic acids (e.g., recombinant expression vectors) encoding the masked TGF-β construct or complex. In one instance, the masked TGF-β construct or complex comprise one or more (e.g., one, two or three) independently selected IL-7 or variant IL-7 MOD polypeptide sequences. A method of treatment or prophylaxis may comprise administering to an individual unable to sufficiently maintain levels of low-affinity CD4+ and/or CD8+ T cells an effective amount of a masked TGF-β construct or complex comprising one or more independently selected IL-7 and/or variant IL-7 polypeptides, or one or more nucleic acids (e.g., recombinant expression vectors) encoding the masked TGF-β construct or complex comprising one or more independently selected IL-7 and/or variant IL-7 polypeptides.

A method of treatment or prophylaxis comprising administering to an individual in which it is desirable to promote apoptosis of specific cells (e.g., cancer cells or cancer cells bearing a specific marker such as cancer antigens 15-3, 27-29, 125, carcinoembryonic antigen, Alpha-fetoprotein and/or Beta 2-microglobulin) an effective amount of a masked TGF-β construct or complex and/or one or more nucleic acids (e.g., recombinant expression vectors) encoding the masked TGF-β construct or complex (e.g., PSM-4033-4039). In one instance, the masked TGF-β construct or complex comprise one or more (e.g., one, two or three) independently selected wt. Fas ligand or variant Fas ligand MOD polypeptide sequences.

A method of treatment or prophylaxis comprising administering to an individual in which it is desirable to induce iTreg (CD4+ FoxP3+) cells (e.g., individuals in which it is desirable to induce peripheral tolerance to actively suppress effector T (T eff) cells and/or inhibit immune-mediated tissue damage) an effective amount of a masked TGF-β construct or complex (e.g., PSM-4033-4039) and/or one or more nucleic acids (e.g., recombinant expression vectors) encoding the masked TGF-β construct or complex. In one instance, the masked TGF-β construct or complex comprise one or more (e.g., one, two or three) independently selected wt. or variant PD-L1 MOD polypeptide sequences. In another instance, the masked TGF-β construct or complex comprise one or more (e.g., one, two or three) independently selected wt. and/or variant PD-L1 MOD polypeptide sequences and one or more wt. and/or variant IL-2 MOD polypeptide sequences. In an embodiment the masked TGF-β construct or complex comprise (i) one independently selected wt. or variant PD-L1 MOD polypeptide sequence and (ii) one wt. or variant IL-2 MOD sequence. See, e.g., Francisco et al., *J. Exp. Med.,* 206(13): 3015-3029 (2009).

A method of treatment or prophylaxis comprising administering to an individual in which it is desirable to inhibit type II innate lymphoid cells (ILC2 cells) (e.g., to suppress asthma, allergic reaction, and/or allergic inflammation) an effective amount of a masked TGF-β construct or complex (e.g., PSM-4033-4039) and/or one or more nucleic acids (e.g., recombinant expression vectors) encoding the masked TGF-β construct or complex. In one instance, the masked TGF-β construct or complex comprise one or more (e.g., one, two or three) independently selected IL-10 or variant IL-10 MOD polypeptide sequences. The masked TGF-β construct or complex and/or one or more nucleic acids (e.g., recombinant expression vectors) encoding the masked TGF-β construct or complex, with or without an IL-10 or variant IL-10 MOD, may be administered before, during (concurrent or combined administration) or after administration of a glucocorticoid (e.g., dexamethasone, prednisone, etc.), antihistamine (e.g., diphenhydramine, chlorpheniramine, etc.), and/or epinephrine.

A method of treatment or prophylaxis comprising administering to an individual having an allergy, allergic inflammation, and/or elevated levels of IgE (circulating or tissue localized) an effective amount of a masked TGF-β construct or complex comprising at least one (e.g., one, two or three) independently selected IL-10 or variant IL-10 MOD polypeptides and/or one or more nucleic acids (e.g., recombinant expression vectors) encoding the masked TGF-β construct or complex. A method of treatment or prophylaxis may comprise administering to an individual with elevated levels of IgE (circulating or tissue localize) an effective amount a masked TGF-β construct or complex comprising at least one (e.g., one, two or three) independently selected IL-10 or variant IL-10 MOD polypeptides and/or one or more nucleic acids (e.g., recombinant expression vectors) encoding the masked TGF-β construct or complex. The masked TGF-β construct or complex and/or one or more nucleic acids (e.g., recombinant expression vectors) encoding the masked TGF-β construct or complex, with or without an IL-10 or variant IL-10 MOD, may be administered before, during (concurrent or combined administration) or after administration of a glucocorticoid (e.g., dexamethasone, prednisone, etc.), antihistamine (e.g., diphenhydramine, chlorpheniramine, etc.), and/or epinephrine. The TGF-β and IL-10 act to suppress expression of the high-affinity IgE receptor (Fc1RI) that activates MAST cells and IL-10 additionally acts to prevent excessive MAST cell activation and the development of chronic inflammation. See, e.g., Kennedy et al. *Journal of Immunology,* 180(5) 2848-2854 (2008).

A method of or prophylaxis comprising administering to an individual diagnosed with or having multiple sclerosis, an effective amount of a masked TGF-β construct or complex (e.g., PSM-4033-4039) and/or one or more nucleic acids (e.g., recombinant expression vectors) encoding the masked TGF-β construct or complex. In one instance, the masked TGF-β construct or complex comprise one or more (e.g., one, two or three) independently selected IL-10 or variant IL-10 MOD polypeptide sequences.

A method of treatment an individual having at least one cutaneous or mucosal burn, the method comprising administering the individual an effective amount of a masked TGF-β construct or complex (e.g., PSM-4033-4039) and/or one or more nucleic acids (e.g., recombinant expression vectors) encoding the masked TGF-β construct or complex. In an instance the method may comprise administering an effective amount of a masked TGF-β construct or complex comprising at least one (e.g., one, two or three) independently selected IL-10 or variant IL-10 MOD polypeptides and/or one or more nucleic acids (e.g., recombinant expression vectors) encoding the masked TGF-β construct or complex. The burns may be first, second, or third-degree burns.

A method of treatment an individual having at least one cutaneous or mucosal wound (an abrasion, avulsion, incision, laceration, or puncture of the epidermis or mucosa), the method comprising administering the individual an effective amount of a masked TGF-β construct or complex (e.g., PSM-4033-4039) and/or one or more nucleic acids (e.g., recombinant expression vectors) encoding the masked TGF-β construct or complex to speed wound closure (reduce time until closure), reduce healing time, or to reduce scar formation relative to an untreated wound. In an instance, the method may comprise administering an effective amount of a masked TGF-β construct or complex comprising at least one (e.g., one, two or three) independently selected IL-10 or variant IL-10 MOD polypeptides and/or one or more nucleic acids (e.g., recombinant expression vectors) encoding the masked TGF-β construct or complex. When the masked TGF-β construct or complex, either with or without an IL-10 MOD polypeptide, comprises TGF-β1 polypeptide, the method may further comprise one or more of: the recruitment of inflammatory cells into the injury site; expression of extracellular matrix proteins such as fibronectin, collagen (e.g., types I and/or III), and/or VEGF; stimulation fibroblasts contraction to enable wound closure; wound site expression of integrins, such as β1, α5, αv, and β5; and keratinocyte migration. When the masked TGF-β construct or complex, either with or without an IL-10 MOD polypeptide, comprises TGF-β2 polypeptide, the method may further comprise one or more of: the recruitment of both fibroblasts and immune cells from circulation and the wound edges into the wounded area; expression of collagen (e.g., types I and/or III); and expression of fibronectin. See, e.g., Pakyari et al *Adv Wound Care,* 2(5): 215-224 (2013). In such methods the masked TGF-β construct or complex may be applied directly to or injected into the wound.

A method of treatment an individual having at least one cutaneous or mucosal wound (an abrasion, avulsion, incision, laceration, or puncture of the epidermis or mucosa), the method comprising administering to the individual an effective amount of a masked TGF-β (e.g., TGF-β3) construct or complex (e.g., PSM-4033-4039) and/or one or more nucleic acids (e.g., recombinant expression vectors) encoding the masked TGF-β3 construct or complex to reduce scar formation relative to an untreated wound. In an instance, the method may comprise administering an effective amount of a masked TGF-β (e.g., TGF-β3) construct or complex comprising at least one (e.g., one, two or three) independently selected IL-10 or variant IL-10 MOD polypeptides and/or one or more nucleic acids (e.g., recombinant expression vectors) encoding the masked TGF-β (e.g., TGF-β3) construct or complex. In such methods the masked TGF-β (e.g., TGF-β3) construct or complex may be applied directly to or injected into the wound. Without being bound by theory, it may be understood that TGF-β3 reduces type/collagen deposition while promoting collagen degradation by MMP-9, leading to decreased scar formation. See, e.g., Pakyari et al *Adv Wound Care,* 2(5): 215-224 (2013).

A method of facilitating organ transplant in an individual, the method comprising administering the individual an effective amount of a masked TGF-β construct or complex (e.g., PSM-4033-4039) and/or one or more nucleic acids (e.g., recombinant expression vectors) encoding the masked TGF-β construct or complex to speed incision closure (reduce time until closure), reduce recovery time, or to reduce scar formation relative to the average time to closure, recovery time or scar formation in untreated individuals matched for the type of organ transplantation, age, sex, smoking habits, and/or body mass index. In an instance, the method may comprise administering an effective amount of a masked TGF-β construct or complex comprising at least one (e.g., one, two or three) independently selected IL-10 or variant IL-10 MOD polypeptides and/or one or more nucleic acids (e.g., recombinant expression vectors) encoding the masked TGF-β construct or complex.

A method of treating an individual with graft vs. host disease (GVHD, including acute GVHD), the method comprising administering the individual an effective amount of a masked TGF-β construct or complex (e.g., PSM-4033-4039) and/or one or more nucleic acids (e.g., recombinant expression vectors) encoding the masked TGF-β construct or complex In any of the foregoing methods, unless specified otherwise, the TGF-β polypeptide of a masked TGF-β construct or complex can be a TGF-β1, TGF-β2, or TGF-β3 polypeptide or a variant thereof as discussed in the preceding section (e.g., a TGF-β3 C77S variant or a TGF-β1 or TGF-β2 variant with a corresponding mutation limiting TGF-β polypeptide dimerization). Similarly, the polypeptide masking the TGF-β polypeptide can be selected from those described above (e.g., antibodies or fragments thereof, single chain antibodies, or TβRI or TβRII ectodomain fragments that bind to TGF-β).

As noted above, in some cases, in carrying out a subject method of treatment or prophylaxis, a masked TGF-β construct or complex is administered to an individual in need thereof, as the polypeptide per se. In other instances, in carrying out a subject method of treatment or prophylaxis, one or more nucleic acids comprising nucleotide sequences encoding a masked TGF-β construct or complex is/are administering to an individual in need thereof. Thus, in other instances, one or more nucleic acids, e.g., one or more recombinant expression vectors, is/are administered to an individual in need thereof.

N. Dosages

A suitable dosage can be determined by an attending physician or other qualified medical personnel, based on various clinical factors. As is well known in the medical arts, dosages for any one patient depend upon many factors, including the patient's size, body surface area, age, the particular polypeptide or nucleic acid to be administered, sex of the patient, time, and route of administration, general health, and other drugs being administered concurrently. A masked TGF-β construct or complex may be administered in amounts between 1 ng/kg body weight and 20 mg/kg body weight per dose, e.g., between 0.1 mg/kg body weight to 10 mg/kg body weight, e.g., between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute. A masked TGF-β construct or complex can be administered in an amount of from about 1 mg/kg body weight to 50 mg/kg body weight, e.g., from about 1 mg/kg body weight to about 5 mg/kg body weight, from about 5 mg/kg body weight to about 10 mg/kg body weight, from about 10 mg/kg body weight to about 15 mg/kg body weight, from about 15 mg/kg body weight to about 20 mg/kg body weight, from about 20 mg/kg body weight to about 25 mg/kg body weight, from about 25 mg/kg body weight to about 30 mg/kg body weight, from about 30 mg/kg body weight to about 35 mg/kg body weight, from about 35 mg/kg body weight to about 40 mg/kg body weight, or from about 40 mg/kg body weight to about 50 mg/kg body weight.

In some cases, a suitable dose of a masked TGF-β construct or complex is from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight. Persons of ordinary skill in the art can easily estimate repetition rates for dosing based on measured residence times and concentrations of the administered agent in bodily fluids or tissues. Following successful treatment, it may be desirable to have the patient undergo maintenance therapy to prevent the recurrence of the disease state, wherein a masked TGF-β construct or complex or a single-chain masked TGF-β construct or complex) is administered in maintenance doses, ranging from 0.01 μg to 100 g per kg of body weight, from 0.1 μg to 10 g per kg of body weight, from 1 μg to 1 g per kg of body weight, from 10 μg to 100 mg per kg of body weight, from 100 μg to 10 mg per kg of body weight, or from 100 μg to 1 mg per kg of body weight.

Those of skill will readily appreciate that dose levels can vary as a function of the specific masked TGF-β construct or complex, the severity of the symptoms and the susceptibility of the subject to side effects. Preferred dosages for a given compound are readily determinable by those of skill in the art by a variety of means.

In some cases, multiple doses of a masked TGF-β construct or complex, a nucleic acid, or a recombinant expression vector are administered. The frequency of administration of a masked TGF-β construct or complex, a nucleic acid, or a recombinant expression vector can vary depending on any of a variety of factors, e.g., severity of the symptoms, etc. For example, in some cases, a masked TGF-β construct or complex, a nucleic acid, or a recombinant expression vectors administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of a masked TGF-β construct or complex, a nucleic acid, or a recombinant expression vector, e.g., the period of time over which a masked TGF-β construct or complex, a nucleic acid, or a recombinant expression vector is administered, can vary, depending on any of a variety of factors, e.g., patient response, etc. For example, a masked TGF-β construct or complex, a nucleic acid, or a recombinant expression vector can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

O. Routes of Administration

An active agent (a masked TGF-β construct or complex, a nucleic acid, or a recombinant expression vector) is administered to an individual using any available method and route suitable for drug delivery, including in vivo and in vitro methods, as well as systemic and localized routes of administration.

Conventional and pharmaceutically acceptable routes of administration include intratumoral, peritumoral, intramuscular, intratracheal, intralymphatic, intracranial, cutaneous, subcutaneous, intradermal, topical application, intravenous, intraarterial, rectal, nasal, oral, and other enteral and parenteral routes of administration. Routes of administration may be combined, if desired, or adjusted depending upon the masked TGF-β construct or complex and/or the desired effect. A masked TGF-β construct or complex, or a nucleic acid or recombinant expression vector, can be administered in a single dose or in multiple doses.

In some cases, a masked TGF-β construct or complex, a nucleic acid, or a recombinant expression vector is administered intravenously. In some cases, a masked TGF-β construct or complex, a nucleic acid, or a recombinant expression vector is administered intramuscularly. In some cases, a masked TGF-β construct or complex, a nucleic acid, or a recombinant expression vector is administered intralymphatically. In some cases, a masked TGF-β construct or complex, a nucleic acid, or a recombinant expression vector is administered locally. In some cases, a masked TGF-β construct or complex, a nucleic acid, or a recombinant expression vector is administered intratumorally. In some cases, a masked TGF-β construct or complex, a nucleic acid, or a recombinant expression vector is administered peritumorally. In some cases, a masked TGF-β construct or complex, a nucleic acid, or a recombinant expression vector is administered intracranially. In some cases, a masked TGF-β construct or complex, a nucleic acid, or a recombinant expression vector is administered cutaneously. In some cases, a masked TGF-β construct or complex, a nucleic acid, or a recombinant expression vector is administered subcutaneously. In some cases, a masked TGF-β construct or complex, a nucleic acid, or a recombinant expression vector is administered to a wound (e.g., a dermal or mucosal wound). In some cases, a masked TGF-β construct or complex, a nucleic acid, or a recombinant expression vector is administered to burned tissue (e.g., a dermal burns).

In some cases, a masked TGF-β construct or complex is administered intravenously. In some cases, a masked TGF-β construct or complex is administered intramuscularly. In some cases, a masked TGF-β construct or complex is administered locally. In some cases, a masked TGF-β construct or complex is administered intratumorally. In some cases, a masked TGF-β construct or complex is administered peritumorally. In some cases, a masked TGF-β construct or complex is administered intracranially. In some cases, a masked TGF-β construct or complex is administered cutaneously. In some cases, a masked TGF-β construct or complex is administered subcutaneously. In some cases, a masked TGF-β construct or complex is administered intralymphatically. In some cases, a masked TGF-β construct or complex is administered to a wound (e.g., a dermal or mucosal wound). In some cases, a masked TGF-β construct or complex is administered to burned tissue (e.g., a dermal burns).

A masked TGF-β construct or complex, a nucleic acid, or a recombinant expression vector can be administered to a host using any available conventional methods and routes suitable for delivery of conventional drugs, including systemic or localized routes. In general, routes of administration contemplated for use in a method include, but are not necessarily limited to, enteral, parenteral, cutaneous, and inhalational routes.

Parenteral routes of administration other than inhalation administration include, but are not necessarily limited to, topical, transdermal, subcutaneous, intramuscular, intraorbital, intracapsular, intraspinal, intrasternal, intratumoral, intralymphatic, peritumoral, and intravenous routes, i.e., any route of administration other than through the alimentary canal. Parenteral administration can be carried to effect systemic or local delivery of a masked TGF-β construct or complex, a nucleic acid, or a recombinant expression vector. Where systemic delivery is desired, administration typically involves invasive or systemically absorbed topical or mucosal administration of pharmaceutical preparations.

P. Subjects Suitable for Treatment

Subjects suitable for treatment with a masked TGF-β construct or complex e.g., PSM-4033-4039), such as by a method described herein, include individuals (e.g., humans) with an autoimmune disease, allergic reaction(s), wounds (e.g., dermal and/or mucosal wounds), and/or burns. Subjects additionally include individuals undergoing organ transplantation. In addition to humans, subjects include non-human mammals including, but not limited to, bovine canine, caprine, cercopithecine, feline, lapine, lapine, murine, ovine, porcine, or simian subjects or patients in need of treatment.

Subjects (individuals) who have an autoimmune disease or conditions and are suitable for treatment with a masked TGF-β construct or complex (e.g., PSM-4033-4039), including individuals those who have been diagnosed as having an autoimmune disease or condition, and individuals who have been treated for an autoimmune disease or condition but who failed to respond to the treatment. Autoimmune diseases and conditions that can be treated with a method of the present disclosure include, but are not limited to, Addison's disease, alopecia areata, ankylosing spondylitis, autoimmune encephalomyelitis, autoimmune colitis, autoimmune gastritis, autoimmune hemolytic anemia, autoimmune hepatitis, autoimmune-associated infertility, autoimmune pancreatitis, autoimmune retinopathy, autoimmune thrombocytopenic purpura, autoimmune urticaria, bullous pemphigoid, celiac disease, Crohn's disease, Goodpasture's syndrome, glomerulonephritis (e.g., crescentic glomerulonephritis, proliferative glomerulonephritis), graft vs. host disease (GVHD, including acute GVHD), Grave's disease, Hashimoto's thyroiditis, inflammatory bowel disease, mixed connective tissue disease, multiple sclerosis, myasthenia gravis (MG), pemphigus (e.g., pemphigus vulgaris), pernicious anemia, polymyositis, psoriasis, psoriatic arthritis, rheumatoid arthritis, scleroderma, Sjögren's syndrome, systemic lupus erythematosus (SLE), transplant rejection, type-1 diabetes (T1D) vasculitis, and vitiligo. In an embodiment, the autoimmune disease is T1D. In an embodiment, the autoimmune disease is celiac disease. Individuals with T1D and/or celiac disease may be excluded from the subjects suitable for treatment. Similarly, T1D and/or celiac disease may be excluded from the autoimmune disease subject to treatment.

In an embodiment, the autoimmune diseases and conditions that can be treated with a method of the present disclosure include, but are not limited to, rheumatoid arthritis (RA), psoriasis/psoriatic arthritis, multiple sclerosis, inflammatory bowel disease, Addison's disease, Graves' disease, Sjögren's syndrome, Hashimoto's thyroiditis, myasthenia gravis, autoimmune vasculitis, and pernicious anemia.

Subjects that have allergic reactions cannot easily categorized by the allergens because allergens are too numerous to recite. By way of example, however, subjects (e.g., individuals previously treated for their allergies or who have never been treated) who have an allergic reaction(s) include those with reactions to: peanuts and tree nuts, plant pollens, latex, and the like. For example, subjects with allergic reactions to peanut allergens include those with reactions to Ara h 1 to 13 proteins that come from seven protein families, include those in Ara h 1 (e.g., PGQFEDFF (SEQ ID NO:161), YLQGFSRN (SEQ ID NO:162), FNAEFNEIRR (SEQ ID NO:163), QEERGQRR (SEQ ID NO:164), DITNPINLRE (SEQ ID NO:165), NNFGKLFEVK (SEQ ID NO:166), GNLELV (SEQ ID NO:167), RRYTARLKEG (SEQ ID NO:168), ELHLLGFGIN (SEQ ID NO:169), HRIFLAGDKD (SEQ ID NO:170), IDQIEKQAKD (SEQ ID NO:171), KDLAFPGSGE (SEQ ID NO:172), KESHFVSARP (SEQ ID NO:173), NEGVIVKVSKEHVEELTKHAKSVSK (SEQ ID NO:174), Ara h 2 (e.g., HASARQQWEL (SEQ ID NO:175), QWELQGDRRC (SEQ ID NO:176), DRRCQSQLER (SEQ ID NO:177), LRPCEQHLMQ (SEQ ID NO:178), KIQRDEDSYE (SEQ ID NO:179), YERDPYSPSQ (SEQ ID NO:180), SQDPYSPSPY (SEQ ID NO:181), DRLQGRQQEQ (SEQ ID NO:182), KRELRNLPQQ (SEQ ID NO:183), QRCDLDVESG (SEQ ID NO:184), and Ara h 3 (e.g., IETWNPNNQEFECAG (SEQ ID NO:185), GNIFSGFTPEFLAQA (SEQ ID NO:186), VTVRGGLRILSPDRK (SEQ ID NO:187), DEDEYEYDEEDRRRG (SEQ ID NO:188). See, e.g., Zhou et al (2013) Intl. J. of Food Sci. 2013 article ID 909140. Subjects with allergic reactions also include those with reactions to hymenoptera proteins (e.g., allergens in bee and wasp venoms such as phospholipase A2, melittin, "antigen 5" found in wasp venom, and hyaluronidases).

Subjects that have wounds include individuals with abrasion, avulsion, incision, laceration, and puncture of skin or mucosa. It may be understood that subjects that have organ transplantation, will, by their nature have one or more of those wound types.

V. CERTAIN ASPECTS

Certain aspects including aspects of the subject matter directed to the TGF-β constructs or complexes described above, may be beneficial alone or in combination, with one or more other aspects, such as those recited below directed to TGF-β constructs and complexes, their method of manufacture, and their methods of use (e.g., as therapeutics).

1. A construct comprising as a first polypeptide:
   - i) a scaffold polypeptide sequence;
   - ii) a TGF-β polypeptide sequence;
   - iii) a masking polypeptide sequence (e.g., a TGF-β receptor polypeptide sequence or anti-TGF-β polypeptide sequence);
   - iv) optionally, one or more (e.g., one, two or more) independently selected MOD polypeptide sequences;

and
   - v) optionally one or more independently selected linker polypeptide sequences (e.g., between any of the foregoing polypeptide sequences);

a construct comprising these elements being collectively referred to as a "masked TGF-β construct,"

wherein the masking polypeptide sequence (e.g., TGF-β receptor polypeptide sequence or anti-TGF-β polypeptide sequence) and the TGF-β polypeptide sequence bind to each other (interact with each other to mask the TGF-β polypeptide sequence). See, e.g., FIG. 1, structure A.

2. The masked TGF-β construct of aspect 1, wherein the first polypeptide comprises, in order from N-terminus to C-terminus:
   i) the scaffold polypeptide sequence, the masking polypeptide sequence (e.g., TGF-β receptor polypeptide sequence), and the TGF-β polypeptide sequence; or
   ii) a first MOD polypeptide sequence, the scaffold polypeptide sequence, the masking polypeptide sequence (e.g., TGF-β receptor polypeptide sequence), and the TGF-β polypeptide sequence; or
   iii) a first independently selected MOD polypeptide sequence, a second independently selected MOD polypeptide sequence (MODs in tandem), the scaffold polypeptide sequence, the masking polypeptide sequence (e.g., TGF-β receptor polypeptide sequence), and the TGF-β polypeptide sequence;

wherein masked TGF-β construct optionally comprise one or more independently selected linker polypeptide sequences (e.g., between any of the foregoing polypeptide sequences).

3. The masked TGF-β construct of aspect 1 or aspect 2, wherein the scaffold polypeptide comprises a dimerization (or multimerization) sequence.

4. The masked TGF-β construct of aspect 3, in the form of a masked TGF-β complex homodimer wherein the scaffold polypeptide sequences optionally have one or more (e.g., one, two or more) covalent attachments (e.g., disulfide bonds) to each other (e.g., wherein a first molecule of the masked TGF-β construct as the first polypeptide is dimerized with a second molecule of the masked TGF-β construct as a second polypeptide through covalent or non-covalent interactions of their scaffold polypeptide sequences to form a homodimer), optionally wherein, the scaffolds comprise Ig Fc polypeptides that include mutations (e.g., the LALA mutations) that substantially reduce or eliminate the ability of the Ig polypeptide to induce cell lysis, e.g., though complement-dependent cytotoxicity (CDC) and/or antibody-dependent cellular cytotoxicity (ADCC). See, e.g., FIG. 1, structure B.

5. The masked TGF-β construct of any of aspects 1-3, wherein the scaffold polypeptide comprises an interspecific dimerization sequence (e.g., a dimerization sequence that preferentially dimerizes with its counterpart interspecific binding sequence as opposed to homodimerizing). See, e.g., FIG. 1, structures C and F.

6. The masked TGF-β construct of aspect 5, further comprising a second polypeptide dimerized with the first polypeptide to form a masked TGF-β complex heterodimer;

wherein the second polypeptide comprises a scaffold polypeptide sequence that comprises a counterpart interspecific dimerization sequence to the interspecific binding sequence of the first polypeptide; and wherein the interspecific binding sequence and the counterpart interspecific binding sequence interact with each other in the heterodimer.

7. The masked TGF-β complex of aspect 6, wherein the second polypeptide comprises:
   (i) a scaffold polypeptide sequence comprising the counterpart interspecific dimerization sequence;
   (ii) one or two (or more) independently selected MOD sequences (e.g., in tandem) and a scaffold polypeptide sequence comprising the counterpart interspecific dimerization sequence;
   (iii) a scaffold polypeptide sequence comprising the counterpart interspecific dimerization sequence, and an independently selected MOD sequence; or
   (iv) one or two (or more) independently selected MOD sequences (e.g., in tandem) and a scaffold polypeptide sequence comprising the counterpart interspecific dimerization sequence;

wherein the first and or second polypeptides optionally comprise one or more independently selected linker polypeptide sequences (e.g., between any of the foregoing polypeptide sequences). See, e.g., FIG. 1, structure F.

8. The masked TGF-β complex of aspect 6 or 7, wherein the second polypeptide comprises, from N-terminus to C-terminus:
   i) a scaffold polypeptide sequence comprising the counterpart interspecific dimerization sequence;
   (ii) one or two (or more) independently selected MOD sequences (e.g., in tandem) and a scaffold polypeptide sequence comprising the counterpart interspecific dimerization sequence;
   (iii) a scaffold polypeptide sequence comprising the counterpart interspecific dimerization sequence, and one or two (or more) independently selected MOD sequences; or
   (iv) one or two (or more) independently selected MOD sequences (e.g., in tandem) and a scaffold polypeptide sequence comprising the counterpart interspecific dimerization sequence wherein first and/or second polypeptides optionally comprises one or more independently selected linker polypeptide sequences (e.g., between any of the foregoing polypeptide sequences). See, e.g., FIG. 1, structure F.

9. The masked TGF-β complex of aspect 6, wherein the second polypeptide comprises:
   i) optionally, one or more (e.g., one, two or more) independently selected MOD polypeptide sequences;
   ii) a scaffold polypeptide sequence comprising the counterpart interspecific dimerization sequence;
   iii) a TGF-β polypeptide sequence;
   iv) a masking polypeptide sequence (e.g., a TGF-β receptor polypeptide sequence or anti-TGF-β polypeptide sequence);

and
   v) optionally one or more independently selected linker polypeptide sequences (e.g., between any of the foregoing polypeptide sequences of the second polypeptide);

wherein the masking polypeptide sequence (e.g., TGF-β receptor polypeptide sequence or anti-TGF-β polypeptide sequence) and the TGF-β polypeptide sequence bind to each other (interact with each to mask the TGF-β polypeptide sequence). See, e.g., FIG. 1, structure C.

10. The masked TGF-β complex heterodimer of aspect 9, wherein the second polypeptide comprises in order from N-terminus to C-terminus:
   i) the scaffold polypeptide sequence comprising the counterpart interspecific dimerization sequence, the masking polypeptide sequence (e.g., TGF-β receptor polypeptide sequence), and the TGF-β polypeptide sequence;
   ii) a first MOD polypeptide sequence, the scaffold polypeptide sequence comprising the counterpart interspecific dimerization sequence, the masking polypeptide sequence (e.g., TGF-β receptor polypeptide sequence), and the TGF-β polypeptide sequence; or iii) a first independently selected MOD polypeptide sequence, a second independently selected MOD polypeptide sequence, the scaffold polypeptide sequence comprising the counterpart interspecific dimerization sequence, the masking polypeptide sequence (e.g., TGF-β receptor polypeptide sequence), and the TGF-β polypeptide sequence. See, e.g., FIG. 1, structure C.

11. A complex comprising a first polypeptide and a second polypeptide as a heterodimer (or multimer), wherein:

(i) the first polypeptide comprises a) a scaffold polypeptide sequence comprising an interspecific dimerization sequence, b) a masking polypeptide sequence (e.g., a TGF-β receptor polypeptide sequence or anti-TGF-β polypeptide sequence), c) optionally, one or more (e.g., one, two or more) independently selected MOD polypeptide sequences, and d) optionally one or more independently selected linker polypeptide sequences (e.g., between any of the foregoing polypeptide sequences of the first polypeptide);

(ii) the second polypeptide comprises a) a scaffold polypeptide sequence comprising a counterpart interspecific dimerization sequence to the interspecific dimerization sequence in the first polypeptide, b) a TGF-β polypeptide sequence, c) optionally, one or more (e.g., one, two or more) independently selected MOD polypeptide sequences, and d) optionally one or more independently selected linker polypeptide sequences (e.g., between any of the foregoing polypeptide sequences of the second polypeptide);

a complex comprising these elements being collectively referred to as a "masked TGF-β complex,"

wherein the masking polypeptide sequence (e.g., TGF-β receptor polypeptide sequence or anti-TGF-β polypeptide sequence) and the TGF-β polypeptide sequence bind to each other (interact with each other to mask the TGF-β polypeptide sequence);

wherein the interspecific binding sequence and the counterpart interspecific binding sequence interact with each other (e.g., bind non-covalently) in the heterodimer; and wherein masked TGF-β first polypeptide and/or the second polypeptide optionally comprise one or more independently selected linker polypeptide sequences (e.g., between any of their polypeptide sequences). See, e.g., FIG. 1, structures D and E.

12. The masked TGF-β complex heterodimer of aspect 11, wherein the first polypeptide comprises, from N-terminus to C-terminus:

a) one or two (or more) independently a) one or two (or more) independently selected MOD sequences, a scaffold polypeptide sequence comprising an interspecific dimerization sequence, and the masking polypeptide sequence (e.g., TGF-β receptor polypeptide sequence), or b) a scaffold polypeptide sequence comprising an interspecific dimerization sequence, and the masking polypeptide sequence (e.g., TGF-β receptor polypeptide sequence); and the second polypeptide comprises, from N-terminus to C-terminus one or two (or more) independently selected MOD sequences, a scaffold polypeptide sequence comprising the counterpart interspecific dimerization sequence, and the TGF-β polypeptide sequence.

13. The masked TGF-β construct or complex of any of aspects 1-12, wherein the scaffold polypeptide sequence(s) are selected from the group consisting of Ig Fc polypeptide sequences (e.g., CH2-CH3 region sequences); Ig heavy chain region 1 (CH1) domains; light chain constant regions ("CL") (e.g., an Ig κ chain (kappa chain) constant region or an Ig λ chain (lambda chain)); leucine zipper polypeptide sequences; Fos or Jun binding pair sequences; collectin polypeptides (e.g., ACRP30 or ACRP30-like proteins); coiled-coil domains; and variants of any of the foregoing (e.g., knob-in-hole and other interspecific sequences in Table 1).

14. The masked TGF-β construct or complex of any of aspects 1-13, wherein the scaffold polypeptide sequence is selected from the group consisting of Ig Fc polypeptide sequences (immunoglobulin sequences); Ig heavy chain sequences (e.g., CH2-CH3 region sequences); Ig heavy chain region 1 (CH1) domains; light chain constant regions ("CL") (e.g., an Ig κ chain (kappa chain) and variants of any of the foregoing. In one embodiment, the scaffold polypeptide are selected from an Ig CH1 domain bearing MD13 substitutions or Ig κ chain sequence bearing MD13 substitutions.

15. The masked TGF-β construct or complex of aspect 14, where the immunoglobulin sequences comprise a sequence having at least about 70%, at least about 80%, at least about 90%, at least about 95%, at least about 98%, at least about 99%, or 100% aa sequence identity to any of SEQ ID NOs: 68 to 83 or 85-87. See, e.g., FIGS. 2A-2H, and 2J-2K (Immunoglobulin sequence can form dimers and in the case of IgM sequence, such as in FIG. 2H, multimers).

16. The masked TGF-β construct or complex of 15, where the immunoglobulin sequences comprise an immunoglobulin heavy chain sequence having at least about 70%, at least about 80%, at least about 90%, at least about 95%, at least about 98%, at least about 99%, or 100% aa sequence identity to any of SEQ ID NOs: 68 to 83. See, e.g., FIGS. 2A-2H (Immunoglobulin sequence can form dimers and in the case of IgM sequence, such as in FIG. 2H, multimers).

17. The masked TGF-β construct or complex of any one of aspects 4 and 6-16, wherein the scaffold polypeptide sequences have one or more (e.g., one, two or more) covalent attachments to each other.

18. The masked TGF-β construct or complex of aspect 17, where at least one (e.g., one, two or more) of the one or more covalent attachments is a disulfide bond between the scaffold polypeptide sequence of the first polypeptide and the scaffold polypeptide sequence of the second polypeptide.

19. The masked TGF-β construct or complex of any of aspects 14-18, wherein the scaffold sequences are immunoglobulin heavy chain constant region (Ig Fc) polypeptide sequences comprising CH2-CH3 immunoglobulin regions that are optionally covalently linked by one or more (e.g., one, two or more) disulfide bonds.

20. The masked TGF-β construct of aspects 5, wherein the scaffold polypeptide comprises an interspecific dimerization sequence selected from the group consisting of: i) an interspecific immunoglobulin (Ig) heavy chain sequence; ii) an Ig CH1 domain; iii) an Ig light chain constant region ("CL") (e.g., an Ig κ chain (kappa chain) or an Ig λ chain (lambda chain) constant region); and (iv) a polypeptide of a Fos/Jun binding pair. In one embodiment the scaffold polypeptide comprises an interspecific dimerization sequence selected from an Ig CH1 domain bearing MD13 substitutions or an Ig κ chain sequence bearing MD13 substitutions.

21. The masked TGF-β construct of aspect 20, wherein the interspecific binding sequence comprises a sequence having at least about 70%, at least about 80%, at least about 90%, at least about 95%, at least about 98%, at least about 99%, or 100% aa sequence identity to any of SEQ ID NOs: 68 to 82 or 85-87. See, e.g., FIGS. 2A-2G, and 2J-2K.

22. The masked TGF-β complex of any of aspects 4 and 6-12, wherein the scaffold polypeptide of the first polypeptide and the second polypeptide comprise an interspecific dimerization sequence and a counterpart interspecific dimerization sequence pair selected from the group consisting of: (i) interspecific immunoglobulin (Ig) heavy chain sequences (e.g., heavy chain CH1-CH2 regions); (ii) an Ig CH1 domain and one of its counterpart interspecific light chain constant region ("CL") (e.g., an Ig κ chain (kappa chain) constant region or an Ig λ chain (lambda chain) constant region); (iii) Fos/Jun binding pairs; and (iv) Ig heavy chain region 1 (CH1) and light chain constant region ("CL") sequences (CH1/CL pairs such as a CH1 sequence paired with a κ or λ Ig light chain constant region sequence). In one embodiment, the scaffold polypeptide of the first polypeptide and the second polypeptide comprise an interspecific dimerization sequence and a counterpart interspecific dimerization sequence pair that comprise an Ig CH1 domain bearing MD13 substitutions and an Ig κ chain sequence bearing MD13 substitutions.

23. The masked TGF-β complex of aspect 22, wherein the scaffold polypeptide sequences have one or more (e.g., one, two or more) covalent attachments to each other.

24. The masked TGF-β complex of aspect 22, where at least one (e.g., one, two or more) of the one or more covalent attachments is a disulfide bond between the scaffold sequence of the first polypeptide and the scaffold sequence of the second polypeptide.

25. The masked TGF-β complex of any of aspects 22-24, wherein the scaffold sequences are immunoglobulin heavy chain constant region (Ig Fc) polypeptide sequences comprising CH2-CH3 immunoglobulin regions that are optionally covalently linked by one or more (e.g., one, two or more) disulfide bonds (between the first and second polypeptides).

26. The masked TGF-β complex of any of aspects 22-25, wherein the interspecific binding sequence and/or the counterpart interspecific binding sequence comprise a sequence having at least about 70%, at least about 80%, at least about 90%, at least about 95%, at least about 98%, at least about 99%, or 100% aa sequence identity to any of SEQ ID NOs: 68 to 82 or 85-87. See, e.g., FIGS. 2A-2G, and 2J-2K.

27. The masked TGF-β complex of 26, where the immunoglobulin sequences comprise an immunoglobulin heavy chain sequence having at least about 70%, at least about 80%, at least about 90%, at least about 95%, at least about 98%, at least about 99%, or 100% aa sequence identity to any of SEQ ID NOs: 68 to 83. See, e.g., FIGS. 2A-2H (Immunoglobulin sequence can form dimers and in the case of IgM sequence, such as in FIG. 2H, multimers).

27. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to at least 150 contiguous aas (at least 175, at least 200, at least 225, at least 250, at least 275, at least 300, at least 325, or at least 350 contiguous aas), or all aas, of the IgA Fc sequence depicted in FIG. 2A (SEQ ID NO:68).

28. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to at least 150 contiguous aas (at least 175, at least 200, at least 225, at least 250, at least 275, at least 300, at least 325, or at least 350 contiguous aas), or all aas, of the IgD Fc sequence depicted in FIG. 2B (SEQ ID NO:69).

29. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to least 125 contiguous aas (at least 150, at least 175, or at least 200 contiguous aas), or all aas, of the IgE Fc sequence depicted in FIG. 2C (SEQ ID NO:70).

30. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to least 125 contiguous aas (at least 150, at least 175, or at least 200 contiguous aas), or all aas, of the wt. IgG Fc polypeptide sequence, such as the IgG1 Fc sequence depicted in FIG. 2D (SEQ ID NOs: 71-78).

31. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to at least 125 contiguous aas (at least 150, at least 175, at least 200, at least 225, at least 250, at least 275, or at least 300), or all aas, of the IgG2 Fc polypeptide sequence depicted in FIG. 2E (SEQ ID NO:79).

32. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to at least 125 contiguous aas (at least 150, at least 175, at least 200, or at least 225), or all aas, of the IgG3 Fc sequence depicted in FIG. 2F (SEQ ID NO:80).

33. The masked TGF-β construct or complex of any of aspects 1-27, comprising a scaffold polypeptide sequence, optionally comprising an interspecific dimerization sequence and/or a counterpart interspecific dimerization sequence, wherein the scaffold polypeptide sequence has at least about 70% (e.g., at least about 80%, at least about 90%, at least about 95%, at least about 98%, at least about 99%, or 100%) aa sequence identity to at least 125 contiguous aas (at least 150, at least 175, at least 200, at least 225, or at least 250,), or all aas, of the IgG4 Fc sequence depicted in FIG. 2G (SEQ ID NO:81 or 82).

34. The masked TGF-β complex of any of aspects 27-33, comprising one or two interchain disulfide bonds between the first and second polypeptides (e.g., between cystines adjacent to their hinge regions of the IgA, IgD, IgE, IgG1, IgG2, IgG3 or IgG4 sequences).

35. The masked TGF-β construct or complex of any of aspects 1-34, wherein one or more scaffold polypeptides comprise an immunoglobulin (Ig) polypeptide sequence bearing one or more substitutions that limits (e.g., reduces) binding of the polypeptide to complement component 1q (C1q) and/or Fc lambda receptor (Fa R) and/or that substantially reduces or eliminates the ability of the Ig polypeptide to induce cell lysis though complement-dependent cytotoxicity (CDC) and/or antibody-dependent cellular cytotoxicity (ADCC).

36. The masked TGF-β construct or complex of aspect 35, wherein each scaffold polypeptide comprises an immunoglobulin (Ig) polypeptide sequence comprising a polypeptide having at least about 70% (e.g., at least about 80%, at least about 85%, at least about 90%, at least about 95%, at least about 98%, at least about 99%, or 100%) aa sequence identity to least 125 contiguous aas (at least 150, at least 175, at least 200, or at least 220 contiguous aas) of wt. IgG1 Fc Sequence (SEQ ID NO:71).

37. The masked TGF-β construct or complex of aspect 36, wherein the immunoglobulin polypeptide sequence comprises a substitution of any one, two, or more of aas 234, 235, 236, 237, 238, and 239 (234-LLGGPS-239).

38. The masked TGF-β construct or complex of aspect 36 or 37, wherein the immunoglobulin polypeptide sequence comprises a substitution at any one, two or more of N297, P331, D270, K322, and/or P329.

39. The masked TGF-β construct or complex of any of aspects 36-38 wherein the immunoglobulin polypeptide sequence comprises an N297 substitution (N77 of SEQ ID NO:71) with an aa other than asparagine (e.g., alanine to give aN297A such as in SEQ ID NO:74).

40. The masked TGF-β construct or complex of any of aspects 36-38 wherein the immunoglobulin polypeptide sequence comprises an L234 and/or L235 (L14 and L15 in SEQ ID NO:71) substitution with an aa other than leucine (e.g., alanine, L234A and/or L235A).

41. The masked TGF-β construct or complex of 39, wherein the immunoglobulin polypeptide sequence comprises an L234A and/or L235A substitutions (see, e.g., SEQ ID NO:75).

42. The masked TGF-β construct or complex of any of aspects 36-41 wherein the immunoglobulin polypeptide sequence comprises P331 (P111 of SEQ ID NO:71)) substituted with an aa other than proline (e.g., serine for a P331S substitution).

43. The masked TGF-β construct or complex of any of aspects 36-38, wherein the immunoglobulin polypeptide sequence comprises substitutions at L234 and/or L235, and a substitution of P331.

44. The masked TGF-β construct or complex of aspect 43 wherein the immunoglobulin polypeptide sequence comprises (i) L234F, L235E, and P331S or (ii) L234A, L235A, and P331S substitutions.

45. The masked TGF-β construct or complex of any of aspects 20-44, comprising an interspecific dimerization sequence of an interspecific dimerization pair selected from the group consisting of KiH, KiHs-s, HA-TF, ZW-1, 7.8.60, DD-KK, EW-RVT, EW-RVTs-s, and A107 sequences (see, e.g., Table 1).

46. The masked TGF-β complex of any of aspects 4 and 22-44, wherein interspecific dimerization sequence and a counterpart interspecific dimerization sequence are a pair of sequences is selected from the group consisting of KiH, KiHs-s, HA-TF, ZW-1, 7.8.60, DD-KK, EW-RVT, EW-RVTs-s, and A107 sequence pairs (see, e.g., Table 1).

47. The masked TGF-β complex of aspect 46, wherein one of the first polypeptide and the second polypeptides comprise an interspecific IgG1 polypeptide sequence (e.g., a sequence of SEQ ID NO:71) comprising a T366Y substitution and the other a Y407T substitution, or corresponding substitutions in other interspecific immunoglobulin heavy chain sequences (e.g., interspecific sequences comprising IgA, IgD, IgE, IgG2, IgG3 or IgG4 heavy chain sequences).

48. The masked TGF-β complex of aspect 46, wherein one of the first polypeptide and the second polypeptides comprise an interspecific IgG1 polypeptide sequence (e.g., a sequence of SEQ ID NO:71) comprising a T366W substitution and the other T366S, L368A and Y407V substitutions, or corresponding substitutions in other interspecific immunoglobulin heavy chain sequences (e.g., interspecific sequences comprising IgA, IgD, IgE, IgG2, IgG3 or IgG4 heavy chain sequences).

49. The masked TGF-β complex of aspect 46, wherein one of the first polypeptide and the second polypeptides comprise an interspecific IgG1 polypeptide sequence (e.g., a sequence of SEQ ID NO:71) comprising Y349C, T366S, L368A, and Y407V substitutions and the other S354C, and T366W substitutions, or corresponding substitutions in other interspecific immunoglobulin heavy chain sequences (e.g., interspecific sequences comprising IgA, IgD, IgE, IgG2, IgG3 or IgG4 heavy chain sequences).

50. The masked TGF-β complex of aspect 46, wherein the first polypeptide comprises an IgG1 scaffold having a T146W KiH sequence substitution, and the second polypeptide comprises an IgG1 scaffold having T146W, L148A, and Y187V KiH sequence substitutions, where the scaffolds comprises a sequence having at least 80%, 90%. 95%, 98%, 99%, or 100% sequence identity to at least 170 (e.g., at least 180, at least 190, at least 200, at least 210, at least 220, or all 227) contiguous aas of the IgG1 of SEQ ID NO:71, and optionally comprises substitutions at one of more of: L14 and L15 (e.g., L14A/L15A "LALA" or L14F/L15E); N77 (e.g., N77A); P111 (e.g., P111S); L131 (e.g., L131K); T146 (e.g., T146S); P175 (e.g., P175V); F185 (e.g., F185R); Y187 (e.g., Y187A); and K189 (e.g., K189Y) as numbered in SEQ ID NO:71.
51. The masked TGF-β complex of aspect 46, wherein the first polypeptide comprises an IgG1 scaffold having a T146W KiH sequence substitution, and the second polypeptide comprises an IgG1 scaffold having T146S, L148A, and Y187V KiH sequence substitutions, where the scaffolds comprises a sequence having at least 80%, 90%. 95%, 98%, 99%, or 100% sequence identity to at least 170 (e.g., at least 180, at least 190, at least 200, at least 210, at least 220, or all 227) contiguous aas of the IgG1 of SEQ ID NO:71; with none, one, or both of the scaffold aa sequences comprising L14 and L15 substitutions (e.g., L234A and L235A "LALA" in Kabat numbering), and/or N77 substitution to remove effector function by blocking interactions with Fcγ receptors (N297 e.g., N297A or N297G in Kabat numbering). See, e.g., FIG. 2D, SEQ ID NOs: 77 and 78.
52. The masked TGF-β complex of aspect 46, wherein the first polypeptide comprises an IgG1 scaffold having T146W and S134C KiHs-s substitutions, and the second polypeptide comprises an IgG1 scaffold having T146S, L148A, Y187V and Y129C KiHs-s substitutions, where the scaffolds comprise a sequence having at least 80%, 90%. 95%, 98%, 99%, or 100% sequence identity to at least 170 (e.g., at least 180, at least 190, at least 200, at least 210, at least 220, or all 227) contiguous aas of the IgG1 of SEQ ID NO:71; with none, one, or both of the scaffold aa sequences of the first and second polypeptide comprising L14 and L15 substitutions (e.g., L234A and L235A "LALA" in Kabat numbering), and/or N77 (N297 in Kabat numbering) substitution to remove effector function by blocking interactions with Fcγ receptors (e.g., N297A or N297G substitutions in Kabat numbering).
53. The masked TGF-β complex of aspect 46, wherein the first and second polypeptide are selected from:
  a first polypeptide comprising an IgG1 scaffold having S144H and F185A substitutions, and a second polypeptide comprising an IgG1 scaffold having Y129T and T174F substitutions;
  a first polypeptide comprising an IgG1 scaffold having T130V, L131Y, F185A, and Y187V substitutions, and a second polypeptide comprising an IgG1 scaffold having 130V, T146L, K172L, and T174W substitutions;
  a first polypeptide comprising an IgG1 scaffold having K140D, D179M, and Y187A substitutions, and a second polypeptide comprising an IgG1 scaffold having E125R, Q127R, T146V, and K189V substitutions;
  a first polypeptide comprising an IgG1 scaffold having K189D, and K172D substitutions, and a second polypeptide comprising an IgG1 scaffold having D179K and E136 substitutions;
  a first polypeptide comprising an IgG1 scaffold having K140E and K189W substitutions, and a second polypeptide comprising an IgG1 scaffold having Q127R, D179V, and F185T substitutions;
  a first polypeptide comprising an IgG1 scaffold having K140E, K189W, and Y129C substitutions, and a second polypeptide comprising an IgG1 scaffold having Q127R, D179V, F185T, and S134C substitutions;
  and
  a first polypeptide comprising an IgG1 scaffold having K150E and K189W substitutions, and a second polypeptide comprising an IgG1 scaffold having E137N, D179V, and F185T substitutions;

wherein the scaffolds comprise a sequence having at least 80%, 90%. 95%, 98%, 99%, or 100% sequence identity to at least 170 (e.g., at least 180, at least 190, at least 200, at least 210, at least 220, or all 227) contiguous aas of the IgG1 of SEQ ID NO:71; and wherein none, one, or both of the scaffold as sequences of the first and second polypeptide comprising L14 and L15 substitutions (e.g., L234A and L235A "LALA" in Kabat numbering), and/or N77 (N297 in Kabat numbering) substitution to remove effector function by blocking interactions with Fey receptors (e.g., N297A or N297G substitutions in Kabat numbering).
54. The masked TGF-β construct of aspects 20, wherein the wherein the scaffold polypeptide comprises an interspecific dimerization sequence selected from the group consisting of:
  (i) an Ig heavy chain CH1 domain (e.g., the polypeptide of SEQ ID NO:85);
  (ii) an Ig κ chain constant region sequence (e.g., SEQ ID NO:86); and
  (iii) an Ig λ chain constant region sequence (e.g., SEQ ID NO:87);

where the scaffold comprises a sequence having at least 80% (85%, 90%. 95%, 98%, 99%, or 100%) sequence identity to at least 70, at least 80, at least 90, or at least 100 contiguous aas of SEQ ID NOs: 85, 86, or 87 respectively. See FIGS. 2J and 2K. The Ig CH1 domain and/or the Ig κ chain sequence optionally comprise their respective MD13 substitutions.
55. The masked TGF-β complex of aspect 22, wherein the scaffold polypeptide of one of the first and second polypeptides comprises an Ig heavy chain CH1 domain (e.g., the polypeptide of SEQ ID NO:85); and the other of the first and second polypeptides comprise either an Ig κ chain constant region sequence (e.g., SEQ ID NO:86 optionally comprising MD13 substitutions) or an Ig λ chain constant region sequence (e.g., SEQ ID NO:87);

wherein the scaffolds comprise a sequence having at least 80% (85%, 90%. 95%, 98%, 99%, or 100%) sequence identity to at least 70, at least 80, at least 90, or at least 100) contiguous aas of SEQ ID NOs: 85, 86, or 87 respectively). See FIGS. 2J and 2K.
56. The masked TGF-β construct or complex of any of aspects 1-56, wherein the masked TGF-β construct or complex comprises at least one (e.g., at least two, or at least three) independently selected linker polypeptide sequences.
57. The masked TGF-β construct or complex of aspect 56, wherein the independently selected linkers have a length from about 1 aa to about 25 aa, (e.g., 1, 2, 3, 4, 5, 6, 7, 8, 9, 10, 11, 12, 13, 14, 15, 16, 17, 18, 19, 20, 21, 22, 23, 24, or 25 aa in length).

58. The masked TGF-β construct or complex of aspect 56, wherein the independently selected linkers have a length from about 25 to about 35 aa in length (e.g., 25, 26, 27, 28, 29, 30, 31, 32, 33, 34, or 35 aa in length).

59. The masked TGF-β construct or complex of aspect 56, wherein the independently selected linkers have a length from about 35 to about 50 aa in length (e.g., 35, 36, 37, 38, 39, 40, 41, 42, 43, 44, 45, 46, 47, 48, 49, or 50, aa in length).

60. The masked TGF-β construct or complex of any of aspects 56 to 59, wherein at least one (e.g., at least two, or at least three) of the independently selected linkers comprises a
   (i) glycine or a polyglycine containing sequence having from about 2 to about 50 contiguous glycine residues (e.g., SEQ ID NO:193);
   (ii) glycine-serine polymer (e.g., $(GS)_n$ (e.g., SEQ ID NO:194), $(GSGGS)_n$ (e.g., SEQ ID NOs:126 and 195), $(GGGGS)_n$ (e.g., SEQ ID NO:136), and $(GGGS)_n$ (e.g., SEQ ID NOs:127 and 196), where n is an integer of at least one (e.g., 1-10, 10-20, or 20-30); or
   (iii) glycine-alanine polymer or alanine-serine polymer (e.g., having a length of 1-10, 10-20, or 20-30 aa).

61. The masked TGF-β construct or complex of any of aspects 56 to 59, wherein at least one (e.g., at least two, or at least three) of the independently selected linkers comprises an aa sequence selected from the group consisting of: GGSG (SEQ ID NO:128), GGSGG (SEQ ID NO:129), GSGSG (SEQ ID NO:130), GSGGG (SEQ ID NO:131), GGGSG (SEQ ID NO:132), GSSSG (SEQ ID NO:133), GGSG (SEQ ID NO:134), GSSSS (SEQ ID NO:135), GGGGS (SEQ ID NO:136), and the like.

62. The masked TGF-β construct or complex of any of aspects 56 to 59, wherein at least one of the independently selected linkers comprises a cysteine residue (e.g., a GCGASGGGGSGGGGS linker aa sequence SEQ ID NO:137) that can or does form a disulfide bond with a cysteine residue present in a second polypeptide (e.g., in a linker of the second polypeptide) of the masked TGF-β construct or complex.

63. The masked TGF-β construct or complex of any of aspects 1 to 62, wherein the one or more (e.g., one, two or more) independently selected MOD polypeptide sequences are selected from the group consisting of: PD-L1, FAS-L, IL-1, IL-2, IL-4, IL-6, IL-7, IL-10, IL-15, IL-21, IL-23 MOD polypeptide sequences, and variants of any thereof (e.g., variants having reduced affinity for their receptor relative to the corresponding wt. MOD polypeptide sequence).

64. The masked TGF-β construct or complex of any of aspects 1 to 62, wherein the one or more (e.g., one, two or more) independently selected MOD polypeptide sequences are selected from the group consisting of: PD-L1, FAS-L, IL-2, IL-4, IL-6, IL-7, IL-10, IL-21, IL-23 MOD polypeptide sequences, and variants of any thereof (e.g., variants having reduced affinity for their receptor relative to the corresponding wt. MOD polypeptide sequence).

65. The masked TGF-β construct or complex of any of aspects 1 to 62, wherein the one or more (e.g., one, two or more) independently selected MOD polypeptide sequences are selected from the group consisting of: PD-L1, FAS-L, IL-2, IL-10 MOD polypeptide sequences, and variants of any thereof (e.g., variants having reduced affinity for their receptor relative to the corresponding wt. MOD polypeptide sequence).

66. The masked TGF-β construct or complex of any of aspects 1 to 62, wherein at least one (e.g., at least two) of the MOD polypeptide sequences is an IL-2 MOD polypeptide sequence or variant IL-2 MOD polypeptide sequence:
   (i) having at least 80% (e.g., at least 85%, at least 90%, at least 95%, at least 98%, or at least 99%) aa sequence identity to at least 80 (e.g., 90, 100, 110, 120, 130 or 133) contiguous aas of SEQ ID NO:9; or
   (ii) having at least 80% (e.g., at least 85%, at least 90%, at least 95%, at least 98%, or at least 99%) aa sequence identity to at least 80 (e.g., 90, 100, 110, 120, 130 or 133) contiguous aas of SEQ ID NOs: 13-27.

67. The masked TGF-β construct or complex of any of aspects 1 to 62, wherein the one or more (e.g., one, two or more) independently selected MOD polypeptide sequences comprise:
   (i) at least one (e.g., at least two) IL-2 MOD polypeptide sequence or variant IL-2 MOD polypeptide sequence (e.g., variant IL-2 MOD polypeptide sequence of aspect 66); and
   (ii) at least one (e.g., at least two) MOD polypeptide sequence selected from the group consisting of PD-L1, FAS-L, IL-1, IL-4, IL-6, IL-7, IL-10, IL-15, IL-21, IL-23 MOD polypeptide sequences, and variants of any thereof (e.g., variants having reduced affinity for their receptor relative to the corresponding wt. MOD polypeptide sequence).

68. The masked TGF-β construct or complex of any of aspects 1 to 62, wherein the one or more (e.g., one, two or more) independently selected MOD polypeptide sequences comprise:
   (i) at least one (e.g., at least two) wt. IL-2 MOD polypeptide sequence or variant IL-2 MOD polypeptide sequence (e.g., variant IL-2 MOD polypeptide sequence of aspect 66); and
   (ii) at least one (e.g., at least two) PD-L1 or PD-L2 MOD polypeptide sequence or variant PD-L1 or PD-L2 MOD polypeptide sequence (e.g., with reduced affinity for the PD1 receptor relative to the corresponding wt. sequence).

69. The masked TGF-β construct or complex of any of aspects 1 to 62, wherein the one or more (e.g., one, two or more) independently selected MOD polypeptide sequences comprise:
   (i) at least one (e.g., at least two) wt. IL-2 MOD polypeptide sequence or variant IL-2 MOD polypeptide sequence (e.g., variant IL-2 MOD polypeptide sequence of aspect 66); and
   (ii) at least one (e.g., at least two) FAS-L MOD polypeptide sequence or variant FAS-L MOD polypeptide sequence (e.g., with reduced affinity for the Fas receptor relative to the corresponding wt. sequence).

70. The masked TGF-β construct or complex of any of aspects 1 to 62, wherein the one or more (e.g., one, two or more) independently selected MOD polypeptide sequences comprise:
   (i) at least one (e.g., at least two) wt. IL-2 MOD polypeptide sequence or variant IL-2 MOD polypeptide sequence (e.g., variant IL-2 MOD polypeptide sequence of aspect 66); and (ii) at least one (e.g., at least two) IL-1 MOD polypeptide sequence or variant IL-1 MOD polypeptide sequence (e.g., with reduced affinity for the IL-1 receptor relative to the corresponding wt. sequence).

71. The masked TGF-β construct or complex of any of aspects 1 to 62, wherein the one or more (e.g., one, two or more) independently selected MOD polypeptide sequences comprise:
(i) at least one (e.g., at least two) IL-2 MOD polypeptide sequence or variant IL-2 MOD polypeptide sequence (e.g., variant IL-2 MOD polypeptide sequence of aspect 66); and
(ii) at least one (e.g., at least two), IL-4 MOD polypeptide sequence or variant, IL-4 MOD polypeptide sequence (e.g., with reduced affinity for the IL-4 receptor relative to the corresponding wt. sequence).

72. The masked TGF-β construct or complex of any of aspects 1 to 62, wherein the one or more (e.g., one, two or more) independently selected MOD polypeptide sequences comprise:
(i) at least one (e.g., at least two) IL-2 MOD polypeptide sequence or variant IL-2 MOD polypeptide sequence (e.g., variant IL-2 MOD polypeptide sequence of aspect 66); and
(ii) at least one (e.g., at least two) IL-6 MOD polypeptide sequence or variant IL-6 MOD polypeptide sequence (e.g., with reduced affinity for the IL-6 receptor relative to the corresponding wt. sequence).

73. The masked TGF-β construct or complex of any of aspects 1 to 62, wherein the one or more (e.g., one, two or more) independently selected MOD polypeptide sequences comprise:
(i) at least one (e.g., at least two) IL-2 MOD polypeptide sequence or variant IL-2 MOD polypeptide sequence (e.g., variant IL-2 MOD polypeptide sequence of aspect 66); and
(ii) at least one (e.g., at least two) IL-7 MOD polypeptide sequence or variant IL-7 MOD polypeptide sequence (e.g., with reduced affinity for the IL-7 receptor relative to the corresponding wt. sequence).

74. The masked TGF-β construct or complex of any of aspects 1 to 62, wherein the one or more (e.g., one, two or more) independently selected MOD polypeptide sequences comprise:
(i) at least one (e.g., at least two) IL-2 MOD polypeptide sequence or variant IL-2 MOD polypeptide sequence (e.g., variant IL-2 MOD polypeptide sequence of aspect 66); and
(ii) at least one (e.g., at least two) IL-10 MOD polypeptide sequence or variant IL-10 MOD polypeptide sequence (e.g., with reduced affinity for the IL-10 receptor relative to the corresponding wt. sequence).

75. The masked TGF-β construct or complex of any of aspects 1 to 62, wherein the one or more (e.g., one, two or more) independently selected MOD polypeptide sequences comprise:
(i) at least one (e.g., at least two) IL-2 MOD polypeptide sequence or variant IL-2 MOD polypeptide sequence (e.g., variant IL-2 MOD polypeptide sequence of aspect 66); and
(ii) at least one (e.g., at least two) IL-15 MOD polypeptide sequence or variant IL-15 MOD polypeptide sequence (e.g., with reduced affinity for the IL-15 receptor relative to the corresponding wt. sequence).

76. The masked TGF-β construct or complex of any of aspects 1 to 62, wherein the one or more (e.g., one, two or more) independently selected MOD polypeptide sequences comprise:
(i) at least one (e.g., at least two) IL-2 MOD polypeptide sequence or variant IL-2 MOD polypeptide sequence (e.g., variant IL-2 MOD polypeptide sequence of aspect 66); and
(ii) at least one (e.g., at least two) IL-21 MOD polypeptide sequence (e.g., a sequence of SEQ ID NO:58 or 60) or variant IL-21 (e.g., with reduced affinity for the IL-21 receptor relative to the corresponding wt. sequence) MOD polypeptide sequence.

77. The masked TGF-β construct or complex of any of aspects 1 to 62, wherein the one or more (e.g., one, two or more) independently selected MOD polypeptide sequences comprise:
(i) at least one (e.g., at least two) wt. IL-2 MOD polypeptide sequence (e.g., comprising the sequence of SEQ ID NO:9) or variant IL-2 MOD polypeptide sequence (e.g., variant IL-2 MOD polypeptide sequence of aspect 66); and
(ii) at least one (e.g., at least two) IL-23 MOD polypeptide sequence (e.g., of SEQ ID NO:63 or 65) or variant IL-23 (e.g., with reduced affinity for the IL-23 receptor relative to the corresponding wt. sequence) MOD polypeptide sequence.

78. The masked TGF-β construct or complex of any of aspects 63 to 77, wherein when the TGF-β polypeptide/polypeptide complex comprises a variant IL-2 MOD polypeptide sequence, the variant IL-MOD polypeptide (e.g., a variant of SEQ ID NO:9) comprises a substitution at any one of, two of, or all of N88, F42 and/or H16.

79. The masked TGF-β construct or complex of aspect 78, wherein at least one variant IL-2 MOD polypeptide sequence comprises an F42A, F42T, H16A, or H16T substitution.

80. The masked TGF-β construct or complex of aspect 78, wherein at least one variant IL-2 MOD polypeptide sequence comprises: (i) F42A and H16A; (ii) F42T and H16A; (iii) F42A and H16T; or (iv) F42T and H16T substitutions.

81. The masked TGF-β construct or complex of aspect 78, wherein at least one variant IL-2 MOD polypeptide sequence comprises: (i) N88R, F42A, and H16A; (ii) N88R, F42T, and H16A; (iii) N88R, F42A, and H16T; or (iv) N88R, F42T, and H16T substitutions.

82. The masked TGF-β construct or complex of any of aspects 1 to 81, wherein the masking polypeptide sequence is a TGF-β receptor ("TβR") polypeptide sequence that comprises an ectodomain fragment of a type I (TORT), type II (TβRII) or type III (TβRIII) TβR.

83. The masked TGF-β construct or complex of aspect 82, wherein the TβRII ectodomain sequence comprises an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, at least 150, or 154) contiguous aas of the TβRII isoform A ectodomain set forth in SEQ ID NO:117.

84. The masked TGF-β construct or complex of aspect 82, wherein the TβRII ectodomain sequence comprises an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, or 143) contiguous aas of the TβRII isoform B ectodomain set forth in SEQ ID NO:119.

85. The masked TGF-β construct or complex of aspect 82, wherein the TβRII ectodomain sequence comprises an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, or 143) contiguous aas of the TβRII isoform B ectodomain set forth in SEQ ID NO:120.

86. The masked TGF-β construct or complex of aspect 82, wherein the TβRII ectodomain sequence comprises an amino acid sequence selected from a TβRII isoform B polypeptide sequence that comprises: the ectodomain fragment of SEQ ID NO:120; the TβRII ectodomain N-terminal Δ14 (delta 14) aa deletion sequence in SEQ ID NO:121; the N-terminal Δ25 (delta 25) aa deletion sequence set forth in SEQ ID NO:122; or a sequence having at least 60% (e.g., at least 70%, at least 80%, at least 90%, at least 95%, at least 98%, at least 99%, or 100%) aa sequence identity to at least 70, at least 80, at least 90, at least 100, at least 110, or 118) contiguous aas of any of those TβRII isoform B polypeptide sequence.

87. The masked TGF-β construct or complex of any of aspects 83-86, wherein the TβRII ectodomain sequence comprises a substitution of any one, two, three, four, or all five of F30, D32, S52, E55, and/or D118 (e.g., with alanine or arginine).

88. The masked TGF-β construct or complex of any of aspects 83-87, comprising:
  a D118A or D118 R substitution (see, e.g., SEQ ID NO:123 for the TβRII ectodomain with an N-terminal Δ25 deletion and a D118 substitution); or
  a D118A or D118R substitution and one, two, three, or all four of a F30A, D32N, S52L and/or E55A substitutions.

89. The masked TGF-β construct or complex of aspect 87, wherein the TβRII ectodomain sequence comprises an N-terminal deletion up to 14 aas (a Δ14 aa deletion) of SEQ ID NO:119 or SEQ ID NO:120 (see, e.g., sequence in SEQ ID NO:121) and an D118 substitution (e.g., D118A or D118R); or a sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or 118) contiguous aas of any of those TβRII polypeptide sequences.

90. The masked TGF-β construct or complex of aspect 89, further comprising one, two, three, or all four of a F30A, D32N, S52L and/or E55A substitution.

91. The masked TGF-β construct or complex of aspect 87, wherein the TβRII ectodomain sequence comprises an N-terminal deletion up 25 aas (a Δ25 aa deletion) of SEQ ID NO:119 or SEQ ID NO:120 and D118 substitution (e.g., D118A or D118R, see SEQ ID NO:123); or a sequence having at least 60% (e.g., at least 70%, at least 80%, at least 90%, at least 95%, at least 98%, at least 99%, or 100%) aa sequence identity to at least 70 (e.g., at least 80, at least 90, or at least 100) contiguous aas of any of those TβRII polypeptide sequences.

92. The masked TGF-β construct or complex of aspect 91, further comprising one, two, three, or all four of a F30A, D32N, S52L and/or E55A substitution.

93. The masked TGF-β construct or complex of aspect 82, wherein the TβR polypeptide sequence comprises a TβRI ectodomain sequence.

94. The masked TGF-β construct or complex of aspect 93, wherein the TβRI ectodomain sequence comprises an amino acid sequence having at least 60% (e.g., at least 70%, at least 80%, at least 90%, at least 95%, at least 98%, at least 99%, or 100%) aa sequence identity to at least 70 (e.g., at least 80, at least 90, or 93) contiguous aas of SEQ ID NO:115.

95. The masked TGF-β construct or complex of aspect 82, wherein the TβR polypeptide sequence comprises a TβRIII ectodomain sequence.

96. The masked TGF-β construct or complex of aspect 95, wherein the TβRIII ectodomain sequence comprises an amino acid sequence having at least 60% (e.g., at least 70%, at least 80%, at least 90%, at least 95%, at least 98%, at least 99%, or 100%) aa sequence identity to at least 70 (e.g., at least 80, 90, 100, 150, 200, 250, 300, 400, 500 or 600) contiguous aas of (aas 27-787 of the A isoform SEQ ID NO:124 or aas 27-786 of the B isoform SEQ ID NO:125).

97. The masked TGF-β construct or complex of any of aspects 1 to 96, wherein the TGF-β polypeptide sequence comprises an amino acid sequence having at least 60% (e.g., at least 70%, at least 80%, at least 80%, at least 85%, at least 90%, at least 95%, at least 98%, at least 99%, or 100%) aa sequence identity to polypeptide comprising at least 70 (e.g., at least 80, at least 90, at least 100, or at least 110) contiguous aas the mature form of a human TGF-β1 polypeptide, a human TGF-β2 polypeptide, or a human TGF-β3 polypeptide.

98. The masked TGF-β construct or complex of any of aspects 1 to 96, wherein the TGF-β polypeptide sequence is a TGF-β1 polypeptide comprising an amino acid sequence having at least 60% (at least 70%, at least 80%, at least 90%, at least 95%, at least 98%, at least 99%, or 100%) aa sequence identity to at least 70 (e.g., at least 80, at least 90, at least 100, at least 110, or 112) contiguous aas of SEQ ID NO:105 (e.g., aas 279-390 of SEQ ID NO:106).

99. The masked TGF-β construct or complex of any of aspects 1 to 96, wherein the TGF-β polypeptide sequence is a TGF-β1 polypeptide bearing a C77S substitution comprising an amino acid sequence having at least 60% (at least 70%, at least 80%, at least 90%, at least 95%, at least 98%, at least 99%, or 100%) contiguous aa sequence identity to at least 70 (e.g., at least 80, at least 90, at least 100, at least 110, or 112) aas of SEQ ID NO:107.

100. The masked TGF-β construct or complex of any of aspects 1 to 96, wherein the TGF-β polypeptide sequence is a TGF-β2 polypeptide comprising an amino acid sequence having at least 60% (at least 70%, at least 80%, at least 90%, at least 95%, at least 98%, at least 99%, or 100%) aa sequence identity to at least 70 (e.g., at least 80, at least 90, at least 100, at least 110, or 112) contiguous aas of (SEQ ID NO:108) (e.g., aas 302-413 of SEQ ID NO:109).

101. The masked TGF-β construct or complex of any of aspects 1 to 96, wherein the TGF-β polypeptide sequence is a TGF-β2 polypeptide bearing a C77S substitution comprising an amino acid sequence having at least 60% (at least 70%, at least 80%, at least 90%, at least 95%, at least 98%, at least 99%, or 100%) contiguous aas sequence identity to at least 70 (e.g., at least 80, at least 90, at least 100, at least 110, or 112) aas of SEQ ID NO:110.

102. The masked TGF-β construct or complex of any of aspects 1 to 96, wherein the TGF-β polypeptide sequence is a TGF-β3 polypeptide comprising an amino acid sequence having at least 60% (at least 70%, at least 80%, at least 90%, at least 95%, at least 98%, at least 99%, or 100%) aa sequence identity to at least 70 (e.g., at least 80, at least 90, at least 100, at least 110, or 112) contiguous aas of SEQ ID NO:111 (e.g., aas 301-412 of SEQ ID NO:112).

103. The masked TGF-β construct or complex of any of aspects 1 to 96, wherein the TGF-β polypeptide sequence is a TGF-β3 polypeptide bearing a C77S substitution comprising an amino acid sequence having at least 60% (at least 70%, at least 80%, at least 90%, at least 95%, at least 98%, at least 99%, or 100%) aa sequence identity to at least 70 (e.g., at least 80, at least 90, at least 100, at least 110, or 112) contiguous aas of SEQ ID NO:113.

104. The masked TGF-β construct or complex of any of aspects 97-103, where in the TGF-β polypeptide sequence comprises a substitution at one or more of positions 25, 92 and/or 94 of the mature TGF-β polypeptide sequence (see, e.g., SEQ ID NO:112 in FIG. 3 and FIG. 4).

105. The masked TGF-β construct or complex of any of aspects 100-101, where in the TGF-β polypeptide sequence comprises a substitution at one or more of positions 25, 92 and/or 94 of the mature TGF-β polypeptide sequence (see, e.g., SEQ ID NO:112 in FIG. 3 and FIG. 4).

106. The masked TGF-β construct or complex of any of aspects 97-105 where in the TGF-β polypeptide sequence comprises:
(i) an aa other than Lys or Arg at position 25
(ii) an aa other than Ile or Val at position 92; and/or
(iii) an aa other than Lys or Arg at position 94 (e.g., based on SEQ ID NO:108 or SEQ ID NO:110).

107. The masked TGF-β construct or complex of any of aspects 1-106, wherein the masked TGF-β construct or complex has the form of any one of structures A-F in FIG. 1.

108. The masked TGF-β construct or complex of aspect 107, wherein the masked TGF-β construct or complex is a masked TGF-β polypeptide having the form of structure A in FIG. 1.

109. The masked TGF-β polypeptide of aspect 108, comprising at least one (e.g., one, two or more) wt. or variant IL-2 MOD polypeptide sequence.

110. The masked TGF-β construct or complex of aspect 107, wherein the masked TGF-β construct or complex is a masked TGF-β complex having the form of structure B in FIG. 1.

111. The masked TGF-β polypeptide of aspect 110, comprising at least one (e.g., one, two or more) wt. or mutant IL-2 MOD polypeptide sequence.

112. The masked TGF-β construct or complex of aspect 107, wherein the masked TGF-β construct or complex is an interspecific masked TGF-β complex having the form of structure C in FIG. 1.

113. The masked TGF-β polypeptide of aspect 112, comprising at least one (e.g., one, two or more) wt. or mutant IL-2 MOD polypeptide sequence.

114. The masked TGF-β construct or complex of aspect 107, wherein the masked TGF-β construct or complex is an interspecific masked TGF-β complex having the form of structure D or E in FIG. 1.

115. The masked TGF-β polypeptide of aspect 114, comprising at least one (e.g., one, two or more) wt. or mutant IL-2 MOD polypeptide sequence.

116. The masked TGF-β construct or complex of aspect 107, wherein the masked TGF-β construct or complex is an interspecific masked TGF-β complex having the form of structure F in FIG. 1.

117. The masked TGF-β polypeptide of aspect 116, comprising at least one (e.g., one, two or more) wt. or mutant IL-2 MOD polypeptide sequence.

118. The masked TGF-β construct or complex of any of aspects 107-117, wherein:
the TGF-β polypeptide sequence comprises a wt. TGF-β3 polypeptide sequence (e.g., comprising the sequence of SEQ ID NO:111) or an amino acid sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or at least 112) contiguous aas of the TGF-β3 sequence set forth in SEQ ID NO:111;
the masking polypeptide sequence is a TβRII polypeptide sequence that comprises a wt. TβRII polypeptide sequence (e.g., comprising the sequence of SEQ ID NO:117) or an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, at least 150, or 154) contiguous aas of the TβRII isoform A ectodomain set forth in SEQ ID NO:117; and
wherein the masked TGF-β construct or complex comprises a wt. IL-2 MOD polypeptide sequence (e.g., comprising the sequence of SEQ ID NO:9).

119. The masked TGF-β construct or complex of any of aspects 107-117, wherein:
the TGF-β polypeptide sequence comprises a wt. TGF-β3 polypeptide sequence (e.g., comprising the sequence of SEQ ID NO:111) or an amino acid sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or at least 112) contiguous aas of the TGF-β3 sequence set forth in SEQ ID NO:111;
the masking polypeptide sequence is a TβRII polypeptide sequence that comprises a wt. TβRII polypeptide sequence (e.g., comprising the sequence of SEQ ID NO:119) or an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, at least 143) contiguous aas of the TβRII isoform B ectodomain set forth in SEQ ID NO:119; and
wherein the masked TGF-β construct or complex comprises a wt. IL-2 MOD polypeptide sequence (e.g., comprising the sequence of SEQ ID NO:9).

120. The masked TGF-β construct or complex of any of aspects 107-117, wherein:

the TGF-β polypeptide sequence comprises a wt. TGF-β3 polypeptide sequence (e.g., comprising the sequence of SEQ ID NO:111) or an amino acid sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or at least 112) contiguous aas of the TGF-β3 sequence set forth in SEQ ID NO:111;

the masking polypeptide sequence is a TβRII polypeptide sequence that comprises a wt. TβRII polypeptide sequence (e.g., comprising the sequence of SEQ ID NO:120) or an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, or at least 129) contiguous aas of the TβRII isoform B ectodomain set forth in SEQ ID NO:120; and wherein the masked TGF-β construct or complex comprises a wt. IL-2 MOD polypeptide sequence (e.g., comprising the sequence of SEQ ID NO:9).

121. The masked TGF-β construct or complex of any of aspects 107-117, wherein:

the TGF-β polypeptide sequence comprises a wt. TGF-β3 polypeptide sequence (e.g., comprising the sequence of SEQ ID NO:111) or an amino acid sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or at least 112) contiguous aas of the TGF-β3 sequence set forth in SEQ ID NO:111;

the masking polypeptide sequence is a TβRII polypeptide sequence that comprises a wt. TβRII polypeptide sequence (e.g., comprising the sequence of SEQ ID NO:117) or an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, at least 150, or 154) contiguous aas of the TβRII isoform A ectodomain set forth in SEQ ID NO:117; and wherein the masked TGF-β construct or complex comprises a variant IL-2 MOD polypeptide sequence comprising an aa sequence having at least 80% (at least 85%, at least 90%, at least 95%, at least 98%, at least 99%, or 100%) aa sequence identity to at least 80 (e.g., 90, 100, 110, 120, 130 or 133) contiguous aas of SEQ ID NO:9.

122. The masked TGF-β construct or complex of any of aspects 107-117, wherein:

the TGF-β polypeptide sequence comprises a wt. TGF-β3 polypeptide sequence (e.g., comprising the sequence of SEQ ID NO:111) or an amino acid sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or at least 112) contiguous aas of the TGF-β3 sequence set forth in SEQ ID NO:111;

the masking polypeptide sequence is a TβRII polypeptide sequence that comprises a wt. TβRII polypeptide sequence (e.g., comprising the sequence of SEQ ID NO:119) or an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, at least 130, at least 140, at least 143) contiguous aas of the TβRII isoform B ectodomain set forth in SEQ ID NO:119; and wherein the masked TGF-β construct or complex comprises a variant IL-2 MOD polypeptide sequence comprising an aa sequence having at least 80% (at least 85%, at least 90%, at least 95%, at least 98%, at least 99%, or 100%) aa sequence identity to at least 80 (e.g., 90, 100, 110, 120, 130 or 133) contiguous aas of SEQ ID NO:9.

123. The masked TGF-β construct or complex of any of aspects 107-117, wherein:

the TGF-β polypeptide sequence comprises a wt. TGF-β3 polypeptide sequence (e.g., comprising the sequence of SEQ ID NO:111) or an amino acid sequence having at least 60% (e.g., at least 70%, at least 80%, at least 90%, at least 95%, at least 98%, at least 99%, or 100%) aa sequence identity to at least 70 (e.g., at least 80, at least 90, at least 100, at least 110, or at least 112) contiguous aas of the TGF-β3 sequence set forth in SEQ ID NO:111;

the masking polypeptide sequence is a TβRII polypeptide sequence that comprises a wt. TβRII polypeptide sequence (e.g., comprising the sequence of SEQ ID NO:120) or an amino acid sequence having at least 60% (e.g., at least 70%, at least 80%, at least 90%, at least 95%, at least 98%, at least 99%, or 100%) aa sequence identity to at least 90 (e.g., at least 100, at least 110, at least 120, or at least 129) contiguous aas of the TβRII isoform B ectodomain set forth in SEQ ID NO:120; and wherein the masked TGF-β construct or complex comprises a variant IL-2 MOD polypeptide sequence comprising an aa sequence having at least 80% (e.g., at least 85%, at least 90%, at least 95%, at least 98%, at least 99%, or 100%) aa sequence identity to at least 80 (e.g., 90, 100, 110, 120, 130 or 133) contiguous aas of SEQ ID NO:9.

124. The masked TGF-β construct or complex of any of aspects 121-123, wherein the TGF-β3 polypeptide sequence comprises a C77S substitution.

125. The masked TGF-β construct or complex of any of aspects 121-124, wherein the TβRII polypeptide sequence comprises a N-terminal Δ14 and either a D118A or a D118R sequence modifications, or a N-terminal Δ25 and either a D118A or a D118R sequence modifications.

126. The masked TGF-β construct or complex of any of aspects 121-125, wherein the IL-2 MOD polypeptide sequence comprises an aa substitution at H16 or an aa substitution at F42.

127. The masked TGF-β construct or complex of any of aspects 121-125, wherein the IL-2 MOD polypeptide sequence comprises an aa substitution at H16 and F42.

128. The masked TGF-β construct or complex of any of aspects 125-127, wherein the substitutions at H16 and F42 are selected from the group consisting of: H16A, H16T, F42A, and F42T (e.g., H16A and F42A or H16T and F42A).

129. The masked TGF-β construct or complex of any of aspects 121-128, wherein the IL-2 MOD polypeptide sequence further comprises an N88R aa substitution.

130a. The masked TGF-β construct or complex of any of aspects 121-129 wherein:

the TGF-β3 polypeptide sequence comprises a C77S substitution;

the TβRII polypeptide sequence comprises either N-terminal Δ14 and D118A or D118R sequence modifications or N-terminal Δ25 and D118A or D118R sequence modifications; and the IL-2 MOD polypeptide sequence comprises an aa substitution at H16 and F42.

130b. The masked TGF-β construct or complex of aspect 130a, wherein the substitutions at H16 and F42 are either an H16A and F42A substitution or an H16T and F42A substitutions.

131. The masked TGF-β construct or complex of any of aspects 1-130b further comprising a wild type or variant MOD polypeptide sequence selected from the group consisting of: PD-L1, FAS-L, IL-1, IL-2, IL-4, IL-6, IL-7, IL-10, IL-15, IL-21 and IL-23.

132. The masked TGF-β construct or complex of any of aspects 1-130b comprising a wild type or variant MOD polypeptide sequence selected from the group consisting of: PD-L1, FAS-L, IL-10.

133. The masked TGF-β construct or complex of any of aspects 1-132, wherein the TGF-β polypeptide/complexes comprises a variant TGF-β polypeptide with reduced affinity for the masking polypeptide (e.g., TGF-β receptor polypeptide) sequence at least 10% less (e.g., at least 20% less, at least 30% less, at least 40% less, at least 50% less, at least 60% less, at least 70% less, at least 80% less, at least 90% less, at least 95% less, or more than 95% less) relative to an otherwise identical wt. TGF-β polypeptide without the sequence variations.

134. The masked TGF-β construct or complex of any of aspects 1-133, wherein the TGF-β polypeptide/complex comprises a TβR polypeptide sequence with one or more sequence variations (e.g., one or more as deletions, insertions or substitutions) with reduced affinity for the TGF-β polypeptide (at least 10% less, at least 20% less, at least 30% less, at least 40% less, at least 50% less, at least 60% less, at least 70% less, at least 80% less, at least 90% less, at least 95% less, or more than 95% less) relative to the corresponding wt. TβR polypeptide sequence without the sequence variations.

135. The masked TGF-β complex PSM-4033-4039.

136. One or more nucleic acids (e.g., expression vector (s)) encoding a masked TGF-β construct or complex of any of aspects 1-135 or encoding a masked TGF-β complex of any of aspects 4 and 6-135.

137. A method of inducing Treg cells in a mammalian (e.g., a human) subject or a cell, tissue, or bodily fluid thereof, the method comprising administering to a subject one or more masked TGF-β constructs or complexes according to any of aspects 1-135.

138. The method of aspect 137, where at least one of the one or more masked TGF-β constructs or complexes comprises a wt. or variant IL-2 MOD polypeptide sequence.

139. The method of aspect 137, where at least one of the one or more masked TGF-β constructs or complexes comprises (i) a wt. or variant IL-2 MOD polypeptide sequence, and (ii) a wt. or variant PL-L1 polypeptide sequence.

140. The method of any of aspects 137-139, wherein the one or more masked TGF-β constructs or complexes is administered before, during (concurrent or combined administration) or after administration of any one or more of vitamin D (e.g., la, 25-dihydroxy vitamin D3 or a vitamin D analog (e.g., vitamin D3), an mTOR inhibitor (e.g., rapamycin), and/or a retinoic acid (e.g., all trans retinoic acid).

141. The method of any of aspects 137-140, wherein the administration leads to an increase in the number of FoxP3+ Treg cells (e.g., any one or more of induced regulatory T cells (iTregs); thymus-derived Treg cells (tTreg), and/or peripheral Treg cells (pTreg)) in a volume of tissue or bodily fluid (e.g., blood or lymph) fluid from a subject relative to the number of those cells either:

(i) before or absent administration of the one or more masked TGF-β constructs or complexes; or (ii) relative to the amount of the Treg cells in the tissue or bodily fluid of a treatment group (e.g., one subject or an average from two or more subjects) that are matched with the subject (e.g., one or more of disease state, age, sex, height, weight, and/or smoking habit) but that have not been administered TGF-β or a masked TGF-β construct or complex.

142. The method of aspect 141, wherein the number of Treg cells (e.g., FoxP3+ cells, iTregs, tTregs, and/or pTregs) increases in a volume of tissue or bodily fluid by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the number of Tregs in a volume of the tissue or the bodily fluid prior to administration of the one or more masked TGF-β constructs or complexes, or relative to the average value of the matched control group that did not receive the one or more masked TGF-β constructs or complexes.

143. A method of inducing Th9 cells a mammalian (e.g., a human) subject or a tissue or bodily fluid thereof, the method comprising administering to the subject one or more masked TGF-β constructs or complexes according to any of aspects 1-134.

144. The method of aspect 143, where at least one of the one or more masked TGF-β constructs or complexes comprises a wt. or variant IL-4 MOD polypeptide sequence.

145. The method of any of aspects 143-144, wherein the administration leads to an increase in the number of Th9 cells in a volume of tissue or bodily fluid (e.g., blood or lymph) fluid from a subject relative to the number of those cells either:

(i) before or absent administration of the one or more masked TGF-β constructs or complexes; or (ii) relative to the amount of Th9 cells in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

146. The method of aspect 145, wherein the number of Th9 cells increases in a volume of tissue or bodily fluid by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the number of Th9 cells in a volume of the tissue or the bodily fluid prior to administration of the one or more masked TGF-β constructs or complexes, or relative to the average value of the matched control group that did not receive the one or more masked TGF-β constructs or complexes.

147. A method of inducing Th17 cells a mammalian (e.g., a human) subject or a tissue or bodily fluid thereof, the method comprising administering to the subject one or more masked TGF-β constructs or complexes according to any of aspects 1-134.

148. The method of aspect 147, where at least one of the one or more masked TGF-β constructs or complexes comprises a wt. or variant IL-6 MOD polypeptide sequence.

149. The method of any of aspects 147-148, wherein the administration leads to an increase in the number of Th17 cells in a volume of tissue or bodily fluid (e.g., blood or lymph) fluid from a subject relative to the number of those cells either:

(i) before or absent administration of the one or more masked TGF-β constructs or complexes; or (ii) relative to the amount of Th17 cells in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

150. The method of aspect 149, wherein the number of Th17 cells increases in a volume of tissue or bodily fluid by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the number of Th17 cells in a volume of the tissue or the bodily fluid prior to administration of the one or more masked TGF-β constructs or complexes, or relative to the average value of the matched control group that did not receive the one or more masked TGF-β constructs or complexes.

151. A method of inducing Thf cells in a mammalian (e.g., a human) subject or a tissue or bodily fluid thereof, the method comprising administering to the subject one or more masked TGF-β constructs or complexes according to any of aspects 1-134.

152. The method of aspect 151, where at least one of the one or more masked TGF-β constructs or complexes comprises at least one wt. or variant IL-21 and/or IL-23 MOD polypeptide sequence.

153. The method of aspect 152, where at least one of the one or more masked TGF-β constructs or complexes comprises at least one wt. or variant IL-21 and at least one wt. or variant IL-23 MOD polypeptide sequence.

154. The method of any of aspects 151-153, wherein the administration leads to an increase in the number of Thf cells in a volume of tissue or bodily fluid (e.g., blood or lymph) fluid from a subject relative to the number of those cells either:

(i) before or absent administration of the one or more masked TGF-β constructs or complexes; or (ii) relative to the number of Thf in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

155. The method of aspect 154, wherein the number of Thf cells increases in a volume of tissue or bodily fluid by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the number of Thf cells in a volume of the tissue or the bodily fluid prior to administration of the one or more masked TGF-β constructs or complexes, or relative to the average value of the matched control group that did not receive the one or more masked TGF-β constructs or complexes.

156. A method of inhibiting the action of Th1 cells in a mammalian subject (or a tissue or bodily fluid thereof), the method comprising administering to the subject one or more masked TGF-β constructs or complexes according to any of aspects 1-134.

157. The method of aspect 156, where at least one of the one or more masked TGF-β constructs or complexes comprises a wt. or variant IL-4 MOD polypeptide sequence.

158. The method of any of aspects 156-157, wherein the administration leads to an inhibition of Th1 mediated release of interferon γ and/or TNF into (or resulting concentration in) a volume of tissue or bodily fluid (e.g., blood or lymph) fluid from a subject relative to amount:

(i) before or absent administration of the one or more masked TGF-β constructs or complexes; or (ii) relative to the amount of interferon γ and/or TNF in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

159. The method of aspect 149, wherein the amount of interferon γ and/or TNF in a volume of tissue or bodily fluid is decreased by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the amount of interferon γ and/or TNF in a volume of the tissue or the bodily fluid prior to administration of the one or more masked TGF-β constructs or complexes, or relative to the average value of the matched control group that did not receive the one or more masked TGF-β constructs or complexes.

160. A method of inhibiting the action and/or proliferation of Th2 cells in a mammalian (e.g., a human) subject or a tissue or bodily fluid thereof, the method comprising administering to the subject one or more masked TGF-β constructs or complexes according to any of aspects 1-134.

161. The method of aspect 160, wherein the administration leads to an inhibition of Th2 mediated release of IL-4, IL-5, and/or IL-13 into (or resulting concentration in) a volume of tissue or bodily fluid (e.g., blood or lymph) fluid from a subject relative to amount:

(i) before or absent administration of the one or more masked TGF-β constructs or complexes; or (ii) relative to the amount in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

162. The method of aspect 161, wherein the amount of IL-4, IL-5, and/or IL-13 in a volume of tissue or bodily fluid is decreased by at least 5% (e.g., at least 10%, at least 15%, at least 20%, at least 25%, at least 30%, at least 40%, at least 50%, at least 60%, at least 70%, at least 80%, or at least 90%) relative to the amount of IL-4, IL-5, and/or IL-13 in a volume of the tissue or the bodily fluid prior to administration of the one or more masked TGF-β constructs or complexes, or relative to the average value of IL-4, IL-5, and/or IL-13 in the tissue, or the bodily fluid from the matched control group that did not receive the one or more masked TGF-β constructs or complexes.

163. A method of inhibiting the action of type II innate lymphoid cells (ILC2 cells) in a mammalian (e.g., a human) subject or a tissue or bodily fluid thereof, the method comprising administering to the subject one or more masked TGF-β constructs or complexes according to any of aspects 1-134, wherein at least one of the one or more masked TGF-β constructs or complexes optionally comprise one or more independently selected wt. or variant IL-10 polypeptide sequences (e.g., a monomeric form such as IL-10M1).

164. The method of aspect 160, wherein the administration leads to an inhibition of ILC2 cells mediated release of IL-5, and/or IL-13 into (or resulting concentration in) a volume of tissue or bodily fluid (e.g., blood or lymph) fluid from a subject relative to amount:
(i) before or absent administration of the treatment with the one or more masked TGF-β constructs or complexes; or
(ii) relative to the amount in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

165. The method of aspect 164, wherein the amount of IL-5, and/or IL-13 in a volume of tissue or bodily fluid is decreased by at least 5% (e.g., at least 10%, at least 15%, at least 20%, at least 25%, at least 30%, at least 40%, at least 50%, at least 60%, at least 70%, at least 80%, or at least 90%) relative to the amount of IL-5 and/or IL-13 in a volume of tissue, or the bodily fluid prior to administration of the one or more masked TGF-β constructs or complexes, or relative to the average value of IL-5 and/or IL-13 in the volume of tissue or the bodily fluid from the matched control group that did not receive the one or more masked TGF-β constructs or complexes.

166. The method of aspect 164, wherein the amount of IL-5, and/or IL-13 in a volume of tissue or bodily fluid is decreased by at least 25%, relative to the amount of IL-5 and/or IL-13 in a volume of tissue, or the bodily fluid prior to administration of the one or more masked TGF-β constructs or complexes, or relative to the average value of IL-5 and/or IL-13 in the volume of tissue or the bodily fluid from the matched control group that did not receive the one or more masked TGF-β constructs or complexes.

167. A method of supporting the development and/or survival of invariant natural killer T (iNKT) cells in a mammalian (e.g., a human) subject, or a tissue or bodily fluid thereof, the method comprising administering to the subject one or more masked TGF-β constructs or complexes according to any of aspects 1-134.

168. The method of aspect 167, where at least one of the one or more masked TGF-β constructs or complexes comprises at least one wt. or variant MOD polypeptide sequence.

169. The method of any of aspects 167-168, wherein the administration leads to an increase in the number of iNKT cells in a volume of tissue or bodily fluid (e.g., blood or lymph) fluid from a subject relative to the number of those cells either:
(i) before or absent administration of the one or more masked TGF-β constructs or complexes; or
(ii) relative to the number of iNKT cells in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

170. The method of aspect 169, wherein the number of iNKT cells increases in a volume of tissue or bodily fluid by at least 5% (e.g., at least 10%, at least 15%, at least 20%, at least 25%, at least 30%, at least 40%, at least 50%, at least 60%, at least 70%, at least 80%, or at least 90%) relative to the number of iNKT cells in a volume of the tissue or the bodily fluid prior to ad ministration of the one or more masked TGF-β constructs or complexes, or relative to the average value of the matched control group that did not receive the one or more masked TGF-β constructs or complexes.

171. The method of aspect 169, wherein the number of iNKT cells increases in a volume of tissue or bodily fluid by at least 25 relative to the number of iNKT cells in a volume of the tissue or the bodily fluid prior to administration of the one or more masked TGF-β constructs or complexes, or relative to the average value of the matched control group that did not receive the one or more masked TGF-β constructs or complexes.

172. A method of blocking an increase in the number of CD4+ T cells or reducing the number of CD4+ T cells in a mammalian (e.g., a human) subject or a tissue or bodily fluid thereof, the method comprising administering to the subject one or more masked TGF-β constructs or complexes according to any of aspects 1-134.

173. The method of aspect 172, where at least one of the one or more masked TGF-β constructs or complexes comprises at least one wt. or variant MOD polypeptide sequence in addition to the TGF-β polypeptide sequence.

174. The method of any of aspects 172-173, wherein the administration leads to a decrease in the number of CD4+ T cells in a volume of tissue or bodily fluid (e.g., blood or lymph) fluid from a subject relative to the number of those cells either:
(i) before or absent administration of the one or more masked TGF-β constructs or complexes; or
(ii) relative to the number of CD4+ T cells in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.

175. The method of aspect 174, wherein the number of CD4+ cells decreases in a volume of tissue or bodily fluid by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the number of CD4+ cells in a volume of the tissue or the bodily fluid prior to administration of the one or more masked TGF-β constructs or complexes, or relative to the average value of the matched control group that did not receive the one or more masked TGF-β constructs or complexes.
176. The method of aspect 174, wherein the number of CD4+ cells decreases in a volume of tissue or bodily fluid by at least 25% relative to the number of CD4+ cells in a volume of the tissue or the bodily fluid prior to administration of the one or more masked TGF-β constructs or complexes, or relative to the average value of the matched control group that did not receive the one or more masked TGF-β constructs or complexes.
177. A method of blocking an increase in the number of $CD8^+$ T cells or reducing the number of CD4+ T cells in a mammalian (e.g., a human) subject or a tissue or bodily fluid thereof, the method comprising administering to the subject one or more masked TGF-β constructs or complexes according to any of aspects 1-134.
178. The method of aspect 172, where at least one of the one or more masked TGF-β constructs or complexes comprises at least one wt. or variant MOD polypeptide sequence in addition to the TGF-β polypeptide sequence.
179. The method of any of aspects 172-173, wherein the administration leads to a decrease in the number of $CD8^+$ T cells in a volume of tissue or bodily fluid (e.g., blood or lymph) fluid from a subject relative to the number of those cells either:
(i) before or absent administration of the one or more masked TGF-β constructs or complexes; or
(ii) relative to the number of $CD8^+$ T cells in the tissue or bodily fluid of a control treatment group (e.g., the average from a group of individuals) matched with the subject (e.g., one or more of disease state, age, sex, height, weight, and/or smoking habit) but that have not been administered TGF-β or a masked TGF-β construct or complex.
180. The method of aspect 174, wherein the number of $CD8^+$ cells decreases in a volume of tissue or bodily fluid by at least 5% (e.g., at least 10%, at least 15%, at least 20%, at least 25%, at least 30%, at least 40%, at least 50%, at least 60%, at least 70%, at least 80%, at least 90%, at least 2-fold, at least 5-fold, at least 10-fold or more) relative to the number of $CD8^+$ cells in a volume of the tissue or the bodily fluid prior to administration of the one or more masked TGF-β constructs or complexes, or relative to the average value of the matched control group that did not receive the one or more masked TGF-β constructs or complexes.
181. A method of providing treatment or prophylaxis of a wound, an allergic reaction, a disease or disorder, the method comprising administering to a subject (e.g., a human) in need thereof either (i) one or more independently selected masked TGF-β constructs or complexes according to any of aspects 1-134, and/or (ii) one more nucleic acids encoding the one or more independently selected masked TGF-β constructs or complexes according to any of aspects 1-134.
182. The method of aspect 181, wherein at least one of the one or more masked TGF-β constructs or complexes comprises at least one (e.g., at least two, or at least three) independently selected wt. or variant IL-2 MOD polypeptide sequences.
183. The method of aspect 182, wherein the independently selected wt. or variant IL-2 MOD polypeptide comprises the IL-2 polypeptide of SEQ ID NO:9 or a variant thereof.
184. The method of aspect 183, wherein the independently selected variant IL-2 MOD polypeptide sequence comprises a sequence having:
(i) at least 80% (e.g., at least 85%, at least 90%, at least 95%, at least 98%, or at least 99%, aa sequence identity to at least 80 (e.g., at least 90, 100, 110, 120, 130 or 133) contiguous aas of SEQ ID NO:9; or
(ii) at least 80% (e.g., at least 85%, at least 90%, at least 95%, at least 98%, or at least 99%) aa sequence identity to at least 80 (e.g., at least 90, 100, 110, 120, 130 or 133) contiguous aas of any of SEQ ID NOs:15-27.
185. The method of any one of aspects 182-184, wherein the independently selected variant IL-2 MOD polypeptide sequence comprises a substitution at any one, two, or all three of N88, F42 and/or H16.
186. The method of any one of aspects 182-185, wherein the independently selected variant IL-2 MOD polypeptide sequence comprises a substitution or pair of substitutions selected from the group consisting of: (i) F42A; (ii) F42T; (iii) H16A; (iv) H16T; (v) F42A and H16A; (vi) F42T and H16A; (vii) F42A and H16T; or (viii) F42T and H16T substitutions.
187. The method of any one of aspects 181-186, wherein the masked TGF-β constructs or complexes comprise at least one (e.g., at least two) independently selected wt. or variant PD-L1 polypeptide sequences.
188. The method of aspect 187, wherein the independently selected variant PD-L1 polypeptide sequence comprises a polypeptide sequences having at least 80% (e.g., at least 85%, at least 90%, at least 95%, at least 98%, or at least 99%) aa sequence identity to at least 170 contiguous aa (e.g., at least 180, 190 or 200 contiguous aa) of SEQ ID NO:2.
189. The method of any one of aspects 181-188, wherein at least one of the one or more masked TGF-β polypeptides comprise an independently selected wt. or variant IL-10 polypeptide sequence (e.g., a monomeric isomer such as IL-10M1).
190. The method of aspect 189, wherein the independently selected wt. or variant IL-10 polypeptide sequence comprise a polypeptide sequence with at least 80% (at least 85%, at least 90%, at least 95%, at least 98%, or at least 99%) aa sequence identity to at least 50 contiguous aa (e.g., at least 60, at least 70, at least 80, at least 90, at least 100, at least 110, at least 120, at least 130, at least 140, at least 150, or at least 160) contiguous aa of SEQ ID NOs: 50 or 51 (e.g., which have at least one aa substitution, deletion or insertion when the sequence is a variant IL-10 sequence); and wherein variant IL-10 polypeptide sequence optionally comprises a 5-7 aa insertion between N49 and K50 of SEQ ID NO:51, or at the equivalent location in SEQ ID NOs:49 or 50 (e.g., IL-10M1 GGGSGG (SEQ ID NO:189) inserted into SEQ ID NO:51 between aa 49 and aa 50).

191. The method of any one of aspects 181-190, wherein at least one of the independently selected masked TGF-β constructs or complexes comprise an independently selected wt. or variant FasL polypeptide sequence.
192. The method of aspect 191, wherein the independently selected wt. or variant FasL polypeptide sequence comprise a polypeptide sequence with at least 80% (e.g., at least 85%, at least 90%, at least 95%, at least 98%, or at least 99%) aa sequence identity to at least 50 contiguous aa (e.g., at least 60, at least 70, at least 80, at least 90, at least 100, at least 110, at least 120, at least 140, at least 160, or at least 180 contiguous aa) of SEQ ID NO:144 (e.g., which have at least one aa substitution, deletion or insertion).
193. The method of any one of aspects 181-192, wherein the one or more masked TGF-β constructs or complexes is administered before, concurrently, combined with, or following administration of any one, two or all three of vitamin D (e.g., 1 α,25-dihydroxy vitamin D3), retinoic acid (e.g., all trans retinoic acid), and/or rapamycin.
194. The method of any one of aspects 181-193, wherein the autoimmune disease is selected from the group consisting of: Addison's disease, alopecia areata, ankylosing spondylitis, autoimmune encephalomyelitis, autoimmune hemolytic anemia, autoimmune hepatitis, autoimmune-associated infertility, autoimmune thrombocytopenic purpura, bullous pemphigoid, celiac disease, Crohn's disease, Goodpasture's syndrome, glomerulonephritis (e.g., crescentic glomerulonephritis, proliferative glomerulonephritis), Grave's disease, Hashimoto's thyroiditis, mixed connective tissue disease, multiple sclerosis, myasthenia gravis (MG), pemphigus (e.g., pemphigus vulgaris), pernicious anemia, polymyositis, psoriasis, psoriatic arthritis, rheumatoid arthritis, scleroderma, Sjögren's syndrome, systemic lupus erythematosus (SLE), type 1 diabetes (T1D), vasculitis, and vitiligo.
195. The method of any of aspects 181-193, wherein the autoimmune disease is T1D or celiac disease.
196. The method of any of aspects 181-193, wherein the autoimmune disease is other than T1D or celiac disease.
197. The method of any one of aspects 181-193, wherein the method is a method of treatment or prophylaxis of an allergic reaction.
198. The method of aspect 197 where the allergic reaction is a reaction to a peanut, tree nut, plant pollens, latex, bee venom or wasp venom allergen.
199. The method of any one of aspects 181-190, wherein the method is a method of providing treatment or prophylaxis for a burn or a wound
200. The method of aspect 199, wherein the wound is an abrasion, avulsion, incision, laceration, or puncture of the epidermis or mucosa.
201. The method of aspect 200, wherein the i) one or more independently selected masked TGF-β constructs or complexes according to any of aspects 1-134, and/or (ii) one more nucleic acids encoding the one or more independently selected masked TGF-β constructs or complexes according to any of aspects 1-134, is administered before, during and/or after formation of the wound.
202. The method of any of aspects 199-201, wherein the burn and/or wound occurs during, or is the result of, a surgical or other medical procedure.
203. The method of any of aspects 199-202, wherein one or more independently selected masked TGF-β constructs or complexes is administered to the site of the wound or burn.
204. The method of any of aspects 199-203, wherein administration of a masked TGF-β construct or complex (an effective amount) and/or one or more nucleic acids (e.g., recombinant expression vectors) encoding the masked TGF-β construct or complex speeds wound closure (reduce time until closure), reduce healing time, or to reduce scar formation relative to an untreated subject or wound.
205. The method of aspect 181, wherein at least one of the masked TGF-β constructs or complexes comprises at least one (e.g., at least two, or at least three) independently selected wt. (e.g., SEQ ID NO:29 or SEQ ID NO:31) or variant IL-4 polypeptide sequences.
206. The method of aspect 205, wherein the variant IL-4 polypeptide sequences comprise a polypeptide sequences having at least 80%, at least 85%, at least 90%, at least 95%, at least 98%, or at least 99% aa sequence identity to at least 80 contiguous aa (e.g., at least 100, or 110 contiguous aa) of SEQ ID NO:29 or SEQ ID NO:31 (e.g., which have at least one aa substitution, deletion or insertion).
207. The method of any of aspects 205-206, wherein the disease or disorder is a helminth infection.
208. The method of aspect 181, wherein at least one of the masked TGF-β constructs or complexes comprises at least one (e.g., at least two, or at least three) independently selected wt. (e.g., the polypeptide of SEQ ID NO:35) or variant IL-6 polypeptide sequences.
209. The method of aspect 208, wherein the variant IL-6 polypeptide sequences comprise a polypeptide sequences having at least 80%, at least 85%, at least 90%, at least 95%, at least 98%, or at least 99% aa sequence identity to at least 80 contiguous aa (e.g., at least 100, or 110 contiguous aa) of SEQ ID NO:35 (e.g., which has at least one aa substitution, deletion or insertion).
210. The method of any of aspects 204-209, wherein the disease or disorder is a bacterial and/or fungal infection (e.g., in the gut).
211. The method of aspect 181, wherein at least one of the masked TGF-β constructs or complexes comprises at least one (e.g., at least two, or at least three) independently selected wt. or variant IL-21 and/or IL-23 polypeptide sequences.
212. The method of aspect 209, wherein the at least one (e.g., at least two) IL-21 MOD polypeptide sequence comprises (i) a polypeptide of sequence of SEQ ID NO:58 or 60) or (ii) a polypeptide sequence having at least 80% (e.g., at least 85%, at least 90%, at least 95%, at least 98%, or at least 99%) aa sequence identity to at least 50 (e.g., at least 60, at least 70, at least 80, at least 90, at least 100, or at least 110) contiguous aa of SEQ ID NO:58 or 60, and which have at least one aa substitution, deletion or insertion.
213. The method of aspect 211 or 212, wherein the at least one (e.g., at least two) IL-23 MOD polypeptide sequence comprises (i) a polypeptide of sequence of SEQ ID NO:63 or 65) or (ii) a polypeptide sequence having at least 80% (e.g., at least 85%, at least 90%, at least 95%, at least 98%, or at least 99%) aa sequence identity to at least 50 (e.g., at least 60, at least 70, at least 80, at least 90, at least 100, at least 110, at least 120, at least 140, at least 160, at least 180, at least 200, at least 220, at least 240, at least 260, at least 280, at least 300, at least 320, or at least 340) contiguous aas of SEQ ID NO:63 and/or 65, and which have at least one aa substitution, deletion or insertion.

214. The method of any of aspects 211-213, wherein the disease or disorder is an inability to produce high affinity antibodies or sufficient amounts of high affinity antibodies.

215. A method of inducing tolerance a mammalian subject, the method comprising administering to the subject:

(i) one or more masked TGF-β constructs or complexes, or one or more nucleic acids (e.g., expression vector(s)) encoding a masked TGF-β construct or complex according to any of aspects 1-136, (ii) one or more masked TGF-β constructs or complexes, or one or more nucleic acids (e.g., expression vector(s)) encoding a masked TGF-β construct or complex according to any of aspects 1-β6, wherein at least one of the one or more masked TGF-β constructs or complexes comprises an wt. or variant IL-2 polypeptide sequence;

(iii) one or more masked TGF-β constructs or complexes, or one or more nucleic acids (e.g., expression vector(s)) encoding a masked TGF-β construct or complex according to any of aspects 1-β6, wherein at least one of the one or more masked TGF-β constructs or complexes comprises an wt. or variant FasL polypeptide sequence; or (iv) one or more masked TGF-β constructs or complexes, or one or more nucleic acids (e.g., expression vector(s)) encoding a masked TGF-β construct or complex according to any of aspects 1-β6, wherein at least one of the one or more masked TGF-β constructs or complexes comprises an wt. or variant IL-2 polypeptide sequence, and wherein at least one of the one or more masked TGF-β constructs or complexes comprises an wt. or variant FasL polypeptide sequence or a wt. or variant IL-10 polypeptide sequence.

216. The method of any of aspects 137-215, further comprising administering a non-steroidal anti-inflammatory drug (NSAID) (e.g., Cox-1 and/or Cox-2 inhibitors such as Celecoxib, Diclofenac, Diflunisal, Etodolac, Ibuprofen, Indomethacin, Ketoprofen, and Naproxen) before, during (concurrent or combined administration) or after administering the one or more masked TGF-β constructs or complexes.

217. The method of any of aspects 137-216, further comprising administering a Corticosteroid (e.g., Cortisone, Dexamethasone, Hydrocortisone, Ethamethasoneb, Fludrocortisone, Methylprednisolone, Prednisone, Prednisolone and Triamcinolone) before, during (concurrent or combined administration) or after administering the one or more masked TGF-β constructs or complexes.

218. The method of any of aspects 137-217, further comprising administering an agent that blocks one or more actions of tumor necrosis factor alpha (e.g., an anti-TNF alpha such as golimumab, infliximab, certolizumab, adalimumab or a TNF alpha decoy receptor such as etanercept) before, during (concurrent or combined administration) or after administering the one or more masked TGF-β constructs or complexes.

219. The method of any of aspects 137-218, further comprising administering an agent that binds to the IL-1 receptor competitively with IL-1 (e.g., anakinra) before, during (concurrent or combined administration) or after administering the one or more masked TGF-β constructs or complexes. This aspect can be subject to the proviso that an agent that binds to the IL-1 receptor competitively with IL-1 is not administered if any of the one or more masked TGF-β constructs or complexes administered to the subject comprises an IL-1 polypeptide.

220. The method of any of aspects 137-219, further comprising administering an agent that binds to the IL-6 receptor and inhibits IL-6 from signaling through the receptor (e.g., tocilizumab) before, during (concurrent or combined administration) or after administering the one or more masked TGF-β constructs or complexes. This aspect can be subject to the proviso that an agent that binds to the IL-6 receptor is not administered if any of the one or more masked TGF-β constructs or complexes administered to the subject comprises an IL-6 polypeptide.

221. The method of any of aspects 137-220, further comprising administering an agent that binds to CD80 or CD86 receptors and inhibits T cell proliferation and/or B cell immune response (e.g., abatacept) before, during (concurrent or combined administration) or after administering the one or more masked TGF-β constructs or complexes.

222. The method of any of aspects 137-221, further comprising administering an agent that binds to CD20 resulting in B-Cell death (e.g., rituximab) before, during (concurrent or combined administration) or after administering the one or more masked TGF-β constructs or complexes.

223. The method of any of aspects 137-222, wherein the mammalian subject is selected from: human, bovine canine, feline, rodent, murine, caprine, simian, ovine, equine, lappine, porcine, etc. subjects.

224. The method of any of aspects 137-223, wherein the subject is a human (e.g., a human patient or a human subject in need of treatment or prophylaxis).

225. A method of delivering a TGF-β polypeptide or a TGF-β polypeptide and an immunomodulatory polypeptide (MOD) to a cell, comprising contacting the cell with (i) a one or more masked TGF-β constructs or complexes of any one of aspects 1-134, (ii) one or more masked TGF-β constructs or complexes comprising one or more independently selected wt. or variant MOD sequences of any one of aspects 1-134, or (iii) one or more nucleic acids encoding one or more masked TGF-β constructs or complexes of any one of aspects 135-136 optionally encoding one or more independently selected wt. or variant MODs.

226. A method of producing cells expressing a masked TGF-β construct or complex, the method comprising introducing one or more nucleic acids (e.g., expression vector(s)) encoding a masked TGF-β construct or complex of any of aspects 1-134 into the cells (e.g., a mammalian cell in vitro), and optionally selecting for cells comprising all or part of the one or more nucleic acids unintegrated and/or integrated into at least one cellular chromosome (e.g., antibiotic selection followed by analysis to determine if any of the one or more nucleic acids had integrated into a cell chromosome).

227. The method of aspect 224, wherein the cell is a cell of a mammalian cell line selected from the HeLa cells, CHO cells, 293 cells, Vero cells, NIH 3T3 cells, Huh-7 cells, BHK cells, PC12, COS cells, COS-7 cells, RAT1 cells, mouse L cells, human embryonic kidney (HEK) cells, and HLHepG2 cells.

228. A cell transiently or stably expressing a masked TGF-β construct or complex prepared by the method of aspect 226 or 227.

229. The cell of aspect 228, wherein cells express from about 25 to about 350 mg/liter or more (e.g., from about 25 to about 100, from about 100 to about 200, from about 200 to about 300, from about 300 to about 350 mg/liter, or greater than 350 mg/liter) of masked TGF-β construct or complex without substantial reduction (less than a 5%, 10%, or 15% reduction) in viability relative to otherwise identical cells not expressing the masked TGF-β construct or complex.

230. The method of any of aspects 138-142, wherein the administering of the masked TGF-β constructs or complexes comprising a wt. or variant IL-2 MOD polypeptide sequence results in modulation of one or more T cells (e.g., inflammatory T cell such as Th1, Th2, Th17 and/or Th22 cells) in the subject, cell, tissue, or bodily fluid.

231. The method of aspect 230, wherein the one or more T cells are Th1 cells and modulation is assessed by a reduction in the number of Th1 cells, a reduction in the expression or secretion of interferon γ by the Th1 cells, or the level of interferon γ in the subject, cell, tissue, or bodily fluid:

(i) before or absent administration of the one or more masked TGF-β constructs or complexes; or (ii) relative to the amount of interferon γ in the subject, cell, tissue, or bodily fluid of a treatment group (e.g., one subject or an average from two or more subjects) that are matched with the subject (e.g., one or more of disease state, age, sex, height, weight, and/or smoking habit) but that have not been administered TGF-β or a masked TGF-β construct or complex.

232. The method of aspect 230, wherein the one or more T cells are Th2 cells, and modulation is assessed by a reduction in the number of Th2 cells, a reduction in the expression or secretion of IL-4, IL-5, and/or IL-13 by the Th2 cells, or the level of L-4, IL-5, and/or IL-13 in the subject, cell, tissue, or bodily fluid:

(i) before or absent administration of the one or more masked TGF-β constructs or complexes; or (ii) relative to the amount of L-4, IL-5, and/or IL-13 in the subject, cell, tissue, or bodily fluid of a treatment group (e.g., one subject or an average from two or more subjects) that are matched with the subject (e.g., one or more of disease state, age, sex, height, weight, and/or smoking habit) but that have not been administered TGF-β or a masked TGF-β construct or complex.

233. The method of aspect 230, wherein the one or more T cells are Th17, cell and modulation is assessed by a reduction in the number of Th17 cells, a reduction in the expression or secretion of IL-17 and/or IL-22 by the Th17 cells, or the level of IL-17 and/or IL-22 in the subject, cell, tissue, or bodily fluid:

(i) before or absent administration of the one or more masked TGF-β constructs or complexes; or (ii) relative to the amount of IL-17 and/or IL-22 in the subject, cell, tissue, or bodily fluid of a treatment group (e.g., one subject or an average from two or more subjects) that are matched with the subject (e.g., one or more of disease state, age, sex, height, weight, and/or smoking habit) but that have not been administered TGF-β or a masked TGF-β construct or complex.

234. The method of aspect 230, wherein the one or more T cells are Th22, cell and modulation is assessed by a reduction in the number of Th22 cells, a reduction in the expression or secretion of at least two or IL-22, IL-13 and/or TNF-alpha by the Th22 cells, or the level of IL-22, IL-13 and/or TNF-alpha in the subject, cell, tissue, or bodily fluid:

(i) before or absent administration of the one or more masked TGF-β constructs or complexes; or (ii) relative to the amount of IL-22, IL-13, and TNF-alpha in the subject, cell, tissue, or bodily fluid of a treatment group (e.g., one subject or an average from two or more subjects) that are matched with the subject (e.g., one or more of disease state, age, sex, height, weight, and/or smoking habit) but that have not been administered TGF-β or a masked TGF-β construct or complex.

235. The method of aspect 234, wherein the method further comprises assessing the expression, secretion of one or more of IL-4, IL-17 and/or interferon γ, or the levels one or more of IL-4, IL-17 and/or interferon γ in the subject, cell, tissue, or bodily fluid.

236. The method of any of aspects 230-235, wherein the T cells are bystander T cells.

237. The method of any of aspects 230-236, wherein the one or more masked TGF-β constructs or complexes is administered before, during (concurrent or combined administration) or after administration of any one or more of vitamin D (e.g., la, 25-dihydroxy vitamin D3 or a vitamin D analog (e.g., vitamin D3), an mTOR inhibitor (e.g., rapamycin), and/or a retinoic acid (e.g., all trans retinoic acid).

238. The method of any of aspects 230-237 wherein the masked-TGF-β constructs or complexes comprising a wt. or variant IL-2 MOD has a structure set forth in FIG. 1 structures A to F.

239. The method of aspect 238, wherein the Fc region lacks immunoglobulin effector sequences (reduced complement component 1q ("C1q") binding compared to the wt. protein, and accordingly a reduction in the ability to participate in complement-dependent cytotoxicity).

VI. EXAMPLES

The following examples are put forth so as to provide those of ordinary skill in the art with a more complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s);); µl, microliter(s); pl, picolitre(s); s or sec, second (s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); wt., wild type; and the like.

A. Example 1

1 Single Polypeptide Chain Masked TGF-β Constructs

Figure 7G:
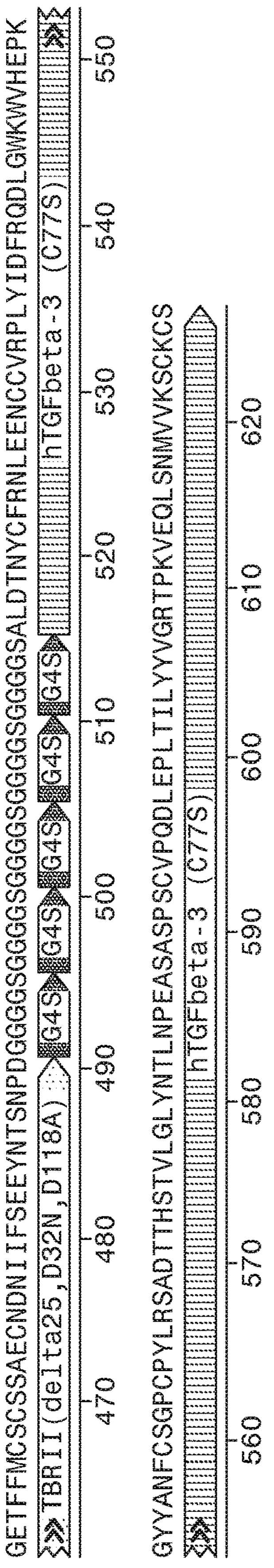
Figure 7H:
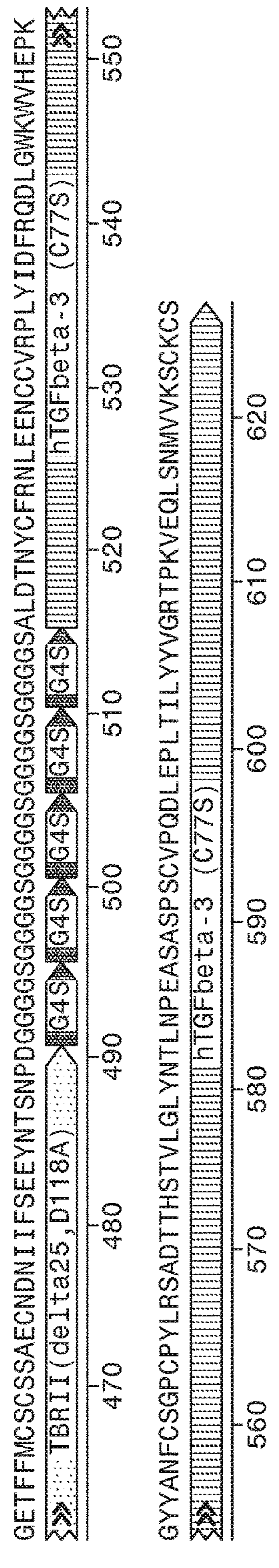
Figure 7I:
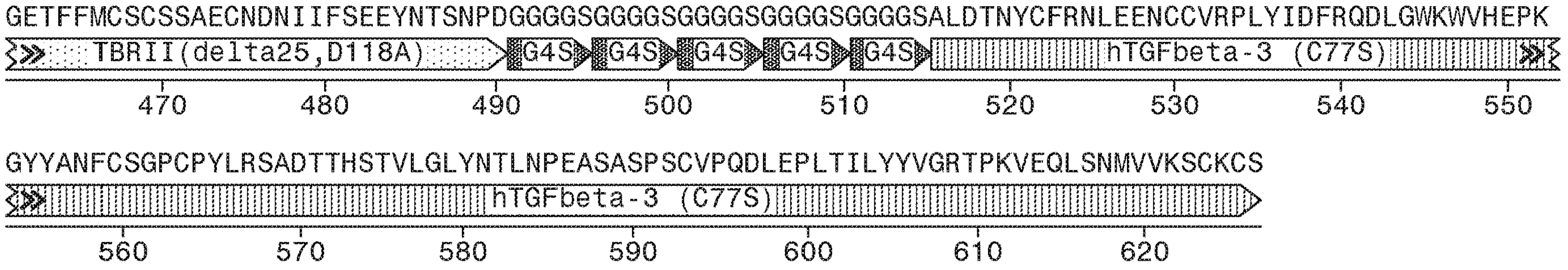

The stable expression of an intact single polypeptide chain presenting a masked TGF-β protein was demonstrated by preparing a nucleic acid encoding the desired components, and driving expression using an expression vector for a mammalian cell. The nucleic acids encode polypeptides comprising, from N- to C-terminus: a MOD polypeptide sequence (e.g., a wt. IL-2 polypeptide sequence, such as SEQ ID NO:20, or a variant of that IL-2 polypeptide bearing substitutions at H16 and/or F42; an IgG/Fc scaffold polypeptide sequence bearing L234A and L235A substitutions along with substitutions that prevent Fc dimerization, a type II TGF-β receptor (e.g., a TGF-βRII B isoform polypeptide sequence with D32N and/or D118A sequence variations), and a TGF-β polypeptide sequence (e.g., wt. TGF-β3 or a C77S sequence variant). A schematic having the overall structure of the expressed proteins is shown in FIG. 1 as structure A, one example of which is shown in FIG. 7A as construct 3470 (SEQ ID NO:146), another example of such a polypeptide's as sequence is construct No. 3472 aligned with the elements labeled is shown in FIG. 7G as SEQ ID NO:157. After constructing the nucleic acid in a plasmid suitable for mammalian protein expression (e.g., in Chinese Hamster Ovary or CHO cells) the proteins were expressed and purified using protein A and size separation chromatography.

In addition to the construction and isolation of constructs 3470 and 3472 two additional single polypeptide chain masked TGF-β constructs, 3466 and 3468 were prepared. Construct 3470, along with constructs 3472, 3466, and 3468 (numbered as (i) to (iii) below) demonstrate the feasibility of preparing single chain masked TGF-β proteins, that do not substantially dimerize, particularly through classical Fc association. The polypeptides comprise, from N- to C-terminus the following polypeptide sequences:

(i) wt. IL-2-IgG Fc-TβRII$_{\Delta 25}$(D32N, D118A) substitutions-TGF-β3 (C77S) (FIG. 7G, Construct No. 3472) SEQ ID NO:157;

(ii) IL-2 (H16T, F42A)-IgG Fc-TβRII$_{\Delta 25}$(D118)-TGF-β3 (C77S) (FIG. 7H, Construct No. 3466) SEQ ID NO:158; and (iii) IL-2 (H16T, F42A)-IgG Fc-TβRII$_{\Delta 25}$(D32N, D118)-TGF-β3 (C77S) (FIG. 7I, Construct No. 3468) SEQ ID NO:159.

As indicated above, single polypeptide chain masked TGF-β constructs may comprise substitutions that prevent the dimerization of the Fc region, for example at L131 (e.g., L131K), T146 (e.g., T146S), P175 (e.g., P175V), F185 (e.g., F185R), Y187 (e.g., Y187A), and K189 (e.g., K189Y) numbered as in the IgG1 sequence of SEQ ID NO:71. Above-mentioned constructs in (i) to (iii) comprise L131K, T146S, P175V, F185R, Y187A, and K189Y as numbered in the IgG1 sequence of SEQ ID NO:71.

2 Heterodimeric Polypeptide Chain

The stable expression of a masked TGF-β complex comprised of two polypeptides was demonstrated masked TGF-β constructs by preparing a nucleic acid encoding a first polypeptide comprising a TGF-β polypeptide sequence, and a second nucleic acid encoding a TGF-β receptor polypeptide sequence, and expressing the polypeptides using mammalian expression vectors (e.g., plasmid expression systems in CHO cells). The first polypeptide comprising, for example, a MOD polypeptide sequence (e.g., a wt. or variant IL-2 polypeptide sequence), an IgG Fc scaffold polypeptide sequence (e.g., a KiH Fc), and a TGF-β polypeptide sequence (e.g., wt. or sequence variant bearing TGF-β1 or wt. TGF-β3) (see, e.g., FIG. 7J, construct 3618). The second polypeptide comprising, for example, a MOD polypeptide sequence (e.g., a wt. or variant IL-2 polypeptide sequence), an IgG Fc scaffold polypeptide sequence (e.g., the counter part of the KiH sequence of the first polypeptide), and a type II TGF-β receptor (TGF-β RII) polypeptide sequence (wt. or with sequence variations) (see, e.g., FIG. 7J, construct 3621). A schematic structure of the expressed protein is shown in FIG. 1 as structure D. Expression and purification (protein A and size separation by chromatography) of one such pair of polypeptides, (iv.a) and (iv.b), comprising, from N- to C-terminus the following polypeptide sequences:

(iv.a) IL-2 (wt. MOD)-knob-in-hole Fc (e.g., knob Fc)-TGF-β3(wt.) see FIG. 7J, construct 3618 (SEQ ID NO:148); and (iv.b) IL-2 (wt. MOD)-knob-in-hole Fc (e.g., hole Fc)-TβRII (D32N) see FIG. 7J, construct 3621 (SEQ ID) NO:160.

In construct (iv.a) or (iv.b), the IL-2 polypeptide may comprise substitutions at H16 and/or H42, such as H16T and F42A substitutions or H16A and F42A substitutions.

3 Activity of Masked TGF-β Constructs

Various concentrations of the purified masked TGF-β polypeptides complexes and constructs (e.g., constructs (i) to (iii) and the complex of polypeptides (vi.a) and (vi.b) prepared in parts 1 and 2 of this example) were tested for their ability to induce naïve CD4 cells to produce FoxP3. For the assays $10^5$ naïve CD4 cells were plated in wells containing 5 μg/ml bound anti-CD3 with 1 μg/ml of anti-CD28 and the masked TGF-β polypeptides complexes or constructs as indicated. After five days in culture the number of FoxP3 CD4+ double positive cells were assessed using fluorescently labeled anti-CD4 and anti-FoxP3 by flow cytometry. Controls providing stimulation by either TGF-β3 or TGF-β3 and recombinant human IL-2 100 U/ml were also run in parallel.

Figure 6A:
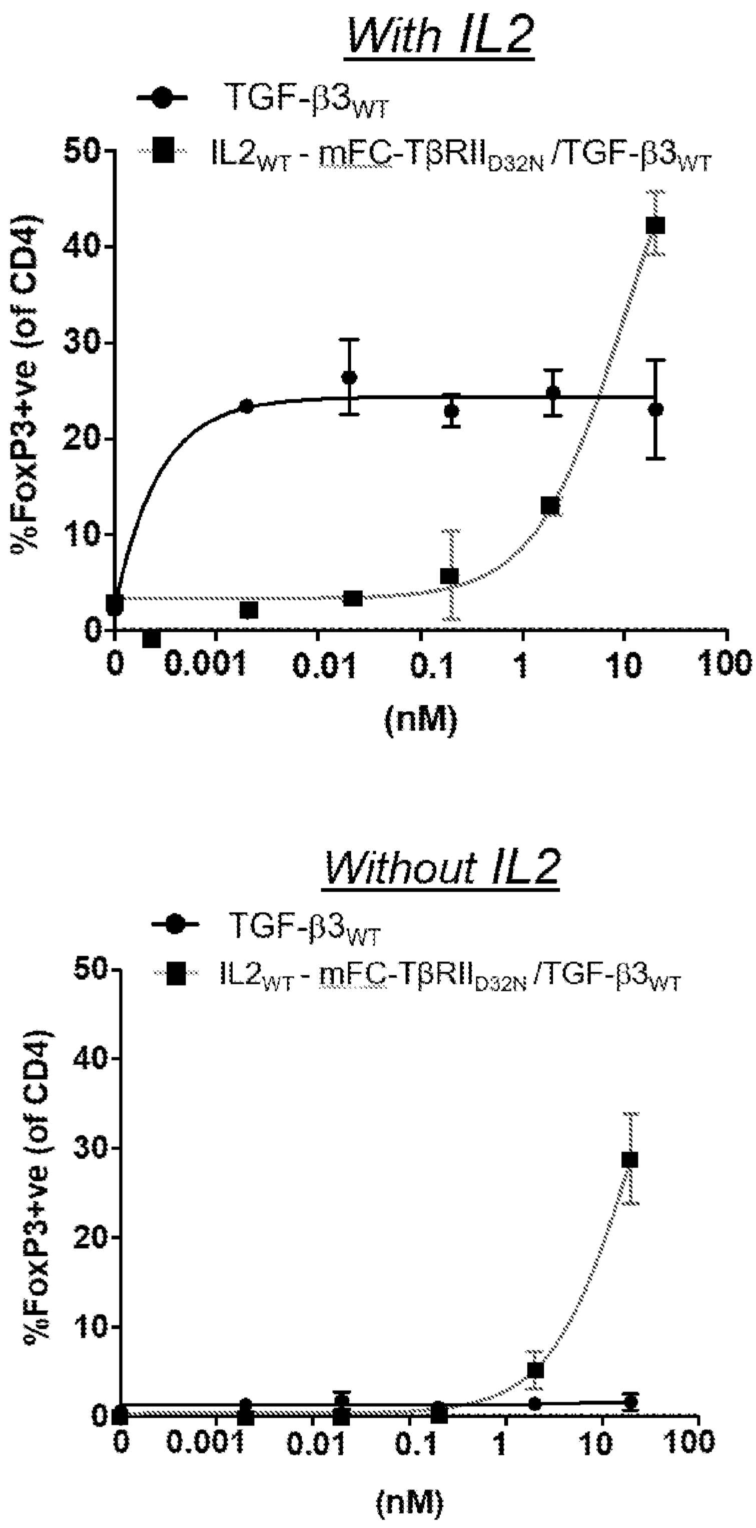

In FIG. 6A a comparison of a masked TGF-β construct having the overall structure shown in FIG. 1 at A comprising wt. IL-2-IgG Fc (mFc)-TβRII with a D32N substitution-TGF-β3 was tested for FoxP3 expression in comparison to the effect of wt. TGF-β3 in the presence or absence of-IL-2. The results shown in FIG. 6A indicate that wt. TGF-β3 does not effectively stimulate FoxP3 under the test conditions, but that wt. IL-2 supplementation can lead to FoxP3 expression.

Figure 6B:
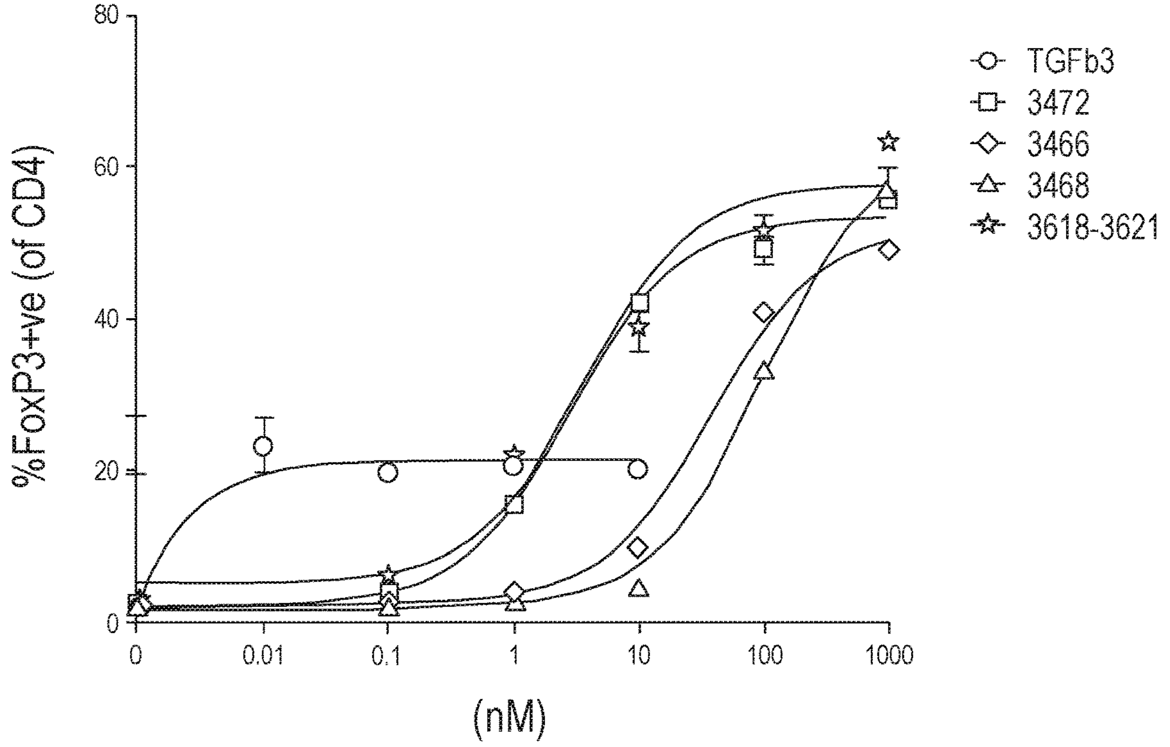

In FIG. 6B a comparison of a masked TGF-β construct (i), (ii) and (iii) from parts 1 and 2 of this example, and masked TGF-β complex comprising polypeptides (iv.a) and (iv.b) were tested for FoxP3 expression in comparison to the effect of wt. TGF-β3 in the presence of IL-2. The results shown in FIG. 6B indicate that masked TGF-β constructs and complexes with wt. IL-2 are more potent than those with the IL-2 substitution H16T and F42A. The substitutions at H16T and F42A shift the potency of the masked complexes by an order of magnitude from about 5 nanomolar to about 50 nanomolar without substantive change in the maximal efficacy based on the number of cells expressing FoxP3. As with the results shown in FIG. 6A, the and masked TGF-β constructs and complexes were more effective at inducing T cells to produce FoxP3 than IL-2 and TGF-β3.

Figure 6C:
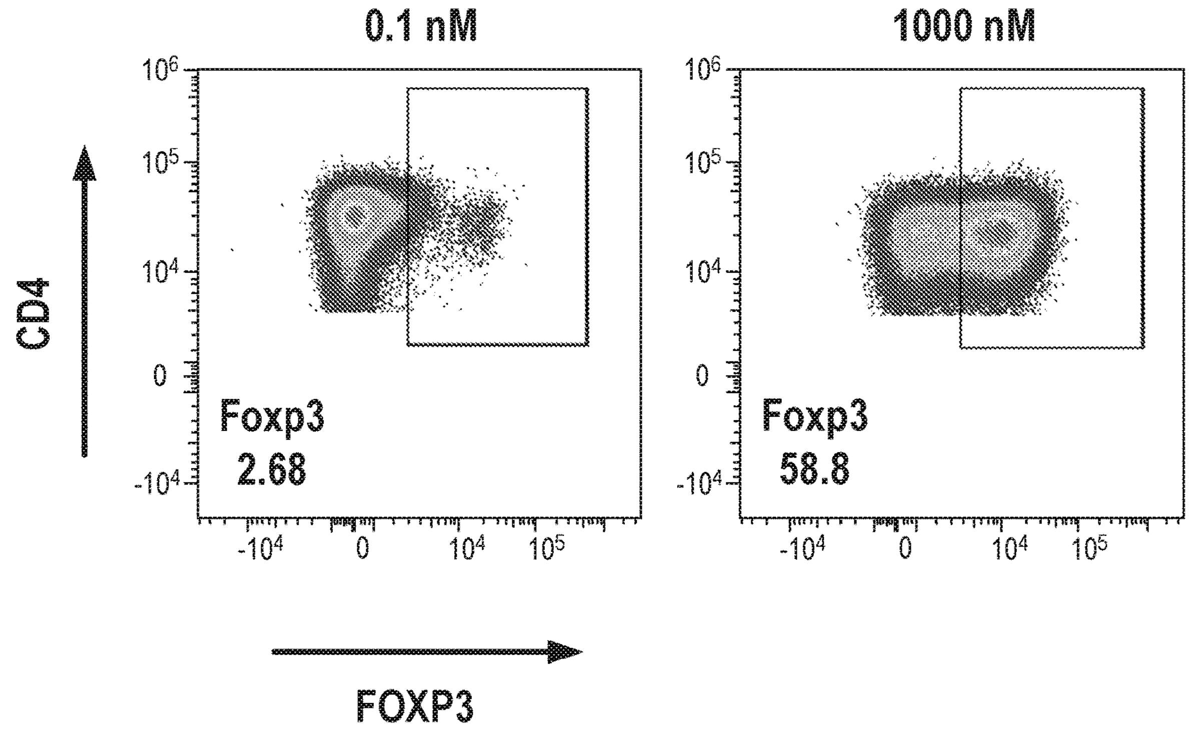

An example of the gating and separation of cells based on CD4+ and FoxP3 is shown in FIG. 6C. The results demonstrate an induction of FoxP3 in cells exposed to a masked TGF-β construct at 1,000 nM show an increase of approximately 30-fold in FoxP3 expression over cells exposed to 0.1 nM of the same construct.

B. Example 2

1 Scaffolds that are Non-Interspecific

This section describes masked TGF beta sequences that do not employ interspecific scaffolds, and accordingly are either monomeric, or if they dimerize, they not preferentially form heterodimers with a counterpart sequence a. Single Polypeptide Chain Masked TGF-β Constructs A nucleic acids encoding a polypeptide comprising, from N- to C-terminus, a MOD polypeptide sequence: a wt. IL-2 polypeptide sequence (SEQ ID NO:20), an IgG1 Fc scaffold polypeptide sequence wt. IgG1 aas 11-215 (Δ10) bearing a L234A and L235A ("LALA"), L351K, T366S, P395V, F405R, Y407A, and K409Y substitutions, a TGF-β RII isoform B polypeptide sequence from aa 26 to 136 aas of the mature protein with a D118A substitution (*D119A see the note in FIG. 5B), and a human TGF-β type 3 isoform 1 polypeptide sequence with a C77S substitution. A schematic structure of the expressed protein is shown in FIG. 1 as structure A (SEQ ID NO:146). The protein was purified by protein A and size chromatography.

b. Homodimeric Polypeptide Complex

A nucleic acids encoding a polypeptide comprising, from N- to C-terminus, a MOD polypeptide sequence (IL-2 SEQ ID NO:20 with H16T and F42A substitutions), an IgG1 Fc scaffold polypeptide sequence (e.g., wt. IgG1 bearing a L234A and L235A ("LALA") substitutions), a TGF-β RII isoform B polypeptide sequence from aa 26 to 136 aas of the mature protein with a D118A substitution (*D119A see the note in FIG. 5B), and a human TGF-β type 3 isoform 1 polypeptide sequence with a C77S substitution. A schematic structure of the expressed protein is shown in FIG. 1 as structure B. The corresponding aa acid sequence aligned with the elements labeled is shown in FIG. 7B (SEQ ID NO:147). The protein was purified by protein A and size chromatograph.

2 Heterodimeric Masked TGF-β Complexes with Interspecific Scaffolds Polypeptides a. Heterodimeric Masked TGF-β Complexes Having Interspecific Scaffolds Each Bearing IL-2 MOD Polypeptides The stable expression of a masked TGF-β complex comprised of two polypeptides was demonstrated masked TGF-β constructs by preparing a nucleic acid encoding a first polypeptide comprising a TGF-β polypeptide sequence, and a second nucleic acid encoding a TGF-β receptor polypeptide sequence, and expressing the polypeptides using mammalian expression vectors (e.g., plasmid expression systems in CHO cells).

The first polypeptide comprising, a wt. IL-2 polypeptide (SEQ ID NO:20), an IgG1 Fc scaffold polypeptide sequence (e.g., wt. IgG1 residues 1-225 bearing L234A and L235A ("LALA") substitutions), and a T366W KiH "knob" substitution, and a human TGF-β type 3 isoform 1 polypeptide sequence with a C77S substitution.

The second polypeptide comprising a wt. IL-2 polypeptide (SEQ ID NO:20), an IgG1 Fc scaffold polypeptide sequence (e.g., wt. IgG1 residues 1-225 bearing L234A and L235A ("LALA") substitutions), and T366S, L368A and Y407V KiH "hole" substitutions, and a TGF-β RII isoform B polypeptide sequence from aa 26 to 136 aas of the mature protein with a D118A substitution. A schematic structure of the expressed protein is shown in FIG. 1 as structure D. The corresponding aa acid sequences are aligned with the elements labeled is shown in FIG. 7C. Expression and purification (protein A followed by size exclusion chromatography) provides the heterodimer complex.

b. Heterodimeric Masked TGF-β Complexes Having Interspecific Scaffolds with a Single Chain Bearing an MOD Polypeptides The stable expression of a masked TGF-β complex comprised of two polypeptides was demonstrated masked TGF-β constructs by preparing a nucleic acid encoding a first polypeptide comprising a TGF-β polypeptide sequence, and a second nucleic acid encoding a TGF-β receptor polypeptide sequence, and expressing the polypeptides using mammalian expression vectors (e.g., plasmid expression systems in CHO cells).

The first polypeptide comprising, a wt. IL-2 polypeptide (SEQ ID NO:20), an IgG1 Fc scaffold polypeptide sequence (e.g., wt. IgG1 residues 1-225 bearing L234A and L235A ("LALA") substitutions, and a T366W (knob) substitution, and a human TGF-β type 3 isoform 1 polypeptide sequence with a C77S substitution.

The second polypeptide comprising an IgG1 Fc scaffold polypeptide sequence (e.g., wt. IgG1 residues 1-225 bearing L234A and L235A ("LALA") substitutions), and T366S, L368A and Y407V "hole" substitutions, and a TGF-β RII isoform B polypeptide sequence from aa 26 to 136 aas of the mature protein with a D118A substitution.

A schematic structure of the expressed protein is shown in FIG. 1 as structure E. The corresponding aa sequence aligned with the elements labeled is shown in FIG. 7D. Expression and purification (protein A followed by size exclusion chromatography) provides the heterodimer complex.

c. Heterodimeric Masked TGF-β Complexes Having Interspecific Scaffold Polypeptide Stabilization, with a Single Chain Bearing MOD Polypeptides The stable expression of a masked TGF-β complex comprised of two polypeptides was demonstrated masked TGF-β constructs by preparing a nucleic acid encoding a first polypeptide comprising a TGF-β polypeptide sequence, and a second nucleic acid encoding a TGF-β receptor polypeptide sequence, and expressing the polypeptides using mammalian expression vectors (e.g., plasmid expression systems in CHO cells).

The first polypeptide comprising an IL-2 polypeptide sequence (SEQ ID NO 20 with H16T and F42A substitutions), an IgG1 Fc scaffold polypeptide sequence (e.g., wt. IgG1 residues 1-225 bearing L234A and L235A ("LALA") substitutions), and a T366W (knob) substitution, a TGF-β RII isoform B polypeptide sequence from aa 26 to 136 aas of the mature protein with a D118A substitution, and a human TGF-β type 3 isoform 1 polypeptide sequence with a C77S substitution.

The second polypeptide comprising an IgG1 Fc scaffold polypeptide sequence (e.g., wt. IgG1 residues 1-225 bearing L234A and L235A ("LALA") substitutions), and T366S, L368A and Y407V "hole" substitutions.

A schematic structure of the expressed protein is shown a variation of the structure in FIG. 1 as structure F, but lacking any immunomodulatory polypeptide sequences on the second polypeptide. The corresponding aa acid sequence aligned with the elements labeled is shown in FIG. 7E. Expression and purification (protein A followed by size exclusion chromatography) provides the heterodimer complex.

C. Example 3 Expression and Purification

Figure 8:
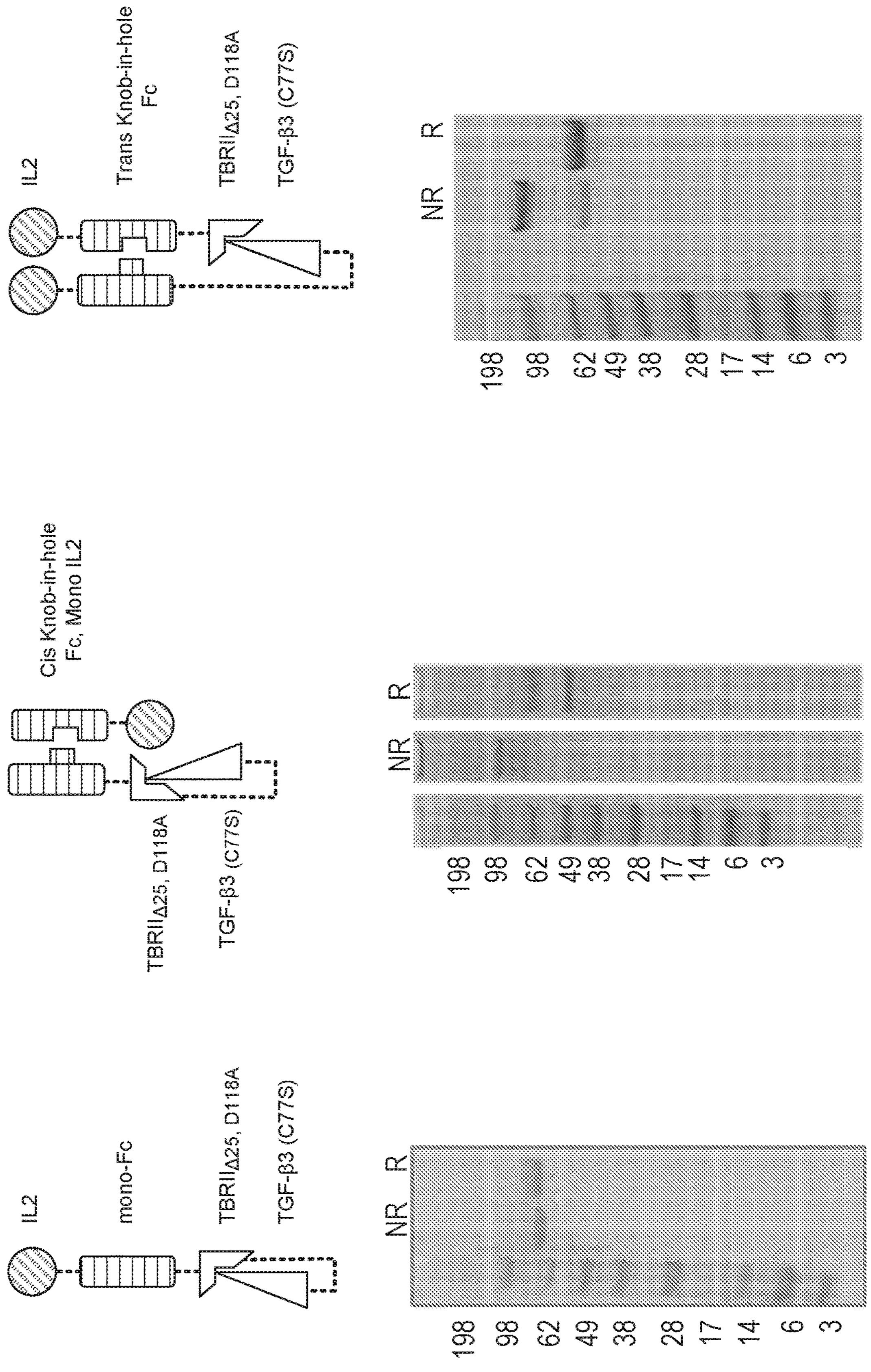

Nucleic acids encoding a masked TGF-β construct nucleic acids encoding two masked TGF-β complexes were prepared (see FIG. 8). Samples of the complexes were prepared by transfecting ExpiCHO cells with the nucleic acid constructs and permitting the cells to expressing the polypeptides. The polypeptides were purified by protein A chromatography followed by size exclusion chromatography. The purified proteins were subjected to SDS-PAGE and the resulting gels were stained with Coomassie blue. NR=not reducing or unreduced samples, and R=reduced samples (reduction with a disulfide reducing agent).

D. Example 4 Biological Activity and Affinity Between the Masking Polypeptide and TGF-β

A series of masked TGF-β constructs were prepared to demonstrate the biological availability of TGF-β, and that its ability to interact with TβRII is inversely proportional to the affinity of the masking polypeptide for the TGF-β polypeptide sequence. The constructs were of the form structure A in FIG. 1, and, from N-terminus to C-terminus, the MOD is an IL-2 polypeptide; the scaffold is an IgG polypeptide; the masking receptor is a TβRII polypeptide of SEQ ID NO:119 with N-terminal aas 1-25 (Δ25) deleted and a D118A substitution (and that comprise the additional substitution E55A, D32N, or S52L as indicated), and a TGF-β3 polypeptide sequence.

Interaction of the masked TGF-β constructs with TβRII was assessed using a capture assay in which a TβRII-Ig Fc fusion was captured in the wells of a microtiter plate and various concentrations of the four constructs were applied to the wells. After rinsing off unbound constructs, the bound construct was detected and measured using biotin labeled anti IL-2 followed by streptavidin-horse radish peroxidase and colorimetric detection (3,3',5,5'-tetramethylbenzidine) at 450 nm. The results, which are shown in FIG. 9, indicate that the Δ25-D118A construct had a dissociation constant of 2.69 μM for the TβRII (TβRII-Ig fusion). Addition of an E55A, D32N or S52L, with have increasingly larger impacts of the dissociation constant for TGF-133-TβRII complexes, provides complexes with increasing affinity for exogenous TβRII (the TβRII-Ig fusion in this case).

Figure 10A:
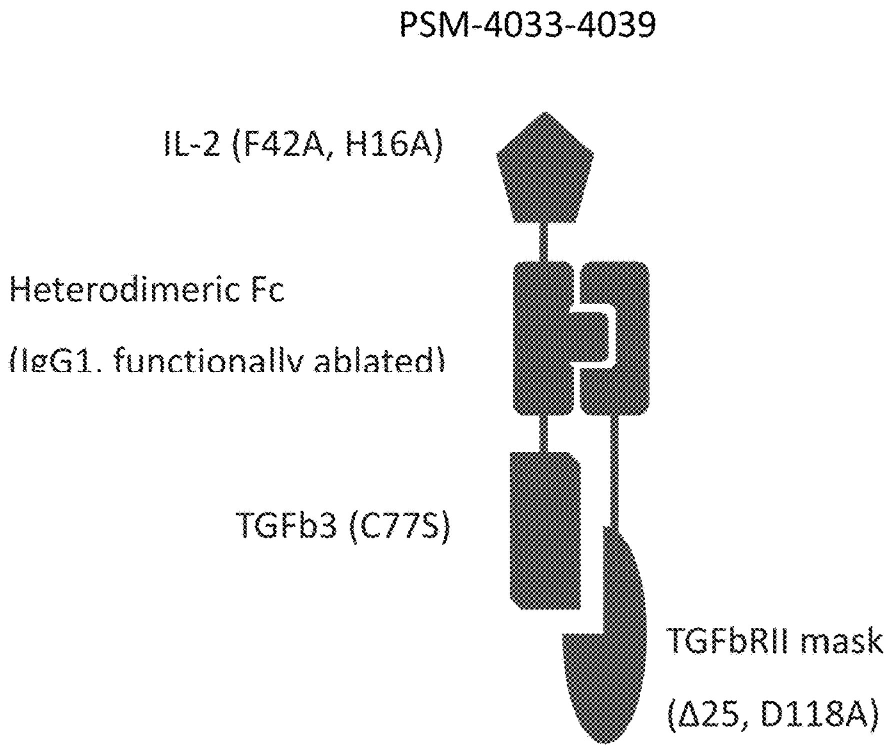

E. Example 5 Biological Activity of Heterodimeric Masked TGF-β Complex (PSM-4033-4039) Having Interspecific Scaffold Polypeptide Stabilization, with a Single Chain Bearing a Variant IL-2 MOD Polypeptide A masked TGF-β complex, PSM-4033-4039, as shown in FIG. 10A was prepared. The complex comprises first and second polypeptides 4033 and 4039 shown in FIGS. 10B and 10C, respectively. A series of experiments then was performed with PSM-4033-4039.

Experiment 1: Induction of Foxp3$^+$ iTregs from Human Peripheral Naïve CD4$^+$ T Cells Naïve CD4$^+$ T cells were sorted from human blood and plated with anti-human CD3 (5 ug/mL), anti-human CD28 (1 ug/mL), and an increasing dose of PSM-4033-4039 or a single dose of recombinant TGFb3 and IL-2 as a positive control. After 5 days in culture, cells were assessed by flow cytometry for expression of the transcription factor Foxp3. n=2, stdev. The results, provided in FIG. 11 show a significant induction of FoxP3 in cells exposed to PSM-4033-4039 at concentrations up to 1,000 nM. These results are similar to those shown in FIG. 6B with other masked TGF-β constructs and complexes, further demonstrating that masked TGF-β3 constructs and complexes disclosed herein can effect a significant induction of FoxP3, which is a master regulator of gene expression in Tregs, including both natural and induced Tregs, and central to Treg identity and function.

Figure 12:
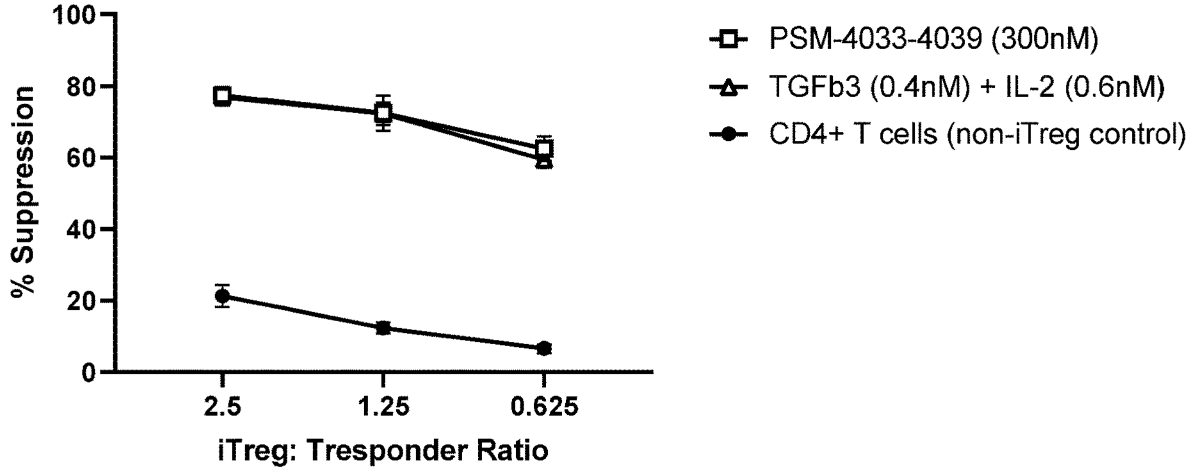
FIG. 12 shows the results of an experiment in which Foxp3$^+$ iTregs induced by PSM-4033-4039 are used to suppress T cell proliferation. See Example 4.

Experiment 2: Suppression of T Cell Proliferation by PSM-4033-4039 Induced Foxp3$^+$ iTregs PSM-4033-4039 induced Foxp3$^+$ T regulatory cells (iTreg) were cultured at different ratios to conventional T cells (T responder) and stimulated with anti-human CD3 (1 ug/mL) and mitomycin C treated peripheral blood mononuclear cells (PBMCs). Proliferation was assessed by flow cytometry after four days by the dilution of cell trace violet (CTV) dye in T responder cells. The data, shown in FIG. 12, represents an average of three donors, each plated in duplicate. TGF-β3 and IL-2 induced T regulatory cells or total peripheral CD4+ T cells were used in place of iTregs, as controls. Suppression is defined as % less CTV dilution compared to no added iTreg controls (avg. 78% CTV diluted). The results of this experiment demonstrate that Foxp3+T regulatory cells induced by the masked TGF-β3 constructs and complexes disclosed herein, e.g., PSM-4033-4039, can suppress the proliferation of T cells activated by CD3 cross-linking and co-stimulation, provided by antigen presenting cells in PBMCs.

A defining characteristic of Tregs beyond their expression of the transcription factor, Foxp3, is their ability to suppress the activation and function of other leukocytes. This experiment demonstrates that iTregs induced by masked TGF-β3 constructs and complexes disclosed herein can indeed suppress the proliferation of T cells activated by CD3 cross-linking and co-stimulation, provided by antigen presenting cells in PBMCs.

Experiment 3: Induction of Foxp3$^+$ Expression from Human Peripheral CD4$^+$ T Cells by PSM-4033-4039

Figure 13A:
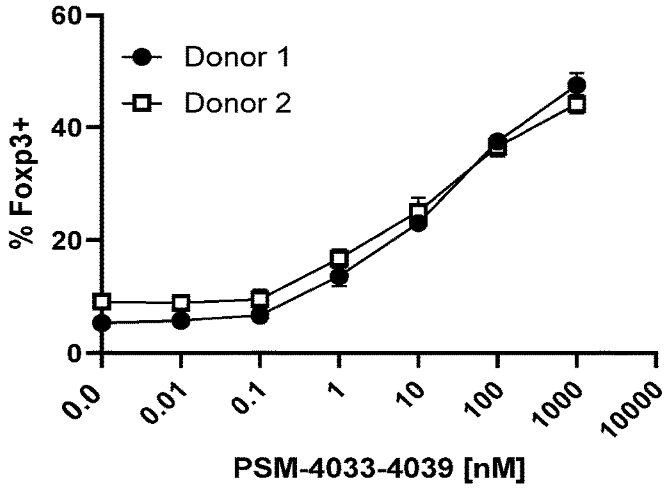
FIGS. 13A and 13B show the results of an experiment in which PSM-4033-4039 is used to induce expression of Foxp3$^+$ iTregs from human peripheral CD4$^+$ T cells, including naïve and memory CD4$^+$ T cells. See Example 4.

Total CD4+ T cells were sorted from human blood and plated with anti-human CD3 (5 ug/mL), anti-human CD28 (1 ug/mL), and an increasing dose of PSM-4033-4039. After 5 days in culture, cells were assessed by flow cytometry for expression of the transcription factor Foxp3. n=2. The data is illustrated in FIG. 13A.

To determine which cell type in a mixture of CD4+ T cell types could differentiate into Foxp3 expressing cells, different populations were sorted and treated with PSM-4033-4039 individually. Accordingly, naïve, total, and memory CD4+ T cells for a different donor than the donors of FIG.

Figure 13B:
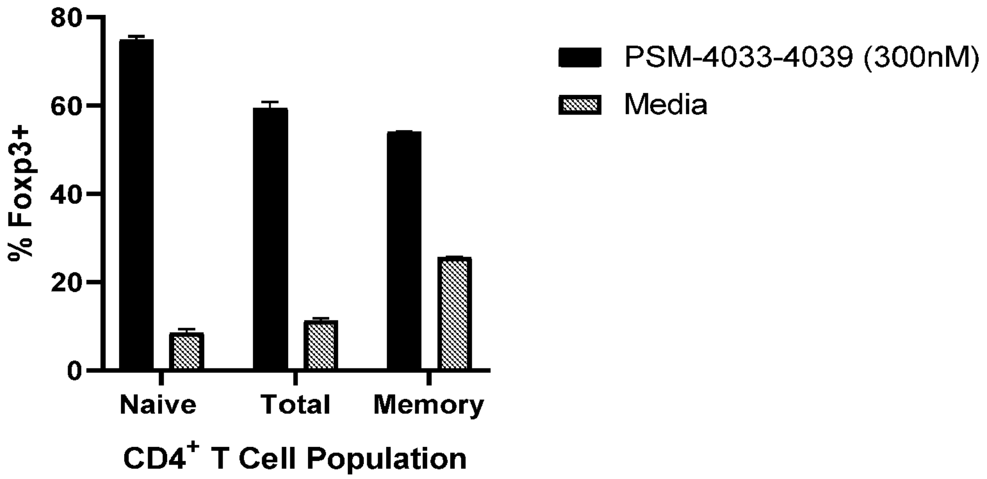

13A were sorted and cultured in the same way as above, with or without PSM-4033-4039 (300 nM), and Foxp3 was assessed by flow cytometry at day 5. The data is illustrated in FIG. 13B.

Total CD4+ T cells, which were differentiated into Foxp3 expressing cells in this experiment, represent both naïve and memory peripheral T cells, a mixture of cell types that masked TGF-β3 constructs and complexes disclosed herein, e.g., PSM-4033-4039, would encounter when administered in vivo. This data shows that even in a mixed T cell population, masked TGF-β3 constructs and complexes disclosed herein, e.g., PSM-4033-4039, can increase the frequency of cells that express Foxp3, a master regulator of a gene expression defining T regulatory cells. The results shown in FIG. 13B show that PSM-4033-4039 can induce memory CD4+ T cells to differentiate into Foxp3+ cells, even if at a lower frequency than naïve CD4+ T cells.

Figure 14A:
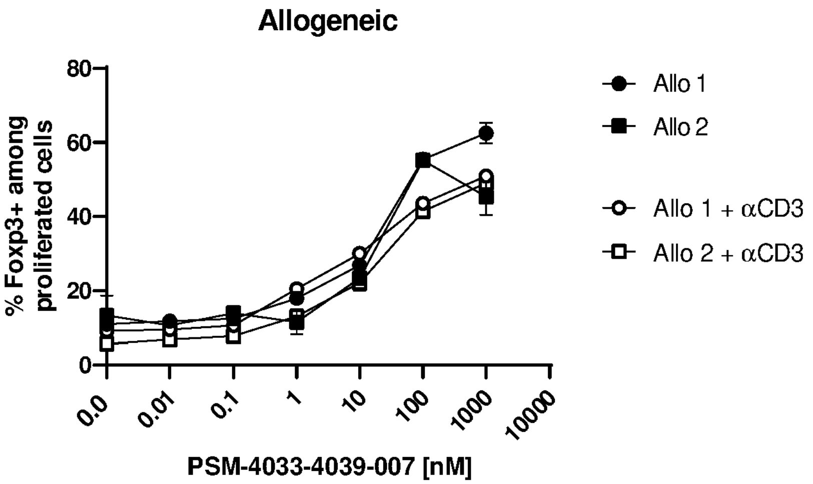
FIGS. 14A and 14B shows the results of an experiment in which PSM-4033-4039 is used to induce Foxp3$^+$ iTregs from CD4$^+$ T cells activated by an allogeneic lymphocyte reaction. See Example 4.
Figure 14B:
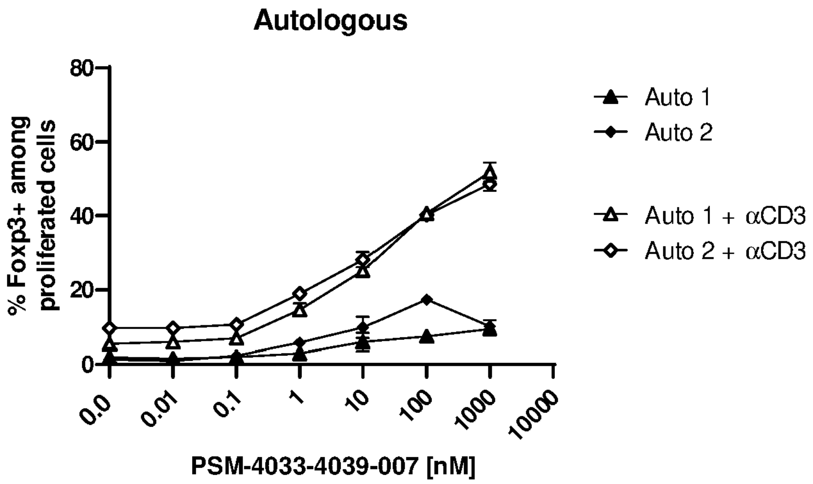

Experiment 4: Induction of Foxp3+ iTregs by PSM-4033-4039 from CD4+ T Cells Activated by an Allogeneic Lymphocyte Reaction Total peripheral CD4+ T cells were sorted from human blood and plated with allogeneic monocyte-derived DCs (moDCs) to induce T cell proliferation. T cells were mixed with autologous moDCs as a control, and both allogeneic or autologous donor combinations were treated with soluble anti-CD3 (1 ug/mL) as an additional control. T cells were labeled with cell trace violet (CTV) dye to track cells which responded to allogeneic activation. Proliferation and expression of Foxp3 were analyzed by flow cytometry on day 5, and the frequency of proliferated cells that express Foxp3 are plotted in FIGS. 14A and 14B. Two donor combinations are shown. n=2, stdev. Among other things, the results demonstrate to potential use of the masked TGF-β3 constructs and complexes disclosed herein, e.g., PSM-4033-4039, for the treatment of graft vs. host disease occurring in bone marrow or stem cell transplantation patients.

Experiment 5: PK Experiment in Mice Using PSM-4033-4039

Figure 15:
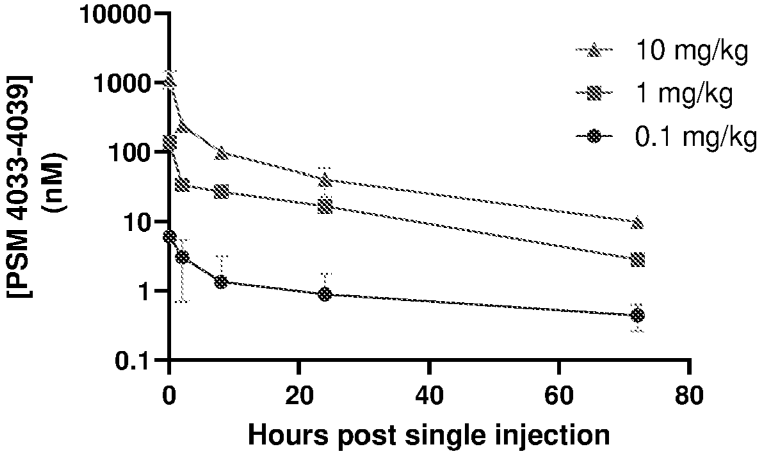
FIG. 15 shows the results of an experiment in which PSM-4033-4039 was administered intravenously to mice in various concentrations to determine serum concentrations in the mice at various intervals up to 72 hours post injection. See Example 4.

PSM-4033-4039 was administered intravenously as single doses to Balb/c mice at 0.1, 1, or 10 mg/kg. Peripheral serum samples were then collected 5 minutes, 2, 8, 24, and 72 hours post-dose. Serum concentrations of PSM-4033-4039 were then determined using a ligand binding assay that captured the molecule using an anti-IL2 antibody, and detected the molecule using an anti-TGFβ3 antibody. The results provided in FIG. 15 show that the masked TGF-β3 constructs and complexes disclosed herein, e.g., PSM-4033-4039, can remain present in the serum at biologically relevant concentrations for more than 72 hours after administration. The sequence of construct 4033 is provided in FIG. 10B (SEQ ID NO:191), and the sequence of construct 4039 is provided in FIG. 10C (SEQ ID NO:192).

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the claims appended hereto.

SEQUENCE LISTING

```
Sequence total quantity: 211
SEQ ID NO: 1            moltype = AA  length = 245
FEATURE                 Location/Qualifiers
REGION                  1..245
                        note = Description of sequence: wild-type human PD-L1
                         polypeptide
source                  1..245
                        mol_type = protein
                        organism = Homo sapiens
SEQUENCE: 1
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPGNI LNVSIKICLT  240
LSPST                                                             245

SEQ ID NO: 2            moltype = AA  length = 219
FEATURE                 Location/Qualifiers
REGION                  1..219
                        note = Description of sequence: wild-type human PD-L1
                         ectodomain  polypeptide
source                  1..219
                        mol_type = protein
                        organism = Homo sapiens
SEQUENCE: 2
FTVTVPKDLY VVEYGSNMTI ECKFPVEKQL DLAALIVYWE MEDKNIIQFV HGEEDLKVQH  60
SSYRQRARLL KDQLSLGNAA LQITDVKLQD AGVYRCMISY GGADYKRITV KVNAPYNKIN  120
QRILVVDPVT SEHELTCQAE GYPKAEVIWT SSDHQVLSGK TTTTNSKREE KLFNVTSTLR  180
INTTTNEIFY CTFRRLDPEE NHTAELVIPG NILNVSIKI                        219

SEQ ID NO: 3            moltype = AA  length = 268
FEATURE                 Location/Qualifiers
REGION                  1..268
                        note = Description of sequence: wild-type PD-1 polypeptide
source                  1..268
```

```
                        mol_type = protein
                        organism = Homo sapiens
SEQUENCE: 3
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV VGVVGGLLGS LVLLVWVLAV ICSRAARGTI  180
GARRTGQPLK EDPSAVPVFS VDYGELDFQW REKTPEPPVP CVPEQTEYAT IVFPSGMGTS  240
SPARRGSADG PRSAQPLRPE DGHCSWPL                                    268

SEQ ID NO: 4            moltype = AA  length = 271
FEATURE                 Location/Qualifiers
REGION                  1..271
                        note = Description of sequence: wild-type human IL-1-alpha
                         precursor polypeptide
source                  1..271
                        mol_type = protein
                        organism = Homo sapiens
SEQUENCE: 4
MAKVPDMFED LKNCYSENEE DSSSIDHLSL NQKSFYHVSY GPLHEGCMDQ SVSLSISETS  60
KTSKLTFKES MVVVATNGKV LKKRRLSLSQ SITDDDLEAI ANDSEEEIIK PRSAPFSFLS  120
NVKYNFMRII KYEFILNDAL NQSIIRANDQ YLTAAALHNL DEAVKFDMGA YKSSKDDAKI  180
TVILRISKTQ LYVTAQDEDQ PVLLKEMPEI PKTITGSETN LLFFWETHGT KNYFTSVAHP  240
NLFIATKQDY WVCLAGGPPS ITDFQILENQ A                                 271

SEQ ID NO: 5            moltype = AA  length = 161
FEATURE                 Location/Qualifiers
REGION                  1..161
                        note = Description of sequence: mature wild-type human
                         IL-1-alpha polypeptide
source                  1..161
                        mol_type = protein
                        organism = Homo sapiens
SEQUENCE: 5
PRSAPFSFLS NVKYNFMRII KYEFILNDAL NQSIIRANDQ YLTAAALHNL DEAVKFDMGA  60
YKSSKDDAKI TVILRISKTQ LYVTAQDEDQ PVLLKEMPEI PKTITGSETN LLFFWETHGT  120
KNYFTSVAHP NLFIATKQDY WVCLAGGPPS ITDFQILENQ A                      161

SEQ ID NO: 6            moltype = AA  length = 269
FEATURE                 Location/Qualifiers
REGION                  1..269
                        note = Description of sequence: wild-type human IL-1Beta-
                         precursor polypeptide
source                  1..269
                        mol_type = protein
                        organism = Homo sapiens
SEQUENCE: 6
MAEVPELASE MMAYYSGNED DLFFEADGPK QMKCSFQDLD LCPLDGGIQL RISDHHYSKG  60
FRQAASVVVA MDKLRKMLVP CPQTFQENDL STFFPFIFEE EPIFFDTWDN EAYVHDAPVR  120
SLNCTLRDSQ QKSLVMSGPY ELKALHLQGQ DMEQQVVFSM SFVQGEESND KIPVALGLKE  180
KNLYLSCVLK DDKPTLQLES VDPKNYPKKK MEKRFVFNKI EINNKLEFES AQFPNWYIST  240
SQAENMPVFL GGTKGGQDIT DFTMQFVSS                                    269

SEQ ID NO: 7            moltype = AA  length = 153
FEATURE                 Location/Qualifiers
REGION                  1..153
                        note = Description of sequence: mature wild-type human
                         IL-1Beta- polypeptide
source                  1..153
                        mol_type = protein
                        organism = Homo sapiens
SEQUENCE: 7
APVRSLNCTL RDSQQKSLVM SGPYELKALH LQGQDMEQQV VFSMSFVQGE ESNDKIPVAL  60
GLKEKNLYLS CVLKDDKPTL QLESVDPKNY PKKKMEKRFV FNKIEINNKL EFESAQFPNW  120
YISTSQAENM PVFLGGTKGG QDITDFTMQF VSS                               153

SEQ ID NO: 8            moltype = AA  length = 569
FEATURE                 Location/Qualifiers
REGION                  1..569
                        note = Description of sequence: IL-1 receptor
source                  1..569
                        mol_type = protein
                        organism = Homo sapiens
SEQUENCE: 8
MKVLLRLICF IALLISSLEA DKCKEREEKI ILVSSANEID VRPCPLNPNE HKGTITWYKD  60
DSKTPVSTEQ ASRIHQHKEK LWFVPAKVED SGHYYCVVRN SSYCLRIKIS AKFVENEPNL  120
CYNAQAIFKQ KLPVAGDGGL VCPYMEFFKN ENNELPKLQW YKDCKPLLLD NIHFSGVKDR  180
LIVMNVAEKH RGNYTCHASY TYLGKQYPIT RVIEFITLEE NKPTRPVIVS PANETMEVDL  240
GSQIQLICNV TGQLSDIAYW KWNGSVIDED DPVLGEDYYS VENPANKRRS TLITVLNISE  300
IESRFYKHPF TCFAKNTHGI DAAYIQLIYP VTNFQKHMIG ICVTLTVIIV CSVFIYKIFK  360
```

-continued

```
IDIVLWYRDS CYDFLPIKAS DGKTYDAYIL YPKTVGEGST SDCDIFVFKV LPEVLEKQCG  420
YKLFIYGRDD YVGEDIVEVI NENVKKSRRL IIILVRETSG FSWLGGSSEE QIAMYNALVQ  480
DGIKVVLLEL EKIQDYEKMP ESIKFIKQKH GAIRWSGDFT QGPQSAKTRF WKNVRYHMPV  540
QRRSPSSKHQ LLSPATKEKL QREAHVPLG                                    569

SEQ ID NO: 9           moltype = AA  length = 133
FEATURE                Location/Qualifiers
REGION                 1..133
                       note = Description of sequence: A wild-type IL-2 amino acid
                        sequence
source                 1..133
                       mol_type = protein
                       organism = Homo sapiens
SEQUENCE: 9
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 10          moltype = AA  length = 251
FEATURE                Location/Qualifiers
REGION                 1..251
                       note = Description of sequence:  Human IL-2R-alpha
source                 1..251
                       mol_type = protein
                       organism = Homo sapiens
SEQUENCE: 10
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SCLVTTTDFQ IQTEMAATME TSIFTTEYQV AVAGCVFLLI SVLLLSGLTW  240
QRRQRKSRRT I                                                       251

SEQ ID NO: 11          moltype = AA  length = 524
FEATURE                Location/Qualifiers
REGION                 1..524
                       note = Description of sequence: Human IL-2RBeta-
source                 1..524
                       mol_type = protein
                       organism = Homo sapiens
SEQUENCE: 11
VNGTSQFTCF YNSRANISCV WSQDGALQDT SCQVHAWPDR RRWNQTCELL PVSQASWACN  60
LILGAPDSQK LTTVDIVTLR VLCREGVRWR VMAIQDFKPF ENLRLMAPIS LQVVHVETHR  120
CNISWEISQA SHYFERHLEF EARTLSPGHT WEEAPLLTLK QKQEWICLET LTPDTQYEFQ  180
VRVKPLQGEF TTWSPWSQPL AFRTKPAALG KDTIPWLGHL LVGLSGAFGF IILVYLLINC  240
RNTGPWLKKV LKCNTPDPSK FFSQLSSEHG GDVQKWLSSP FPSSSFSPGG LAPEISPLEV  300
LERDKVTQLL LQQDKVPEPA SLSSNHSLTS CFTNQGYFFF HLPDALEIEA CQVYFTYDPY  360
SEEDPDEGVA GAPTGSSPQP LQPLSGEDDA YCTFPSRDDL LLFSPSLLGG PSPPSTAPGG  420
SGAGEERMPP SLQERVPRDW DPQPLGPPTP GVPDLVDFQP PPELVLREAG EEVPDAGPRE  480
GVSFPWSRPP GQGEFRALNA RLPLNTDAYL SLQELQGQDP THLV                   524

SEQ ID NO: 12          moltype = AA  length = 347
FEATURE                Location/Qualifiers
REGION                 1..347
                       note = Description of sequence: Human IL-2R-gamma
source                 1..347
                       mol_type = protein
                       organism = Homo sapiens
SEQUENCE: 12
LNTTILTPNG NEDTTADFFL TTMPTDSLSV STLPLPEVQC FVFNVEYMNC TWNSSSEPQP  60
TNLTLHYWYK NSDNDKVQKC SHYLFSEEIT SGCQLQKKEI HLYQTFVVQL QDPREPRRQA  120
TQMLKLQNLV IPWAPENLTL HKLSESQLEL NWNNRFLNHC LEHLVQYRTD WDHSWTEQSV  180
DYRHKFSLPS VDGQKRYTFR VRSRFNPLCG SAQHWSEWSH PIHWGSNTSK ENPFLFALEA  240
VVISVGSMGL IISLLCVYFW LERTMPRIPT LKNLEDLVTE YHGNFSAWSG VSKGLAESLQ  300
PDYSERLCLV SEIPPKGGAL GEGPGASPCN QHSPYWAPPC YTLKPET                347

SEQ ID NO: 13          moltype = AA  length = 133
FEATURE                Location/Qualifiers
REGION                 1..133
                       note = Description of sequence: a variant IL-2 polypeptide
source                 1..133
                       mol_type = protein
                       organism = Homo sapiens
VARIANT                15
                       note = X is any amino acid other than Glu. In some cases X
                        is Ala
SEQUENCE: 13
APTSSSTKKT QLQLXHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133
```

```
SEQ ID NO: 14          moltype = AA  length = 133
FEATURE                Location/Qualifiers
REGION                 1..133
                       note = Description of sequence: a variant IL-2 polypeptide
source                 1..133
                       mol_type = protein
                       organism = Homo sapiens
VARIANT                20
                       note = X is any amino acid other than Asp. In some cases X
                        is Ala
SEQUENCE: 14
APTSSSTKKT QLQLEHLLLX LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 15          moltype = AA  length = 133
FEATURE                Location/Qualifiers
REGION                 1..133
                       note = Description of sequence: a variant IL-2 polypeptide
source                 1..133
                       mol_type = protein
                       organism = Homo sapiens
VARIANT                16
                       note = X is any amino acid other than His. In some cases X
                        is Ala (H16A)  Arg Asn Asp Cys Glu Gln Gly Ile  Lys Leu
                        Met Phe Pro Ser Thr (H16T) Tyr Trp or Val.
SEQUENCE: 15
APTSSSTKKT QLQLEXLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 16          moltype = AA  length = 133
FEATURE                Location/Qualifiers
REGION                 1..133
                       note = Description of sequence: a variant IL-2 polypeptide
source                 1..133
                       mol_type = protein
                       organism = Homo sapiens
VARIANT                42
                       note = X is any amino acid other than Phe. In some cases X
                        is Ala (F42A). In some cases X is Thr (F42T)
SEQUENCE: 16
APTSSSTKKT QLQLEHLLLD LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 17          moltype = AA  length = 133
FEATURE                Location/Qualifiers
REGION                 1..133
                       note = Description of sequence: a variant IL-2 polypeptide
source                 1..133
                       mol_type = protein
                       organism = Homo sapiens
VARIANT                45
                       note = X is any amino acid other than Tyr. In some cases X
                        is Ala
SEQUENCE: 17
APTSSSTKKT QLQLEHLLLD LQMILNGINN YKNPKLTRML TFKFXMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 18          moltype = AA  length = 133
FEATURE                Location/Qualifiers
REGION                 1..133
                       note = Description of sequence: a variant IL-2 polypeptide
source                 1..133
                       mol_type = protein
                       organism = Homo sapiens
VARIANT                88
                       note = X is any amino acid other than Asn. In some cases X
                        is Ala; in some cases X is Arg
SEQUENCE: 18
APTSSSTKKT QLQLEHLLLD LQMILNGINN YKNPKLTRML TFKFYMPKKA TELKHLQCLE  60
EELKPLEEVL NLAQSKNFHL RPRDLISXIN VIVLELKGSE TTFMCEYADE TATIVEFLNR  120
WITFCQSIIS TLT                                                     133

SEQ ID NO: 19          moltype = AA  length = 133
FEATURE                Location/Qualifiers
```

```
REGION                  1..133
                        note = Description of sequence: a variant IL-2 polypeptide
source                  1..133
                        mol_type = protein
                        organism = Homo sapiens
VARIANT                 126
                        note = where X is any amino acid other than Gln. In some
                         cases X is Ala
SEQUENCE: 19
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCXSIIS TLT                                                     133

SEQ ID NO: 20           moltype = AA  length = 133
FEATURE                 Location/Qualifiers
REGION                  1..133
                        note = Description of sequence: a variant IL-2 polypeptide
source                  1..133
                        mol_type = protein
                        organism = Homo sapiens
VARIANT                 16
                        note = X at position 16 is any amino acid other than His
VARIANT                 42
                        note = X at position 42 is any amino acid other than Phe
REGION                  16..42
                        note = X at position 16 is any amino acid other than His  an
                         d X at position 42 is any amino acid other than Phe. In
                         some cases positon 16 is Ala. In some cases position 42 is
                         Ala. In some cases position 16 is Ala and position 42 is
                         Ala (H16A F42A). In some cases position 16 is Thr; and
                         position 42 is Ala (H16T F42A). In some casesposition 16
                         is Ala; and position 42 is Thr (H16A F42T). In some cases
                         position 16 is Thr; and position 42 is Thr (H16T F42T).
SEQUENCE: 20
APTSSSTKKT QLQLEXLLLD LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 21           moltype = AA  length = 133
FEATURE                 Location/Qualifiers
REGION                  1..133
                        note = Description of sequence: a variant IL-2 polypeptide
source                  1..133
                        mol_type = protein
                        organism = Homo sapiens
VARIANT                 16
                        note = X at position 16  is any amino acid other than His
VARIANT                 42
                        note = X at position 42 is any amino acid other than Phe
REGION                  16..42
                        note = Sequence 21 comprises an N88R substitution and where
                         position 16  is any amino acid other than His and  position
                          42 is any amino acid other than Phe. In some cases  positi
                         on 16 is Ala. In some cases  position 42 is Ala. In some
                         cases  position 16 is Ala and  position 42 is Ala. In some
                         cases  position 16 is Thr and  position 42 is Ala. In some
                         cases  position 16 is Ala and  position 42 is Thr. In some
                         cases  position 16 is Thr; and  position 42 is Thr.
SEQUENCE: 21
APTSSSTKKT QLQLEXLLLD LQMILNGINN YKNPKLTRML TXKFYMPKKA TELKHLQCLE  60
EELKPLEEVL NLAQSKNFHL RPRDLISRIN VIVLELKGSE TTFMCEYADE TATIVEFLNR  120
WITFCQSIIS TLT                                                     133

SEQ ID NO: 22           moltype = AA  length = 133
FEATURE                 Location/Qualifiers
REGION                  1..133
                        note = Description of sequence: a variant IL-2 polypeptide
source                  1..133
                        mol_type = protein
                        organism = Homo sapiens
VARIANT                 20
                        note = X at position 20 is any amino acid other than Asp
VARIANT                 42
                        note = X at position 42 is any amino acid other than Phe
REGION                  20..42
                        note = X at position 20 is any amino acid other than Asp;
                         and where X at position 42 is any amino acid other than
                         Phe. In some cases position 20 is Ala. In some cases
                         position 42 is Ala. In some cases position 20 is Ala; and
```

```
                        position 42 is Ala
SEQUENCE: 22
APTSSSTKKT QLQLEHLLLX LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 23           moltype = AA  length = 133
FEATURE                 Location/Qualifiers
REGION                  1..133
                        note = Description of sequence: a variant IL-2 polypeptide
source                  1..133
                        mol_type = protein
                        organism = Homo sapiens
VARIANT                 15
                        note = X at position 15 is any amino acid other than  Glu
VARIANT                 20
                        note = X at position 20 is any amino acid other than Asp
REGION                  15..42
                        note = X at position 15 is any amino acid other than  Glu;
                         where X at position 20 is any amino acid other than Asp;
                         and where X position 42 is any amino acid other than Phe.
                         In some cases X at position 15 is Ala. In some cases X at
                         position 20 is Ala. In some cases X at position 20 is Ala.
                         In some cases any two or all three of positions 15 20
                         and42 are Ala.
SEQUENCE: 23
APTSSSTKKT QLQLXHLLLX LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 24           moltype = AA  length = 133
FEATURE                 Location/Qualifiers
REGION                  1..133
                        note = Description of sequence: a variant IL-2 polypeptide
source                  1..133
                        mol_type = protein
                        organism = Homo sapiens
VARIANT                 16
                        note = X at position 16 is any amino acid other than His
VARIANT                 20
                        note = X at position 20 is any amino acid other than Asp
VARIANT                 42
                        note = X at position 42 is any amino acid other than Phe
REGION                  16..42
                        note = X at position 16 is any amino acid other than His;
                         where X at position 20 is any amino acid other than Asp;
                         and X at position 42 is any amino acid other than Phe. In
                         some cases position 16 is Ala. In some cases position 20
                         is Ala. In some cases position 42 is Ala. In some cases
                         positions 16 20 and 42 are Ala.
SEQUENCE: 24
APTSSSTKKT QLQLEXLLLX LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 25           moltype = AA  length = 133
FEATURE                 Location/Qualifiers
REGION                  1..133
                        note = Description of sequence: a variant IL-2 polypeptide
source                  1..133
                        mol_type = protein
                        organism = Homo sapiens
VARIANT                 20
                        note = X at position 20 is an amino acid other than Asp
VARIANT                 42
                        note = X at position 42 is any amino acid other than Phe
VARIANT                 126
                        note = X at position 126 is any amino acid other than Gln
REGION                  20..126
                        note = X at position 20 is an amino acid other than Asp; X
                         at position 42 is any amino acid other than Phe; and X at
                         position 126 is any amino acid other than Gln. In some
                         cases position 20 Ala. In some cases position 42 is Ala.
                         In some cases position 126 is Ala.n some cases positions
                         16 20 and 126 are Ala.
SEQUENCE: 25
APTSSSTKKT QLQLEHLLLX LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCXSIIS TLT                                                     133
```

```
SEQ ID NO: 26           moltype = AA  length = 133
FEATURE                 Location/Qualifiers
REGION                  1..133
                        note = Description of sequence: a variant IL-2 polypeptide
source                  1..133
                        mol_type = protein
                        organism = Homo sapiens
VARIANT                 20
                        note = X at position 20 is any amino acid other than Asp
VARIANT                 42
                        note = X at position 42 is any amino acid other than Phe
VARIANT                 45
                        note = X at position 45 is any amino acid other than Tyr
REGION                  20..45
                        note = X at position 20 is any amino acid other than Asp; X
                         at position 42 is any amino acid other than Phe; and X at
                         position 45 is any amino acid other than Tyr. In some
                         casesX at position 20 is Ala. In some cases X at position
                         42 is Ala. In some cases X at position 45 is Ala. In some
                         cases positions 20 42 and 45 are Ala.
SEQUENCE: 26
APTSSSTKKT QLQLEHLLLX LQMILNGINN YKNPKLTRML TXKFXMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 27           moltype = AA  length = 133
FEATURE                 Location/Qualifiers
REGION                  1..133
                        note = Description of sequence: a variant IL-2 polypeptide
source                  1..133
                        mol_type = protein
                        organism = Homo sapiens
VARIANT                 16
                        note = X at position 16 is any amino acid other than His
VARIANT                 20
                        note = X at position 20  is any amino acid other than Asp
VARIANT                 42
                        note = X at position 42 is any amino acid other than Phe
VARIANT                 45
                        note = X at position 45 is any amino acid other than Tyr.
REGION                  16..45
                        note = X at position 16 is any amino acid other than His;  X
                          at position 20  is any amino acid other than Asp; X at
                         position 42 is any amino acid other than Phe; and X at
                         position 45 is any amino acid other than Tyr. In some
                         cases position 16 is Ala. In some cases position 20  is
                         Ala. In some cases position 42 is Ala. In some cases
                         position 45 is Ala. In some cases positions 16 20 42 and
                         45 are  Ala
SEQUENCE: 27
APTSSSTKKT QLQLEXLLLX LQMILNGINN YKNPKLTRML TXKFXMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 28           moltype = AA  length = 153
FEATURE                 Location/Qualifiers
REGION                  1..153
                        note = Description of sequence: A wild-type human IL-4
                         isoform 1 precursor polypeptide
source                  1..153
                        mol_type = protein
                        organism = Homo sapiens
SEQUENCE: 28
MGLTSQLLPP LFFLLACAGN FVHGHKCDIT LQEIIKTLNS LTEQKTLCTE LTVTDIFAAS  60
KNTTEKETFC RAATVLRQFY SHHEKDTRCL GATAQQFHRH KQLIRFLKRL DRNLWGLAGL  120
NSCPVKEANQ STLENFLERL KTIMREKYSK CSS                               153

SEQ ID NO: 29           moltype = AA  length = 128
FEATURE                 Location/Qualifiers
REGION                  1..128
                        note = Description of sequence: A mature wild-type human
                         IL-4 isoform 1 polypeptide
source                  1..128
                        mol_type = protein
                        organism = Homo sapiens
SEQUENCE: 29
KCDITLQEII KTLNSLTEQK TLCTELTVTD IFAASKNTTE KETFCRAATV LRQFYSHHEK  60
DTRCLGATAQ QFHRHKQLIR FLKRLDRNLW GLAGLNSCPV KEANQSTLEN FLERLKTIMR  120
```

```
EKYSKCSS                                                          128

SEQ ID NO: 30          moltype = AA  length = 137
FEATURE                Location/Qualifiers
REGION                 1..137
                       note = Description of sequence: A wild-type human IL-4
                        isoform 2 precursor polypeptide
source                 1..137
                       mol_type = protein
                       organism = Homo sapiens
SEQUENCE: 30
MGLTSQLLPP LFFLLACAGN FVHGHKCDIT LQEIIKTLNS LTEQKNTTEK ETFCRAATVL  60
RQFYSHHEKD TRCLGATAQQ FHRHKQLIRF LKRLDRNLWG LAGLNSCPVK EANQSTLENF  120
LERLKTIMRE KYSKCSS                                                137

SEQ ID NO: 31          moltype = AA  length = 112
FEATURE                Location/Qualifiers
REGION                 1..112
                       note = Description of sequence: A mature wild-type human
                        IL-4 isoform 2 polypeptide
source                 1..112
                       mol_type = protein
                       organism = Homo sapiens
SEQUENCE: 31
KCDITLQEII KTLNSLTEQK NTTEKETFCR AATVLRQFYS HHEKDTRCLG ATAQQFHRHK  60
QLIRFLKRLD RNLWGLAGLN SCPVKEANQS TLENFLERLK TIMREKYSKC SS          112

SEQ ID NO: 32          moltype = AA  length = 825
FEATURE                Location/Qualifiers
REGION                 1..825
                       note = Description of sequence: Membrane bound IL-4 receptor
source                 1..825
                       mol_type = protein
                       organism = Homo sapiens
DOMAIN                 26..825
                       note =  aas 26 to 825 forming the mature polypeptide
DOMAIN                 233..256
                       note = aas 233-256 the transmembrane region
SEQUENCE: 32
MGWLCSGLLF PVSCLVLLQV ASSGNMKVLQ EPTCVSDYMS ISTCEWKMNG PTNCSTELRL  60
LYQLVFLLSE AHTCIPENNG GAGCVCHLLM DDVVSADNYT LDLWAGQQLL WKGSFKPSEH  120
VKPRAPGNLT VHTNVSDTLL LTWSNPYPPD NYLYNHLTYA VNIWSENDPA DFRIYNVTYL  180
EPSLRIAAST LKSGISYRAR VRAWAQCYNT TWSEWSPSTK WHNSYREPFE QHLLLGVSVS  240
CIVILAVCLL CYVSITKIKK EWWDQIPNPA RSRLVAIIIQ DAQGSQWEKR SRGQEPAKCP  300
HWKNCLTKLL PCFLEHNMKR DEDPHKAAKE MPFQGSGKSA WCPVEISKTV LWPESISVVR  360
CVELFEAPVE CEEEEEVEEE KGSFCASPES SRDDFQEGRE GIVARLTESL FLDLLGEENG  420
GFCQQDMGES CLLPPSGSTS AHMPWDEFPS AGPKEAPPWG KEQPLHLEPS PPASPTQSPD  480
NLTCTETPLV IAGNPAYRSF SNSLSQSPCP RELGPDPLLA RHLEEVEPEM PCVPQLSEPT  540
TVPQPEPETW EQILRRNVLQ HGAAAAPVSA PTSGYQEFVH AVEQGGTQAS AVVGLGPPGE  600
AGYKAFSSLL ASSAVSPEKC GFGASSGEEG YKPFQDLIPG CPGDPAPVPV PLFTGFLDRE  660
PPRSPQSSHL PSSSPEHLGL EPGEKVEDMP KPPLPQEQAT DPLVDSLGSG IVYSALTCHL  720
CGHLKQCHGQ EDGGQTPVMA SPCCGCCCGD RSSPPTTPLR APDPSPGGVP LEASLCPASL  780
APSGISEKSK SSSSFHPAPG NAQSSSQTPK IVNFVSVGPT YMRVS                 825

SEQ ID NO: 33          moltype = AA  length = 227
FEATURE                Location/Qualifiers
REGION                 1..227
                       note = Description of sequence: IL-4R soluble isoform 2
source                 1..227
                       mol_type = protein
                       organism = Homo sapiens
SEQUENCE: 33
MGWLCSGLLF PVSCLVLLQV ASSGNMKVLQ EPTCVSDYMS ISTCEWKMNG PTNCSTELRL  60
LYQLVFLLSE AHTCIPENNG GAGCVCHLLM DDVVSADNYT LDLWAGQQLL WKGSFKPSEH  120
VKPRAPGNLT VHTNVSDTLL LTWSNPYPPD NYLYNHLTYA VNIWSENDPA DFRIYNVTYL  180
EPSLRIAAST LKSGISYRAR VRAWAQCYNT TWSEWSPSTK WHNSNIC               227

SEQ ID NO: 34          moltype = AA  length = 212
FEATURE                Location/Qualifiers
REGION                 1..212
                       note = Description of sequence: A wild-type human IL-6
                        precursor polypeptide
source                 1..212
                       mol_type = protein
                       organism = Homo sapiens
SEQUENCE: 34
MNSFSTSAFG PVAFSLGLLL VLPAAFPAPV PPGEDSKDVA APHRQPLTSS ERIDKQIRYI  60
LDGISALRKE TCNKSNMCES SKEALAENNL NLPKMAEKDG CFQSGFNEET CLVKIITGLL  120
EFEVYLEYLQ NRFESSEEQA RAVQMSTKVL IQFLQKKAKN LDAITTPDPT TNASLLTKLQ  180
```

-continued

```
AQNQWLQDMT THLILRSFKE FLQSSLRALR QM                         212

SEQ ID NO: 35          moltype = AA  length = 183
FEATURE                Location/Qualifiers
REGION                 1..183
                       note = Description of sequence: A mature wild-type human
                        IL-6 polypeptide
source                 1..183
                       mol_type = protein
                       organism = Homo sapiens
SEQUENCE: 35
VPPGEDSKDV AAPHRQPLTS SERIDKQIRY ILDGISALRK ETCNKSNMCE SSKEALAENN  60
LNLPKMAEKD GCFQSGFNEE TCLVKIITGL LEFEVYLEYL QNRFESSEEQ ARAVQMSTKV  120
LIQFLQKKAK NLDAITTPDP TTNASLLTKL QAQNQWLQDM TTHLILRSFK EFLQSSLRAL  180
RQM                                                         183

SEQ ID NO: 36          moltype = AA  length = 468
FEATURE                Location/Qualifiers
REGION                 1..468
                       note = Description of sequence: human IL-6R alpha subunit
source                 1..468
                       mol_type = protein
                       organism = Homo sapiens
SEQUENCE: 36
MLAVGCALLA ALLAAPGAAL APRRCPAQEV ARGVLTSLPG DSVTLTCPGV EPEDNATVHW  60
VLRKPAAGSH PSRWAGMGRR LLLRSVQLHD SGNYSCYRAG RPAGTVHLLV DVPPEEPQLS  120
CFRKSPLSNV VCEWGPRSTP SLTTKAVLLV RKFQNSPAED FQEPCQYSQE SQKFSCQLAV  180
PEGDSSFYIV SMCVASSVGS KFSKTQTFQG CGILQPDPPA NITVTAVARN PRWLSVTWQD  240
PHSWNSSFYR LRFELRYRAE RSKTFTTWMV KDLQHHCVIH DAWSGLRHVV QLRAQEEFGQ  300
GEWSEWSPEA MGTPWTESRS PPAENEVSTP MQALTTNKDD DNILFRDSAN ATSLPVQDSS  360
SVPLPTFLVA GGSLAFGTLL CIAIVLRFKK TWKLRALKEG KTSMHPPYSL GQLVPERPRP  420
TPVLVPLISP PVSPSSLGSD NTSSHNRPDA RDPRSPYDIS NTDYFFPR        468

SEQ ID NO: 37          moltype = AA  length = 918
FEATURE                Location/Qualifiers
REGION                 1..918
                       note = Description of sequence: human IL-6R beta subunit
source                 1..918
                       mol_type = protein
                       organism = Homo sapiens
SEQUENCE: 37
MLTLQTWLVQ ALFIFLTTES TGELLDPCGY ISPESPVVQL HSNFTAVCVL KEKCMDYFHV  60
NANYIVWKTN HFTIPKEQYT IINRTASSVT FTDIASLNIQ LTCNILTGFQ LEQNVYGITI  120
ISGLPPEKPK NLSCIVNEGK KMRCEWDGGR ETHLETNFTL KSEWATHKFA DCKAKRDTPT  180
SCTVDYSTVY FVNIEVWVEA ENALGKVTSD HINFDPVYKV KPNPPHNLSV INSEELSSIL  240
KLTWTNPSIK SVIILKYNIQ YRTKDASTWS QIPPEDTAST RSSFTVQDLK PFTEYVFRIR  300
CMKEDGKGYW SDWSEEASGI TYEDRPSKAP SFWYKIDPSH TQGYRTVQLV WKTLPPFEAN  360
GKILDYEVTL TRWKSHLQNY TVNATKLTVN LTNDRYLATL TVRNLVGKSD AAVLTIPACD  420
FQATHPVMDL KAFPKDNMLW VEWTTPRESV KKYILEWCVL SDKAPCITDW QQEDGTVHRT  480
YLRGNLAESK CYLITVTPVY ADGPGSPESI KAYLKQAPPS KGPTVRTKKV GKNEAVLEWD  540
QLPVDVQNGF IRNYTIFYRT IIGNETAVNV DSSHTEYTLS SLTSDTLYMV RMAAYTDEGG  600
KDGPEFTFTT PKFAQGEIEA IVVPVCLAFL LTTLLGVLFC FNKRDLIKKH IWPNVPDPSK  660
SHIAQWSPHT PPRHNFNSKD QMYSDGNFTD VSVVEIEAND KKPFPEDLKS LDLFKKEKIN  720
TEGHSSGIGG SSCMSSSRPS ISSSDENESS QNTSSTVQYS TVVHSGYRHQ VPSVQVFSRS  780
ESTQPLLDSE ERPEDLQLVD HVDGGDGILP RQQYFKQNCS QHESSPDISH FERSKQVSSV  840
NEEDFVRLKQ QISDHISQSC GSGQMKMFQE VSAADAFGPG TEGQVERFET VGMEAATDEG  900
MPKSYLPQTV RQGGYMPQ                                         918

SEQ ID NO: 38          moltype = AA  length = 468
FEATURE                Location/Qualifiers
REGION                 1..468
                       note = Description of sequence: mature soluble form of the
                        IL-6R alpha subunit
source                 1..468
                       mol_type = protein
                       organism = Homo sapiens
SEQUENCE: 38
MLAVGCALLA ALLAAPGAAL APRRCPAQEV ARGVLTSLPG DSVTLTCPGV EPEDNATVHW  60
VLRKPAAGSH PSRWAGMGRR LLLRSVQLHD SGNYSCYRAG RPAGTVHLLV DVPPEEPQLS  120
CFRKSPLSNV VCEWGPRSTP SLTTKAVLLV RKFQNSPAED FQEPCQYSQE SQKFSCQLAV  180
PEGDSSFYIV SMCVASSVGS KFSKTQTFQG CGILQPDPPA NITVTAVARN PRWLSVTWQD  240
PHSWNSSFYR LRFELRYRAE RSKTFTTWMV KDLQHHCVIH DAWSGLRHVV QLRAQEEFGQ  300
GEWSEWSPEA MGTPWTESRS PPAENEVSTP MQALTTNKDD DNILFRDSAN ATSLPVQDSS  360
SVPLPTFLVA GGSLAFGTLL CIAIVLRFKK TWKLRALKEG KTSMHPPYSL GQLVPERPRP  420
TPVLVPLISP PVSPSSLGSD NTSSHNRPDA RDPRSPYDIS NTDYFFPR        468

SEQ ID NO: 39          moltype = AA  length = 177
FEATURE                Location/Qualifiers
REGION                 1..177
```

```
                        note = Description of sequence: A wild-type human IL-7
                         isoform 1 precursor polypeptide
source                  1..177
                        mol_type = protein
                        organism = Homo sapiens
SEQUENCE: 39
MFHVSFRYIF GLPPLILVLL PVASSDCDIE GKDGKQYESV LMVSIDQLLD SMKEIGSNCL  60
NNEFNFFKRH ICDANKEGMF LFRAARKLRQ FLKMNSTGDF DLHLLKVSEG TTILLNCTGQ  120
VKGRKPAALG EAQPTKSLEE NKSLKEQKKL NDLCFLKRLL QEIKTCWNKI LMGTKEH     177

SEQ ID NO: 40           moltype = AA  length = 152
FEATURE                 Location/Qualifiers
REGION                  1..152
                        note = Description of sequence: A mature wild-type human
                         IL-7 isoform 1 polypeptide
source                  1..152
                        mol_type = protein
                        organism = Homo sapiens
SEQUENCE: 40
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EH                               152

SEQ ID NO: 41           moltype = AA  length = 133
FEATURE                 Location/Qualifiers
REGION                  1..133
                        note = Description of sequence:  A wild-type human IL-7
                         isoform 2 precursor polypeptide
source                  1..133
                        mol_type = protein
                        organism = Homo sapiens
SEQUENCE: 41
MFHVSFRYIF GLPPLILVLL PVASSDCDIE GKDGKQYESV LMVSIDQLLD SMKEIGSNCL  60
NNEFNFFKRH ICDANKVKGR KPAALGEAQP TKSLEENKSL KEQKKLNDLC FLKRLLQEIK  120
TCWNKILMGT KEH                                                    133

SEQ ID NO: 42           moltype = AA  length = 109
FEATURE                 Location/Qualifiers
REGION                  1..109
                        note = Description of sequence: A mature wild-type human
                         IL-7 isoform 2 polypeptide
source                  1..109
                        mol_type = protein
                        organism = Homo sapiens
SEQUENCE: 42
SDCDIEGKDG KQYESVLMVS IDQLLDSMKE IGSNCLNNEF NFFKRHICDA NKVKGRKPAA  60
LGEAQPTKSL EENKSLKEQK KLNDLCFLKR LLQEIKTCWN KILMGTKEH             109

SEQ ID NO: 43           moltype = AA  length = 159
FEATURE                 Location/Qualifiers
REGION                  1..159
                        note = Description of sequence: A wild-type human IL-7
                         isoform 3 precursor polypeptide
source                  1..159
                        mol_type = protein
                        organism = Homo sapiens
SEQUENCE: 43
MFHVSFRYIF GLPPLILVLL PVASSDCDIE GKDGKQYESV LMVSIDQLLD SMKEIGSNCL  60
NNEFNFFKRH ICDANKEGMF LFRAARKLRQ FLKMNSTGDF DLHLLKVSEG TTILLNCTGQ  120
EENKSLKEQK KLNDLCFLKR LLQEIKTCWN KILMGTKEH                        159

SEQ ID NO: 44           moltype = AA  length = 133
FEATURE                 Location/Qualifiers
REGION                  1..133
                        note = Description of sequence: A mature wild-type human
                         IL-7 isoform 3 polypeptide
source                  1..133
                        mol_type = protein
                        organism = Homo sapiens
SEQUENCE: 44
CDIEGKDGKQ YESVLMVSID QLLDSMKEIG SNCLNNEFNF FKRHICDANK EGMFLFRAAR  60
KLRQFLKMNS TGDFDLHLLK VSEGTTILLN CTGQEENKSL KEQKKLNDLC FLKRLLQEIK  120
TCWNKILMGT KEH                                                    133

SEQ ID NO: 45           moltype = AA  length = 115
FEATURE                 Location/Qualifiers
REGION                  1..115
                        note = Description of sequence: A wild-type human IL-7
                         isoform 4 precursor polypeptide
```

```
source                  1..115
                        mol_type = protein
                        organism = Homo sapiens
SEQUENCE: 45
MFHVSFRYIF GLPPLILVLL PVASSDCDIE GKDGKQYESV LMVSIDQLLD SMKEIGSNCL  60
NNEFNFFKRH ICDANKEENK SLKEQKKLND LCFLKRLLQE IKTCWNKILM GTKEH       115

SEQ ID NO: 46           moltype = AA  length = 91
FEATURE                 Location/Qualifiers
REGION                  1..91
                        note = Description of sequence: A mature wild-type human
                         IL-7 isoform 4 polypeptide
source                  1..91
                        mol_type = protein
                        organism = Homo sapiens
SEQUENCE: 46
SDCDIEGKDG KQYESVLMVS IDQLLDSMKE IGSNCLNNEF NFFKRHICDA NKEENKSLKE  60
QKKLNDLCFL KRLLQEIKTC WNKILMGTKE H                                 91

SEQ ID NO: 47           moltype = AA  length = 459
FEATURE                 Location/Qualifiers
REGION                  1..459
                        note = Description of sequence: An IL-7 receptor alpha
                         subunit
source                  1..459
                        mol_type = protein
                        organism = Homo sapiens
SEQUENCE: 47
MTILGTTGFM VFSLLQVVSG ESGYAQNGDL EDAELDDYSF SCYSQLEVNG SQHSLTCAFE  60
DPDVNITNLE FEICGALVEV KCLNFRKLQE IYFIETKKFL LIGKSNICVK VGEKSLTCKK  120
IDLTTIVKPE APFDLSVVYR EGANDFVVTF NTSHLQKKYV KVLMHDVAYR QEKDENKWTH  180
VNLSSTKLTL LQRKLQPAAM YEIKVRSIPD HYFKGFWSEW SPSYYFRTPE INNSSGEMDP  240
ILLTISILSF FSVALLVILA CVLWKKRIKP IVWPSLPDHK KTLEHLCKKP RKNLNVSFNP  300
ESFLDCQIHR VDDIQARDEV EGFLQDTFPQ QLEESEKQRL GGDVQSPNCP SEDVVITPES  360
FGRDSSLTCL AGNVSACDAP ILSSSRSLDC RESGKNGPHV YQDLLLSLGT TNSTLPPPFS  420
LQSGILTLNP VAQGQPILTS LGSNQEEAYV TMSSFYQNQ                         459

SEQ ID NO: 48           moltype = AA  length = 369
FEATURE                 Location/Qualifiers
REGION                  1..369
                        note = Description of sequence: IL-7R common-gamma subunit
                         (IL-7RG or IL-R7?-gamma)
source                  1..369
                        mol_type = protein
                        organism = Homo sapiens
SEQUENCE: 48
MLKPSLPFTS LLFLQLPLLG VGLNTTILTP NGNEDTTADF FLTTMPTDSL SVSTLPLPEV  60
QCFVFNVEYM NCTWNSSSEP QPTNLTLHYW YKNSDNDKVQ KCSHYLFSEE ITSGCQLQKK  120
EIHLYQTFVV QLQDPREPRR QATQMLKLQN LVIPWAPENL TLHKLSESQL ELNWNNRFLN  180
HCLEHLVQYR TDWDHSWTEQ SVDYRHKFSL PSVDGQKRYT FRVRSRFNPL CGSAQHWSEW  240
SHPIHWGSNT SKENPFLFAL EAVVISVGSM GLIISLLCVY FWLERTMPRI PTLKNLEDLV  300
TEYHGNFSAW SGVSKGLAES LQPDYSERLC LVSEIPPKGG ALGEGPGASP CNQHSPYWAP  360
PCYTLKPET                                                          369

SEQ ID NO: 49           moltype = AA  length = 178
FEATURE                 Location/Qualifiers
REGION                  1..178
                        note = Description of sequence: A wild-type human IL-10
                         isoform 1 precursor polypeptide
source                  1..178
                        mol_type = protein
                        organism = Homo sapiens
SEQUENCE: 49
MHSSALLCCL VLLTGVRASP GQGTQSENSC THFPGNLPNM LRDLRDAFSR VKTFFQMKDQ  60
LDNLLLKESL LEDFKGYLGC QALSEMIQFY LEEVMPQAEN QDPDIKAHVN SLGENLKTLR  120
LRLRRCHRFL PCENKSKAVE QVKNAFNKLQ EKGIYKAMSE FDIFINYIEA YMTMKIRN    178

SEQ ID NO: 50           moltype = AA  length = 160
FEATURE                 Location/Qualifiers
REGION                  1..160
                        note = Description of sequence: A mature wild-type human
                         IL-10 polypeptide
source                  1..160
                        mol_type = protein
                        organism = Homo sapiens
SEQUENCE: 50
SPGQGTQSEN SCTHFPGNLP NMLRDLRDAF SRVKTFFQMK DQLDNLLLKE SLLEDFKGYL  60
GCQALSEMIQ FYLEEVMPQA ENQDPDIKAH VNSLGENLKT LRLRLRRCHR FLPCENKSKA  120
VEQVKNAFNK LQEKGIYKAM SEFDIFINYI EAYMTMKIRN                        160
```

```
SEQ ID NO: 51          moltype = AA  length = 74
FEATURE                Location/Qualifiers
REGION                 1..74
                       note = Description of sequence: A human IL-10 polypeptide
source                 1..74
                       mol_type = protein
                       organism = Homo sapiens
SEQUENCE: 51
MIQFYLEEVM PQAENQDPDI KAHVNSLGEN LKTLRLRLRR CHRFLPCENK SKAVEQVKNA  60
FNKLQEKGIY KAMS                                                    74

SEQ ID NO: 52          moltype = AA  length = 578
FEATURE                Location/Qualifiers
REGION                 1..578
                       note = Description of sequence: An IL-10 receptor alpha
                        subunit
source                 1..578
                       mol_type = protein
                       organism = Homo sapiens
SEQUENCE: 52
MLPCLVVLLA ALLSLRLGSD AHGTELPSPP SVWFEAEFFH HILHWTPIPN QSESTCYEVA  60
LLRYGIESWN SISNCSQTLS YDLTAVTLDL YHSNGYRARV RAVDGSRHSN WTVTNTRFSV  120
DEVTLTVGSV NLEIHNGFIL GKIQLPRPKM APANDTYESI FSHFREYEIA IRKVPGNFTF  180
THKKVKHENF SLLTSGEVGE FCVQVKPSVA SRSNKGMWSK EECISLTRQY FTVTNVIIFF  240
AFVLLLSGAL AYCLALQLYV RRRKKLPSVL LFKKPSPFIF ISQRPSPETQ DTIHPLDEEA  300
FLKVSPELKN LDLHGSTDSG FGSTKPSLQT EEPQFLLPDP HPQADRTLGN REPPVLGDSC  360
SSGSSNSTDS GICLQEPSLS PSTGPTWEQQ VGSNSRGQDD SGIDLVQNSE GRAGDTQGGS  420
ALGHHSPPEP EVPGEEDPAA VAFQGYLRQT RCAEEKATKT GCLEEESPLT DGLGPKFGRC  480
LVDEAGLHPP ALAKGYLKQD PLEMTLASSG APTGQWNQPT EEWSLLALSS CSDLGISDWS  540
FAHDLAPLGC VAAPGGLLGS FNSDLVTLPL ISSLQSSE                          578

SEQ ID NO: 53          moltype = AA  length = 325
FEATURE                Location/Qualifiers
REGION                 1..325
                       note = Description of sequence: An IL-10 receptor beta
                        subunit
source                 1..325
                       mol_type = protein
                       organism = Homo sapiens
SEQUENCE: 53
MAWSLGSWLG GCLLVSALGM VPPPENVRMN SVNFKNILQW ESPAFAKGNL TFTAQYLSYR  60
IFQDKCMNTT LTECDFSSLS KYGDHTLRVR AEFADEHSDW VNITFCPVDD TIIGPPGMQV  120
EVLADSLHMR FLAPKIENEY ETWTMKNVYN SWTYNVQYWK NGTDEKFQIT PQYDFEVLRN  180
LEPWTTYCVQ VRGFLPDRNK AGEWSEPVCE QTTHDETVPS WMVAVILMAS VFMVCLALLG  240
CFALLWCVYK KTKYAFSPRN SLPQHLKEFL GHPHHNTLLF FSFPLSDEND VFDKLSVIAE  300
DSESGKQNPG DSCSLGTPPG QGPQS                                        325

SEQ ID NO: 54          moltype = AA  length = 162
FEATURE                Location/Qualifiers
REGION                 1..162
                       note = Description of sequence: A wt. IL-15 polypeptide
source                 1..162
                       mol_type = protein
                       organism = Homo sapiens
SEQUENCE: 54
MRISKPHLRS ISIQCYLCLL LNSHFLTEAG IHVFILGCFS AGLPKTEANW VNVISDLKKI  60
EDLIQSMHID ATLYTESDVH PSCKVTAMKC FLLELQVISL ESGDASIHDT VENLIILANN  120
SLSSNGNVTE SGCKECEELE EKNIKEFLQS FVHIVQMFIN TS                     162

SEQ ID NO: 55          moltype = AA  length = 114
FEATURE                Location/Qualifiers
REGION                 1..114
                       note = Description of sequence: A mature IL-15 polypeptide
source                 1..114
                       mol_type = protein
                       organism = Homo sapiens
SEQUENCE: 55
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 56          moltype = AA  length = 267
FEATURE                Location/Qualifiers
REGION                 1..267
                       note = Description of sequence: A human an IL-15R-alpha
                        isoform 1 precursor protein
source                 1..267
                       mol_type = protein
                       organism = Homo sapiens
```

```
SEQUENCE: 56
MAPRRARGCR TLGLPALLLL LLLRPPATRG ITCPPPMSVE HADIWVKSYS LYSRERYICN  60
SGFKRKAGTS SLTECVLNKA TNVAHWTTPS LKCIRDPALV HQRPAPPSTV TTAGVTPQPE  120
SLSPSGKEPA ASSPSSNNTA ATTAAIVPGS QLMPSKSPST GTTEISSHES SHGTPSQTTA  180
KNWELTASAS HQPPGVYPQG HSDTTVAIST STVLLCGLSA VSLLACYLKS RQTPPLASVE  240
MEAMEALPVT WGTSSRDEDL ENCSHHL                                      267

SEQ ID NO: 57          moltype = AA  length = 162
FEATURE                Location/Qualifiers
REGION                 1..162
                       note = Description of sequence: A wild type (wt.) IL-21
                        isoform 1 polypeptide
source                 1..162
                       mol_type = protein
                       organism = Homo sapiens
SEQUENCE: 57
MRSSPGNMER IVICLMVIFL GTLVHKSSSQ GQDRHMIRMR QLIDIVDQLK NYVNDLVPEF  60
LPAPEDVETN CEWSAFSCFQ KAQLKSANTG NNERIINVSI KKLKRKPPST NAGRRQKHRL  120
TCPSCDSYEK KPPKEFLERF KSLLQKMIHQ HLSSRTHGSE DS                     162

SEQ ID NO: 58          moltype = AA  length = 133
FEATURE                Location/Qualifiers
REGION                 1..133
                       note = Description of sequence: A mature IL-21 isoform 1
                        polypeptide
source                 1..133
                       mol_type = protein
                       organism = Homo sapiens
SEQUENCE: 58
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDS                                                     133

SEQ ID NO: 59          moltype = AA  length = 162
FEATURE                Location/Qualifiers
REGION                 1..162
                       note = Description of sequence: A wild type (wt.) IL-21
                        isoform 2 polypeptide
source                 1..162
                       mol_type = protein
                       organism = Homo sapiens
SEQUENCE: 59
MRSSPGNMER IVICLMVIFL GTLVHKSSSQ GQDRHMIRMR QLIDIVDQLK NYVNDLVPEF  60
LPAPEDVETN CEWSAFSCFQ KAQLKSANTG NNERIINVSI KKLKRKPPST NAGRRQKHRL  120
TCPSCDSYEK KPPKEFLERF KSLLQKMIHQ HLSSRTHGSE DS                     162

SEQ ID NO: 60          moltype = AA  length = 153
FEATURE                Location/Qualifiers
REGION                 1..153
                       note = Description of sequence: A mature IL-21 isoform 2
                        polypeptide
source                 1..153
                       mol_type = protein
                       organism = Homo sapiens
SEQUENCE: 60
MRSSPGNMER IVICLMVIFL GTLVHKSSSQ GQDRHMIRMR QLIDIVDQLK NYVNDLVPEF  60
LPAPEDVETN CEWSAFSCFQ KAQLKSANTG NNERIINVSI KKLKRKPPST NAGRRQKHRL  120
TCPSCDSYEK KPPKEFLERF KSLLQKVSTL SFI                               153

SEQ ID NO: 61          moltype = AA  length = 538
FEATURE                Location/Qualifiers
REGION                 1..538
                       note = Description of sequence: A human IL-21R isoform 1
                        precursor protein
source                 1..538
                       mol_type = protein
                       organism = Homo sapiens
DOMAIN                 1..19
                       note = aas 1-19 forming the signal sequence
DOMAIN                 20..538
                       note = aas 20-538 forming the mature polypeptide
DOMAIN                 233..253
                       note = aas 233..253 forming the transmembrane domain
DOMAIN                 20..232
                       note = aas 20-232 forming the ectodomain
SEQUENCE: 61
MPRGWAAPLL LLLLQGGWGC PDLVCYTDYL QTVICILEMW NLHPSTLTLT WQDQYEELKD  60
EATSCSLHRS AHNATHATYT CHMDVFHFMA DDIFSVNITD QSGNYSQECG SFLLAESIKP  120
APPFNVTVTF SGQYNISWRS DYEDPAFYML KGKLQYELQY RNRGDPWAVS PRRKLISVDS  180
```

```
RSVSLLPLEF RKDSSYELQV RAGPMPGSSY QGTWSEWSDP VIFQTQSEEL KEGWNPHLLL  240
LLLLVIVFIP AFWSLKTHPL WRLWKKIWAV PSPERFFMPL YKGCSGDFKK WVGAPFTGSS  300
LELGPWSPEV PSTLEVYSCH PPRSPAKRLQ LTELQEPAEL VESDGVPKPS FWPTAQNSGG  360
SAYSEERDRP YGLVSIDTVT VLDAEGPCTW PCSCEDDGYP ALDLDAGLEP SPGLEDPLLD  420
AGTTVLSCGC VSAGSPGLGG PLGSLLDRLK PPLADGEDWA GGLPWGGRSP GGVSESEAGS  480
PLAGLDMDTF DSGFVGSDCS SPVECDFTSP GDEGPPRSYL RQWVVIPPPL SSPGPQAS    538

SEQ ID NO: 62          moltype = AA  length = 189
FEATURE                Location/Qualifiers
REGION                 1..189
                       note = Description of sequence: A wild type IL-23A
                        polypeptide
source                 1..189
                       mol_type = protein
                       organism = Homo sapiens
DOMAIN                 1..19
                       note = aa 1 to 19 as the signal peptide
DOMAIN                 20..189
                       note = 20-189 as the mature peptide
SEQUENCE: 62
MLGSRAVMLL LLLPWTAQGR AVPGGSSPAW TQCQQLSQKL CTLAWSAHPL VGHMDLREEG  60
DEETTNDVPH IQCGDGCDPQ GLRDNSQFCL QRIHQGLIFY EKLLGSDIFT GEPSLLPDSP  120
VGQLHASLLG LSQLLQPEGH HWETQQIPSL SPSQPWQRLL LRFKILRSLQ AFVAVAARVF  180
AHGAATLSP                                                        189

SEQ ID NO: 63          moltype = AA  length = 170
FEATURE                Location/Qualifiers
REGION                 1..170
                       note = Description of sequence: A mature IL-23A polypeptide
source                 1..170
                       mol_type = protein
                       organism = Homo sapiens
DOMAIN                 1..22
                       note = aas 1-22 forming the signal sequence
DOMAIN                 23..170
                       note = aas 23-170 forming the mature polypeptide
SEQUENCE: 63
RAVPGGSSPA WTQCQQLSQK LCTLAWSAHP LVGHMDLREE GDEETTNDVP HIQCGDGCDP  60
QGLRDNSQFC LQRIHQGLIF YEKLLGSDIF TGEPSLLPDS PVGQLHASLL GLSQLLQPEG  120
HHWETQQIPS LSPSQPWQRL LLRFKILRSL QAFVAVAARV FAHGAATLSP            170

SEQ ID NO: 64          moltype = AA  length = 328
FEATURE                Location/Qualifiers
REGION                 1..328
                       note = Description of sequence: A wild type (wt) IL-12B
                        polypeptide
source                 1..328
                       mol_type = protein
                       organism = Homo sapiens
SEQUENCE: 64
MCHQQLVISW FSLVFLASPL VAIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCS                                   328

SEQ ID NO: 65          moltype = AA  length = 306
FEATURE                Location/Qualifiers
REGION                 1..306
                       note = Description of sequence: A mature IL-12B polypeptide
source                 1..306
                       mol_type = protein
                       organism = Homo sapiens
SEQUENCE: 65
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCS                                                           306

SEQ ID NO: 66          moltype = AA  length = 629
FEATURE                Location/Qualifiers
REGION                 1..629
                       note = Description of sequence:  An IL-23R isoform 1
                        precursor protein
source                 1..629
                       mol_type = protein
```

```
                         organism = Homo sapiens
DOMAIN                   1..23
                         note = aas 1-23 forming the signal sequence
DOMAIN                   24..629
                         note = aas 24-629 forming the mature polypeptide
DOMAIN                   356..376
                         note = aas 356 to 376 forming the transmembrane domain
DOMAIN                   24..355
                         note = aas 24-355 forming the ectodomain
SEQUENCE: 66
MNQVTIQWDA VIALYILFSW CHGGITNINC SGHIWVEPAT IFKMGMNISI YCQAAIKNCQ  60
PRKLHFYKNG IKERFQITRI NKTTARLWYK NFLEPHASMY CTAECPKHFQ ETLICGKDIS  120
SGYPPDIPDE VTCVIYEYSG NMTCTWNAGK LTYIDTKYVV HVKSLETEEE QQYLTSSYIN  180
ISTDSLQGGK KYLVWVQAAN ALGMEESKQL QIHLDDIVIP SAAVISRAET INATVPKTII  240
YWDSQTTIEK VSCEMRYKAT TNQTWNVKEF DTNFTYVQQS EFYLEPNIKY VFQVRCQETG  300
KRYWQPWSSL FFHKTPETVP QVTSKAFQHD TWNSGLTVAS ISTGHLTSDN RGDIGLLLGM  360
IVFAVMLSIL SLIGIFNRSF RTGIKRRILL LIPKWLYEDI PNMKNSNVVK MLQENSELMN  420
NNSSEQVLYV DPMITEIKEI FIPEHKPTDY KKENTGPLET RDYPQNSLFD NTTVVYIPDL  480
NTGYKPQISN FLPEGSHLSN NNEITSLTLK PPVDSLDSGN NPRLQKHPNF AFSVSSVNSL  540
SNTIFLGELS LILNQGECSS PDIQNSVEEE TTMLLENDSP SETIPEQTLL PDEFVSCLGI  600
VNEELPSINT YFPQNILESH FNRISLLEK                                  629

SEQ ID NO: 67            moltype = AA  length = 662
FEATURE                  Location/Qualifiers
REGION                   1..662
                         note = Description of sequence: An 12RB1 isoform 1
                          precursor protein aa sequence
source                   1..662
                         mol_type = protein
                         organism = Homo sapiens
DOMAIN                   1..23
                         note = aas 1-23 forming the signal sequence
DOMAIN                   24..662
                         note = aas 24-662 forming the mature polypeptide
DOMAIN                   546..570
                         note = aas 546 to 570 forming the transmembrane domain
DOMAIN                   24..545
                         note = aas forming 24-545 the ectodomain
SEQUENCE: 67
MEPLVTWVVP LLFLFLLSRQ GAACRTSECC FQDPPYPDAD SGSASGPRDL RCYRISSDRY  60
ECSWQYEGPT AGVSHFLRCC LSSGRCCYFA AGSATRLQFS DQAGVSVLYT VTLWVESWAR  120
NQTEKSPEVT LQLYNSVKYE PPLGDIKVSK LAGQLRMEWE TPDNQVGAEV QFRHRTPSSP  180
WKLGDCGPQD DDTESCLCPL EMNVAQEFQL RRRQLGSQGS SWSKWSSPVC VPPENPPQPQ  240
VRFSVEQLGQ DGRRRLTLKE QPTQLELPEG CQGLAPGTEV TYRLQLHMLS CPCKAKATRT  300
LHLGKMPYLS GAAYNVAVIS SNQFGPGLNQ TWHIPADTHT EPVALNISVG TNGTTMYWPA  360
RAQSMTYCIE WQPVGQDGGL ATCSLTAPQD PDPAGMATYS WSRESGAMGQ EKCYYITIFA  420
SAHPEKLTLW STVLSTYHFG GNASAAGTPH HVSVKNHSLD SVSVDWAPSL LSTCPGVLKE  480
YVVRCRDEDS KQVSEHPVQP TETQVTLSGL RAGVAYTVQV RADTAWLRGV WSQPQRFSIE  540
VQVSDWLIFF ASLGSFLSIL LVGVLGYLGL NRAARHLCPP LPTPCASSAI EFPGGKETWQ  600
WINPVDFQEE ASLQEALVVE MSWDKGERTE PLEKTELPEG APELALDTEL SLEDGDRCKA  660
KM                                                               662

SEQ ID NO: 68            moltype = AA  length = 353
FEATURE                  Location/Qualifiers
REGION                   1..353
                         note = Description of sequence: an IgA Fc
source                   1..353
                         mol_type = protein
                         organism = Homo sapiens
SEQUENCE: 68
ASPTSPKVFP LSLCSTQPDG NVVIACLVQG FFPQEPLSVT WSESGQGVTA RNFPPSQDAS  60
GDLYTTSSQL TLPATQCLAG KSVTCHVKHY TNPSQDVTVP CPVPSTPPTP SPSTPPTPSP  120
SCCHPRLSLH RPALEDLLLG SEANLTCTLT GLRDASGVTF TWTPSSGKSA VQGPPERDLC  180
GCYSVSSVLP GCAEPWNHGK TFTCTAAYPE SKTPLTATLS KSGNTFRPEV HLLPPPSEEL  240
ALNELVTLTC LARGFSPKDV LVRWLQGSQE LPREKYLTWA SRQEPSQGTT TFAVTSILRV  300
AAEDWKKGDT FSCMVGHEAL PLAFTQKTID RLAGKPTHVN VSVVMAEVDG TCY        353

SEQ ID NO: 69            moltype = AA  length = 383
FEATURE                  Location/Qualifiers
REGION                   1..383
                         note = Description of sequence: an IgD Fc
source                   1..383
                         mol_type = protein
                         organism = Homo sapiens
SEQUENCE: 69
PTKAPDVFPI ISGCRHPKDN SPVVLACLIT GYHPTSVTVT WYMGTQSQPQ RTFPEIQRRD  60
SYYMTSSQLS TPLQQWRQGE YKCVVQHTAS KSKKEIFRWP ESPKAQASSV PTAQPQAEGS  120
LAKATTAPAT TRNTGRGGEE KKKEKEKEEQ EERETKTPEC PSHTQPLGVY LLTPAVQDLW  180
LRDKATFTCF VVGSDLKDAH LTWEVAGKVP TGGVEEGLLE RHSNGSQSQH SRLTLPRSLW  240
```

```
NAGTSVTCTL NHPSLPPQRL MALREPAAQA PVKLSLNLLA SSDPPEAASW LLCEVSGFSP  300
PNILLMWLED QREVNTSGFA PARPPPQPRS TTFWAWSVLR VPAPPSPQPA TYTCVVSHED  360
SRTLLNASRS LEVSYVTDHG PMK                                          383

SEQ ID NO: 70          moltype = AA  length = 222
FEATURE                Location/Qualifiers
REGION                 1..222
                       note = Description of sequence: an IgE Fc
source                 1..222
                       mol_type = protein
                       organism = Homo sapiens
SEQUENCE: 70
ADPCDSNPRG VSAYLSRPSP FDLFIRKSPT ITCLVVDLAP SKGTVNLTWS RASGKPVNHS  60
TRKEEKQRNG TLTVTSTLPV GTRDWIEGET YQCRVTHPHL PRALMRSTTK TSGPRAAPEV  120
YAFATPEWPG SRDKRTLACL IQNFMPEDIS VQWLHNEVQL PDARHSTTQP RKTKGSGFFV  180
FSRLEVTRAE WEQKDEFICR AVHEAASPSQ TVQRAVSVNP GK                     222

SEQ ID NO: 71          moltype = AA  length = 227
FEATURE                Location/Qualifiers
REGION                 1..227
                       note = Description of sequence: an IgG1 Fc
source                 1..227
                       mol_type = protein
                       organism = Homo sapiens
SEQUENCE: 71
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 72          moltype = AA  length = 227
FEATURE                Location/Qualifiers
REGION                 1..227
                       note = Description of sequence: an IgG1 Fc
source                 1..227
                       mol_type = protein
                       organism = Homo sapiens
SEQUENCE: 72
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 73          moltype = AA  length = 227
FEATURE                Location/Qualifiers
REGION                 1..227
                       note = Description of sequence: IgG1 Fc Mutant:
                        L234F/L235E/P331S (Triple Mutant TM)
source                 1..227
                       mol_type = protein
                       organism = Homo sapiens
SEQUENCE: 73
DKTHTCPPCP APEFEGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA SIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 74          moltype = AA  length = 227
FEATURE                Location/Qualifiers
REGION                 1..227
                       note = Description of sequence: IgG1 Fc Mutant: N297A
source                 1..227
                       mol_type = protein
                       organism = Homo sapiens
SEQUENCE: 74
DKTHTCPPCP APELLGGPSV FLFPPKPKDT LMISRTPEVT CVVVDVSHED PEVKFNWYVD  60
GVEVHNAKTK PREEQYASTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 75          moltype = AA  length = 227
FEATURE                Location/Qualifiers
REGION                 1..227
                       note = Description of sequence: IgG1 Fc Mutant: L234A/L235A
                        (LALA)
source                 1..227
                       mol_type = protein
                       organism = Homo sapiens
SEQUENCE: 75
```

```
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 76          moltype = AA  length = 215
FEATURE                Location/Qualifiers
REGION                 1..215
                       note = Description of sequence: IgG1 Fc Mutant: (N-terminal
                        Delta-10) L234A/L235A (LALA) L351K, T366S, P395V, F405R,
                        Y407A, and K409Y
source                 1..215
                       mol_type = protein
                       organism = Homo sapiens
SEQUENCE: 76
APEAAGGPSV FLFPPKPKDT LMISRTPEVT CVVVDVSHED PEVKFNWYVD GVEVHNAKTK  60
PREEQYNSTY RVVSVLTVLH QDWLNGKEYK CKVSNKALPA PIEKTISKAK GQPREPQVYT  120
KPPSREEMTK NQVSLSCLVK GFYPSDIAVE WESNGQPENN YKTTVPVLDS DGSFRLASYL  180
TVDKSRWQQG NVFSCSVMHE ALHNHYTQKS LSLSP                             215

SEQ ID NO: 77          moltype = AA  length = 225
FEATURE                Location/Qualifiers
REGION                 1..225
                       note = Description of sequence: IgG1 Fc Mutant: L234A/L235A
                        (LALA) and  T366W Knob-in-Hole Knob
source                 1..225
                       mol_type = protein
                       organism = Homo sapiens
SEQUENCE: 77
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLWCLVK GFYPSDIAVE WESNGQPENN YKTTPPVLDS  180
DGSFFLYSKL TVDKSRWQQG NVFSCSVMHE ALHNHYTQKS LSLSP                  225

SEQ ID NO: 78          moltype = AA  length = 225
FEATURE                Location/Qualifiers
REGION                 1..225
                       note = Description of sequence: IgG1 Fc Mutant: L234A/L235A
                        (LALA) and T366S and L368A Knob-in-Hole Hole
source                 1..225
                       mol_type = protein
                       organism = Homo sapiens
SEQUENCE: 78
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSP                  225

SEQ ID NO: 79          moltype = AA  length = 325
FEATURE                Location/Qualifiers
REGION                 1..325
                       note = Description of sequence: IgG2 Fc GenBank AAN76044
                        (amino acids 99-325)
source                 1..325
                       mol_type = protein
                       organism = Homo sapiens
SEQUENCE: 79
STKGPSVFPL APCSRSTSES TAALGCLVKD YFPEPVTVSW NSGALTSGVH TFPAVLQSSG  60
LYSLSSVVTV PSSNFGTQTY TCNVDHKPSN TKVDKTVERK CCVECPPCPA PPVAGPSVFL  120
FPPKPKDTLM ISRTPEVTCV VVDVSHEDPE VQFNWYVDGV EVHNAKTKPR EEQFNSTFRV  180
VSVLTVVHQD WLNGKEYKCK VSNKGLPAPI EKTISKTKGQ PREPQVYTLP PSREEMTKNQ  240
VSLTCLVKGF YPSDIAVEWE SNGQPENNYK TTPPMLDSDG SFFLYSKLTV DKSRWQQGNV  300
FSCSVMHEAL HNHYTQKSLS LSPGK                                        325

SEQ ID NO: 80          moltype = AA  length = 246
FEATURE                Location/Qualifiers
REGION                 1..246
                       note = Description of sequence: IgG3 Fc GenBank
                        AAW65947(amino acids 19-246)
source                 1..246
                       mol_type = protein
                       organism = Homo sapiens
SEQUENCE: 80
HKPSNTKVDK RVELKTPLGD TTHTCPPCPA PELLGGPSVF LFPPKPKDTL MISRTPEVTC  60
VVVDVSHEDP EVKFNWYVDG VEVHNAKTKP REEQYNSTYR VVSVLTVLHQ DWLNGKEYKC  120
KVSNKALPAP IEKTISKAKG QPREPQVYTL PPSRDELTKN QVSLTCLVKG FYPSDIAVEW  180
ESNGQPENNY KTTPPVLDSD GSFFLYSKLT VDKSRWQQGN VFSCSVMHEA LHNHYTQKSL  240
SLSPGK                                                             246
```

```
SEQ ID NO: 81          moltype = AA  length = 327
FEATURE                Location/Qualifiers
REGION                 1..327
                       note = Description of sequence: IgG4 Fc GenBank P01861
source                 1..327
                       mol_type = protein
                       organism = Homo sapiens
SEQUENCE: 81
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 82          moltype = AA  length = 223
FEATURE                Location/Qualifiers
REGION                 1..223
                       note = Description of sequence: IgG4 Fc Segment
source                 1..223
                       mol_type = protein
                       organism = Homo sapiens
SEQUENCE: 82
PPCPSCPAPE FLGGPSVFLF PPKPKDTLMI SRTPEVTCVV VDVSQEDPEV QFNWYVDGVE  60
VHNAKTKPRE EQFNSTYRVV SVLTVLHQDW LNGKEYKCKV SNKGLPSSIE KTISKAKGQP  120
REPQVYTLPP SQEEMTKNQV SLTCLVKGFY PSDIAVEWES NGQPENNYKT TPPVLDSDGS  180
FFLYSRLTVD KSRWQEGNVF SCSVMHEALH NHYTQKSLSL SPG                    223

SEQ ID NO: 83          moltype = AA  length = 276
FEATURE                Location/Qualifiers
REGION                 1..276
                       note = Description of sequence: IgM Fc regions
source                 1..276
                       mol_type = protein
                       organism = Homo sapiens
SEQUENCE: 83
VTSTLTIKZS DWLGESMFTC RVDHRGLTFQ QNASSMCVPD QDTAIRVFAI PPSFASIFLT  60
KSTKLTCLVT DLTTYBSVTI SWTREENGAV KTHTNISESH PNATFSAVGE ASICEDBDWS  120
GERFTCTVTH TDLPSPLKQT ISRPKGVALH RPBVYLLPPA RZZLNLRESA TITCLVTGFS  180
PADVFVEWMQ RGEPLSPQKY VTSAPMPEPQ APGRYFAHSI LTVSEEEWNT GGTYTCVVAH  240
EALPNRVTER TVDKSTGKPT LYNVSLVMSD TAGTCY                            276

SEQ ID NO: 84          moltype = AA  length = 159
FEATURE                Location/Qualifiers
REGION                 1..159
                       note = Description of sequence: j-chain sequences
source                 1..159
                       mol_type = protein
                       organism = Homo sapiens
SEQUENCE: 84
MKNHLLFWGV LAVFIKAVHV KAQEDERIVL VDNKCKCARI TSRIIRSSED PNEDIVERNI  60
RIIVPLNNRE NISDPTSPLR TRFVYHLSDL CKKCDPTEVE LDNQIVTATQ SNICDEDSAT  120
ETCYTYDRNK CYTAVVPLVY GGETKMVETA LTPDACYPD                         159

SEQ ID NO: 85          moltype = AA  length = 112
FEATURE                Location/Qualifiers
REGION                 1..112
                       note = Description of sequence: Ig CH1 domain
source                 1..112
                       mol_type = protein
                       organism = Homo sapiens
SEQUENCE: 85
FTVRETASTK GPSVFPLAPS SKSTSGGTAA LGCLVKDYFP EPVTVSWNSG ALTSGVHTFP  60
AVLQSSGLYS LSSVVTVPSS SLGTQTYICN VNHKPSNTKV DKKVEPKSCD KT          112

SEQ ID NO: 86          moltype = AA  length = 106
FEATURE                Location/Qualifiers
REGION                 1..106
                       note = Description of sequence: Ig Kappa chain constant
                        region
source                 1..106
                       mol_type = protein
                       organism = Homo sapiens
SEQUENCE: 86
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC                 106

SEQ ID NO: 87          moltype = AA  length = 106
FEATURE                Location/Qualifiers
```

```
REGION                  1..106
                        note = Description of sequence: Ig Lambda chain constant
                         region
source                  1..106
                        mol_type = protein
                        organism = Homo sapiens
SEQUENCE: 87
GQPKANPTVT LFPPSSEELQ ANKATLVCLI SDFYPGAVTV AWKADGSPVK AGVETTKPSK  60
QSNNKYAASS YLSLTPEQWK SHRSYSCQVT HEGSTVEKTV APTECS                106

SEQ ID NO: 88           moltype = AA  length = 33
FEATURE                 Location/Qualifiers
REGION                  1..33
                        note = Description of sequence: leucine-zipper polypeptide
source                  1..33
                        mol_type = protein
                        organism = Homo sapiens
SEQUENCE: 88
RMKQIEDKIE EILSKIYHIE NEIARIKKLI GER                               33

SEQ ID NO: 89           moltype = AA  length = 32
FEATURE                 Location/Qualifiers
REGION                  1..32
                        note = Description of sequence: leucine-zipper polypeptide
source                  1..32
                        mol_type = protein
                        organism = Homo sapiens
SEQUENCE: 89
LSSIEKKQEE QTSWLIWISN ELTLIRNELA QS                                32

SEQ ID NO: 90           moltype = AA  length = 31
FEATURE                 Location/Qualifiers
REGION                  1..31
                        note = Description of sequence: leucine-zipper polypeptide
source                  1..31
                        mol_type = protein
                        organism = Homo sapiens
SEQUENCE: 90
LSSIEKKLEE ITSQLIQISN ELTLIRNELA Q                                 31

SEQ ID NO: 91           moltype = AA  length = 31
FEATURE                 Location/Qualifiers
REGION                  1..31
                        note = Description of sequence: leucine-zipper polypeptide
source                  1..31
                        mol_type = protein
                        organism = Homo sapiens
SEQUENCE: 91
LSSIEKKLEE ITSQLIQIRN ELTLIRNELA Q                                 31

SEQ ID NO: 92           moltype = AA  length = 31
FEATURE                 Location/Qualifiers
REGION                  1..31
                        note = Description of sequence: leucine-zipper polypeptide
source                  1..31
                        mol_type = protein
                        organism = Homo sapiens
SEQUENCE: 92
LSSIEKKLEE ITSQLQQIRN ELTLIRNELA Q                                 31

SEQ ID NO: 93           moltype = AA  length = 31
FEATURE                 Location/Qualifiers
REGION                  1..31
                        note = Description of sequence: leucine-zipper polypeptide
source                  1..31
                        mol_type = protein
                        organism = Homo sapiens
SEQUENCE: 93
LSSLEKKLEE LTSQLIQLRN ELTLLRNELA Q                                 31

SEQ ID NO: 94           moltype = AA  length = 31
FEATURE                 Location/Qualifiers
REGION                  1..31
                        note = Description of sequence: leucine-zipper polypeptide
source                  1..31
                        mol_type = protein
                        organism = Homo sapiens
SEQUENCE: 94
ISSLEKKIEE LTSQIQQLRN EITLLRNEIA Q                                 31
```

```
SEQ ID NO: 95          moltype = AA  length = 47
FEATURE                Location/Qualifiers
REGION                 1..47
                       note = Description of sequence: leucine-zipper polypeptide
source                 1..47
                       mol_type = protein
                       organism = Homo sapiens
SEQUENCE: 95
LEIEAAFLER ENTALETRVA ELRQRVQRLR NRVSQYRTRY GPLGGGK                47

SEQ ID NO: 96          moltype = AA  length = 31
FEATURE                Location/Qualifiers
REGION                 1..31
                       note = Description of sequence: coiled-coil polypeptide
source                 1..31
                       mol_type = protein
                       organism = Homo sapiens
SEQUENCE: 96
LKSVENRLAV VENQLKTVIE ELKTVKDLLS N                                 31

SEQ ID NO: 97          moltype = AA  length = 31
FEATURE                Location/Qualifiers
REGION                 1..31
                       note = Description of sequence: coiled-coil polypeptide
source                 1..31
                       mol_type = protein
                       organism = Homo sapiens
SEQUENCE: 97
LARIEEKLKT IKAQLSEIAS TLNMIREQLA Q                                 31

SEQ ID NO: 98          moltype = AA  length = 31
FEATURE                Location/Qualifiers
REGION                 1..31
                       note = Description of sequence: coiled-coil polypeptide
source                 1..31
                       mol_type = protein
                       organism = Homo sapiens
SEQUENCE: 98
VSRLEEKVKT LKSQVTELAS TVSLLREQVA Q                                 31

SEQ ID NO: 99          moltype = AA  length = 30
FEATURE                Location/Qualifiers
REGION                 1..30
                       note = Description of sequence: coiled-coil polypeptide
source                 1..30
                       mol_type = protein
                       organism = Homo sapiens
SEQUENCE: 99
IQSEKKIEDI SSLIGQIQSE ITLIRNEIAQ                                   30

SEQ ID NO: 100         moltype = AA  length = 31
FEATURE                Location/Qualifiers
REGION                 1..31
                       note = Description of sequence: coiled-coil polypeptide
source                 1..31
                       mol_type = protein
                       organism = Homo sapiens
SEQUENCE: 100
LMSLEKKLEE LTQTLMQLQN ELSMLKNELA Q                                 31

SEQ ID NO: 101         moltype = AA  length = 18
FEATURE                Location/Qualifiers
REGION                 1..18
                       note = Description of sequence: FasL polypeptide
source                 1..18
                       mol_type = protein
                       organism = Homo sapiens
SEQUENCE: 101
VDLEGSTSNG RQCAGIRL                                                18

SEQ ID NO: 102         moltype = AA  length = 27
FEATURE                Location/Qualifiers
REGION                 1..27
                       note = Description of sequence: FasL polypeptide
source                 1..27
                       mol_type = protein
                       organism = Homo sapiens
SEQUENCE: 102
```

```
EDDVTTTEEL APALVPPPKG TCAGWMA                                 27

SEQ ID NO: 103         moltype = AA  length = 27
FEATURE                Location/Qualifiers
REGION                 1..27
                       note = Description of sequence: FasL polypeptide
source                 1..27
                       mol_type = protein
                       organism = Homo sapiens
SEQUENCE: 103
GHDQETTTQG PGVLLPLPKG ACTGQMA                                 27

SEQ ID NO: 104         moltype = AA  length = 64
FEATURE                Location/Qualifiers
REGION                 1..64
                       note = Description of sequence: collagen oligomerization
                        peptide
source                 1..64
                       mol_type = protein
                       organism = Homo sapiens
SEQUENCE: 104
VTAFSNMDDM LQKAHLVIEG TFIYLRDSTE FFIRVRDGWK KLQLGELIPI PADSPPPPAL  60
SSNP                                                          64

SEQ ID NO: 105         moltype = AA  length = 112
FEATURE                Location/Qualifiers
REGION                 1..112
                       note = Description of sequence: A TGF-beta-1 amino acid
                        sequence
source                 1..112
                       mol_type = protein
                       organism = Homo sapiens
SEQUENCE: 105
ALDTNYCFSS TEKNCCVRQL YIDFRKDLGW KWIHEPKGYH ANFCLGPCPY IWSLDTQYSK  60
VLALYNQHNP GASAAPCCVP QALEPLPIVY YVGRKPKVEQ LSNMIVRSCK CS          112

SEQ ID NO: 106         moltype = AA  length = 390
FEATURE                Location/Qualifiers
REGION                 1..390
                       note = Description of sequence: TGF-Beta-1 preproprotein
                        NCBI Ref. Seq. NP_000651.3
source                 1..390
                       mol_type = protein
                       organism = Homo sapiens
DOMAIN                 1..29
                       note = 1..29 forming the Signal Peptide
DOMAIN                 29..261
                       note = 29..261 forming the TGF-Beta propeptide
DOMAIN                 244..246
                       note = 244..246 forming the Cell attachment site
DOMAIN                 279..390
                       note = 279..390 forming the mature peptide
SEQUENCE: 106
MPPSGLRLLP LLLPLLWLLV LTPGRPAAGL STCKTIDMEL VKRKRIEAIR GQILSKLRLA  60
SPPSQGEVPP GPLPEAVLAL YNSTRDRVAG ESAEPEPEPE ADYYAKEVTR VLMVETHNEI  120
YDKFKQSTHS IYMFFNTSEL REAVPEPVLL SRAELRLLRL KLKVEQHVEL YQKYSNNSWR  180
YLSNRLLAPS DSPEWLSFDV TGVVRQWLSR GGEIEGFRLS AHCSCDSRDN TLQVDINGFT  240
TGRRGDLATI HGMNRPFLLL MATPLERAQH LQSSRHRRAL DTNYCFSSTE KNCCVRQLYI  300
DFRKDLGWKW IHEPKGYHAN FCLGPCPYIW SLDTQYSKVL ALYNQHNPGA SAAPCCVPQA  360
LEPLPIVYYV GRKPKVEQLS NMIVRSCKCS                              390

SEQ ID NO: 107         moltype = AA  length = 112
FEATURE                Location/Qualifiers
REGION                 1..112
                       note = Description of sequence: A TGF-Beta-1 polypeptide
source                 1..112
                       mol_type = protein
                       organism = Homo sapiens
SEQUENCE: 107
ALDTNYCFSS TEKNCCVRQL YIDFRKDLGW KWIHEPKGYH ANFCLGPCPY IWSLDTQYSK  60
VLALYNQHNP GASAAPSCVP QALEPLPIVY YVGRKPKVEQ LSNMIVRSCK CS          112

SEQ ID NO: 108         moltype = AA  length = 112
FEATURE                Location/Qualifiers
REGION                 1..112
                       note = Description of sequence: A TGF-Beta-2 amino acid
                        sequence
source                 1..112
                       mol_type = protein
```

```
                        organism = Homo sapiens
SEQUENCE: 108
ALDAAYCFRN VQDNCCLRPL YIDFKRDLGW KWIHEPKGYN ANFCAGACPY LWSSDTQHSR  60
VLSLYNTINP EASASPCCVS QDLEPLTILY YIGKTPKIEQ LSNMIVKSCK CS          112

SEQ ID NO: 109          moltype = AA  length = 413
FEATURE                 Location/Qualifiers
REGION                  1..413
                        note = Description of sequence:A TGF-Beta-2 preproprotein
                         GenBank: AAA50405.1
source                  1..413
                        mol_type = protein
                        organism = Homo sapiens
DOMAIN                  1..20
                        note = 1..20 forming the Signal Peptide
DOMAIN                  21..227
                        note = 21..227 forming the TGF-Beta- propeptide
DOMAIN                  302..413
                        note =  302..413 forming the mature peptide
SEQUENCE: 109
MHYCVLSAFL ILHLVTVALS LSTCSTLDMD QFMRKRIEAI RGQILSKLKL TSPPEDYPEP  60
EEVPPEVISI YNSTRDLLQE KASRRAAACE RERSDEEYYA KEVYKIDMPP FFPSEAIPPT  120
FYRPYFRIVR FDVSAMEKNA SNLVKAEFRV FRLQNPKARV PEQRIELYQI LKSKDLTSPT  180
QRYIDSKVVK TRAEGEWLSF DVTDAVHEWL HHKDRNLGFK ISLHCPCCTF VPSNNYIIPN  240
KSEELEARFA GIDGTSTYTS GDQKTIKSTR KKNSGKTPHL LLMLLPSYRL ESQQTNRRKK  300
RALDAAYCFR NVQDNCCLRP LYIDFKRDLG WKWIHEPKGY NANFCAGACP YLWSSDTQHS  360
RVLSLYNTIN PEASASPCCV SQDLEPLTIL YYIGKTPKIE QLSNMIVKSC KCS         413

SEQ ID NO: 110          moltype = AA  length = 112
FEATURE                 Location/Qualifiers
REGION                  1..112
                        note = Description of sequence: A TGF-Beta-2 amino acid
                         sequence
source                  1..112
                        mol_type = protein
                        organism = Homo sapiens
SEQUENCE: 110
ALDAAYCFRN VQDNCCLRPL YIDFKRDLGW KWIHEPKGYN ANFCAGACPY LWSSDTQHSR  60
VLSLYNTINP EASASPSCVS QDLEPLTILY YIGKTPKIEQ LSNMIVKSCK CS          112

SEQ ID NO: 111          moltype = AA  length = 112
FEATURE                 Location/Qualifiers
REGION                  1..112
                        note = Description of sequence: Mature TGF-Beta--3 isoform
                         1 NCBI Ref. Seq. NP_001316868.1  UniProt Ref.: P10600.1
source                  1..112
                        mol_type = protein
                        organism = Homo sapiens
SEQUENCE: 111
ALDTNYCFRN LEENCCVRPL YIDFRQDLGW KWVHEPKGYY ANFCSGPCPY LRSADTTHST  60
VLGLYNTLNP EASASPCCVP QDLEPLTILY YVGRTPKVEQ LSNMVVKSCK CS          112

SEQ ID NO: 112          moltype = AA  length = 412
FEATURE                 Location/Qualifiers
REGION                  1..412
                        note = Description of sequence: TGF-Beta-3 preproprotein
                         isoform 1 NCBI Ref. Seq. NP_001316868.1  UniProt Ref.:
                         P10600.1
source                  1..412
                        mol_type = protein
                        organism = Homo sapiens
DOMAIN                  1..23
                        note = 1..23 forming the Signal Peptide
DOMAIN                  24..300
                        note = 24..300 forming the mature latency associated
                         peptide
DOMAIN                  24..230
                        note = 24..230 forming the TGF-beta propeptide'
DOMAIN                  261..263
                        note = 261..263 forming the Cell attachment site
DOMAIN                  301..412
                        note =  301..412 forming the mature peptide
SEQUENCE: 112
MKMHLQRALV VLALLNFATV SLSLSTCTTL DFGHIKKKRV EAIRGQILSK LRLTSPPEPT  60
VMTHVPYQVL ALYNSTRELL EEMHGEREEG CTQENTESEY YAKEIHKFDM IQGLAEHNEL  120
AVCPKGITSK VFRFNVSSVE KNRTNLFRAE FRVLRVPNPS SKRNEQRIEL FQILRPDEHI  180
AKQRYIGGKN LPTRGTAEWL SFDVTDTVRE WLLRRESNLG LEISIHCPCH TFQPNGDILE  240
NIHEVMEIKF KGVDNEDDHG RGDLGRLKKQ KDHHNPHLIL MMIPPHRLDN PGQGGQRKKR  300
ALDTNYCFRN LEENCCVRPL YIDFRQDLGW KWVHEPKGYY ANFCSGPCPY LRSADTTHST  360
```

```
VLGLYNTLNP EASASPCCVP QDLEPLTILY YVGRTPKVEQ LSNMVVKSCK CS          412

SEQ ID NO: 113          moltype = AA  length = 112
FEATURE                 Location/Qualifiers
REGION                  1..112
                        note = Description of sequence: Mature TGF-Beta--3 isoform
                         1 Mutant: C77S
source                  1..112
                        mol_type = protein
                        organism = Homo sapiens
SEQUENCE: 113
ALDTNYCFRN LEENCCVRPL YIDFRQDLGW KWVHEPKGYY ANFCSGPCPY LRSADTTHST  60
VLGLYNTLNP EASASPSCVP QDLEPLTILY YVGRTPKVEQ LSNMVVKSCK CS          112

SEQ ID NO: 114          moltype = AA  length = 503
FEATURE                 Location/Qualifiers
REGION                  1..503
                        note = Description of sequence: TGF-Beta- receptor type-1
                         isoform 1 precursor, NCBI Ref. Seq.  NP_004603.1 and
                         UniProtKB/Swiss-Prot: P36897.1
source                  1..503
                        mol_type = protein
                        organism = Homo sapiens
DOMAIN                  1..33
                        note = 1..33 forming the signal peptide
DOMAIN                  34..126
                        note = 34-126 forming the extracellular region (ectodomain)

DOMAIN                  127..147
                        note = 127-147 forming the transmembrane region
DOMAIN                  176..203
                        note = 176..203 forming the Transforming growth factor beta
                         type I GS-motif
DOMAIN                  205..492
                        note = 205..492 forming the Protein tyrosine kinase
DOMAIN                  205..496
                        note = 209..496 forming the Catalytic domain of the
                         Serine/Threonine Kinases
SEQUENCE: 114
MEAAVAAPRP RLLLLVLAAA AAAAAALLPG ATALQCFCHL CTKDNFTCVT DGLCFVSVTE  60
TTDKVIHNSM CIAEIDLIPR DRPFVCAPSS KTGSVTTTYC CNQDHCNKIE LPTTVKSSPG  120
LGPVELAAVI AGPVCFVCIS LMLMVYICHN RTVIHHRVPN EEDPSLDRPF ISEGTTLKDL  180
IYDMTTSGSG SGLPLLVQRT IARTIVLQES IGKGRFGEVW RGKWRGEEVA VKIFSSREER  240
SWFREAEIYQ TVMLRHENIL GFIAADNKDN GTWTQLWLVS DYHEHGSLFD YLNRYTVTVE  300
GMIKLALSTA SGLAHLHMEI VGTQGKPAIA HRDLKSKNIL VKKNGTCCIA DLGLAVRHDS  360
ATDTIDIAPN HRVGTKRYMA PEVLDDSINM KHFESFKRAD IYAMGLVFWE IARRCSIGGI  420
HEDYQLPYYD LVPSDPSVEE MRKVVCEQKL RPNIPNRWQS CEALRVMAKI MRECWYANGA  480
ARLTALRIKK TLSQLSQQEG IKM                                          503

SEQ ID NO: 115          moltype = AA  length = 93
FEATURE                 Location/Qualifiers
REGION                  1..93
                        note = Description of sequence: TGF-Beta- receptor type-1
                         isoform 1 ectodomain
source                  1..93
                        mol_type = protein
                        organism = Homo sapiens
SEQUENCE: 115
LQCFCHLCTK DNFTCVTDGL CFVSVTETTD KVIHNSMCIA EIDLIPRDRP FVCAPSSKTG  60
SVTTTYCCNQ DHCNKIELPT TVKSSPGLGP VEL                               93

SEQ ID NO: 116          moltype = AA  length = 592
FEATURE                 Location/Qualifiers
REGION                  1..592
                        note = Description of sequence: sapiens TGF-Beta- receptor
                         type-2 (TBeta-RII) isoform A precursor
source                  1..592
                        mol_type = protein
                        organism = Homo sapiens
DOMAIN                  1..23
                        note = 1..23 forming the signal peptide
DOMAIN                  24..592
                        note = 24..592 forming the mature peptide
DOMAIN                  24..177
                        note = 24..177 forming the extracellular region (ectodomain)
SEQUENCE: 116
MGRGLLRGLW PLHIVLWTRI ASTIPPHVQK SDVEMEAQKD EIICPSCNRT AHPLRHINND  60
MIVTDNNGAV KFPQLCKFCD VRFSTCDNQK SCMSNCSITS ICEKPQEVCV AVWRKNDENI  120
TLETVCHDPK LPYHDFILED AASPKCIMKE KKKPGETFFM CSCSSDECND NIIFSEEYNT  180
```

```
SNPDLLLVIF QVTGISLLPP LGVAISVIII FYCYRVNRQQ KLSSTWETGK TRKLMEFSEH  240
CAIILEDDRS DISSTCANNI NHNTELLPIE LDTLVGKGRF AEVYKAKLKQ NTSEQFETVA  300
VKIFPYEEYA SWKTEKDIFS DINLKHENIL QFLTAEERKT ELGKQYWLIT AFHAKGNLQE  360
YLTRHVISWE DLRKLGSSLA RGIAHLHSDH TPCGRPKMPI VHRDLKSSNI LVKNDLTCCL  420
CDFGLSLRLD PTLSVDDLAN SGQVGTARYM APEVLESRMN LENVESFKQT DVYSMALVLW  480
EMTSRCNAVG EVKDYEPPFG SKVREHPCVE SMKDNVLRDR GRPEIPSFWL NHQGIQMVCE  540
TLTECWDHDP EARLTAQCVA ERFSELEHLD RLSGRSCSEE KIPEDGSLNT TK          592

SEQ ID NO: 117         moltype = AA  length = 154
FEATURE                Location/Qualifiers
REGION                 1..154
                       note = Description of sequence: TGF-Beta- receptor type-2
                        (TBeta-RII) isoform A ectodomain
source                 1..154
                       mol_type = protein
                       organism = Homo sapiens
SEQUENCE: 117
IPPHVQKSDV EMEAQKDEII CPSCNRTAHP LRHINNDMIV TDNNGAVKFP QLCKFCDVRF  60
STCDNQKSCM SNCSITSICE KPQEVCVAVW RKNDENITLE TVCHDPKLPY HDFILEDAAS  120
PKCIMKEKKK PGETFFMCSC SSDECNDNII FSEE                              154

SEQ ID NO: 118         moltype = AA  length = 567
FEATURE                Location/Qualifiers
REGION                 1..567
                       note = Description of sequence: TGF-Beta- receptor type-2
                        (TBeta-RII) isoform B precursor, UniProtKB Ref. P37173,
                        NCBI Ref. Seq. NP_003233.4
source                 1..567
                       mol_type = protein
                       organism = Homo sapiens
DOMAIN                 1..23
                       note = 1..23 foming the Signal peptide  24..567 foming the
                        Mature peptide  24..166 foming the Transforming growth
                        factor beta receptor 2 ectodomain
DOMAIN                 24..567
                       note = 24..567 foming the Mature peptide
DOMAIN                 24..166
                       note = 24..166 foming the Transforming growth factor beta
                        receptor 2 ectodomain
SEQUENCE: 118
MGRGLLRGLW PLHIVLWTRI ASTIPPHVQK SVNNDMIVTD NNGAVKFPQL CKFCDVRFST  60
CDNQKSCMSN CSITSICEKP QEVCVAVWRK NDENITLETV CHDPKLPYHD FILEDAASPK  120
CIMKEKKKPG ETFFMCSCSS DECNDNIIFS EEYNTSNPDL LLVIFQVTGI SLLPPLGVAI  180
SVIIIFYCYR VNRQQKLSST WETGKTRKLM EFSEHCAIIL EDDRSDISST CANNINHNTE  240
LLPIELDTLV GKGRFAEVYK AKLKQNTSEQ FETVAVKIFP YEEYASWKTE KDIFSDINLK  300
HENILQFLTA EERKTELGKQ YWLITAFHAK GNLQEYLTRH VISWEDLRKL GSSLARGIAH  360
LHSDHTPCGR PKMPIVHRDL KSSNILVKND LTCCLCDFGL SLRLDPTLSV DDLANSGQVG  420
TARYMAPEVL ESRMNLENVE SFKQTDVYSM ALVLWEMTSR CNAVGEVKDY EPPFGSKVRE  480
HPCVESMKDN VLRDRGRPEI PSFWLNHQGI QMVCETLTEC WDHDPEARLT AQCVAERFSE  540
LEHLDRLSGR SCSEEKIPED GSLNTTK                                      567

SEQ ID NO: 119         moltype = AA  length = 143
FEATURE                Location/Qualifiers
REGION                 1..143
                       note = Description of sequence: TGF-Beta- receptor type-2
                        (TBeta-RII) isoform B, ectodomain sequence
source                 1..143
                       mol_type = protein
                       organism = Homo sapiens
SEQUENCE: 119
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDLLLV IFQ                                          143

SEQ ID NO: 120         moltype = AA  length = 129
FEATURE                Location/Qualifiers
REGION                 1..129
                       note = Description of sequence: TGF-Beta- receptor type-2
                        (TBeta-RII) isoform B, ectodomain fragment sequence
source                 1..129
                       mol_type = protein
                       organism = Homo sapiens
SEQUENCE: 120
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEE                                                          129

SEQ ID NO: 121         moltype = AA  length = 115
FEATURE                Location/Qualifiers
```

```
REGION                  1..115
                        note = Description of sequence: TGF-Beta- receptor type-2
                         isoform B, ectodomain fragment Delta14 (N-terminus) with a
                          D118A substitution
source                  1..115
                        mol_type = protein
                        organism = Homo sapiens
SEQUENCE: 121
VTDNNGAVKF PQLCKFCDVR FSTCDNQKSC MSNCSITSIC EKPQEVCVAV WRKNDENITL  60
ETVCHDPKLP YHDFILEDAA SPKCIMKEKK KPGETFFMCS CSSDECNDNI IFSEE       115

SEQ ID NO: 122          moltype = AA  length = 104
FEATURE                 Location/Qualifiers
REGION                  1..104
                        note = Description of sequence: TGF-Beta- receptor type-2
                         (TBeta-RII) isoform B, ectodomain fragment Delta25
                         (N-terminus) with a D118A substitution
source                  1..104
                        mol_type = protein
                        organism = Homo sapiens
SEQUENCE: 122
QLCKFCDVRF STCDNQKSCM SNCSITSICE KPQEVCVAVW RKNDENITLE TVCHDPKLPY  60
HDFILEDAAS PKCIMKEKKK PGETFFMCSC SSDECNDNII FSEE                  104

SEQ ID NO: 123          moltype = AA  length = 111
FEATURE                 Location/Qualifiers
REGION                  1..111
                        note = Description of sequence: TGF-Beta- receptor type-2
                         (TBeta-RII) isoform B, ectodomain fragment Delta25
                         (N-terminus) with D118A substitution.  Position Asp at 7
                         (D32 of the precursor protein) may be substituted by
                         asparagine.
source                  1..111
                        mol_type = protein
                        organism = Homo sapiens
VARIANT                 7
                        note = position 7 may be asparagine
SEQUENCE: 123
QLCKFCDVRF STCDNQKSCM SNCSITSICE KPQEVCVAVW RKNDENITLE TVCHDPKLPY  60
HDFILEDAAS PKCIMKEKKK PGETFFMCSC SSAECNDNII FSEEYNTSNP D           111

SEQ ID NO: 124          moltype = AA  length = 851
FEATURE                 Location/Qualifiers
REGION                  1..851
                        note = Description of sequence: A TGF-Beta- receptor type 3
                         isoform A precursor, (BETA Glycan)
source                  1..851
                        mol_type = protein
                        organism = Homo sapiens
DOMAIN                  1..18
                        note = 1..18 forming the Signal peptide
DOMAIN                  27..787
                        note = 27..787 forming the Extracellular domain
                         (ectodomain)
DOMAIN                  788..809
                        note = 788-809 forming the Transmembrane domain
DOMAIN                  567..724
                        note = 567..724 forming the Zona pellucida-like domain
DOMAIN                  737..751
                        note = 737..751 forming the Interaction with TGF-beta
                         ligand
DOMAIN                  788..809
                        note = 788..809 forming the transmembrane region
SEQUENCE: 124
MTSHYVIAIF ALMSSCLATA GPEPGALCEL SPVSASHPVQ ALMESFTVLS GCASRGTTGL  60
PQEVHVLNLR TAGQGPGQLQ REVTLHLNPI SSVHIHHKSV VFLLNSPHPL VWHLKTERLA  120
TGVSRLFLVS EGSVVQFSSA NFSLTAETEE RNFPHGNEHL LNWARKEYGA VTSFTELKIA  180
RNIYIKVGED QVFPPKCNIG KNFLSLNYLA EYLQPKAAEG CVMSSQPQNE EVHIIELITP  240
NSNPYSAFQV DITIDIRPSQ EDLEVVKNLI LILKCKKSVN WVIKSFDVKG SLKIIAPNSI  300
GFGKESERSM TMTKSIRDDI PSTQGNLVKW ALDNGYSPIT SYTMAPVANR FHLRLENNAE  360
EMGDEEVHTI PPELRILLDP GALPALQNPP IRGGEGQNGG LPFPFPDISR RVWNEEGEDG  420
LPRPKDPVIP SIQLFPGLRE PEEVQGSVDI ALSVKCDNEK MIVAVEKDSF QASGYSGMDV  480
TLLDPTCKAK MNGTHFVLES PLNGCGTRPR WSALDGVVYY NSIVIQVPAL GDSSGWPDGY  540
EDLESGDNGF PGDMDEGDAS LFTRPEIVVF NCSLQQVRNP SSFQEQPHGN ITFNMELYNT  600
DLFLVPSQGV FSVPENGHVY VEVSVTKAEQ ELGFAIQTCF ISPYSNPDRM SHYTIIENIC  660
PKDESVKFYS PKRVHFPIPQ ADMDKKRFSF VFKPVFNTSL LFLQCELTLC TKMEKHPQKL  720
PKCVPPDEAC TSLDASIIWA MMQNKKTFTK PLAVIHHEAE SKEKGPSMKE PNPISPPIFH  780
GLDTLTVMGI AFAAFVIGAL LTGALWYIYS HTGETAGRQQ VPTSPPASEN SSAAHSIGST  840
QSTPCSSSST A                                                      851
```

```
SEQ ID NO: 125          moltype = AA  length = 850
FEATURE                 Location/Qualifiers
REGION                  1..850
                        note = Description of sequence: A TGF-Beta- receptor type 3
                         isoform B precursor, (BETA Glycan)
source                  1..850
                        mol_type = protein
                        organism = Homo sapiens
DOMAIN                  1..18
                        note = 1..18 forming the Signal peptide
DOMAIN                  27..786
                        note = 27..786 forming the Extracellular domain
                         (ectodomain)
DOMAIN                  566..723
                        note = 566..723 forming the Zona pellucida-like domain
DOMAIN                  726..750
                        note = 736..750 forming the Interaction with TGF-beta
                         ligand
DOMAIN                  787..808
                        note = 787..808 forming the transmembrane region
SEQUENCE: 125
MTSHYVIAIF ALMSSCLATA GPEPGALCEL SPVSASHPVQ ALMESFTVLS GCASRGTTGL  60
PQEVHVLNLR TAGQGPGQLQ REVTLHLNPI SSVHIHHKSV VFLLNSPHPL VWHLKTERLA  120
TGVSRLFLVS EGSVVQFSSA NFSLTAETEE RNFPHGNEHL LNWARKEYGA VTSFTELKIA  180
RNIYIKVGED QVFPPKCNIG KNFLSLNYLA EYLQPKAAEG CVMSSQPQNE EVHIIELITP  240
NSNPYSAFQV DITIDIRPSQ EDLEVVKNLI LILKCKKSVN WVIKSFDVKG SLKIIAPNSI  300
GFGKESERSM TMTKSIRDDI PSTQGNLVKW ALDNGYSPIT SYTMAPVANR FHLRLENNEE  360
MGDEEVHTIP PELRILLDPG ALPALQNPPI RGGEGQNGGL PFPFPDISRR VWNEEGEDGL  420
PRPKDPVIPS IQLFPGLREP EEVQGSVDIA LSVKCDNEKM IVAVEKDSFQ ASGYSGMDVT  480
LLDPTCKAKM NGTHFVLESP LNGCGTRPRW SALDGVVYYN SIVIQVPALG DSSGWPDGYE  540
DLESGDNGFP GDMDEGDASL FTRPEIVVFN CSLQQVRNPS SFQEQPHGNI TFNMELYNTD  600
LFLVPSQGVF SVPENGHVYV EVSVTKAEQE LGFAIQTCFI SPYSNPDRMS HYTIIENICP  660
KDESVKFYSP KRVHFPIPQA DMDKKRFSFV FKPVFNTSLL FLQCELTLCT KMEKHPQKLP  720
KCVPPDEACT SLDASIIWAM MQNKKTFTKP LAVIHHEAES KEKGPSMKEP NPISPPIFHG  780
LDTLTVMGIA FAAFVIGALL TGALWYIYSH TGETAGRQQV PTSPPASENS SAAHSIGSTQ  840
STPCSSSSTA                                                         850

SEQ ID NO: 126          moltype = AA  length = 150
FEATURE                 Location/Qualifiers
REGION                  1..150
                        note = Description of sequence: A linker sequence
source                  1..150
                        mol_type = protein
                        organism = synthetic construct
REGION                  1..150
                        note = Unit GGGSG repeated fom 1 to 30 times
SEQUENCE: 126
GSGGSGSGGS GSGGSGSGGS GSGGSGSGGS GSGGSGSGGS GSGGSGSGGS GSGGSGSGGS  60
GSGGSGSGGS GSGGSGSGGS GSGGSGSGGS GSGGSGSGGS GSGGSGSGGS GSGGSGSGGS  120
GSGGSGSGGS GSGGSGSGGS GSGGSGSGGS                                   150

SEQ ID NO: 127          moltype = AA  length = 120
FEATURE                 Location/Qualifiers
REGION                  1..120
                        note = Description of sequence: A linker sequence
source                  1..120
                        mol_type = protein
                        organism = synthetic construct
REGION                  1..120
                        note = Unit GGSG repeated fom 1 to 30 times
SEQUENCE: 127
GGGSGGGSGG GSGGGSGGGS GGGSGGGSGG GSGGGSGGGS GGGSGGGSGG GSGGGSGGGS  60
GGGSGGGSGG GSGGGSGGGS GGGSGGGSGG GSGGGSGGGS GGGSGGGSGG GSGGGSGGGS  120

SEQ ID NO: 128          moltype = AA  length = 40
FEATURE                 Location/Qualifiers
REGION                  1..40
                        note = Description of sequence: A linker sequence
source                  1..40
                        mol_type = protein
                        organism = synthetic construct
REGION                  1..40
                        note = Unit GGSG repeated fom 1 to 10 times
SEQUENCE: 128
GGSGGGSGGG SGGGSGGGSG GGSGGGSGGG SGGGSGGGSG                        40

SEQ ID NO: 129          moltype = AA  length = 50
FEATURE                 Location/Qualifiers
```

```
REGION                  1..50
                        note = Description of sequence: A linker sequence
source                  1..50
                        mol_type = protein
                        organism = synthetic construct
REGION                  1..50
                        note = Unit GGSGG repeated fom 1 to 10 times
SEQUENCE: 129
GGSGGGGSGG GGSGGGGSGG GGSGGGGSGG GGSGGGGSGG GGSGGGGSGG            50

SEQ ID NO: 130          moltype = AA  length = 50
FEATURE                 Location/Qualifiers
REGION                  1..50
                        note = Description of sequence: A linker sequence
source                  1..50
                        mol_type = protein
                        organism = synthetic construct
REGION                  1..50
                        note = Unit GSGGG repeated fom 1 to 10 times
SEQUENCE: 130
GSGSGGSGSG GSGSGGSGSG GSGSGGSGSG GSGSGGSGSG GSGSGGSGSG            50

SEQ ID NO: 131          moltype = AA  length = 50
FEATURE                 Location/Qualifiers
REGION                  1..50
                        note = Description of sequence: A linker sequence
source                  1..50
                        mol_type = protein
                        organism = synthetic construct
REGION                  1..50
                        note = Unit GSGSG repeated fom 1 to 10 times
SEQUENCE: 131
GSGGGGSGGG GSGGGGSGGG GSGGGGSGGG GSGGGGSGGG GSGGGGSGGG            50

SEQ ID NO: 132          moltype = AA  length = 50
FEATURE                 Location/Qualifiers
REGION                  1..50
                        note = Description of sequence: A linker sequence
source                  1..50
                        mol_type = protein
                        organism = synthetic construct
REGION                  1..50
                        note = Unit GGGSG repeated fom 1 to 10 times
SEQUENCE: 132
GGGSGGGGSG GGGSGGGGSG GGGSGGGGSG GGGSGGGGSG GGGSGGGGSG            50

SEQ ID NO: 133          moltype = AA  length = 50
FEATURE                 Location/Qualifiers
REGION                  1..50
                        note = Description of sequence: A linker sequence
source                  1..50
                        mol_type = protein
                        organism = synthetic construct
REGION                  1..50
                        note = Unit GSSSG repeated fom 1 to 10 times
SEQUENCE: 133
GSSSGGSSSG GSSSGGSSSG GSSSGGSSSG GSSSGGSSSG GSSSGGSSSG            50

SEQ ID NO: 134          moltype = AA  length = 40
FEATURE                 Location/Qualifiers
REGION                  1..40
                        note = Description of sequence: A linker sequence
source                  1..40
                        mol_type = protein
                        organism = synthetic construct
REGION                  1..40
                        note = Unit GGSG repeated fom 1 to 10 times
SEQUENCE: 134
GGSGGGSGGG SGGGSGGGSG GGSGGGSGGG SGGGSGGGSG                       40

SEQ ID NO: 135          moltype = AA  length = 50
FEATURE                 Location/Qualifiers
REGION                  1..50
                        note = Description of sequence: A linker sequence
source                  1..50
                        mol_type = protein
                        organism = synthetic construct
REGION                  1..50
                        note = Unit GSSSS repeated fom 1 to 10 times
```

```
SEQUENCE: 135
GSSSSGSSSS GSSSSGSSSS GSSSSGSSSS GSSSSGSSSS GSSSSGSSSS             50

SEQ ID NO: 136          moltype = AA  length = 50
FEATURE                 Location/Qualifiers
REGION                  1..50
                        note = Description of sequence: A linker sequence
source                  1..50
                        mol_type = protein
                        organism = synthetic construct
REGION                  1..50
                        note = Unit GSSSS repeated fom 1 to 10 times
SEQUENCE: 136
GGGGSGGGGS GGGGSGGGGS GGGGSGGGGS GGGGSGGGGS GGGGSGGGGS             50

SEQ ID NO: 137          moltype = AA  length = 150
FEATURE                 Location/Qualifiers
REGION                  1..150
                        note = Description of sequence: A linker sequence
source                  1..150
                        mol_type = protein
                        organism = synthetic construct
REGION                  1..150
                        note = Unit GCGASGGGGSGGGGS repeated fom 1 to 10 times
SEQUENCE: 137
GCGASGGGGS GGGGSGCGAS GGGGSGGGGS GCGASGGGGS GGGGSGCGAS GGGGSGGGGS  60
GCGASGGGGS GGGGSGCGAS GGGGSGGGGS GCGASGGGGS GGGGSGCGAS GGGGSGGGGS  120
GCGASGGGGS GGGGSGCGAS GGGGSGGGGS                                   150

SEQ ID NO: 138          moltype = AA  length = 124
FEATURE                 Location/Qualifiers
REGION                  1..124
                        note = Description of sequence: wild-type PD-1 polypeptide
source                  1..124
                        mol_type = protein
                        organism = Homo sapiens
SEQUENCE: 138
AFTVTVPKDL YVVEYGSNMT IECKFPVEKQ LDLAALIVYW EMEDKNIIQF VHGEEDLKTQ  60
HSSYRQRARL LKDQLSLGNA ALQITDVKLQ DAGVYRCMIS YGGADYKRIT VKVNAPYAAA  120
LHEH                                                               124

SEQ ID NO: 139          moltype = AA  length = 133
FEATURE                 Location/Qualifiers
REGION                  1..133
                        note = Description of sequence: Human Peptide
source                  1..133
                        mol_type = protein
                        organism = Homo sapiens
VARIANT                 20
                        note = X at position 20 is any amino acid other than Asp
VARIANT                 42
                        note = X at position 42 is any amino acid other than Phe
VARIANT                 45
                        note = X at position 45 is any amino acid other than Tyr
VARIANT                 126
                        note = X at position 126 is any amino acid other than Gln
REGION                  20..126
                        note =  In some cases position 20 is Ala. In some cases
                         position 42 is Ala. In some cases position 45 is Ala. In
                         some cases position 126 is Ala. In some cases postions 20
                         42 45 and 126 are Ala
SEQUENCE: 139
APTSSSTKKT QLQLEHLLLX LQMILNGINN YKNPKLTRML TXKFXMPKKA TELKHLQCLE  60
EELKPLEEVL NLAQSKNFHL RPRDLISNIN VIVLELKGSE TTFMCEYADE TATIVEFLNR  120
WITFCXSIIS TLT                                                     133

SEQ ID NO: 140          moltype = AA  length = 133
FEATURE                 Location/Qualifiers
REGION                  1..133
                        note = Description of sequence: Human Peptide
source                  1..133
                        mol_type = protein
                        organism = Homo sapiens
VARIANT                 16
                        note = X at position 16  is any amino acid other than His
VARIANT                 20
                        note = X at position 20 is any amino acid other than Asp
VARIANT                 42
                        note = X at position 42 is any amino acid other than Phe
```

```
VARIANT                 45
                        note = X at position 45 is any amino acid other than Tyr
VARIANT                 126
                        note = X at position 126 is any amino acid other than Gln
REGION                  16..126
                        note = In some cases position 16 is Ala. In some cases
                         position 20 is Ala. In some cases position 42 is Ala. In
                         some cases position 45 is Ala. In some cases position 126
                         is Ala. In some cases any two three four or all five of
                         postions 16 20 42 45 and 126 are Ala.
SEQUENCE: 140
APTSSSTKKT QLQLEXLLLX LQMILNGINN YKNPKLTRML TXKFXMPKKA TELKHLQCLE  60
EELKPLEEVL NLAQSKNFHL RPRDLISNIN VIVLELKGSE TTFMCEYADE TATIVEFLNR  120
WITFCXSIIS TLT                                                     133

SEQ ID NO: 141          moltype = AA  length = 133
FEATURE                 Location/Qualifiers
REGION                  1..133
                        note = Description of sequence: Human Peptide
source                  1..133
                        mol_type = protein
                        organism = Homo sapiens
VARIANT                 16
                        note = X at position 16  is any amino acid other than His
VARIANT                 42
                        note = X at position 42 is any amino acid other than Phe
VARIANT                 126
                        note = X at position 126 is any amino acid other than Gln
REGION                  16..126
                        note =  In some cases position 20 is Ala. In some cases
                         position 42 is Ala. In some cases position 126 is Ala. In
                         some cases any two or all three of postions 20 42 and 126
                         are Ala.
SEQUENCE: 141
APTSSSTKKT QLQLEXLLLD LQMILNGINN YKNPKLTRML TXKFYMPKKA TELKHLQCLE  60
EELKPLEEVL NLAQSKNFHL RPRDLISNIN VIVLELKGSE TTFMCEYADE TATIVEFLNR  120
WITFCXSIIS TLT                                                     133

SEQ ID NO: 142          moltype = AA  length = 8
FEATURE                 Location/Qualifiers
REGION                  1..8
                        note = Description of sequence: insertion element between
                         N49 and K50 of human IL-10
source                  1..8
                        mol_type = protein
                        organism = Homo sapiens
SEQUENCE: 142
GGGGSGGG                                                           8

SEQ ID NO: 143          moltype = AA  length = 281
FEATURE                 Location/Qualifiers
REGION                  1..281
                        note = Description of sequence: A wild-type Homo sapiens
                         FasL protein
source                  1..281
                        mol_type = protein
                        organism = Homo sapiens
DOMAIN                  1..80
                        note = 1-80 forms the cytoplasmic domain
DOMAIN                  81..102
                        note = 81-102 forms the transmembrane domain
DOMAIN                  103..281
                        note = aas 103-281 forms the extracellular (ectodomain)
                         domain
SEQUENCE: 143
MQQPFNYPYP QIYWVDSSAS SPWAPPGTVL PCPTSVPRRP GQRRPPPPPP PPPLPPPPPP  60
PPLPPLPLPP LKKRGNHSTG LCLLVMFFMV LVALVGLGLG MFQLFHLQKE LAELRESTSQ  120
MHTASSLEKQ IGHPSPPPEK KELRKVAHLT GKSNSRSMPL EWEDTYGIVL LSGVKYKKGG  180
LVINETGLYF VYSKVYFRGQ SCNNLPLSHK VYMRNSKYPQ DLVMMEGKMM SYCTTGQMWA  240
RSSYLGAVFN LTSADHLYVN VSELSLVNFE ESQTFFGLYK L                      281

SEQ ID NO: 144          moltype = AA  length = 179
FEATURE                 Location/Qualifiers
REGION                  1..179
                        note = Description of sequence: A FasL polypeptide
source                  1..179
                        mol_type = protein
                        organism = Homo sapiens
SEQUENCE: 144
```

```
QLFHLQKELA ELRESTSQMH TASSLEKQIG HPSPPPEKKE LRKVAHLTGK SNSRSMPLEW  60
EDTYGIVLLS GVKYKKGGLV INETGLYFVY SKVYFRGQSC NNLPLSHKVY MRNSKYPQDL  120
VMMEGKMMSY CTTGQMWARS SYLGAVFNLT SADHLYVNVS ELSLVNFEES QTFFGLYKL   179

SEQ ID NO: 145         moltype = AA  length = 335
FEATURE                Location/Qualifiers
REGION                 1..335
                       note = Description of sequence: A Fas recptor sequence
source                 1..335
                       mol_type = protein
                       organism = Homo sapiens
DOMAIN                 26..173
                       note = aas 26-173 forms the ectodomain (extracellular
                        domain)
DOMAIN                 174..190
                       note = aas 174-190 forms the transmembrane domain
DOMAIN                 191..335
                       note = 191-335 forms the cytoplasmic domain
SEQUENCE: 145
MLGIWTLLPL VLTSVARLSS KSVNAQVTDI NSKGLELRKT VTTVETQNLE GLHHDGQFCH  60
KPCPPGERKA RDCTVNGDEP DCVPCQEGKE YTDKAHFSSK CRRCRLCDEG HGLEVEINCT  120
RTQNTKCRCK PNFFCNSTVC EHCDPCTKCE HGIIKECTLT SNTKCKEEGS RSNLGWLCLL  180
LLPIPLIVWV KRKEVQKTCR KHRKENQGSH ESPTLNPETV AINLSDVDLS KYITTIAGVM  240
TLSQVKGFVR KNGVNEAKID EIKNDNVQDT AEQKVQLLRN WHQLHGKKEA YDTLIKDLKK  300
ANLCTLAEKI QTIILKDITS DSENSNFRNE IQSLV                            335

SEQ ID NO: 146         moltype = AA  length = 627
FEATURE                Location/Qualifiers
REGION                 1..627
                       note = Description of sequence: Chimeric peptide
source                 1..627
                       mol_type = protein
                       organism = synthetic construct
DOMAIN                 1..133
                       note = 1..133 is wt human IL-2
DOMAIN                 134..148
                       note = 134..148  is a linker
DOMAIN                 149..364
                       note = 149..364 is Mono(67) (LALA)
DOMAIN                 365..379
                       note = 365..379 is a linker
DOMAIN                 380..490
                       note = 380..490 is TBRII (delta 25 D1118A)
DOMAIN                 491..515
                       note = 491..515 is a linker
SEQUENCE: 146
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSAP EAAGGPSVFL FPPKPKDTLM ISRTPEVTCV  180
VVDVSHEDPE VKFNWYVDGV EVHNAKTKPR EEQYNSTYRV VSVLTVLHQD WLNGKEYKCK  240
VSNKALPAPI EKTISKAKGQ PREPQVYTKP PSREEMTKNQ VSLSCLVKGF YPSDIAVEWE  300
SNGQPENNYK TTVPVLDSDG SFRLASYLTV DKSRWQQGNV FSCSVMHEAL HNHYTQKSLS  360
LSPGGGGGSG GGGSGGGGSQ LCKFCDVRFS TCDNQKSCMS NCSITSICEK PQEVCVAVWR  420
KNDENITLET VCHDPKLPYH DFILEDAASP KCIMKEKKKP GETFFMCSCS SAECNDNIIF  480
SEEYNTSNPD GGGGSGGGGS GGGGSGGGGS GGGGSALDTN YCFRNLEENC CVRPLYIDFR  540
QDLGWKWVHE PKGYYANFCS GPCPYLRSAD TTHSTVLGLY NTLNPEASAS PSCVPQDLEP  600
LTILYYVGRT PKVEQLSNMV VKSCKCS                                     627

SEQ ID NO: 147         moltype = AA  length = 637
FEATURE                Location/Qualifiers
REGION                 1..637
                       note = Description of sequence: Chimeric peptide
source                 1..637
                       mol_type = protein
                       organism = synthetic construct
DOMAIN                 1..133
                       note = 1..133 is human IL-2 (H16T F42A)
DOMAIN                 134..148
                       note = 134..148  is a linker
DOMAIN                 149..374
                       note = 149..374 is hIgG1 (LALA)
DOMAIN                 375..389
                       note = 375..389 is a linker
DOMAIN                 390..500
                       note = 390..500 is TBRII (delta 25 D1118A)
DOMAIN                 501..525
                       note = 501..525 is a  linker
SEQUENCE: 147
APTSSSTKKT QLQLETLLLD LQMILNGINN YKNPKLTRML TAKFYMPKKA TELKHLQCLE  60
```

```
EELKPLEEVL NLAQSKNFHL RPRDLISNIN VIVLELKGSE TTFMCEYADE TATIVEFLNR  120
WITFCQSIIS TLTGGGGSGG GGSGGGGSDK THTCPPCPAP EAAGGPSVFL FPPKPKDTLM  180
ISRTPEVTCV VVDVSHEDPE VKFNWYVDGV EVHNAKTKPR EEQYNSTYRV VSVLTVLHQD  240
WLNGKEYKCK VSNKALPAPI EKTISKAKGQ PREPQVYTLP PSREEMTKNQ VSLTCLVKGF  300
YPSDIAVEWE SNGQPENNYK TTPPVLDSDG SFFLYSKLTV DKSRWQQGNV FSCSVMHEAL  360
HNHYTQKSLS LSPGGGGGSG GGGSGGGGSQ LCKFCDVRFS TCDNQKSCMS NCSITSICEK  420
PQEVCVAVWR KNDENITLET VCHDPKLPYH DFILEDAASP KCIMKEKKKP GETFFMCSCS  480
SAECNDNIIF SEEYNTSNPD GGGGSGGGGS GGGGSGGGGS GGGGSALDTN YCFRNLEENC  540
CVRPLYIDFR QDLGWKWVHE PKGYYANFCS GPCPYLRSAD TTHSTVLGLY NTLNPEASAS  600
PCCVPQDLEP LTILYYVGRT PKVEQLSNMV VKSCKCS                          637

SEQ ID NO: 148         moltype = AA  length = 511
FEATURE                Location/Qualifiers
REGION                 1..511
                       note = Description of sequence: Chimeric peptide
source                 1..511
                       mol_type = protein
                       organism = synthetic construct
DOMAIN                 1..133
                       note = 1..133 is human IL-2 (wt)
DOMAIN                 134..148
                       note = 134..148 is a linker
DOMAIN                 149..374
                       note = 149..374 is hIgG1 Fc (LALA) KiH chain A
DOMAIN                 375..399
                       note = 375..399 is a linker
DOMAIN                 400..511
                       note = 400..511 is hTGF Beta-3 (C77S)
SEQUENCE: 148
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSDK THTCPPCPAP EAAGGPSVFL FPPKPKDTLM  180
ISRTPEVTCV VVDVSHEDPE VKFNWYVDGV EVHNAKTKPR EEQYNSTYRV VSVLTVLHQD  240
WLNGKEYKCK VSNKALPAPI EKTISKAKGQ PREPQVYTLP PSREEMTKNQ VSLWCLVKGF  300
YPSDIAVEWE SNGQPENNYK TTPPVLDSDG SFFLYSKLTV DKSRWQQGNV FSCSVMHEAL  360
HNHYTQKSLS LSPGGGGGSG GGGSGGGGSG GGGSGGGGSA LDTNYCFRNL EENCCVRPLY  420
IDFRQDLGWK WVHEPKGYYA NFCSGPCPYL RSADTTHSTV LGLYNTLNPE ASASPSCVPQ  480
DLEPLTILYY VGRTPKVEQL SNMVVKSCKC S                                511

SEQ ID NO: 149         moltype = AA  length = 500
FEATURE                Location/Qualifiers
REGION                 1..500
                       note = Description of sequence: Chimeric peptide
source                 1..500
                       mol_type = protein
                       organism = synthetic construct
DOMAIN                 1..133
                       note = 1..133 is human IL-2 (wt)
DOMAIN                 134..148
                       note = 134..148 is a linker
DOMAIN                 149..374
                       note = 149..374 is hIgG1 Fc (LALA) KiH chain B
DOMAIN                 375..389
                       note = 375..389 is a linker
DOMAIN                 390..500
                       note = 390..500 is TBRII (delta 25 D1118A)
SEQUENCE: 149
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSDK THTCPPCPAP EAAGGPSVFL FPPKPKDTLM  180
ISRTPEVTCV VVDVSHEDPE VKFNWYVDGV EVHNAKTKPR EEQYNSTYRV VSVLTVLHQD  240
WLNGKEYKCK VSNKALPAPI EKTISKAKGQ PREPQVYTLP PSREEMTKNQ VSLSCAVKGF  300
YPSDIAVEWE SNGQPENNYK TTPPVLDSDG SFFLVSKLTV DKSRWQQGNV FSCSVMHEAL  360
HNHYTQKSLS LSPGGGGGSG GGGSGGGGSQ LCKFCDVRFS TCDNQKSCMS NCSITSICEK  420
PQEVCVAVWR KNDENITLET VCHDPKLPYH DFILEDAASP KCIMKEKKKP GETFFMCSCS  480
SAECNDNIIF SEEYNTSNPD                                             500

SEQ ID NO: 150         moltype = AA  length = 511
FEATURE                Location/Qualifiers
REGION                 1..511
                       note = Description of sequence: Chimeric peptide
source                 1..511
                       mol_type = protein
                       organism = synthetic construct
DOMAIN                 1..133
                       note = 1..133 is human IL-2 (wt)
DOMAIN                 134..148
                       note = 134..148  is linker
DOMAIN                 149..374
```

```
                        note =  149..374 is hIgG1 Fc (LALA) KiH chain A
DOMAIN                  375..399
                        note = 375..399 is a linker;
DOMAIN                  400..511
                        note = 400..511 is hTGF Beta-3 (C77S)
SEQUENCE: 150
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSDK THTCPPCPAP EAAGGPSVFL FPPKPKDTLM  180
ISRTPEVTCV VVDVSHEDPE VKFNWYVDGV EVHNAKTKPR EEQYNSTYRV VSVLTVLHQD  240
WLNGKEYKCK VSNKALPAPI EKTISKAKGQ PREPQVYTLP PSREEMTKNQ VSLWCLVKGF  300
YPSDIAVEWE SNGQPENNYK TTPPVLDSDG SFFLYSKLTV DKSRWQQGNV FSCSVMHEAL  360
HNHYTQKSLS LSPGGGGGSG GGGSGGGGSG GGGSGGGGSA LDTNYCFRNL EENCCVRPLY  420
IDFRQDLGWK WVHEPKGYYA NFCSGPCPYL RSADTTHSTV LGLYNTLNPE ASASPSCVPQ  480
DLEPLTILYY VGRTPKVEQL SNMVVKSCKC S                                511

SEQ ID NO: 151          moltype = AA  length = 352
FEATURE                 Location/Qualifiers
REGION                  1..352
                        note = Description of sequence: Chimeric peptide
source                  1..352
                        mol_type = protein
                        organism = synthetic construct
DOMAIN                  1..226
                        note = 1..226 is hIgG1 Fc (LALA) KiH chain B (T366S L368A
                         Y407V)
DOMAIN                  227..241
                        note = 227.. 241 is a linker
DOMAIN                  242..352
                        note = 242..352 is TBRII (delta 25 D118A)
SEQUENCE: 151
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGGGGG SGGGGSGGGG  240
SQLCKFCDVR FSTCDNQKSC MSNCSITSIC EKPQEVCVAV WRKNDENITL ETVCHDPKLP  300
YHDFILEDAA SPKCIMKEKK KPGETFFMCS CSSAECNDNI IFSEEYNTSN PD          352

SEQ ID NO: 152          moltype = AA  length = 637
FEATURE                 Location/Qualifiers
REGION                  1..637
                        note = Description of sequence: Chimeric peptide
source                  1..637
                        mol_type = protein
                        organism = synthetic construct
DOMAIN                  1..133
                        note = 1..133 is human IL-2 (H16T F42A);
DOMAIN                  134..148
                        note = 134..148 is a linker
DOMAIN                  149..374
                        note = 149..374 is hIgG1 Fc (LALA) KiH (T366W) chain A;
DOMAIN                  375..389
                        note = 375..389 is a linker
DOMAIN                  390..500
                        note = 390..500 is TBRII (delta 25 D118A)
DOMAIN                  501..525
                        note = 501..525 is a linker
SEQUENCE: 152
APTSSSTKKT QLQLETLLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSDK THTCPPCPAP EAAGGPSVFL FPPKPKDTLM  180
ISRTPEVTCV VVDVSHEDPE VKFNWYVDGV EVHNAKTKPR EEQYNSTYRV VSVLTVLHQD  240
WLNGKEYKCK VSNKALPAPI EKTISKAKGQ PREPQVYTLP PSREEMTKNQ VSLWCLVKGF  300
YPSDIAVEWE SNGQPENNYK TTPPVLDSDG SFFLYSKLTV DKSRWQQGNV FSCSVMHEAL  360
HNHYTQKSLS LSPGGGGGSG GGGSGGGGSQ LCKFCDVRFS TCDNQKSCMS NCSITSICEK  420
PQEVCVAVWR KNDENITLET VCHDPKLPYH DFILEDAASP KCIMKEKKKP GETFFMCSCS  480
SAECNDNIIF SEEYNTSNPD GGGGSGGGGS GGGGSGGGGS GGGGSALDTN YCFRNLEENC  540
CVRPLYIDFR QDLGWKWVHE PKGYYANFCS GPCPYLRSAD TTHSTVLGLY NTLNPEASAS  600
PSCVPQDLEP LTILYYVGRT PKVEQLSNMV VKSCKCS                          637

SEQ ID NO: 153          moltype = AA  length = 226
FEATURE                 Location/Qualifiers
REGION                  1..226
                        note = Description of sequence:  hIgG1 Fc (LALA) KiH chain B
source                  1..226
                        mol_type = protein
                        organism = synthetic construct
SEQUENCE: 153
DKTHTCPPCP APEAAGGPSV FLFPPKPKDT LMISRTPEVT CVVVDVSHED PEVKFNWYVD  60
```

-continued

```
GVEVHNAKTK PREEQYNSTY RVVSVLTVLH QDWLNGKEYK CKVSNKALPA PIEKTISKAK  120
GQPREPQVYT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPG                226

SEQ ID NO: 154         moltype = AA  length = 11
FEATURE                Location/Qualifiers
REGION                 1..11
                       note = Description of sequence: Myc epitope
source                 1..11
                       mol_type = protein
                       organism = Homo sapiens
SEQUENCE: 154
CEQKLISEED L                                                      11

SEQ ID NO: 155         moltype = AA  length = 374
FEATURE                Location/Qualifiers
REGION                 1..374
                       note = Description of sequence: Chimeric peptide
source                 1..374
                       mol_type = protein
                       organism = synthetic construct
DOMAIN                 1..226
                       note = 1..226  is hIgG1 Fc  (LALA) KiH chain A
DOMAIN                 227..241
                       note = 227..241 is a linker
DOMAIN                 242..374
                       note = 242..374 is  hIL-2 (wt)
SEQUENCE: 155
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLWCLVK GFYPSDIAVE WESNGQPENN YKTTPPVLDS  180
DGSFFLYSKL TVDKSRWQQG NVFSCSVMHE ALHNHYTQKS LSLSPGGGGG SGGGGSGGGG  240
SAPTSSSTKK TQLQLEHLLL DLQMILNGIN NYKNPKLTRM LTFKFYMPKK ATELKHLQCL  300
EEELKPLEEV LNLAQSKNFH LRPRDLISNI NVIVLELKGS ETTFMCEYAD ETATIVEFLN  360
RWITFCQSII STLT                                                   374

SEQ ID NO: 156         moltype = AA  length = 489
FEATURE                Location/Qualifiers
REGION                 1..489
                       note = Description of sequence: Chimeric peptide
source                 1..489
                       mol_type = protein
                       organism = synthetic construct
DOMAIN                 1..226
                       note = 1..226  is hIgG1 Fc  (LALA) KiH chain B
DOMAIN                 227..241
                       note = 227..241 is a linker
DOMAIN                 242..352
                       note = 242..352  is TBRII (delta 25 D32N D118A)
DOMAIN                 353..377
                       note = 353..377 is a linker
DOMAIN                 378..489
                       note = 378..489 is hTGF Beta-3 (C77S)
SEQUENCE: 156
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGGGGG SGGGGSGGGG  240
SQLCKFCNVR FSTCDNQKSC MSNCSITSIC EKPQEVCVAV WRKNDENITL ETVCHDPKLP  300
YHDFILEDAA SPKCIMKEKK KPGETFFMCS CSSAECNDNI IFSEEYNTSN PDGGGGSGGG  360
GSGGGGSGGG GSGGGGSALD TNYCFRNLEE NCCVRPLYID FRQDLGWKWV HEPKGYYANF  420
CSGPCPYLRS ADTTHSTVLG LYNTLNPEAS ASPSCVPQDL EPLTILYYVG RTPKVEQLSN  480
MVVKSCKCS                                                         489

SEQ ID NO: 157         moltype = AA  length = 627
FEATURE                Location/Qualifiers
REGION                 1..627
                       note = Description of sequence: Chimeric peptide
source                 1..627
                       mol_type = protein
                       organism = synthetic construct
DOMAIN                 1..133
                       note = 1..133 is human IL-2 (wt)
DOMAIN                 134..148
                       note = 134..148 is a linker
DOMAIN                 149..364
                       note = 149..364 is Mono Fc (LALA)
DOMAIN                 365..379
                       note = 365..379 is a linker;
```

```
DOMAIN                  380..490
                        note = 380..490 is TBRII (delta 25 D32N D118A)
DOMAIN                  491..515
                        note = 491..515 is a linker
SEQUENCE: 157
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSAP EAAGGPSVFL FPPKPKDTLM ISRTPEVTCV  180
VVDVSHEDPE VKFNWYVDGV EVHNAKTKPR EEQYNSTYRV VSVLTVLHQD WLNGKEYKCK  240
VSNKALPAPI EKTISKAKGQ PREPQVYTKP PSREEMTKNQ VSLSCLVKGF YPSDIAVEWE  300
SNGQPENNYK TTVPVLDSDG SFRLASYLTV DKSRWQQGNV FSCSVMHEAL HNHYTQKSLS  360
LSPGGGGGSG GGGSGGGGSQ LCKFCNVRFS TCDNQKSCMS NCSITSICEK PQEVCVAVWR  420
KNDENITLET VCHDPKLPYH DFILEDAASP KCIMKEKKKP GETFFMCSCS SAECNDNIIF  480
SEEYNTSNPD GGGGSGGGGS GGGGSGGGGS GGGGSALDTN YCFRNLEENC CVRPLYIDFR  540
QDLGWKWVHE PKGYYANFCS GPCPYLRSAD TTHSTVLGLY NTLNPEASAS PSCVPQDLEP  600
LTILYYVGRT PKVEQLSNMV VKSCKCS                                    627

SEQ ID NO: 158          moltype = AA  length = 627
FEATURE                 Location/Qualifiers
REGION                  1..627
                        note = Description of sequence: Chimeric peptide
source                  1..627
                        mol_type = protein
                        organism = synthetic construct
DOMAIN                  1..133
                        note = 1..133 is human IL-2 (H16T F42A)
DOMAIN                  134..148
                        note = 134..148  is a linker
DOMAIN                  149..364
                        note = 149..364 is Mono Fc (LALA);
DOMAIN                  365..379
                        note = 365..379 is a linker
DOMAIN                  380..490
                        note = 380..490 is TBRII (delta 25 D118A)
DOMAIN                  491..515
                        note = 491..515 is a linker
SEQUENCE: 158
APTSSSTKKT QLQLETLLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSAP EAAGGPSVFL FPPKPKDTLM ISRTPEVTCV  180
VVDVSHEDPE VKFNWYVDGV EVHNAKTKPR EEQYNSTYRV VSVLTVLHQD WLNGKEYKCK  240
VSNKALPAPI EKTISKAKGQ PREPQVYTKP PSREEMTKNQ VSLSCLVKGF YPSDIAVEWE  300
SNGQPENNYK TTVPVLDSDG SFRLASYLTV DKSRWQQGNV FSCSVMHEAL HNHYTQKSLS  360
LSPGGGGGSG GGGSGGGGSQ LCKFCDVRFS TCDNQKSCMS NCSITSICEK PQEVCVAVWR  420
KNDENITLET VCHDPKLPYH DFILEDAASP KCIMKEKKKP GETFFMCSCS SAECNDNIIF  480
SEEYNTSNPD GGGGSGGGGS GGGGSGGGGS GGGGSALDTN YCFRNLEENC CVRPLYIDFR  540
QDLGWKWVHE PKGYYANFCS GPCPYLRSAD TTHSTVLGLY NTLNPEASAS PSCVPQDLEP  600
LTILYYVGRT PKVEQLSNMV VKSCKCS                                    627

SEQ ID NO: 159          moltype = AA  length = 627
FEATURE                 Location/Qualifiers
REGION                  1..627
                        note = Description of sequence: Chimeric peptide
source                  1..627
                        mol_type = protein
                        organism = synthetic construct
DOMAIN                  1..133
                        note = 1..133 is human IL-2 (H16T F42A)
DOMAIN                  134..148
                        note = 134..148 is a linker
DOMAIN                  149..364
                        note = 149..364 is Mono (67) Fc (LALA)
DOMAIN                  365..379
                        note = 365..379 is a linker
DOMAIN                  380..490
                        note = 380..490 is TBRII (delta 25D32N  D118A)
DOMAIN                  491..515
                        note = 491..515is a linker
SEQUENCE: 159
APTSSSTKKT QLQLETLLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSAP EAAGGPSVFL FPPKPKDTLM ISRTPEVTCV  180
VVDVSHEDPE VKFNWYVDGV EVHNAKTKPR EEQYNSTYRV VSVLTVLHQD WLNGKEYKCK  240
VSNKALPAPI EKTISKAKGQ PREPQVYTKP PSREEMTKNQ VSLSCLVKGF YPSDIAVEWE  300
SNGQPENNYK TTVPVLDSDG SFRLASYLTV DKSRWQQGNV FSCSVMHEAL HNHYTQKSLS  360
LSPGGGGGSG GGGSGGGGSQ LCKFCNVRFS TCDNQKSCMS NCSITSICEK PQEVCVAVWR  420
KNDENITLET VCHDPKLPYH DFILEDAASP KCIMKEKKKP GETFFMCSCS SAECNDNIIF  480
SEEYNTSNPD GGGGSGGGGS GGGGSGGGGS GGGGSALDTN YCFRNLEENC CVRPLYIDFR  540
QDLGWKWVHE PKGYYANFCS GPCPYLRSAD TTHSTVLGLY NTLNPEASAS PSCVPQDLEP  600
```

```
LTILYYVGRT PKVEQLSNMV VKSCKCS                                   627

SEQ ID NO: 160          moltype = AA  length = 500
FEATURE                 Location/Qualifiers
REGION                  1..500
                        note = Description of sequence: Chimeric peptide
source                  1..500
                        mol_type = protein
                        organism = synthetic construct
DOMAIN                  1..213
                        note = 1..213 is h IgG1 Fc (functionally ablated) KiH chain
                         B
DOMAIN                  214..229
                        note = 214..229 is a linker
DOMAIN                  230..340
                        note = 230..340 is TBRII (delta 25 D1118A)
SEQUENCE: 160
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSDK THTCPPCPAP EAAGGPSVFL FPPKPKDTLM  180
ISRTPEVTCV VVDVSHEDPE VKFNWYVDGV EVHNAKTKPR EEQYNSTYRV VSVLTVLHQD  240
WLNGKEYKCK VSNKALPAPI EKTISKAKGQ PREPQVYTLP PSREEMTKNQ VSLSCAVKGF  300
YPSDIAVEWE SNGQPENNYK TTPPVLDSDG SFFLVSKLTV DKSRWQQGNV FSCSVMHEAL  360
HNHYTQKSLS LSPGGGGGSG GGGSGGGGSQ LCKFCNVRFS TCDNQKSCMS NCSITSICEK  420
PQEVCVAVWR KNDENITLET VCHDPKLPYH DFILEDAASP KCIMKEKKKP GETFFMCSCS  480
SAECNDNIIF SEEYNTSNPD                                           500

SEQ ID NO: 161          moltype = AA  length = 8
FEATURE                 Location/Qualifiers
REGION                  1..8
                        note = Description of sequence: Arachis hypogaea peptide
source                  1..8
                        mol_type = protein
                        organism = Arachis hypogaea
SEQUENCE: 161
PGQFEDFF                                                        8

SEQ ID NO: 162          moltype = AA  length = 8
FEATURE                 Location/Qualifiers
REGION                  1..8
                        note = Description of sequence: Arachis hypogaea peptide
source                  1..8
                        mol_type = protein
                        organism = Arachis hypogaea
SEQUENCE: 162
YLQGFSRN                                                        8

SEQ ID NO: 163          moltype = AA  length = 10
FEATURE                 Location/Qualifiers
REGION                  1..10
                        note = Description of sequence: Arachis hypogaea peptide
source                  1..10
                        mol_type = protein
                        organism = Arachis hypogaea
SEQUENCE: 163
FNAEFNEIRR                                                      10

SEQ ID NO: 164          moltype = AA  length = 8
FEATURE                 Location/Qualifiers
REGION                  1..8
                        note = Description of sequence: Arachis hypogaea peptide
source                  1..8
                        mol_type = protein
                        organism = Arachis hypogaea
SEQUENCE: 164
QEERGQRR                                                        8

SEQ ID NO: 165          moltype = AA  length = 10
FEATURE                 Location/Qualifiers
REGION                  1..10
                        note = Description of sequence: Arachis hypogaea peptide
source                  1..10
                        mol_type = protein
                        organism = Arachis hypogaea
SEQUENCE: 165
DITNPINLRE                                                      10

SEQ ID NO: 166          moltype = AA  length = 10
FEATURE                 Location/Qualifiers
```

```
REGION                  1..10
                        note = Description of sequence: Arachis hypogaea peptide
source                  1..10
                        mol_type = protein
                        organism = Arachis hypogaea
SEQUENCE: 166
NNFGKLFEVK                                                              10

SEQ ID NO: 167          moltype = AA  length = 6
FEATURE                 Location/Qualifiers
REGION                  1..6
                        note = Description of sequence: Arachis hypogaea peptide
source                  1..6
                        mol_type = protein
                        organism = Arachis hypogaea
SEQUENCE: 167
GNLELV                                                                  6

SEQ ID NO: 168          moltype = AA  length = 10
FEATURE                 Location/Qualifiers
REGION                  1..10
                        note = Description of sequence: Arachis hypogaea peptide
source                  1..10
                        mol_type = protein
                        organism = Arachis hypogaea
SEQUENCE: 168
RRYTARLKEG                                                              10

SEQ ID NO: 169          moltype = AA  length = 10
FEATURE                 Location/Qualifiers
REGION                  1..10
                        note = Description of sequence: Arachis hypogaea peptide
source                  1..10
                        mol_type = protein
                        organism = Arachis hypogaea
SEQUENCE: 169
ELHLLGFGIN                                                              10

SEQ ID NO: 170          moltype = AA  length = 10
FEATURE                 Location/Qualifiers
REGION                  1..10
                        note = Description of sequence: Arachis hypogaea peptide
source                  1..10
                        mol_type = protein
                        organism = Arachis hypogaea
SEQUENCE: 170
HRIFLAGDKD                                                              10

SEQ ID NO: 171          moltype = AA  length = 10
FEATURE                 Location/Qualifiers
REGION                  1..10
                        note = Description of sequence: Arachis hypogaea peptide
source                  1..10
                        mol_type = protein
                        organism = Arachis hypogaea
SEQUENCE: 171
IDQIEKQAKD                                                              10

SEQ ID NO: 172          moltype = AA  length = 10
FEATURE                 Location/Qualifiers
REGION                  1..10
                        note = Description of sequence: Arachis hypogaea peptide
source                  1..10
                        mol_type = protein
                        organism = Arachis hypogaea
SEQUENCE: 172
KDLAFPGSGE                                                              10

SEQ ID NO: 173          moltype = AA  length = 10
FEATURE                 Location/Qualifiers
REGION                  1..10
                        note = Description of sequence: Arachis hypogaea peptide
source                  1..10
                        mol_type = protein
                        organism = Arachis hypogaea
SEQUENCE: 173
KESHFVSARP                                                              10

SEQ ID NO: 174          moltype = AA  length = 25
```

```
FEATURE                Location/Qualifiers
REGION                 1..25
                       note = Description of sequence: Arachis hypogaea peptide
source                 1..25
                       mol_type = protein
                       organism = Arachis hypogaea
SEQUENCE: 174
NEGVIVKVSK EHVEELTKHA KSVSK                                        25

SEQ ID NO: 175         moltype = AA  length = 10
FEATURE                Location/Qualifiers
REGION                 1..10
                       note = Description of sequence: Arachis hypogaea peptide
source                 1..10
                       mol_type = protein
                       organism = Arachis hypogaea
SEQUENCE: 175
HASARQQWEL                                                         10

SEQ ID NO: 176         moltype = AA  length = 10
FEATURE                Location/Qualifiers
REGION                 1..10
                       note = Description of sequence: Arachis hypogaea peptide
source                 1..10
                       mol_type = protein
                       organism = Arachis hypogaea
SEQUENCE: 176
QWELQGDRRC                                                         10

SEQ ID NO: 177         moltype = AA  length = 10
FEATURE                Location/Qualifiers
REGION                 1..10
                       note = Description of sequence: Arachis hypogaea peptide
source                 1..10
                       mol_type = protein
                       organism = Arachis hypogaea
SEQUENCE: 177
DRRCQSQLER                                                         10

SEQ ID NO: 178         moltype = AA  length = 10
FEATURE                Location/Qualifiers
REGION                 1..10
                       note = Description of sequence: Arachis hypogaea peptide
source                 1..10
                       mol_type = protein
                       organism = Arachis hypogaea
SEQUENCE: 178
LRPCEQHLMQ                                                         10

SEQ ID NO: 179         moltype = AA  length = 10
FEATURE                Location/Qualifiers
REGION                 1..10
                       note = Description of sequence: Arachis hypogaea peptide
source                 1..10
                       mol_type = protein
                       organism = Arachis hypogaea
SEQUENCE: 179
KIQRDEDSYE                                                         10

SEQ ID NO: 180         moltype = AA  length = 10
FEATURE                Location/Qualifiers
REGION                 1..10
                       note = Description of sequence: Arachis hypogaea peptide
source                 1..10
                       mol_type = protein
                       organism = Arachis hypogaea
SEQUENCE: 180
YERDPYSPSQ                                                         10

SEQ ID NO: 181         moltype = AA  length = 10
FEATURE                Location/Qualifiers
REGION                 1..10
                       note = Description of sequence: Arachis hypogaea peptide
source                 1..10
                       mol_type = protein
                       organism = Arachis hypogaea
SEQUENCE: 181
SQDPYSPSPY                                                         10
```

```
SEQ ID NO: 182          moltype = AA  length = 10
FEATURE                 Location/Qualifiers
REGION                  1..10
                        note = Description of sequence: Arachis hypogaea peptide
source                  1..10
                        mol_type = protein
                        organism = Arachis hypogaea
SEQUENCE: 182
DRLQGRQQEQ                                                    10

SEQ ID NO: 183          moltype = AA  length = 10
FEATURE                 Location/Qualifiers
REGION                  1..10
                        note = Description of sequence: Arachis hypogaea peptide
source                  1..10
                        mol_type = protein
                        organism = Arachis hypogaea
SEQUENCE: 183
KRELRNLPQQ                                                    10

SEQ ID NO: 184          moltype = AA  length = 10
FEATURE                 Location/Qualifiers
REGION                  1..10
                        note = Description of sequence: Arachis hypogaea peptide
source                  1..10
                        mol_type = protein
                        organism = Arachis hypogaea
SEQUENCE: 184
QRCDLDVESG                                                    10

SEQ ID NO: 185          moltype = AA  length = 15
FEATURE                 Location/Qualifiers
REGION                  1..15
                        note = Description of sequence: Arachis hypogaea peptide
source                  1..15
                        mol_type = protein
                        organism = Arachis hypogaea
SEQUENCE: 185
IETWNPNNQE FECAG                                              15

SEQ ID NO: 186          moltype = AA  length = 15
FEATURE                 Location/Qualifiers
REGION                  1..15
                        note = Description of sequence: Arachis hypogaea peptide
source                  1..15
                        mol_type = protein
                        organism = Arachis hypogaea
SEQUENCE: 186
GNIFSGFTPE FLAQA                                              15

SEQ ID NO: 187          moltype = AA  length = 15
FEATURE                 Location/Qualifiers
REGION                  1..15
                        note = Description of sequence: Arachis hypogaea peptide
source                  1..15
                        mol_type = protein
                        organism = Arachis hypogaea
SEQUENCE: 187
VTVRGGLRIL SPDRK                                              15

SEQ ID NO: 188          moltype = AA  length = 15
FEATURE                 Location/Qualifiers
REGION                  1..15
                        note = Description of sequence: Arachis hypogaea peptide
source                  1..15
                        mol_type = protein
                        organism = Arachis hypogaea
SEQUENCE: 188
DEDEYEYDEE DRRRG                                              15

SEQ ID NO: 189          moltype = AA  length = 6
FEATURE                 Location/Qualifiers
REGION                  1..6
                        note = Description of sequence: Linker
source                  1..6
                        mol_type = protein
                        organism = Homo sapiens
SEQUENCE: 189
GGGSGG                                                        6
```

```
SEQ ID NO: 190          moltype = AA  length = 390
FEATURE                 Location/Qualifiers
REGION                  1..390
                        note = Description of sequence: TGF-Beta- -1 preproprotein
                         UniProtKB - P01137 having a P10L substitution in the
                         signal sequence
source                  1..390
                        mol_type = protein
                        organism = Homo sapiens
DOMAIN                  1..29
                        note = 1..29 is a Signal Peptide
DOMAIN                  29..261
                        note = 29..261 is TGF-beta propeptide
DOMAIN                  29..261
                        note = 29..261 is TGF-beta propeptide
DOMAIN                  244..246
                        note = 244..246 is a Cell attachment site
DOMAIN                  279..390
                        note = 279..390 is the mature peptide
SEQUENCE: 190
MPPSGLRLLL LLLPLLWLLV LTPGRPAAGL STCKTIDMEL VKRKRIEAIR GQILSKLRLA  60
SPPSQGEVPP GPLPEAVLAL YNSTRDRVAG ESAEPEPEPE ADYYAKEVTR VLMVETHNEI  120
YDKFKQSTHS IYMFFNTSEL REAVPEPVLL SRAELRLLRL KLKVEQHVEL YQKYSNNSWR  180
YLSNRLLAPS DSPEWLSFDV TGVVRQWLSR GGEIEGFRLS AHCSCDSRDN TLQVDINGFT  240
TGRRGDLATI HGMNRPFLLL MATPLERAQH LQSSRHRRAL DTNYCFSSTE KNCCVRQLYI  300
DFRKDLGWKW IHEPKGYHAN FCLGPCPYIW SLDTQYSKVL ALYNQHNPGA SAAPCCVPQA  360
LEPLPIVYYV GRKPKVEQLS NMIVRSCKCS                                   390

SEQ ID NO: 191          moltype = AA  length = 511
FEATURE                 Location/Qualifiers
REGION                  1..511
                        note = Description of sequence: Protein construct
source                  1..511
                        mol_type = protein
                        organism = synthetic construct
DOMAIN                  1..133
                        note = 1..133 is human IL-2 (H16A F42A)
DOMAIN                  134..148
                        note = 134..148 is a  linker
DOMAIN                  149..374
                        note = 149..374 is IgG1 KiH A chain functionally ablated
DOMAIN                  375..399
                        note = 375..399 is a linker
DOMAIN                  400..511
                        note =  400..511 is TGF Beta-3 (C77S)
SEQUENCE: 191
APTSSSTKKT QLQLEALLLD LQMILNGINN YKNPKLTRML TAKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTGGGGSGG GGSGGGGSDK THTCPPCPAP EAAGGPSVFL FPPKPKDTLM  180
ISRTPEVTCV VVDVSHEDPE VKFNWYVDGV EVHNAKTKPR EEQYNSTYRV VSVLTVLHQD  240
WLNGKEYKCK VSNKALPAPI EKTISKAKGQ PREPQVYTLP PCREEMTKNQ VSLWCLVKGF  300
YPSDIAVEWE SNGQPENNYK TTPPVLDSDG SFFLYSKLTV DKSRWQQGNV FSCSVMHEAL  360
HNHYTQKSLS LSPGGGGGSG GGGSGGGGSG GGGSGGGGSA LDTNYCFRNL EENCCVRPLY  420
IDFRQDLGWK WVHEPKGYYA NFCSGPCPYL RSADTTHSTV LGLYNTLNPE ASASPSCVPQ  480
DLEPLTILYY VGRTPKVEQL SNMVVKSCKC S                                 511

SEQ ID NO: 192          moltype = AA  length = 352
FEATURE                 Location/Qualifiers
REGION                  1..352
                        note = Description of sequence: Protein construct
source                  1..352
                        mol_type = protein
                        organism = synthetic construct
DOMAIN                  1..226
                        note = 1..226  is IgG1 KiH B chain functionally ablated
DOMAIN                  227..241
                        note = 227..241 is a linker; 242..352 is TGFbRII (delta 25
                         D118A)
DOMAIN                  242..352
                        note = 242..352 is TGFbRII (delta 25 D118A)
SEQUENCE: 192
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGGGGG SGGGGSGGGG  240
SQLCKFCDVR FSTCDNQKSC MSNCSITSIC EKPQEVCVAV WRKNDENITL ETVCHDPKLP  300
YHDFILEDAA SPKCIMKEKK KPGETFFMCS CSSAECNDNI IFSEEYNTSN PD          352
```

```
SEQ ID NO: 193          moltype = AA  length = 50
FEATURE                 Location/Qualifiers
REGION                  1..50
                        note = Description of sequence: Linker
source                  1..50
                        mol_type = protein
                        organism = synthetic construct
SEQUENCE: 193
GGGGGGGGGG GGGGGGGGGG GGGGGGGGGG GGGGGGGGGG GGGGGGGGGG             50

SEQ ID NO: 194          moltype = AA  length = 60
FEATURE                 Location/Qualifiers
REGION                  1..60
                        note = Description of sequence: Linker
source                  1..60
                        mol_type = protein
                        organism = synthetic construct
SEQUENCE: 194
GSGSGSGSGS GSGSGSGSGS GSGSGSGSGS GSGSGSGSGS GSGSGSGSGS GSGSGSGSGS  60

SEQ ID NO: 195          moltype = AA  length = 150
FEATURE                 Location/Qualifiers
REGION                  1..150
                        note = Description of sequence: Linker
source                  1..150
                        mol_type = protein
                        organism = synthetic construct
SEQUENCE: 195
GSGGSGSGGS GSGGSGSGGS GSGGSGSGGS GSGGSGSGGS GSGGSGSGGS GSGGSGSGGS  60
GSGGSGSGGS GSGGSGSGGS GSGGSGSGGS GSGGSGSGGS GSGGSGSGGS GSGGSGSGGS  120
GSGGSGSGGS GSGGSGSGGS GSGGSGSGGS                                   150

SEQ ID NO: 196          moltype = AA  length = 120
FEATURE                 Location/Qualifiers
REGION                  1..120
                        note = Description of sequence: Linker
source                  1..120
                        mol_type = protein
                        organism = synthetic construct
SEQUENCE: 196
GGGSGGGSGG GSGGGSGGGS GGGSGGGSGG GSGGGSGGGS GGGSGGGSGG GSGGGSGGGS  60
GGGSGGGSGG GSGGGSGGGS GGGSGGGSGG GSGGGSGGGS GGGSGGGSGG GSGGGSGGGS  120

SEQ ID NO: 197          moltype = AA  length = 40
FEATURE                 Location/Qualifiers
REGION                  1..40
                        note = Description of sequence: Linker
source                  1..40
                        mol_type = protein
                        organism = synthetic construct
SEQUENCE: 197
GGSGGGSGGG SGGGSGGGSG GGSGGGSGGG SGGGSGGGSG                        40

SEQ ID NO: 198          moltype = AA  length = 10
FEATURE                 Location/Qualifiers
REGION                  1..10
                        note = Description of sequence: Linker
source                  1..10
                        mol_type = protein
                        organism = synthetic construct
SEQUENCE: 198
GSSSSGSSSS                                                         10

SEQ ID NO: 199          moltype = AA  length = 15
FEATURE                 Location/Qualifiers
REGION                  1..15
                        note = Description of sequence: Linker
source                  1..15
                        mol_type = protein
                        organism = synthetic construct
SEQUENCE: 199
GSSSSGSSSS GSSSS                                                   15

SEQ ID NO: 200          moltype = AA  length = 25
FEATURE                 Location/Qualifiers
REGION                  1..25
                        note = Description of sequence: Linker
source                  1..25
                        mol_type = protein
```

```
                       organism = synthetic construct
SEQUENCE: 200
GSSSSGSSSS GSSSSGSSSS GSSSS                                             25

SEQ ID NO: 201         moltype = AA  length = 30
FEATURE                Location/Qualifiers
REGION                 1..30
                       note = Description of sequence: Linker
source                 1..30
                       mol_type = protein
                       organism = synthetic construct
SEQUENCE: 201
GSSSSGSSSS GSSSSGSSSS GSSSSGSSSS                                        30

SEQ ID NO: 202         moltype = AA  length = 10
FEATURE                Location/Qualifiers
REGION                 1..10
                       note = Description of sequence: Linker
source                 1..10
                       mol_type = protein
                       organism = synthetic construct
SEQUENCE: 202
GGGGSGGGGS                                                              10

SEQ ID NO: 203         moltype = AA  length = 15
FEATURE                Location/Qualifiers
REGION                 1..15
                       note = Description of sequence: Linker
source                 1..15
                       mol_type = protein
                       organism = synthetic construct
SEQUENCE: 203
GGGGSGGGGS GGGGS                                                        15

SEQ ID NO: 204         moltype = AA  length = 20
FEATURE                Location/Qualifiers
REGION                 1..20
                       note = Description of sequence: Linker
source                 1..20
                       mol_type = protein
                       organism = synthetic construct
SEQUENCE: 204
GGGGSGGGGS GGGGSGGGGS                                                   20

SEQ ID NO: 205         moltype = AA  length = 25
FEATURE                Location/Qualifiers
REGION                 1..25
                       note = Description of sequence: Linker
source                 1..25
                       mol_type = protein
                       organism = synthetic construct
SEQUENCE: 205
GGGGSGGGGS GGGGSGGGGS GGGGS                                             25

SEQ ID NO: 206         moltype = AA  length = 30
FEATURE                Location/Qualifiers
REGION                 1..30
                       note = Description of sequence: Linker
source                 1..30
                       mol_type = protein
                       organism = synthetic construct
SEQUENCE: 206
GGGGSGGGGS GGGGSGGGGS GGGGSGGGGS                                        30

SEQ ID NO: 207         moltype = AA  length = 35
FEATURE                Location/Qualifiers
REGION                 1..35
                       note = Description of sequence: Linker
source                 1..35
                       mol_type = protein
                       organism = synthetic construct
SEQUENCE: 207
GGGGSGGGGS GGGGSGGGGS GGGGSGGGGS GGGGS                                  35

SEQ ID NO: 208         moltype = AA  length = 40
FEATURE                Location/Qualifiers
REGION                 1..40
                       note = Description of sequence: Linker
source                 1..40
```

-continued

```
                      mol_type = protein
                      organism = synthetic construct
SEQUENCE: 208
GGGGSGGGGS GGGGSGGGGS GGGGSGGGGS GGGGSGGGGS                        40

SEQ ID NO: 209        moltype = AA  length = 45
FEATURE               Location/Qualifiers
REGION                1..45
                      note = Description of sequence: Linker
source                1..45
                      mol_type = protein
                      organism = synthetic construct
SEQUENCE: 209
GGGGSGGGGS GGGGSGGGGS GGGGSGGGGS GGGGSGGGGS GGGGS                  45

SEQ ID NO: 210        moltype = AA  length = 50
FEATURE               Location/Qualifiers
REGION                1..50
                      note = Description of sequence: Linker
source                1..50
                      mol_type = protein
                      organism = synthetic construct
SEQUENCE: 210
GGGGSGGGGS GGGGSGGGGS GGGGSGGGGS GGGGSGGGGS GGGGSGGGGS             50

SEQ ID NO: 211        moltype = AA  length = 6
FEATURE               Location/Qualifiers
REGION                1..6
                      note = Description of sequence: Linker
source                1..6
                      mol_type = protein
                      organism = synthetic construct
SEQUENCE: 211
GGGGGS                                                             6
```

The invention claimed is:

1. A construct comprising a first polypeptide, wherein the first polypeptide comprises:

i) a scaffold polypeptide sequence having at least about 95% sequence identity to an IgG1 sequence selected from SEQ ID NOs: 71 to 78;

ii) a TGF-β3 polypeptide sequence having at least 95% sequence identity to SEQ ID NO: 111; and iii) a masking polypeptide sequence comprising a TGF-β receptor polypeptide sequence having at least 95% sequence identity to SEQ ID NO:122;

wherein the construct comprises one or more independently selected immunomodulatory polypeptide sequences, and the TGF-β receptor polypeptide sequence and the TGF-β3 polypeptide sequence of the first polypeptide interact with each other to reversibly mask the TGF-β3 polypeptide sequence.

2. The construct of claim 1, wherein the one or more independently selected immunomodulatory polypeptide sequences are one or more independently selected IL-2 immunomodulatory polypeptide sequences having at least 95% sequence identity to SEQ ID NO:9.

3. The construct of claim 2, wherein:

i) the TGF-β receptor polypeptide sequence comprises a substitution of any one, any two, any three, any four, or all five of amino acids F30, D32, S52, E55, and D118;

ii) at least one of the IL-2 immunomodulatory polypeptide sequences comprises an amino acid other than histidine at position 16 and an amino acid other than phenylalanine at position 42; and iii) the scaffold polypeptide comprises a substitution that reduces or eliminates the ability of the IgG1 sequence to induce cell lysis through either or both of complement-dependent cytotoxicity (CDC) and antibody-dependent cellular cytotoxicity (ADCC).

4. The construct of claim 2, wherein the scaffold polypeptide comprises a dimerization sequence.

5. The construct of claim 4, wherein the construct forms a homodimer.

6. The construct of claim 5, wherein:

i) the TGF-β receptor polypeptide sequences comprise a substitution of any one, any two, any three, any four, or all five of amino acids F30, D32, S52, E55, and D118; or ii) the one or more IL-2 immunomodulatory polypeptide sequences comprise an amino acid other than histidine at position 16 and an amino acid other than phenylalanine at position 42.

7. The construct of claim 6, wherein each scaffold polypeptide of the homodimer comprises a substitution that reduces or eliminates the ability of the IgG1 sequence to induce cell lysis through either or both of complement-dependent cytotoxicity (CDC) and antibody-dependent cellular cytotoxicity (ADCC).

8. The construct of claim 1, wherein:

the scaffold sequence of the first polypeptide comprises a first interspecific dimerization sequence, the construct further comprises a second polypeptide comprising a scaffold sequence that comprises a counterpart interspecific dimerization sequence and that has at least about 95% sequence identity to an IgG1 sequence selected from SEQ ID NOs: 71 to 78; and the first polypeptide and second polypeptide form a heterodimer through interactions between the interspecific and counterpart interspecific dimerization sequences of their scaffold sequences.

9. The construct of claim 8, wherein the one or more independently selected immunomodulatory polypeptide sequences are one or more independently selected IL-2 immunomodulatory polypeptide sequences having at least 95% sequence identity to SEQ ID NO:9.

10. The construct of claim 9, wherein:

i) the TGF-β receptor polypeptide sequence comprises a substitution of any one, any two, any three, any four, or all five of amino acids F30, D32, S52, E55, and D118;

ii) at least one of the one or more IL-2 immunomodulatory polypeptide sequences comprises an amino acid other than histidine at position 16 and an amino acid other than phenylalanine at position 42; and iii) each scaffold polypeptide comprises a substitution that reduces or eliminates the ability of the IgG1 sequence to induce cell lysis through either or both of complement-dependent cytotoxicity (CDC) and antibody-dependent cellular cytotoxicity (ADCC).

11. The construct of claim 9, wherein the second polypeptide further comprises:

i) a TGF-β3 polypeptide sequence having at least 95% sequence identity to SEQ ID NO: 111; and ii) a masking polypeptide sequence comprising a TGF-β receptor polypeptide sequence having at least 95% sequence identity to SEQ ID NO:122.

12. The construct of claim 11, wherein the first polypeptide, the second polypeptide, or both the first polypeptide and second polypeptide comprise the one or more independently selected IL-2 immunomodulatory polypeptide sequences having at least 95% sequence identity to SEQ ID NO:9.

13. The construct of claim 12, wherein:

i) the TGF-β receptor polypeptide sequence of the first polypeptide and/or second polypeptide comprises a substitution of any one, any two, any three, any four, or all five of amino acids F30, D32, S52, E55, and D118;

ii) at least one of the one or more independently selected IL-2 immunomodulatory polypeptide sequences comprises an amino acid other than histidine at position 16 and an amino acid other than phenylalanine at position 42; and iii) each scaffold polypeptide comprises a substitution that reduces or eliminates the ability of the IgG1 sequence to induce cell lysis through either or both of complement-dependent cytotoxicity (CDC) and antibody-dependent cellular cytotoxicity (ADCC).

14. The construct of claim 12, wherein the first polypeptide comprises, in order in the N-terminal to C-terminal direction:

i) the scaffold polypeptide sequence comprising the first interspecific dimerization sequence, the masking polypeptide sequence, and the TGF-β3 polypeptide sequence;

ii) a first independently selected IL-2 immunomodulatory polypeptide sequence having at least 95% sequence identity to SEQ ID NO:9, and the scaffold polypeptide sequence comprising the first interspecific dimerization sequence, the masking polypeptide sequence, and the TGF-β3 polypeptide sequence; or iii) a first independently selected IL-2 immunomodulatory polypeptide sequence and a second independently selected IL-2 immunomodulatory polypeptide sequence, each IL-2 immunomodulatory polypeptide sequence having at least 95% sequence identity to SEQ ID NO:9, and the scaffold polypeptide sequence comprising the first interspecific dimerization sequence, the masking polypeptide sequence, and the TGF-β3 polypeptide sequence.

15. The construct of claim 14, wherein the second polypeptide comprises in the N-terminal to C-terminal direction:

i) the scaffold polypeptide sequence comprising the counterpart interspecific dimerization sequence and having at least about 95% sequence identity to an IgG1 sequence selected from SEQ ID NOs: 71 to 78;

ii) the TGF-β3 polypeptide sequence; and iii) the masking polypeptide sequence comprising a TGF-β receptor polypeptide sequence having at least 95% sequence identity to SEQ ID NO:122;

wherein the TGF-β receptor polypeptide sequence and the TGF-β3 polypeptide sequence of the second polypeptide interact with each other to reversibly mask the TGF-β3 polypeptide sequence of the second polypeptide.

16. The construct of claim 15, wherein the second polypeptide further comprises one or more independently selected IL-2 immunomodulatory polypeptide sequences having at least 95% sequence identity to SEQ ID NO:9.

17. The construct of claim 16, wherein:

i) the TGF-β receptor polypeptide sequence comprises a substitution of any one, any two, any three, any four, or all five of amino acids F30, D32, S52, E55, and D118;

ii) at least one of the one or more independently selected IL-2 immunomodulatory polypeptide sequences comprises an amino acid other than histidine at position 16 and an amino acid other than phenylalanine at position 42; and iii) each scaffold polypeptide comprises a substitution that reduces or eliminates the ability of the IgG1 sequence to induce cell lysis through either or both of complement-dependent cytotoxicity (CDC) and antibody-dependent cellular cytotoxicity (ADCC).

* * * * *